US012655211B2

(12) United States Patent
Brentjens et al.

(10) Patent No.: US 12,655,211 B2
(45) Date of Patent: *Jun. 16, 2026

(54) ANTIBODIES TARGETING G-PROTEIN COUPLED RECEPTOR AND METHODS OF USE

(71) Applicants: MEMORIAL SLOAN-KETTERING CANCER CENTER, New York, NY (US); EUREKA THERAPEUTICS, INC., Emeryville, CA (US)

(72) Inventors: Renier J. Brentjens, New York, NY (US); Eric L. Smith, New York, NY (US); Cheng Liu, Emeryville, CA (US); Hong Liu, Emeryville, CA (US)

(73) Assignees: MEMORIAL SLOAN-KETTERING CANCER CENTER, New York, NY (US); EUREKA THERAPEUTICS, INC., Emeryville, CA (US)

( * ) Notice: Subject to any disclaimer, the term of this patent is extended or adjusted under 35 U.S.C. 154(b) by 391 days.

This patent is subject to a terminal disclaimer.

(21) Appl. No.: 18/145,254

(22) Filed: Dec. 22, 2022

(65) Prior Publication Data

US 2024/0076370 A1 Mar. 7, 2024

Related U.S. Application Data

(60) Continuation of application No. 16/732,022, filed on Dec. 31, 2019, now Pat. No. 11,566,071, which is a division of application No. 15/614,290, filed on Jun. 5, 2017, now Pat. No. 10,590,196, which is a continuation of application No. PCT/US2015/064122, filed on Dec. 4, 2015.

(60) Provisional application No. 62/088,228, filed on Dec. 5, 2014.

(51) Int. Cl.

| | |
|---|---|
| *C07K 16/30* | (2006.01) |
| *A61K 47/68* | (2017.01) |
| *A61P 35/00* | (2006.01) |
| *C07K 16/28* | (2006.01) |
| *G01N 33/68* | (2006.01) |

(52) U.S. Cl.
CPC .......... *C07K 16/28* (2013.01); *A61K 47/6849* (2017.08); *A61P 35/00* (2018.01); *C07K 16/2809* (2013.01); *G01N 33/6872* (2013.01); *C07K 2317/21* (2013.01); *C07K 2317/24* (2013.01); *C07K 2317/31* (2013.01); *C07K 2317/34* (2013.01); *C07K 2317/622* (2013.01); *C07K 2317/92* (2013.01); *C07K 2319/21* (2013.01); *G01N 2333/705* (2013.01)

(58) Field of Classification Search
CPC ........................ C07K 2317/622; C07K 16/30
USPC ...................................................... 424/136.1
See application file for complete search history.

(56) References Cited

U.S. PATENT DOCUMENTS

| | | | |
|---|---|---|---|
| 4,956,778 | A | 9/1990 | Naito |
| 5,091,513 | A | 2/1992 | Huston et al. |
| 5,132,405 | A | 7/1992 | Huston et al. |
| 5,399,346 | A | 3/1995 | Anderson et al. |
| 6,588,543 | B1 | 7/2003 | Tchilinguirian et al. |
| 7,083,785 | B2 | 8/2006 | Browning et al. |
| 7,446,190 | B2 | 11/2008 | Sadelain et al. |
| 7,483,544 | B2 | 1/2009 | Wright et al. |
| 7,605,236 | B2 | 10/2009 | Ruben et al. |
| 7,807,163 | B2 | 10/2010 | Law et al. |
| 8,389,282 | B2 | 3/2013 | Sadelain et al. |
| 9,994,633 | B2 | 6/2018 | Deshpande et al. |
| 10,098,951 | B2 | 10/2018 | Lu et al. |
| 10,464,988 | B2 | 11/2019 | Lu et al. |
| 10,590,196 | B2 * | 3/2020 | Brentjens ................ C07K 16/28 |
| 10,633,426 | B2 * | 4/2020 | Brentjens ........... C07K 14/7051 |
| 10,906,956 | B2 * | 2/2021 | Brentjens ................ A61P 35/00 |
| 11,566,071 | B2 * | 1/2023 | Brentjens ................ A61P 35/00 |
| 11,820,806 | B2 * | 11/2023 | Brentjens ........... A61K 40/4211 |
| 11,866,478 | B2 * | 1/2024 | Brentjens ........... A61K 40/4202 |
| 12,077,592 | B2 * | 9/2024 | Attar ....................... C07K 16/28 |
| 2003/0207288 | A1 | 11/2003 | Lewin et al. |
| 2004/0110139 | A1 | 6/2004 | Monia et al. |
| 2005/0019320 | A1 | 1/2005 | Sugaru et al. |
| 2005/0196754 | A1 | 9/2005 | Drmanac et al. |
| 2008/0057063 | A1 | 3/2008 | Rinkenberger et al. |
| 2011/0166330 | A1 | 7/2011 | Kobilka et al. |
| 2013/0130379 | A1 | 5/2013 | Adams et al. |
| 2014/0322183 | A1 | 10/2014 | Milone et al. |
| 2015/0306141 | A1 | 10/2015 | Jensen et al. |
| 2016/0158359 | A1 | 6/2016 | Gilbert |
| 2016/0289293 | A1 | 10/2016 | Pule et al. |
| 2016/0303230 | A1 | 10/2016 | Ahmed et al. |
| 2016/0333114 | A1 | 11/2016 | Williams |
| 2017/0335281 | A1 | 11/2017 | Loew et al. |
| 2018/0110002 | A1 | 4/2018 | Kim et al. |
| 2018/0118803 | A1 | 5/2018 | Brentjens et al. |

(Continued)

FOREIGN PATENT DOCUMENTS

| | | |
|---|---|---|
| CN | 103483452 | 1/2014 |
| CN | 103483453 | 1/2014 |

(Continued)

OTHER PUBLICATIONS

Almagro & Franssen, Frontiers in Bioscience, 13:1619-33 (2008).*
Edwards et al., J Mol Biol 334:103-118 (2003).*
Marchalonis et al., Dev & Comp Immunol. 30:223-247 (2006).*
Lippow et al., Nature Biotechnology, 25(10):1171-1176 (2007).*
Sulea et al., Scientific Reports, 8(260):1-11 (2018).*
Hasegawa et al.,MABS, vol. 9, No. 5, pp. 854-873 (2017).*
Altshuler et al., Biochemistry (Moscow), 75(13):1584-1605 (2010).*
Vajda et al., Current Opinion in Structural Biology, 67 pp. 226-231 (2021).*
Marks et al., J. Biol. Chem. 295(29) 9823-9837 (2020).*

(Continued)

*Primary Examiner* — Lynn A Bristol
(74) *Attorney, Agent, or Firm* — Baker Botts L.L.P.

(57) ABSTRACT
The presently disclosed subject matter provides antibodies that bind to GPRC5D and methods of using the same.

22 Claims, 17 Drawing Sheets

Specification includes a Sequence Listing.

(56) References Cited

U.S. PATENT DOCUMENTS

| 2018/0118822 A1 | 5/2018 | Brentjens et al. |
| 2018/0258149 A1 | 9/2018 | Motz et al. |
| 2019/0107537 A1 | 4/2019 | Chaudhary |
| 2019/0112380 A1 | 4/2019 | Chaudhary |
| 2019/0248865 A1 | 8/2019 | Lu et al. |
| 2019/0367612 A1 | 12/2019 | Chaen et al. |
| 2020/0123249 A1 | 4/2020 | Brentjens et al. |
| 2020/0270326 A1 | 8/2020 | Brentjens et al. |
| 2020/0270327 A1 | 8/2020 | Brentjens et al. |
| 2020/0270328 A1 | 8/2020 | Brentjens et al. |
| 2021/0393689 A1 | 12/2021 | Sather et al. |
| 2024/0294599 A1* | 9/2024 | Brentjens ........... A61K 40/4211 |

FOREIGN PATENT DOCUMENTS

| CN | 105647873 | | 6/2016 |
| CN | 108239144 | | 7/2018 |
| EP | 1 468 694 | A1 | 10/2004 |
| EP | 4582449 | A1 * | 7/2025 |
| RU | 2 526 517 | C2 | 8/2014 |
| WO | WO 03/055507 | A1 | 7/2003 |
| WO | WO 2004/072117 | A2 | 8/2004 |
| WO | WO 2005/019258 | A2 | 3/2005 |
| WO | WO 2005/097185 | | 10/2005 |
| WO | WO 2009/039192 | A2 | 3/2009 |
| WO | WO 2009/101611 | A1 | 8/2009 |
| WO | WO 2011/083088 | A2 | 7/2011 |
| WO | WO 2012/009790 | A1 | 1/2012 |
| WO | WO 2012/079000 | A1 | 6/2012 |
| WO | WO 2013/033626 | A2 | 3/2013 |
| WO | WO 2013/185552 | | 12/2013 |
| WO | WO 2014/031687 | | 2/2014 |
| WO | WO 2014/087010 | A1 | 6/2014 |
| WO | WO 2014/114800 | A1 | 7/2014 |
| WO | WO 2014/127261 | A1 | 8/2014 |
| WO | WO 2014/191128 | A1 | 12/2014 |
| WO | WO 2015/095895 | | 6/2015 |
| WO | WO 2015/105522 | | 7/2015 |
| WO | WO 2015/121454 | | 8/2015 |
| WO | WO 2015/142675 | A2 | 9/2015 |
| WO | WO 2016/001810 | A1 | 1/2016 |
| WO | WO 2016/014530 | A1 | 1/2016 |
| WO | WO 2016/090312 | A1 | 6/2016 |
| WO | WO 2016/090327 | | 6/2016 |
| WO | WO 2016/090329 | | 6/2016 |
| WO | WO 2016/126608 | | 8/2016 |
| WO | WO 2016/210293 | | 12/2016 |
| WO | WO 2017/049166 | | 3/2017 |
| WO | WO 2017/062628 | | 4/2017 |
| WO | WO 2017/070608 | | 4/2017 |
| WO | WO 2017/149515 | | 9/2017 |
| WO | WO 2017/172981 | | 10/2017 |
| WO | WO 2017/181119 | | 10/2017 |
| WO | WO 2017/222593 | | 12/2017 |
| WO | WO 2018/017786 | | 1/2018 |
| WO | WO 2019/154890 | | 8/2019 |
| WO | WO 2020/092854 | | 7/2020 |

OTHER PUBLICATIONS

Akbar et al., Cell Reports 34, 108856, Mar. 16, 2021.*

Lo et al., BMC Genomics vol. 22, Article No. 116 (2021).*

Ali et al., "T cells expressing an anti-B-cell maturation antigen chimeric antigen receptor cause remissions of multiple myeloma," Blood (2016) 128(13):1688-1700.

Almagro et al., "Humanization of antibodies," Front Biosci (Jan. 2008) 13:1619-33.

Barderas et al., "Affinity maturation of antibodies assisted by in silico modeling," Proc Natl Acad Sciences, Natl Aca Sci USA (2008) 105(26):9029-34.

Berahovich et al., "CAR-T Cells Based on Novel BCMA Mono-clonal Antibody Block Multiple Myeloma Cell Growth," Cancers (Basel) (2018) 10(9):323, 16 pages.

Brentjens et al., 2016 (Geneseq Accession No. BDB11168, com-puter printout, p. 1) (Brentjens SEQ ID No. 21).

Brentjens et al., 2016 (Geneseq Accession No. BDB11169, com-puter printout, p. 1) (Brentjens SEQ ID No. 22).

Brudno J et al., "T Cells Genetically Modified to Express an Anti-B-Cell Maturation Antigen Chimeric Antigen Receptor Cause Remissions of Poor-Prognosis Relapsed Multiple Myeloma," J Clin. Oncol. (2018) 36(22):2267-80.

Carpenter et al., "B-cell Maturation Antigen is a Promising Target for Adoptive T-cell Therapy of Multiple Myeloma," Clin Cancer Res. 19(8):2048-2060 (2013).

Chen et al., "Enhancement and destruction of antibody function by somatic mutation: unequal occurrence is controlled by V gene combinatorial associations," EMBO J (Jun. 1995) 14(12):2784-94.

Cho et al., "BCMA CAR T-cell therapy arrives for multiple myeloma: a reality," Ann Transl Med (2018) 6(Suppl 2):S93, 5 pages.

Curran et al., "Chimeric antigen receptors for T cell immunotherapy: current understanding and future directions," J Gene Med (2012) 14(6):405-415.

Ebert et al., "Logic-gated approaches to extend the utility of chimeric antigen receptor T-cell technology," Biochem Soc Trans (Apr. 2018) 46(2):391-401.

Hudecek et al., "Receptor affinity and extracellular domain modi-fications affect tumor recognition by ROR1-specific chimeric anti-gen receptor T cells," Clin. Cancer Res. (2013) 19:3153-3164.

Hudecek et al., "The nonsignaling extracellular spacer domain of chimeric antigen receptors is decisive for in vivo antitumor activ-ity," Cancer Immunol Res (Feb. 2015, e-pub. Sep. 11, 2014) 3(2):125-135.

Koenig et al., "Mutational landscape of antibody variable domains reveals a switch modulating the interdomain conformational dynam-ics and antigen binding," Proc Natl Acad Sci USA (Jan. 2017) 114(4):E486-E495.

Kussie et al., "A Single Engineered Amino Acid Substitution Changes Antibody Fine Specificity," J Immunol. (Jan. 1994) 152(1):146-52.

Maynard et al., "Protection against anthrax toxin by recombinant antibody fragments correlates with antigen affinity," Nature Biotech (2002) 20(6):597-601.

Smith et al., "CAR T Cell Therapy Targeting G Protein-Coupled Receptor Class C Group 5 Member D (GPRC5D), a Novel Target for Immunotherapy of Myelom," ASH Annual Meeting 2018. Presentation. Presented on Dec. 3, 2018, 27 pages.

Smith et al., "Development and Evaluation of a Human scFv Derived BCMA Targeted CAR T Cell Vector Leads to a High Objective Response Rate in Patients with Advanced MM," Pre-sented at 2017 ASH annual meeting. Presentation Dec. 11, 2017 [23 pages].

Smith et al., "Development and Evaluation of a Human Single Chain Variable Fragment (scFv) Derived BCMA Targeted Car T Cell Vector Leads to a High Objective Response Rate in Patients with Advanced MM," Blood (2017) 130:742, 6 pages.

Smith et al., "Development and Evaluation of an Optimal Human Single-Chain Variable Fragment-Derived BCMA-Targeted Car T Cell Vector," Mol Ther. (2018) 26:1447-1456.

Smith et al., "Car T Cell Therapy Targeting G Protein-Coupled Receptor Class C Group 5 Member D (GPRC5D), a Novel Target for the Immunotherapy of Multiple Myeloma," ASH 2018. Abstract 589. Presented on Dec. 3, 2018.

Tai et al., "Antibody-Based Therapies in Multiple Myeloma," Bone Marrow Research (2011) Article ID: 924058, 14 pages.

Tai et al., "Novel anti-B-cell maturation antigen antibody-drug conjugate (GSK2857916) selectively induces killing of multiple myeloma," Blood (May 15, 2014, e-pub. Feb. 25, 2014) 123(20):3128-38.

Tai et al., "Targeting B-cell maturation antigen in multiple myeloma," Immunotherapy (2015) 7(11):1187-1199.

Wahl et al., "Molecular Hybridization of Immobilized Nucleic Acids: Theoretical Concepts and Practical Considerations," Meth-ods Enzymol. 152:399-407 (1987).

Winkler et al., "Changing the antigen binding specificity by single point mutations of an anti-pp24 (HIV-1) antibody," J Immunol (2000) 165(8):4505-14.

(56) References Cited

OTHER PUBLICATIONS

Pearson, "An Introduction to Sequence Similarity ("Homology") Searching," Current Protocols in Bioinformatics, 42(1):3.1.1-3.1.8 (2013).

Anonymous, "GPRC5D Antibody (N-Terminus, APC) IHC-plus(TM) ILSA105978I LSBio—Bio-Connect," Jan. 1, 2014 (Jan. 1, 2014), pp. 1-2, XP093046783, Retrieved from the Internet: URL:https://shop.bio-connect.nl/antibodies/gprc5d-antibody-n-terminusapc-ihc-plus/ls-al0S978-100/sfid/8943903 [retrieved on May 15, 2023].

U.S. Appl. No. 15/613,800 (US 2018/0118803), filed Jun. 5, 2017 (May 3, 2018).

U.S. Appl. No. 15/614,290 (U.S. Pat. No. 10,590,196), filed Jun. 5, 2017 (Mar. 17, 2020).

U.S. Appl. No. 16/731,973 (Abandoned), filed Dec. 31, 2019.

U.S. Appl. No. 16/732,022 (U.S. Pat. No. 11,566,071), filed Dec. 31, 2019 (Jan. 31, 2023).

U.S. Appl. No. 16/732,022, Dec. 22, 2022 Issue Fee Payment.

U.S. Appl. No. 16/732,022, Sep. 30, 2022 Notice of Allowance.

U.S. Appl. No. 16/732,022, Jul. 21, 2022 Response to Non-Final Office Action.

U.S. Appl. No. 16/732,022, Apr. 25, 2022 Non-Final Office Action.

U.S. Appl. No. 15/613,800, Jan. 17, 2020 Amendment after Notice of Allowance.

U.S. Appl. No. 15/613,800, Jan. 30, 2020 Response to Amendment after Notice of Allowance.

U.S. Appl. No. 15/613,800, Feb. 5, 2020 Notice of Allowance.

U.S. Appl. No. 15/613,800, Feb. 21, 2020 Issue Fee Payment.

U.S. Appl. No. 15/613,800, Feb. 27, 2020 Notice of Allowance.

U.S. Appl. No. 15/613,800, Nov. 21, 2019 Notice of Allowance.

U.S. Appl. No. 15/613,800, Nov. 1, 2019 Response to Non-Final Office Action.

U.S. Appl. No. 15/613,800, Aug. 2, 2019 Non-Final Office Action.

U.S. Appl. No. 15/613,800, May 1, 2019 Response to Restriction Requirement.

U.S. Appl. No. 15/613,800, Feb. 5, 2019 Restriction Requirement.

U.S. Appl. No. 15/614,290, Dec. 5, 2019 Amendment after Notice of Allowance.

U.S. Appl. No. 15/614,290, Dec. 9, 2019 Amendment after Notice of Allowance.

U.S. Appl. No. 15/614,290, Dec. 31, 2019 Issue Fee Payment.

U.S. Appl. No. 15/614,290, Oct. 2, 2019 Notice of Allowance.

U.S. Appl. No. 15/614,290, Aug. 22, 2019 Response to Non-Final Office Action.

U.S. Appl. No. 15/614,290, May. 22, 2019 Non-Final Office Action.

U.S. Appl. No. 15/614,290, Mar. 19, 2019 Response to Restriction Requirement.

U.S. Appl. No. 15/614,290, Feb. 19, 2019 Applicant Initiated Interview Summary.

U.S. Appl. No. 15/614,290, Sep. 20, 2018 Restriction Requirement.

U.S. Appl. No. 16/731,973, Aug. 24, 2020 Notice of Abandonment.

U.S. Appl. No. 16/731,973, Aug. 10, 2020 Applicant Initiated Interview Summary.

U.S. Appl. No. 16/731,973, Feb. 14, 2020 Non-Final Office Action.

"Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-316 (Academic Press 1985).

Abbas et al., Cellular and Molecular Immunology, p. 54 (1991).

Abdiche et al., "Probing the binding mechanism and affinity of tanezumab, a recombinant humanized anti-NGF monoclonal antibody, using a repertoire of biosensors," Protein Science 17:1326-1335 (2008).

Allen, "Ligand-Targeted Therapeutics in Anticancer Therapy," Nat. Rev. Cancer 2:750-763 (2002).

Altschul et al., "Gapped BLAST and PSI-BLAST: a new generation of protein database search programs," Nucleic Acids Res. 25(17):3389-3402 (1997).

Altschul, et al., "Basic Local Alignment Search Tool," J. Mol. Biol. 215:403-410 (1990).

Amon et al., "Monoclonal Antibodies for Immunotargeting Of Drugs In Cancer Therapy," in Monoclonal Antibodies And Cancer Therapy, Reisfeld et al. (eds.), pp. 243-256 (1985).

Anderson, "Prospects for Human Gene Therapy," Science 226(4673):401-409 (1984).

Arnon et al., "Monoclonal Antibodies For Immunotargeting Of Drugs In Cancer Therapy", in Monoclonal Antibodies And Cancer Therapy, Reisfeld et al. (eds.), pp. 243-256 (Alan R. Liss, Inc. 1985).

Atamaniuk et al., "Overexpression of G protein-coupled receptor 5D in the bone marrow is associated with poor prognosis in patients with multiple myeloma," European Journal of Clinical Investigation, 42(9):953-960 (2012).

Azinovic et al., "Survival benefit associated with human anti-mouse antibody (HAMA) in patients with B-cell malignancies," Cancer Immunol Immunother 55:1451-1458 (2006).

Baeuerle et al., "Bispecific T-cell Engaging Antibodies for Cancer Therapy," Cancer Res., 69(12):4941-4944 (2009).

Bam et al., "GPRC5D Is a Cell Surface Plasma Cell Marker Whose Expression Is High In Myeloma Cells and Reduced Following Coculture With Osteoclasts," Blood 122:3099 (2013).

Bataille et al., "The phenotype of normal, reactive and malignant plasma cells. Identification of "many and multiple myelomas" and of new targets for myeloma therapy," Haematologica 91:1234-1240 (2006).

Beckman et al., "Antibody constructs in cancer therapy: protein engineering strategies to improve exposure in solid tumors," Can. 109:170-179 (2007).

Benton et al., "Screening Xgt Recombinant Clones by Hybridization to Single Plaques in situ," Science 196(4286):180-182 (1977).

Bertilaccio et al., "Low-Dose Lenalidomide Improves CAR-Based Immunotherapy In CLL By Reverting T-Cell Defects In Vivo," Blood 122:4171 (2013).

Bird et al., "Single-Chain Antigen-Binding Proteins," Science 242(4877):423-426 (1988).

Blömer et al., "Highly Efficient and Sustained Gene Transfer in Adult Neurons with a Lentivirus Vector," Journal of Virology 71(9):6641-6649 (1997).

Boyd et al., "The Clinical Impact and Molecular Biology of del(17p) in Multiple Myeloma Treated with Conventional or Thalidomide-Based Therapy," Genes, Chromosomes & Cancer 50:765-774 (2011).

Bregni et al., "Human Peripheral Blood Hematopoietic Progenitors Are Optimal Targets of Retroviral-Mediated Gene Transfer," Blood 80(6):1418-1422 (1992).

Brennan et al., "Preparation of Bispecific Antibodies by Chemical Recombination of Monoclonal Immunoglobulin G1 Fragments," Science 229:81-83 (1985).

Brentjens et al., "CD19-Targeted T Cells Rapidly Induce Molecular Remissions in Adults with Chemotherapy-Refractory Acute Lymphoblastic Leukemia," Science Translational Medicine 5:177ra38 (2013).

Brentjens et al., "Eradication of systemic B-cell tumors by genetically targeted human T lymphocytes co-stimulated by CD80 and interleukin-15," Nature Medicine 9(3):279-286 (2003).

Brentjens et al., "Genetically Targeted T Cells Eradicate Systemic Acute Lymphoblastic Leukemia Xenografts," Clin Cancer Res 13(18):5426-5435 (2007).

Brentjens et al., "Safety and persistence of adoptively transferred autologous CD19-targeted T cells in patients with relapsed or chemotherapy refractory B-cell leukemias," Blood 118(18):4817-4828 (2011).

Brigham et al., "Rapid Communication: In vivo Transfection of Murine Lungs with a Functioning Prokaryotic Gene Using a Liposome Vehicle," Am. J. Med. Sci. 298(4):278-281 (1989).

Brocks et al., "A TNF receptor antagonistic scFv, which is not secreted in mammalian cells, is expressed as a soluble mono- and bivalent scFv derivative in insect cells," Immunotechnology 3:173-184 (1997).

Brown et al., "Tolerance to Single, but not Multiple, Amino Acid Replacements in Antibody V-H CDR2: A Means of Minimizing B

(56) References Cited

OTHER PUBLICATIONS

Cell Wastage from Somatic Hypermutation?" The Journal of Immunology, The American Association of Immunologists, 156:3285-3291 (1996).

Caron et al., "Engineered Humanized Dimeric Forms of IgG are More Effective Antibodies," J Exp. Med 176:1191-1195 (1992).

Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).

Cespedes et al., "Mouse models in oncogenesis and cancer therapy," Clin. Transl. Oncol. 8(5):318-329 (2006).

Chen et al., "Selection and Analysis of an Optimized Anti-VEGF Antibody: Crystal Structure of an Affinity-matured Fab in Complex with Antigen," J. Mol. Biol. 293:865-881(1999).

Clinical Immunology and Allergology: in 3 volumes / edited by L. Yeger; translated from German by S.S. Kirzon, A.P. Portnova, Editor Academician R. V.Petrov—[2nd edition, reworked and updated].—Moscow: Meditsina, 1990. 1:219-222 (with full English translation).

Cohen et al., "GPRC5D is a promising marker for monitoring the tumor load and to target multiple myeloma cells," Hematology 18(6):348-351 (2013).

Cornetta et al., "Gene Transfer into Primates and Prospects for Gene Therapy in Humans," Progress in Nucleic Acid Research and Molecular Biology 36:311-322 (1987).

Cuesta et al., "Multivalent antibodies: when design surpasses evolution," Trends in Biotechnology 28(7):355-362 (2010).

Culture of Animal Cells: A Manual of Basic Technique And Specialized Applications, Sixth Edition, Freshney, 2010 (Table of Contents).

Danos et al., "Safe and efficient generation of recombinant retroviruses with amphotropic and ecotropic host ranges," PNAS USA 85:6460-6464 (1988).

Davila et al., "Efficacy and Toxicity Management of 19-28z CAR T Cell Therapy in B Cell Acute Lymphoblastic Leukemia," Science Translational Medicine 6:224ra25 (2014).

Dennis et al., "Cancer: Off by a Whisker," Nature 442:739-741 (2006).

Dudley et al., "Adoptive Cell Therapy for Patients with Metastatic Melanoma: Evaluation of Intensive Myeloablative Chemoradiation Preparative Regimens," J Clin Oncol 26:5233-5239 (2008).

Dupont et al., "Artificial Antigen-Presenting Cells Transduced with Telomerase Efficiently Expand Epitope-Specific, Human Leukocyte Antigen-Restricted Cytotoxic T Cells," Cancer Res 65:5417-5427 (2005).

Edwards et al., "The Remarkable Flexibility of the Human Antibody Repertoire; Isolation of Over One Thousand Different Antibodies to a Single Protein, BLyS," J. Mol. Biol. 334:103-118 (2003).

Eglitis et al., "Retroviral Vectors for Introduction of Genes into Mammalian Cells," BioTechniques 6(7):608-614 (1988).

Extended European Search Report dated Jul. 10, 2018 in Application No. EP 15865633.

Felgner et al., "Lipofection: A highly efficient, lipid-mediated DNA-transfection procedure," PNAS USA 84:7413-7417 (1987).

Fife et al., "Inhibition of T cell activation and autoimmune diabetes using a B cell surface-linked CTLA-4 agonist," J Clin Invest 116(8):2252-2261 (2006).

Flatman et al., "Process analytics for purification of monoclonal antibodies," J. Chromatogr. B 848:79-87 (2007).

Friedmann, "Progress toward Human Gene Therapy," Science 244(4910):1275-1281 (1989).

Frigyesi et al., "Robust isolation of malignant plasma cells in multiple myeloma," Blood 123(9):1336-1340 (2014).

Fujimori et al., "A Modeling Analysis of Monoclonal Antibody Percolation through Tumors: a Binding-Site Barrier," J. Nucl. Med. 31:1191-I 198 (1990).

Gade et al., "Targeted Elimination of Prostate Cancer by Genetically Directed Human T Lymphocytes," Cancer Res 65(19):9080-9088 (2005).

Gahrton et al., "Allogeneic Bone Marrow Transplantation in Multiple Myeloma," N Engl J Med 325:1267-1273 (1991).

Gerd R, et al. Serological Analysis of Human Anti-Human Antibody Responses in Colon Cancer Patients Treated with Repeated Doses of Humanized Monoclonal Antibody A33. Cancer Res 2001; 61, 6851-6859.

Gershoni et al., "Epitope mapping—The first step in developing epitope-based vaccines," Biod, Adis International Ltd., NZ, 21(3):145-156 (2007).

Giomarelli et al., "Inhibition of thrombin-induced platelet aggregation using human single-chain Fv antibodies specific for TREM-like transcript-I," Thromb Haemost 97:955-963 (2007).

Glennie et al., "Preparation and performance of bispecific F(ab' gamma)2 antibody containing thioether-linked Fab' gamma fragments," J. Immunol. 139:2367-2375 (1987).

Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia 1(2):123-127 (1999).

Grunstein et al., "Colony hybridization: A method for the isolation of cloned DNAs that contain a specific gene," PNAS USA 72(10):3961-3965 (1975).

Harris et al., "Crystallographic Structure of an Intact IgG1 Monoclonal Antibody," Journal of Molecular Biology 275:861-872 (1998).

Hellstrom et al., "Antibodies for Drug Delivery," in Controlled Drug Delivery (2nd Ed.), Robinson et al. (eds.), pp. 623-653 (1987).

Hirano et al., "Novel reciprocal regulation of cAMP signaling and apoptosis by orphan G-protein-coupled receptor GPRCSA gene expression," Biochemical and Biophysical Research Communications 351:185-191(2006).

Ho et al., "Inhibition of Cocaine Binding to the Human Dopamine Transporter by a Single Chain Anti-Idiotypic Antibody: Its Cloning, Expression and Functional Properties," BioChim Biophys Acta 1638(3):257-266 (2003).

Hollyman et al., "Manufacturing Validation of Biologically Functional T Cells Targeted to CD19 Antigen for Autologous Adoptive Cell Therapy," J Immunother 32:169-180 (2009).

Huang et al., "Application in Antibody Research," An Introduction to Bioinformatics, University of Electronic Science and Technology Press, pp. 160, (2014) (with full English translation).

Huang et al., "Recombinant immunotherapeutics: current state and perspectives regarding the feasibility and market," Appl. Microbiol Biotechnol 87:401-410 (2010).

Hughes et al., "Retroviral Gene Transfer to Primitive Normal and Leukemic Hematopoietic Cells Using Clinically Applicable Procedures," J. Clin. Invest. 89:1817-1824 (1992).

Hunder et al., "Treatment of Metastatic Melanoma with Autologous CD4+ T Cells against NY-ESO-1," N Engl J Med 358:2698-2703 (2008).

Huston et al., "Protein engineering of antibody binding sites: Recovery of specific activity in an anti-digoxin single-chain Fv analogue produced in *Escherichia coli*," PNAS USA 85:5879-5883 (1988).

International Search Report and Written Opinion dated Jul. 14, 2017 in International Patent Application No. PCT/US2017/032539, 12 pages.

International Search Report dated Apr. 8, 2016 in International Application No. PCT/US15/64102.

International Search Report dated May 19, 2016 in International Application No. PCT/US15/64122.

Johnson, "Gene Therapy for Cystic Fibrosis," Chest 107:77S-83S (1995).

Kabat et al., Sequences of Proteins of Immunological Interest, 4th U. S. Department of Health and Human Services, National Institutes of Health (1987).

Kabat, E. A., et al. (1991) Sequences of Proteins of Immunological Interest, Fifth Edition, U.S. Department of Health and Human Services, NIH Publication No. 91-3242.

Karpovsky et al., "Production of Target-Specific Effector Cells Using Hetero-Cross-Linked Aggregates Containing Anti-Target Cell and Anti-Fcy Receptor Antibodies," J. Exp. Med. 160:1686-1701 (1984).

(56)                   References Cited

OTHER PUBLICATIONS

Kershaw et al., "Gene-Engineered T cells as a Superior Adjuvant Therapy for Metastatic Cancer," J Immunol 173:2143-2150 (2004).

Kido et al., "Use of a retroviral vector with an internal opsin promoter to direct gene expression to retinal photoreceptor cells," Current Eye Research 15:833-844 (1996).

Klechevsky et al., "Antitumor activity of immunotoxins with T-cell receptor-like specificity against human melanoma xenografts," Cancer Res 68(15):6360-6367 (2008).

Kochenderfer et al., "Adoptive transfer of syngeneic T cells transduced with a chimeric antigen receptor that recognizes murine CD19 can eradicate lymphoma and normal B cells," Blood (2010) 116(19):3875-3886.

Kodama et al., "Anti-GPRC5D/CD3 Bispecific T-Cell-Redirecting Antibody for the Treatment of Multiple Myeloma," Mol. Cancer Ther. 18:1555-1564 (2019), Published Online first Jul. 3, 2019.

Koyko, R. Immunology: Textbook for Post-Graduate Education of Physicians / R. Koyko, D. Sunshine, E. Benjamin; translated from English, Editor N.B. Serebryanaya.—Moscow: Akademiya; Saint-Petersburg: Philology Department of The S.-Petersburg State University, 2008, 1:156 and 160 (with full English translation).

Koyko, R. Immunology: Textbook for Post-Graduate Education of Physicians / R. Koyko, D. Sunshine, E. Benjamin; translated from English, Editor N.B. Serebryanaya.—Moscow Akademiya; Saint-Petersburg: Philology Department of The S.-Petersburg State University, 2008, 1:37 (with full English translation).

Krause et al., "Antigen-dependent CD28 Signaling Selectively Enhances Survival and Proliferation in Genetically Modified Activated Human Primary T Lymphocytes," J. Exp. Med. 188(4):619-626 (1998).

Le Gal La Salle et al., "An Adenovirus Vector for Gene Transfer into Neurons and Glia in the Brain," Science 259(5097):988-990 (1993).

Ledbetter et al., "Agonistic Activity of a CD40-Specific Single-Chain Fv Constructed from the Variable Regions of mAb G28-5," Crit Rev Immunol. 17:427-435 (1997).

Lidij a P, et al. An integrated vector system for the eukaryotic expression of antibodies or their fragments after selection from phage display libraries. Gene 1997; 187(1 ): 9-18.

Lippincott-Schwartz et al., "Antibodies as Cell Biological Tools," Chapter 16 in Current Protocols in Cell Biology Supplement 13, 16.0.1-16.0.2 (2002), 2 pages.

Lisa et al. Crystallographic structure of an intact IgG1 monoclonal antibody. Journal of Molecular Biology 1998; 275 (5): 861-872.

Liu et al., "Practical Internal Medicine Diagnosis and Treatment", Multiple Myeloma, Hebei Science and Technology Press, p. 416 (2013).

Liu et al., "Heteroantibody duplexes target cells for lysis by cytotoxic T lymphocytes," Proc. Natl. Acad. Sci. USA 82:8648-8652 (1985).

Lloyd et al., "Modelling the human immune response: performance of a 10^11 human antibody repertoire against a broad panel of therapeutically relevant antigens," Protein Engineering, Design & Selection 22(3):159-168 (2009).

Lyddane et al., "Cutting Edge: CD28 Controls Dominant Regulatory T Cell Activity During Active Immunization," J. Immunol. 176:3306-3310 (2006).

Maher et al., "Human T-lymphocyte cytotoxicity and proliferation directed by a single chimeric TCRζ/CD28 receptor," Nat. Biotechnol. 20:70-75 (2002).

Mariuzza et al., "The Structural Basis Of Antigen-Antibody Recognition," Annual Review of Biophysis and Biophysical Chemistry 16:139-159 (1987).

McCafferty et al., "Phage antibodies: filamentous phage displaying antibody variable domains," Nature 348:552-554 (1990).

Myers et al., "Optimal alignments in linear space," Cabios 4(1):11-17 (1988).

Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).

Miller et al., "Improved Retroviral Vectors for Gene Transfer and Expression," Biotechniques 7(9):980-990 (1989).

Miller et al., "Redesign of Retrovirus Packaging Cell Lines to Avoid Recombination Leading to Helper Virus Production," Mol. Cell. Biol. 6(8):2895-2902 (1986).

Miller, "Retrovirus Packaging Cells," Human Gene Therapy 1:5-14 (1990).

Miyoshi et al., "Stable and efficient gene transfer into the retina using an HIV-based lentiviral vector," PNAS USA 94:10319-10323 (1997).

Moen, "Directions in Gene Therapy," Blood Cells 17:407-416 (1991).

Moosmayer et al., "A single-chain TNF receptor antagonist is an effective inhibitor of TNF mediated cytotoxicity," Therapeutic Immunol. 2:31-40 (1995).

Morgan et al., "Cancer Regression in Patients After Transfer of Genetically Engineered Lymphocytes," Science 314:126-129 (2006).

Morgan et al., "Case Report of a Serious Adverse Event Following the Administration of T Cells Transduced with a Chimeric Antigen Receptor Recognizing ERBB2," Molecular Therapy 18(4):843-851 (2010).

Naldini et al., "In Vivo Gene Delivery and Stable Transduction of Nondividing Cells by a Lentiviral Vector," Science 272(5259):263-267 (1996).

Needleman et al., "A General Method Applicable to the Search for Similarities in the Amino Acid Sequence of Two Proteins," J. Mol. Biol. 48:443-453 (1970).

Ono et al., "Plasmid DNAs directly injected into mouse brain with lipofectin can be incorporated and expressed by brain cells," Neuroscience Letters, 117:259-263 (1990).

Ozhegov, S.I. The Thesaurus of the Russian Language: 80,000 words and idioms / S.I. Ozhegov and N. Yu Shvedova; Russian Academy of Sciences, Institute of the Russian Language named after V.V. Vinogradov.—4th Edition, updated—Moscow: [A TEIVIP}, 2006. 1:375 (with full English translation).

Panelli et al., "A Tumor-Infiltrating Lymphocyte from a Melanoma Metastasis with Decreased Expression of Melanoma Differentiation Antigens Recognizes MAGE-12," J Immunol 164:4382-4392 (2000).

Panelli et al., "Expansion of Tumor-T Cell Pairs from Fine Needle Aspirates of Melanoma Metastases," J Immunol 164:495-504 (2000).

Papanicolaou et al., "Rapid expansion of cytomegalovirus-specific cytotoxic T lymphocytes by artificial antigen-presenting cells expressing a single HLA allele," Blood 102:2498-2505 (2003).

Parkman, R., "Clonal analysis of murine graft-vs-host disease. I. Phenotypic and functional analysis of T lymphocyte clones," J. Immunol. 136:3543-3548 (1986).

Pastan et al., "Immunotoxins in cancer therapy," Curr. Opin. Investig. Drugs 3(7):1089-1091 (2002).

Paulus, "Preparation and Biomedical Applications of Bi specific Antibodies," Behring Ins. Mitt. 78: 118-132 (1985).

Payne, "Progress in immunoconjugate cancer therapeutics," Cancer Cell 3:207-212 (2003).

Pegram et al., "Tumor-targeted T cells modified to secrete IL-12 eradicate systemic tumors without need for prior conditioning," Blood 119(18):4133-4141 (2012).

Persic et al., "An integrated vector system for the eukaryotic expression of antibodies or their fragments after selection from phage display libraries," Gene 187:9-18 (1997).

Peter et al., "Protective effects of an anti-melanocortin-4 receptor scFv derivative in lipopolysaccharide-induced cachexia in rats," J Cachexia Sarcopenia Muscle 4:79-88 (2013).

Peter et al., "scFv Single Chain Antibody Variable Fragment as Inverse Agonist of the 132-Adrenergic Receptor," J Biol. Chem. 278(38):36740-36747 (2003).

Posthumus et al., "Analysis and Simulation of a Neutralizing Epitope of Transmissible Gastroenteritis Virus," J. Virology, 64(7):3304-3309 (1990).

Queen et al., "A humanized antibody that binds to the interleukin 2 receptor," Proc Natl Acad Sci USA 86:10029-10033 (1989).

Riechmann et al., "Reshaping human antibodies for therapy," Nature 332:323-327 (1988).

(56)     References Cited

OTHER PUBLICATIONS

Ritter et al., "Serological Analysis of Human Anti-Human Antibody Responses in Colon Cancer Patients Treated with Repeated Doses of Humanized Monoclonal Antibody A33," Cancer Res 61:6851-6859 (2001).

Riviere et al., "Novel Strategies for Cancer Therapy: The Potential of Genetically Modified T Lymphocytes," Curr Hematol Rep 3:290-297 (2004).

Roberts et al., "Vaccination with CD20 peptides induces a biologically active, specific immune response in mice," Blood 99: 3748-3755 (2002).

Rosenberg et al., "Adoptive cell transfer: a clinical path to effective cancer immunotherapy," Nature Reviews Cancer 8:299-308 (2008).

Rosenberg et al., "Gene Transfer into Humans," N. Engl. J. Med 323(9):570-578 (1990).

Rudnick et al., "Affinity and Avidity in Antibody-Based Tumor Targeting," Can. Biotherp. & Radiopharm 24(2):155-162 (2009).

Sadelain et al., "Targeting Tumours With Genetically Enhanced T Lymphocytes," Nat Rev Cancer 3:35-45 (2003).

Sadelain et al., "The basic principles of chimeric antigen receptor (CAR) design," Cancer Discovery 3(4):388-398 (2013).

Sadelain et al., "The promise and potential pitfalls of chimeric antigen receptors," Curr Opin Immunol 21:215-223 (2009).

Saito et al., "Drug delivery strategy utilizing conjugation via reversible disulfide linkages: role and site of cellular reducing activities," Adv. Drug Deliv. Rev. 55:199-215 (2003).

Saito, G. et al. (2003) Adv. Drug Deliv. Rev. 55:199-215.

Sambrook et al., Molecular Cloning: A Laboratory Manual, 2nd ed. Cold Spring Harbor Laboratory Press, New York (1989).

Search Report in Russian Application No. 2017123545 received by Applicant on Dec. 11, 2019.

Senter et al., "Selective activation of anticancer prodrugs by monoclonal antibody-enzyme conjugates," Adv. Drug Deliv. Rev. 53:247-264 (2001).

Sharp, "Gene Therapy," The Lancet 337: 1277-1278 (1991).

Shaughnessy, Jr., et al., "A validated gene expression model of high-risk multiple myeloma is defined by deregulated expression of genes mapping to chromosome 1," Blood 109:2276-2284 (2007).

Shen et al., "Engineering Peptide Linkers for scFv Immunosensors," Anal Chem. 80(6):1910-1917 (2008).

Shieh et al., "Transgenic Expression of Single-Chain Anti-CTLA-4 Fv on β Cells Protects Nonobese Diabetic Mice from Autoimmune Diabetes," J Immunol 183:2277-2285 (2009).

Siegel et al., "Cancer Statistics, 2013," CA Cancer J Clin 63:11-30 (2013).

Smith et al. (Sci Transl. Med. 11:1-14 (2019).

Stephan et al., "T cell-encoded CD80 and 4-1BBL induce auto- and transcostimulation, resulting in potent tumor rejection," Nat. Med 13(12):1440-1449 (2007).

Straubinger et al., "Liposomes as Carriers for Intracellular Delivery of Nucleic Acids," Methods in Enzymology, 101:512-527 (1983).

Supplemental Partial European Search Report dated May 4, 2018 in Application No. EP 15865989.

Talmadge et al., "Murine Models to Evaluate Novel and Conventional Therapeutic Strategies for Cancer," Am. J. Pathol. 170(3):793-804 (2007).

Tang et al., "The Foxp+ regulatory T cell: a jack of all trades, master of regulation," Nat Inmmunol 9(3):239-244 (2008).

The Polymerase Chain Reaction. Mullis, 1994 (Foreword and Table of Contents).

Thorpe et al., "The Preparation and Cytotoxic Properties of Antibody-Toxin Conjugates," Immunol. Rev., 62:119-158 (1982).

Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985).

Thurber et al., "Antibody tumor penetration: transport opposed by systemic and antigen-mediated clearance," Adv. Drug Deliv. Rev. 60:1421-1434 (2008).

Timmerman et al., "Functional reconstruction and synthetic mimicry of a conformational epitope using CLIPS™ technology," J. Mol. Recognit. 20:283-299 (2007).

Tjandra et al., "Development of human anti-murine antibody (HAMA) response in patients," Immunol Cell Biol. 68:367-376 (1990).

Tolstoshev et al., "Gene expression using retroviral vectors," Current Opinion in Biotechnology 1:55-61 (1990).

Tomimatsu et al., "Production of Human Monoclonal Antibodies against FcεRIα by a Method Combining in Vitro Immunization with Phage Display," Biosci Biotechnol Biochem 73(7):1465-1469 (2009).

Trail et al., "Monoclonal antibody drug immunoconjugates for targeted treatment of cancer," Cancer Immunol. Immunother. 52:328-337 (2003).

Voskoglou-Nomikos et al., "Clinical Predictive Value of the in Vitro Cell Line, Human Xenograft, and Mouse Allograft Preclinical Cancer Models," Clin Can. Res. 9:4227-4239 (2003).

Wahl et al., "Improved Radioimaging and Tumor Localization with Monoclonal F(ab')2," J. Nucl. Med. 24:316-325 (1983).

Wang et al., "Single-Chain Antibody (scFv)," Antibody Technology, Military Medical Science Press, Beijing, pp. 75 (2009) (with full English translation).

Ward et al., "Binding activities of a repertoire of single immunoglobulin variable domains secreted from *Escherichia coli*," Nature 341:544-546 (1989).

Wels et al., "Recombinant immunotoxins and retargeted killer cells: employing engineered antibody fragments for tumor-specific targeting of cytotoxic effectors," Cancer Immunol Immunother 53:217-226 (2004).

Wolff et al., "Direct Gene Transfer into Mouse Muscle in Vivo," Science 247(4949):1465-1468 (1990).

Written Opinion of Singapore Application No. 11201704547R, dated Jun. 25, 2018.

Wu et al., "Receptor-mediated Gene Delivery and Expression in Vivo," Journal of Biological Chemistry, 263(29):14621-14624 (1988).

Wu et al., "Targeting Genes: Delivery and Persistent Expression of a Foreign Gene Driven by Mammalian Regulatory Elements in Vivo," Journal of Biological Chemistry 264(29):16985-16987 (1989).

Xie et al., "Direct demonstration of MuSK involvement in acetylcholine receptor clustering through identification of agonist ScFv," Nat Biotech 15:768-771 (1997).

Xu et al., "Correction of the enzyme deficiency in hematopoietic cells of Gaucher patients using a clinically acceptable retroviral supernatant transduction protocol," Exp. Hemat. 22:223-230 (1994).

Yasmina Na, et al. Probing the binding mechanism and affinity of tanezumab, a recombinant humanized anti-NGF monoclonal antibody, using a repertoire of biosensors. Protein Science 2008; 17(8):1326-1335.

Zhao et al., "Characteristics of an scFv Antibody Fragment That Binds to Immunoglobulin G of Graves' Disease Patients and Inhibits Autoantibody-Mediated Thyroid-Stimulating Activity," Hybridoma 27(6):445-451 (2008).

Zhong et al., "Chimeric Antigen Receptors Combining 4-1BB and CD28 Signaling Domains Augment P13kinase/AKT/Bc1-XL Activation and CD8+ T Cell-mediated Tumor Eradication," Molecular Therapy, pp. 413-420 (2010).

Rabia et al., "Understanding and overcoming trade-offs between antibody affinity, specificity, stability and solubility," Biochem Eng J (Sep. 15, 2018, e-pub. Jun. 5, 2018) 137:365-374.

* cited by examiner

| Loop 1 | Loop 2 | ELISA |
|---|---|---|
| C (SEQ ID NO.: 416) MDYDFKVKLSSERER C | (SEQ ID NO.: 420) WAIGCIFAELLTSEP C | −0.01 |
| C (SEQ ID NO.: 416) MDYDFKVKLSSERER C | (SEQ ID NO.: 421) CIFAELLTSEPIFHC C | 0.79 |
| C (SEQ ID NO.: 416) MDYDFKVKLSSERER C | (SEQ ID NO.: 422) ELLTSEPIFHCRQED C | 1.21 |
| C (SEQ ID NO.: 416) MDYDFKVKLSSERER C | (SEQ ID NO.: 423) SEPIFHCRQEDIKTS C | 0.36 |
| C (SEQ ID NO.: 417) FKVKLSSERERVEDL C | (SEQ ID NO.: 420) WAIGCIFAELLTSEP C | 0.17 |
| C (SEQ ID NO.: 417) FKVKLSSERERVEDL C | (SEQ ID NO.: 421) CIFAELLTSEPIFHC C | 1.19 |
| C (SEQ ID NO.: 417) FKVKLSSERERVEDL C | (SEQ ID NO.: 422) ELLTSEPIFHCRQED C | 1.24 |
| C (SEQ ID NO.: 417) FKVKLSSERERVEDL C | (SEQ ID NO.: 423) SEPIFHCRQEDIKTS C | 0.56 |
| C (SEQ ID NO.: 418) LSSERERVEDLFEYE C | (SEQ ID NO.: 420) WAIGCIFAELLTSEP C | 0.61 |
| C (SEQ ID NO.: 418) LSSERERVEDLFEYE C | (SEQ ID NO.: 421) CIFAELLTSEPIFHC C | 1.21 |
| C (SEQ ID NO.: 418) LSSERERVEDLFEYE C | (SEQ ID NO.: 422) ELLTSEPIFHCRQED C | 1.41 ← |
| C (SEQ ID NO.: 418) LSSERERVEDLFEYE C | (SEQ ID NO.: 423) SEPIFHCRQEDIKTS C | 0.58 |
| C (SEQ ID NO.: 419) RERVEDLFEYEGCKV C | (SEQ ID NO.: 420) WAIGCIFAELLTSEP C | 0.10 |
| C (SEQ ID NO.: 419) RERVEDLFEYEGCKV C | (SEQ ID NO.: 421) CIFAELLTSEPIFHC C | 0.83 |
| C (SEQ ID NO.: 419) RERVEDLFEYEGCKV C | (SEQ ID NO.: 422) ELLTSEPIFHCRQED C | 1.21 |
| C (SEQ ID NO.: 419) RERVEDLFEYEGCKV C | (SEQ ID NO.: 423) SEPIFHCRQEDIKTS C | −0.02 |

FIG. 5A

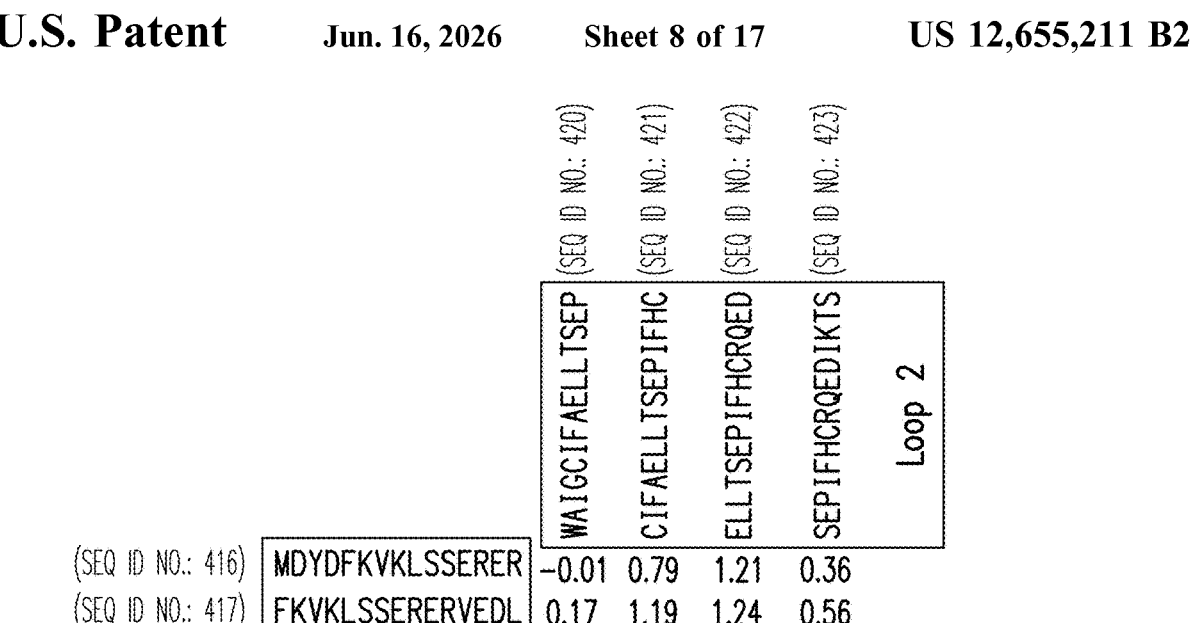

| | WAIGCIFAELLTSEP (SEQ ID NO.: 420) | CIFAELLTSEPIFHC (SEQ ID NO.: 421) | ELLTSEPIFHCRQED (SEQ ID NO.: 422) | SEPIFHCRQEDIKTS (SEQ ID NO.: 423) |
|---|---|---|---|---|
| | | | Loop 2 | |
| (SEQ ID NO.: 416) MDYDFKVKLSSERER | −0.01 | 0.79 | 1.21 | 0.36 |
| (SEQ ID NO.: 417) FKVKLSSERERVEDL | 0.17 | 1.19 | 1.24 | 0.56 |
| (SEQ ID NO.: 418) LSSERERVEDLFEYE | 0.61 | 1.21 | 1.41 | 0.58 |
| (SEQ ID NO.: 419) RERVEDLFEYEGCKV | 0.10 | 0.83 | 1.21 | −0.02 |
| Loop 1 | | | | |

FIG. 5B low                    Average                    high

FIG. 5C

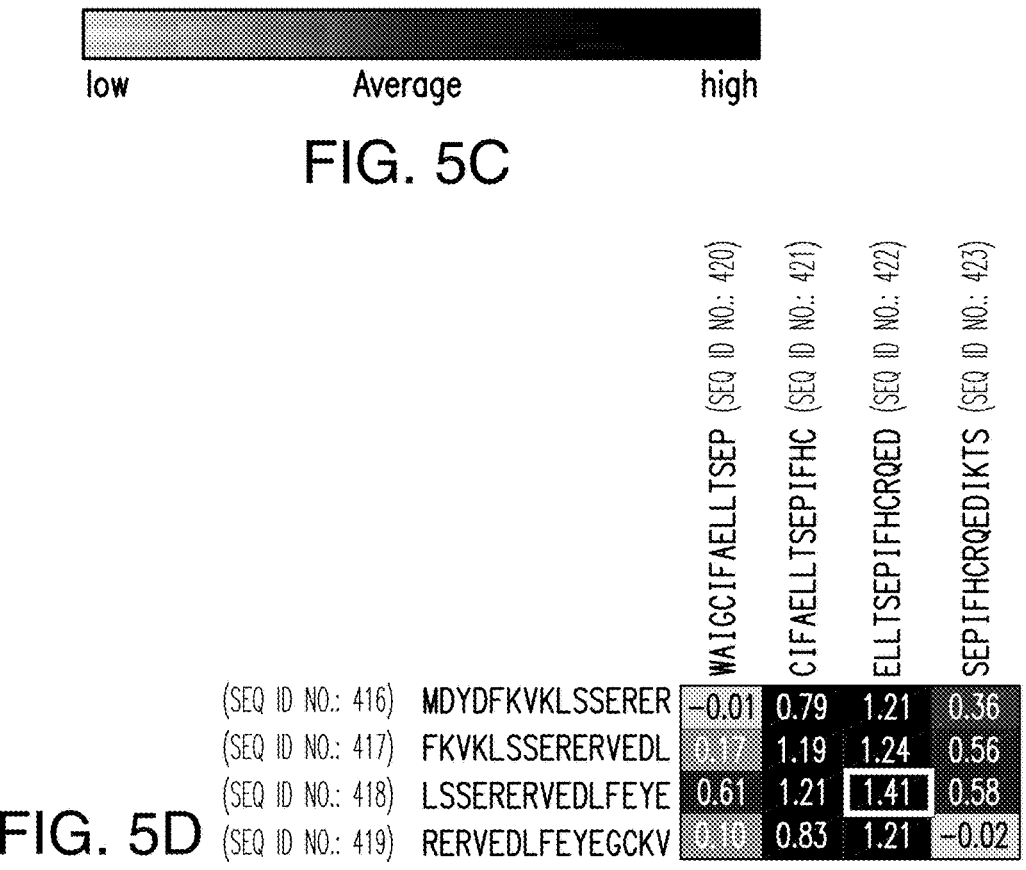

| | WAIGCIFAELLTSEP (SEQ ID NO.: 420) | CIFAELLTSEPIFHC (SEQ ID NO.: 421) | ELLTSEPIFHCRQED (SEQ ID NO.: 422) | SEPIFHCRQEDIKTS (SEQ ID NO.: 423) |
|---|---|---|---|---|
| (SEQ ID NO.: 416) MDYDFKVKLSSERER | −0.01 | 0.79 | 1.21 | 0.36 |
| (SEQ ID NO.: 417) FKVKLSSERERVEDL | 0.17 | 1.19 | 1.24 | 0.56 |
| (SEQ ID NO.: 418) LSSERERVEDLFEYE | 0.61 | 1.21 | 1.41 | 0.58 |
| (SEQ ID NO.: 419) RERVEDLFEYEGCKV | 0.10 | 0.83 | 1.21 | −0.02 |

FIG. 5D

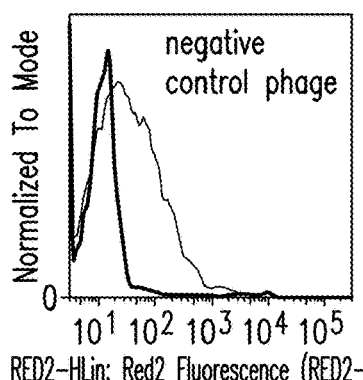
| Sample Name | Median, RED2-HLin |
|---|---|
| B01 3T3-ET150+ K07 fcs | 23.5 |
| A04 anti-M13+ APC mIgG fcs | 10.9 |
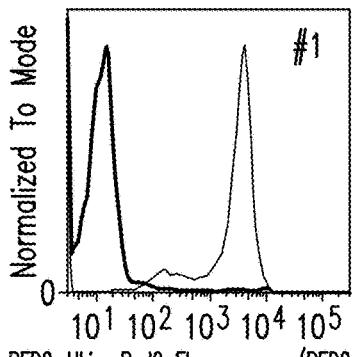
| Sample Name | Median, RED2-HLin |
|---|---|
| B02 3T3-ET150+ ET150-1 fcs | 3232 |
| A04 anti-M13+ APC mIgG fcs | 10.9 |
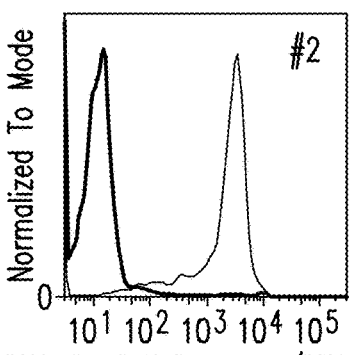
| Sample Name | Median, RED2-HLin |
|---|---|
| B03 3T3-ET150+ ET150-2 fcs | 2404 |
| A04 anti-M13+ APC mIgG fcs | 10.9 |
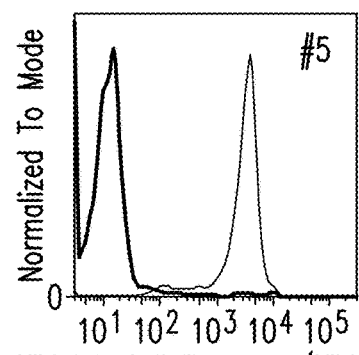
| Sample Name | Median, RED2-HLin |
|---|---|
| B04 3T3-ET150+ ET150-5 fcs | 3216 |
| A04 anti-M13+ APC mIgG fcs | 10.9 |
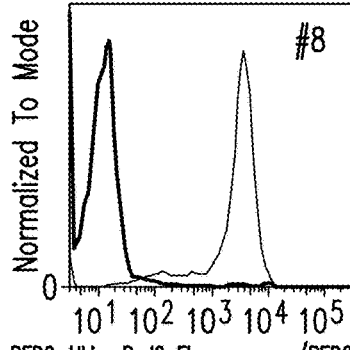
| Sample Name | Median, RED2-HLin |
|---|---|
| B05 3T3-ET150+ ET150-8 fcs | 3113 |
| A04 anti-M13+ APC mIgG fcs | 10.9 |
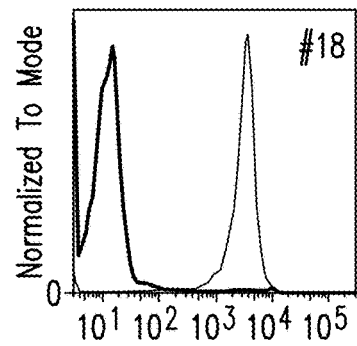
| Sample Name | Median, RED2-HLin |
|---|---|
| B07 3T3-ET150+ ET150-18 fcs | 3176 |
| A04 anti-M13+ APC mIgG fcs | 10.9 |
FIG. 12

SEQUENCE LISTING

```
Sequence total quantity: 415
SEQ ID NO: 1            moltype = AA  length = 120
FEATURE                 Location/Qualifiers
REGION                  1..120
                        note = Description of Artificial Sequence: Synthetic
                        polypeptide
source                  1..120
                        mol_type = protein
                        organism = synthetic construct
SEQUENCE: 1
QVQLVQSGSE LKKPGASVRV SCTASGYTFT SYYMHWVRQA PGQGLEWMGV INPNAGSTRY  60
AQKFQGRVTM STDTSTSTAY MDLSSLRSED TAVYYCARGM YRSLLFYDPW GQGTLVTVSS 120

SEQ ID NO: 2            moltype = AA  length = 111
FEATURE                 Location/Qualifiers
REGION                  1..111
                        note = Description of Artificial Sequence: Synthetic
```

```
                                 polypeptide
source                           1..111
                                 mol_type = protein
                                 organism = synthetic construct
SEQUENCE: 2
QSVLTQPPSV SAAPGQKVTI PCSGSRSNVG NYYVSWYQQL PGTAPKLLIY DNNKRPSGIP    60
DRFSGSKSGT SATLGITGLQ TGDEADYFCG TWDGSLSAHV FGTGTKVTVL G            111

SEQ ID NO: 3                     moltype = DNA   length = 360
FEATURE                          Location/Qualifiers
misc_feature                     1..360
                                 note = Description of Artificial Sequence: Synthetic
                                  polynucleotide
source                           1..360
                                 mol_type = other DNA
                                 organism = synthetic construct
SEQUENCE: 3
caggtgcagc tggtgcagtc tgggtctgag ttgaagaagc ctggggcctc agtcagagtc    60
tcctgcacgg cttctggata caccttcacc agttactata tgcactgggt gcgacaggcc   120
cctgacaaag ggcttgagtg gatgggagta atcaaccCta atgctggcag cacaagatac   180
gcacagaaat tccagggcag agtcaccatg agcactgaca cgtccacgag cacagcctac   240
atggacctga gcagtctgag atctgaggac acggccgtgt attactgtgc gcgcggtatg   300
taccgttctc tgctgttcta cgatccgtgg ggtcaaggta ctctggtgac cgtctcctca   360

SEQ ID NO: 4                     moltype = DNA   length = 333
FEATURE                          Location/Qualifiers
misc_feature                     1..333
                                 note = Description of Artificial Sequence: Synthetic
                                  polynucleotide
source                           1..333
                                 mol_type = other DNA
                                 organism = synthetic construct
SEQUENCE: 4
cagtctgtgt tgacgcagcc gccctcagtg tctgcggccc caggacagaa ggtcaccatc    60
ccctgctctg gaagccgttc caacgttggg aattattatg tgtcctggta ccagcaactc   120
ccaggaacag cccccaaact cctcatttat gacaataata agcgaccctc agggattcct   180
gaccgattct ctggctccaa gtctggcacg tcagccaccc tgggcatcac cggactccag   240
actggggacg aggccgatta tttctgcgga acatgggatg gcagcctgag tgcccatgtc   300
ttcggaactg ggaccaaggt caccgtccta ggt                                333

SEQ ID NO: 5                     moltype = AA   length = 116
FEATURE                          Location/Qualifiers
REGION                           1..116
                                 note = Description of Artificial Sequence: Synthetic
                                  polypeptide
source                           1..116
                                 mol_type = protein
                                 organism = synthetic construct
SEQUENCE: 5
EVQLVESGGG LVQPGGSLRL SCAASGFTFS NYAMSWVRQA PGKGLEWVSA ISGSGNTYYA    60
DSVKGRFTIS RDNSKNTLYL QMNSLRAEDT AVYYCARGSV RYTDIWGQGT LVTVSS        116

SEQ ID NO: 6                     moltype = AA   length = 113
FEATURE                          Location/Qualifiers
REGION                           1..113
                                 note = Description of Artificial Sequence: Synthetic
                                  polypeptide
source                           1..113
                                 mol_type = protein
                                 organism = synthetic construct
SEQUENCE: 6
NFMLTQPHSV SESPGKTVSI SCTRTSGAIA GAYVQWFQQR PGSAPTTVIY DDNKRPSGVP    60
DRFSGSIDKS SNSASLTISG LKTEDEADYY CQSYDYDSSN VLFGGGTKLT VLG           113

SEQ ID NO: 7                     moltype = DNA   length = 348
FEATURE                          Location/Qualifiers
misc_feature                     1..348
                                 note = Description of Artificial Sequence: Synthetic
                                  polynucleotide
source                           1..348
                                 mol_type = other DNA
                                 organism = synthetic construct
SEQUENCE: 7
gaggtgcagc tggtggagtc tggggggaggc ttggtacagc ctggggggtc cctgagactc    60
tcctgtgcag cctctggatt caccttTagc aactatgcca tgagttgggt ccgccaggct   120
ccagggaagg gactggagtg ggtctcagct attagtggta gtggtaacac atactacgca   180
gactccgtga agggccggtt caccatctcc agagacaatt ccaagaacac gctgtatctg   240
caaatgaaca gcctgagagc cgaggacacg gccgtatatt actgtgcgcg cggttctgtt   300
cgttacactg atatctgggg tcaaggtact ctggtgaccg tctcctca                348
```

-continued

```
SEQ ID NO: 8              moltype = DNA  length = 339
FEATURE                   Location/Qualifiers
misc_feature              1..339
                          note = Description of Artificial Sequence: Synthetic
                          polynucleotide
source                    1..339
                          mol_type = other DNA
                          organism = synthetic construct
SEQUENCE: 8
aattttatgc tgactcagcc ccactcagtg tcggagtctc cggggaagac ggtaagcatc   60
tcctgcaccc gcaccagtgg cgccattgcc ggcgcctatg tgcagtggtt ccagcagcgc  120
ccgggcagtg cccccaccac tgtgatctat gacgataaca aaagaccctc tggggtccct  180
gatcggttct ctgggtccat cgacaagtcc tccaactctg cctccctcac catctctgga  240
ctgaagactg aggacgaggc tgactattat tgtcagtctt atgattatga tagcagcaat  300
gtgctattcg gcggagggac caagctgacc gtcctaggt                         339

SEQ ID NO: 9              moltype = AA  length = 119
FEATURE                   Location/Qualifiers
REGION                    1..119
                          note = Description of Artificial Sequence: Synthetic
                          polypeptide
source                    1..119
                          mol_type = protein
                          organism = synthetic construct
SEQUENCE: 9
EVQLVQSGGG LVQPGGSLRL SCATSGFTFN NYWMSWVRQA PGKGLEWVAN IKQDGSEKYY   60
ADSVRGRFTI SRDNAKNSLS LQLNNLRAED TAVYYCARSM STAWGYDEWG QGTLVTVSS    119

SEQ ID NO: 10             moltype = AA  length = 108
FEATURE                   Location/Qualifiers
REGION                    1..108
                          note = Description of Artificial Sequence: Synthetic
                          polypeptide
source                    1..108
                          mol_type = protein
                          organism = synthetic construct
SEQUENCE: 10
DIQLTQSPSS LSASVGDRVT ITCRASQSIS SYLNWYQQKP GKAPKLLIYA ASSLQSGVPS   60
RFSGSGSGTD FTLTISSLQP ADFATYYCQQ SYSVPYTFGQ GTKLEIKR                108

SEQ ID NO: 11             moltype = DNA  length = 357
FEATURE                   Location/Qualifiers
misc_feature              1..357
                          note = Description of Artificial Sequence: Synthetic
                          polynucleotide
source                    1..357
                          mol_type = other DNA
                          organism = synthetic construct
SEQUENCE: 11
gaggtgcagc tggtgcagtc tggggggaggc ttggtccagc ctggggggtc cctgagactc   60
tcctgtgcaa cctctggatt cacctttaat aactattgga tgagttgggt ccgccaggct  120
ccagggaagg ggctggagtg ggtggccaac ataaagcaag atggaagtga gaaatactac  180
gcggactctg tgaggggccg attcaccatc tccagagaca cgccaagaa ctcactgtct   240
ctgcaattga caacctgag agccgaggac acggccgtgt attactgtgc gcgctctatg   300
tctactgctt ggggttacga tgaatggggt caaggtactc tggtgaccgt ctcctca     357

SEQ ID NO: 12             moltype = DNA  length = 324
FEATURE                   Location/Qualifiers
misc_feature              1..324
                          note = Description of Artificial Sequence: Synthetic
                          polynucleotide
source                    1..324
                          mol_type = other DNA
                          organism = synthetic construct
SEQUENCE: 12
gacatccagt tgacccagtc tccatcctcc ctgtctgcat ctgtcggaga cagagtcacc   60
atcacttgcc gggcaagtca gagcattagc agctatttaa attggtatca acagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gcagattttg caacttacta ctgtcaacag agttacagtg tcccgtacac ttttggccag  300
gggaccaagc tggagatcaa acgt                                         324

SEQ ID NO: 13             moltype = AA  length = 121
FEATURE                   Location/Qualifiers
REGION                    1..121
                          note = Description of Artificial Sequence: Synthetic
                          polypeptide
source                    1..121
```

```
                          mol_type = protein
                          organism = synthetic construct
SEQUENCE: 13
QVQLVQSGAE VKKPGASVKV SCKASGYTFT SYYMHWVRQA PGQGLEWMGI INPSGGSTRY  60
AQKFQGRVTM TRDTSTSTVY MELSSLRSED TAVYYCARGS SRWGGWTGDY WGQGTLVTVS  120
S                                                                 121

SEQ ID NO: 14            moltype = AA  length = 111
FEATURE                  Location/Qualifiers
REGION                   1..111
                          note = Description of Artificial Sequence: Synthetic
                          polypeptide
source                   1..111
                          mol_type = protein
                          organism = synthetic construct
SEQUENCE: 14
QSALTQPASV SGSPGQSITI SCTGTSSDVG GYNFVSWYQQ HPGKAPKVMI YDVSKRPSGI  60
SNRFSGSKSG NTASLTISGL QVEDEAEYYC SSYTSTRTVI FAGGTKVTVL G           111

SEQ ID NO: 15            moltype = DNA  length = 363
FEATURE                  Location/Qualifiers
misc_feature             1..363
                          note = Description of Artificial Sequence: Synthetic
                          polynucleotide
source                   1..363
                          mol_type = other DNA
                          organism = synthetic construct
SEQUENCE: 15
caggtgcagc tggtgcagtc tggggctgag gtgaagaagc ctgggggctc agtgaaggtt  60
tcctgcaagg catctggata caccttcacc agctactata tgcactgggt gcgacaggcc  120
cctggacaag ggcttgagtg gatgggaata tcaaccctaa gtggtggtag cacaaggtac  180
gcacagaagt tccagggcag agtcaccatg accaggggaca cgtcaacgag cacagtctac  240
atggagctga gcagcctgag atctgaggac acggccgtgt attactgtgc gcgcggttcc  300
tctcgctggg gtggttggac tggtgattac tggggtcaag gtactctggt gaccgtctcc  360
tca                                                               363

SEQ ID NO: 16            moltype = DNA  length = 333
FEATURE                  Location/Qualifiers
misc_feature             1..333
                          note = Description of Artificial Sequence: Synthetic
                          polynucleotide
source                   1..333
                          mol_type = other DNA
                          organism = synthetic construct
SEQUENCE: 16
caatctgccc tgactcagcc tgcctccgtg tctgggtctc ctggacagtc gatcaccatc  60
tcctgcactg gaaccagcag tgacgttggt ggttataact ttgtctcctg gtaccaacag  120
cacccaggca aagcccccaa agtcatgatt tatgatgtca gtaagcggcc ctcaggagtt  180
tctaatcgct tctctggctc caagtctggc aacacggcct ccctgaccat ctctgggctc  240
caggttgagg acgaggctga atattactgc agctcatata caagcactag aactgtgata  300
ttcgccggag ggaccaaggt caccgtccta ggt                              333

SEQ ID NO: 17            moltype = AA  length = 117
FEATURE                  Location/Qualifiers
REGION                   1..117
                          note = Description of Artificial Sequence: Synthetic
                          polypeptide
source                   1..117
                          mol_type = protein
                          organism = synthetic construct
SEQUENCE: 17
EVQLVETGGG LVQPGGSLRL SCAASGSTFS SYAMSWVRQA PGKGLEWVSA ISGRGRSTYY  60
ADSVKGRFTI SRDNSKNTLY LQMNSLRAED TAVYYCARYY KSSKDHWGQG TLVTVSS     117

SEQ ID NO: 18            moltype = AA  length = 111
FEATURE                  Location/Qualifiers
REGION                   1..111
                          note = Description of Artificial Sequence: Synthetic
                          polypeptide
MOD_RES                  37
                          note = Any amino acid
source                   1..111
                          mol_type = protein
                          organism = synthetic construct
SEQUENCE: 18
QSVLTQPPSL SGAPGQRVTI SCSGSRSNIG TNYVSWXQQL PGTAPKLLIY RNHQWPSGVP  60
DRFTGSKSGT SASLAISGLR SEDEADYYCA AWDDNLSGVV FGGGTKLTVL G           111

SEQ ID NO: 19            moltype = DNA  length = 351
```

```
FEATURE              Location/Qualifiers
misc_feature         1..351
                     note = Description of Artificial Sequence: Synthetic
                      polynucleotide
source               1..351
                     mol_type = other DNA
                     organism = synthetic construct
SEQUENCE: 19
gaggtgcagc tggtggagac tgggggaggc ttggtacagc ctgggggtc cctgagactc    60
tcctgtgcag cctctggatc cacctttagc agctatgcca tgagctgggt ccgccaggct   120
ccagggaagg ggctggagtg ggtctcagct attagtggtc gtggtcgtag cacatactac   180
gcagactccg tgaagggccg gttcaccatc tccagagaca attccaagaa cacgctgtat   240
ctgcaaatga acagcctgag agccgaggac acggccgtat attactgtgc gcgctactac   300
aaatcttcta aagatcattg gggtcaaggt actctggtga ccgtctcctc a            351

SEQ ID NO: 20          moltype = DNA   length = 333
FEATURE              Location/Qualifiers
misc_feature         1..333
                     note = Description of Artificial Sequence: Synthetic
                      polynucleotide
modified_base        109
                     mod_base = x
                     note = a, c, t, g, unknown or other
source               1..333
                     mol_type = other DNA
                     organism = synthetic construct
SEQUENCE: 20
cagtctgtgt tgacgcagcc gccctcactg tctggggccc cagggcagag ggtcaccatc    60
tcttgttccg gaagcaggtc caacatcgga actaattatg tatcctggna ccagcaactc   120
ccaggaacgg cccccaaact cctcatctat aggaatcatc agtggccctc aggggtccct   180
gaccgattca ctggctccaa gtctggcacc tcagcctccc tggccatcag tgggctccgg   240
tccgaggatg aggctgatta ctactgtgca gcatgggatg acaatttgag tggtgtggtg   300
ttcggcggag ggaccaagct gaccgtccta ggt                                333

SEQ ID NO: 21          moltype = AA   length = 121
FEATURE              Location/Qualifiers
REGION               1..121
                     note = Description of Artificial Sequence: Synthetic
                      polypeptide
source               1..121
                     mol_type = protein
                     organism = synthetic construct
SEQUENCE: 21
QVQLVQSGAE VQRPGASVRV SCKAIAYTFT DYYIHWVRQA PGQGPEWMGW INPKSGRTQY    60
APKFQDRVTL ARETPISTAS MELRGLTSDD TAVYYCARVY GYSRWSGFDL WGQGTLVTVS   120
S                                                                    121

SEQ ID NO: 22          moltype = AA   length = 111
FEATURE              Location/Qualifiers
REGION               1..111
                     note = Description of Artificial Sequence: Synthetic
                      polypeptide
source               1..111
                     mol_type = protein
                     organism = synthetic construct
SEQUENCE: 22
QAVLTQPPSA SGTPGQRVTI SCSGSSSNIG SNYVYWYQQL PGTAPKLLIY RNNQRPSGVP    60
DRFSGSKSGT SASLAISGLR SEDEADYYCA AWDDSLSGYV FGTGTKVTVL G             111

SEQ ID NO: 23          moltype = DNA   length = 363
FEATURE              Location/Qualifiers
misc_feature         1..363
                     note = Description of Artificial Sequence: Synthetic
                      polynucleotide
source               1..363
                     mol_type = other DNA
                     organism = synthetic construct
SEQUENCE: 23
caggtccagc tggtgcagtc tggggctgag gtgcagaggc ctggggcctc agtgagggtc    60
tcctgcaagg ctattgcgta caccttcacc gactactata tccactgggt gcgacaggcc   120
cctggacaag ggcctgagtg gatggggtgg atcaaccta aaagtggtcg cacacagtat   180
gcaccgaagt tcaagacag ggtcaccctg gccagggaga cgcccatcag cacagcctcc   240
atggagctgc gcggactgac atctgacgac acggccgtgt attactgtgc gcgcgtttac   300
ggttactctc gttggtctgg tttcgatctg tggggtcaag gtactctggt gaccgtctcc   360
tca                                                                  363

SEQ ID NO: 24          moltype = DNA   length = 333
FEATURE              Location/Qualifiers
misc_feature         1..333
```

```
                           note = Description of Artificial Sequence: Synthetic
                            polynucleotide
source                     1..333
                           mol_type = other DNA
                           organism = synthetic construct
SEQUENCE: 24
caggctgtgc tgactcagcc accctcagcg tctgggaccc ccgggcagag ggtcaccatc    60
tcttgttctg gaagcagctc caacatcgga agtaattatg tatactggta ccagcagctc   120
ccaggaacgg cccccaaact cctcatctat aggaataatc agcggccctc aggggtccct   180
gaccgattct ctggctccaa gtctggcacc tcagcctccc tggccatcag tgggctccgg   240
tccgaggatg aggctgatta ttactgtgca gcatgggatg acagcctgag tggttatgtc   300
ttcggaactg ggaccaaggt caccgtccta ggt                                333

SEQ ID NO: 25             moltype = AA  length = 124
FEATURE                   Location/Qualifiers
REGION                    1..124
                          note = Description of Artificial Sequence: Synthetic
                           polypeptide
source                    1..124
                          mol_type = protein
                          organism = synthetic construct
SEQUENCE: 25
QVQLVQSGAE VKQPGASVKV SCQASGYTFT TYYMHWVRQA PGQGLEWMGI INPNGGGTFY    60
AQKFQDRVTM TRDTSTGTVY MELSSLRSDD TAVYYCARGH KVYKSHPTGG YDRWGQGTLV   120
TVSS                                                                124

SEQ ID NO: 26             moltype = AA  length = 111
FEATURE                   Location/Qualifiers
REGION                    1..111
                          note = Description of Artificial Sequence: Synthetic
                           polypeptide
source                    1..111
                          mol_type = protein
                          organism = synthetic construct
SEQUENCE: 26
QSALTQPASV SGSPGQSITI SCTGTSRDVG GYNYVSWYQQ YPGKAPKLMI YEVSKRPSGV    60
SNRFSGSKSG NTASLTISGL QAEDEADYYC SSYTSSSTLD FGTGTKVTVL G            111

SEQ ID NO: 27             moltype = DNA  length = 372
FEATURE                   Location/Qualifiers
misc_feature              1..372
                          note = Description of Artificial Sequence: Synthetic
                           polynucleotide
source                    1..372
                          mol_type = other DNA
                          organism = synthetic construct
SEQUENCE: 27
caggtgcagc tggtgcaatc tggggctgag gtgaagcagc ctggggcctc agtgaaggtt    60
tcctgccagg catctggata caccttcacc acttattata tgcactgggt gcgacaggcc   120
cctgacaag ggcttgagtg gatgggaata atcaacccta atggtggtgg cacattctac   180
gcacagaagt tccaggacag agtcaccatg accagggaca cgtccacggg cacagtctac   240
atggaactga gcagcctgag atctgacgac actgccgtgt attactgtgc gcgcggtcat   300
aaagtttaca aatctcatcc gactggtggt tacgatcgtt ggggtcaagg tactctggtg   360
accgtctcct ca                                                       372

SEQ ID NO: 28             moltype = DNA  length = 333
FEATURE                   Location/Qualifiers
misc_feature              1..333
                          note = Description of Artificial Sequence: Synthetic
                           polynucleotide
source                    1..333
                          mol_type = other DNA
                          organism = synthetic construct
SEQUENCE: 28
caatctgccc tgactcagcc tgcctccgtg tctgggtctc ctggacagtc gatcaccatc    60
tcctgcactg gaaccagccg tgacgttggt ggttataact atgtctcctg gtaccaacag   120
tacccaggca aagcccccaa actcatgatt tatgaggtca gtaagcggcc ctcaggggtt   180
tctaatcgct tctctggctc caagtctggc aacacggccc ccctgaccat ctctgggctc   240
caggctgagg acgaggctga ttattactgc agctcatata ccagtagcag cactttagac   300
ttcggaactg ggaccaaggt caccgtccta ggt                                333

SEQ ID NO: 29             moltype = AA  length = 119
FEATURE                   Location/Qualifiers
REGION                    1..119
                          note = Description of Artificial Sequence: Synthetic
                           polypeptide
source                    1..119
                          mol_type = protein
                          organism = synthetic construct
```

```
SEQUENCE: 29
EVQLVQSGAE VKKPGSSVKV SCKASGGTFS SYAISWVRQA PGQGLEWMGG IIPIFGTAKY   60
AQKFQGRVTI TADESTSTAY MELSSLRSED TAVYYCARSH VAWSLLDYWG QGTLVTVSS   119

SEQ ID NO: 30            moltype = AA  length = 111
FEATURE                  Location/Qualifiers
REGION                   1..111
                         note = Description of Artificial Sequence: Synthetic
                          polypeptide
source                   1..111
                         mol_type = protein
                         organism = synthetic construct
SEQUENCE: 30
SYELTQPPSA SGTPGQRVTI SCSGSSSNIG SNYVSWYQQL PGTAPKLLIY RNNQRPSGVP   60
DRFSGSKSGT SASLAISGLR SEDEADYYCA AWDDSLSGVV FGGGTKLTVL G            111

SEQ ID NO: 31            moltype = DNA  length = 357
FEATURE                  Location/Qualifiers
misc_feature             1..357
                         note = Description of Artificial Sequence: Synthetic
                          polynucleotide
source                   1..357
                         mol_type = other DNA
                         organism = synthetic construct SEQUENCE: 31
gaggtccagc tggtgcagtc tggggctgag gtgaagaagc ctgggtcctc ggtgaaggtc   60
tcctgcaagg cttctggagg caccttcagc agctatgcta tcagctgggt gcgacaggcc  120
cctggacaag ggcttgagtg gatgggaggg attatcccta tctttggtac agcaaaatat  180
gcacagaagt tccagggcag agtcacgatt accgcggacg aatccacgag cacagcctac  240
atggagctga gcagcctgag atctgaggac acggccgtgt attactgtgc gcgctctcat  300
gttgcttggt ctctgctgga ttactggggt caaggtactc tggtgaccgt ctcctca     357

SEQ ID NO: 32            moltype = DNA  length = 333
FEATURE                  Location/Qualifiers
misc_feature             1..333
                         note = Description of Artificial Sequence: Synthetic
                          polynucleotide
source                   1..333
                         mol_type = other DNA
                         organism = synthetic construct SEQUENCE: 32
tcctatgagc tgactcagcc accctcagcg tctgggaccc ccgggcagag ggtcaccatc   60
tcttgttctg gaagcagctc caacatcgga agtaattatg tatcctggta ccagcagctc  120
ccaggaacgg cccccaaact cctcatctat aggaataatc agcggccctc aggggtccct  180
gaccgattct ctggctccaa gtctggcacc tcagcctccc tggccatcag tgggctccgg  240
tccgaggatg aggctgatta ttactgtgca gcatgggatg acagcctgag tggtgtggta  300
ttcggcggag ggaccaagct gaccgtccta ggt                                333

SEQ ID NO: 33            moltype = AA  length = 120
FEATURE                  Location/Qualifiers
REGION                   1..120
                         note = Description of Artificial Sequence: Synthetic
                          polypeptide
source                   1..120
                         mol_type = protein
                         organism = synthetic construct
SEQUENCE: 33
QVQLVQSGAE VKKPGSSVKV SCKASGGTFS SYAISWVRQA PGQGLEWMGW MNPNSGNTGY   60
AQKFQGRVTM TRNTSISTAY MELSSLRSED TAVYYCARYQ SYKGSQSDSW GQGTLVTVSS  120

SEQ ID NO: 34            moltype = AA  length = 111
FEATURE                  Location/Qualifiers
REGION                   1..111
                         note = Description of Artificial Sequence: Synthetic
                          polypeptide
source                   1..111
                         mol_type = protein
                         organism = synthetic construct
SEQUENCE: 34
QSVLTQPPSA SGTPGQRVTI SCSGSSSNIG SNYVYWYQQL PGTAPKLLIY RNNQRPSGVP   60
DRFSGSKSGT SASLAISGLR SEDEADYYCA AWDDSLSGWV FGGGTKLTVL G            111

SEQ ID NO: 35            moltype = DNA  length = 360
FEATURE                  Location/Qualifiers
misc_feature             1..360
                         note = Description of Artificial Sequence: Synthetic
                          polynucleotide
source                   1..360
                         mol_type = other DNA
```

```
                        organism = synthetic construct
SEQUENCE: 35
caggtgcagc tggtgcagtc tggggctgag gtgaagaagc ctgggtcctc agtgaaggtc   60
tcctgcaagg cttctggagg caccttcagc agctatgcta tcagctgggt gcgacaggcc  120
cctggacaag ggcttgagtg gatgggatgg atgaacccta acagtggtaa cacaggctat  180
gcacagaagt tccagggcag agtcaccatg accaggaaca cctccataag cacagcctac  240
atggagctga gcagcctgag atctgaggac acggccgtgt attactgtgc gcgctaccag  300
tcttacaaag gttctcagtc tgattcttgg ggtcaaggta ctctggtgac cgtctcctca  360

SEQ ID NO: 36             moltype = DNA  length = 333
FEATURE                   Location/Qualifiers
misc_feature              1..333
                          note = Description of Artificial Sequence: Synthetic
                           polynucleotide
source                    1..333
                          mol_type = other DNA
                          organism = synthetic construct
SEQUENCE: 36
cagtctgtgt tgacgcagcc accctcagcg tctgggaccc ccgggcagag ggtcaccatc   60
tcttgttctg gaagcagctc caacatcgga agtaattatg tatactggta ccagcagctc  120
ccaggaacgg cccccaaact cctcatctat aggaataatc agcggccctc aggggtccct  180
gaccgattct ctggctccaa gtctggcacc tcagcctccc tggccatcag tgggctccgg  240
tccgaggatg aggctgatta ttactgtgca gcatgggatg acagcctgag tggttgggtg  300
ttcggcggag ggaccaagct gaccgtccta ggt                               333

SEQ ID NO: 37             moltype = AA  length = 127
FEATURE                   Location/Qualifiers
REGION                    1..127
                          note = Description of Artificial Sequence: Synthetic
                           polypeptide
source                    1..127
                          mol_type = protein
                          organism = synthetic construct
SEQUENCE: 37
EVQLVQSGAE VKKPGASVKV SCKASGYTFT SYYMHWVRQA PGQGLEWMGI INPSGGSTSY   60
AQKFQGRVTM TRDTSTSTVY MELSSLRSED TAVYYCARGG SKKWSGEKWR RENFDYWGQG  120
TLVTVSS                                                            127

SEQ ID NO: 38             moltype = AA  length = 111
FEATURE                   Location/Qualifiers
REGION                    1..111
                          note = Description of Artificial Sequence: Synthetic
                           polypeptide
source                    1..111
                          mol_type = protein
                          organism = synthetic construct
SEQUENCE: 38
QSALTQPASV SGSPGQSITI SCTGTSSDVG GYNYVSWYQQ HPGKAPKLMI YDVSKRPSGV   60
SNRFSGSKSG NTASLTISGL QAEDEADYYC SSYTRSSTEV FGGGTKLTVL G           111

SEQ ID NO: 39             moltype = DNA  length = 381
FEATURE                   Location/Qualifiers
misc_feature              1..381
                          note = Description of Artificial Sequence: Synthetic
                           polynucleotide
source                    1..381
                          mol_type = other DNA
                          organism = synthetic construct
SEQUENCE: 39
gaggtccagc tggtacagtc tggggctgag gtgaagaagc ctggggcctc agtgaaggtt   60
tcctgcaagg catctggata caccttcacc agctactata tgcactgggt gcgacaggcc  120
cctggacaag ggcttgagtg gatgggaata atcaacccta gtggtggtag cacaagctac  180
gcacagaagt tccagggcag agtcaccatg accagggaca cgtccacgag cacagtctac  240
atggagctga gcagcctgag atctgaggac acggccgtgt attactgtgc gcgcggtggt  300
tctaaaaaat ggtctggtga aaaatggcgt cgtgaaaact cgattactg gggtcaaggt   360
actctggtga ccgtctcctc a                                            381

SEQ ID NO: 40             moltype = DNA  length = 333
FEATURE                   Location/Qualifiers
misc_feature              1..333
                          note = Description of Artificial Sequence: Synthetic
                           polynucleotide
source                    1..333
                          mol_type = other DNA
                          organism = synthetic construct
SEQUENCE: 40
caatctgccc tgactcagcc tgcctccgtg tctgggtctc ctggacagtc gatcaccatc   60
tcctgcactg gaaccagcag tgacgttggt ggttataact atgtctcctg gtaccaacag  120
cacccaggca aagcccccaa actcatgatt tatgatgtca gtaagcggcc ctcagggggtt  180
```

```
tctaatcgct tctctggctc caagtctggc aacacggcct ccctgaccat ctctgggctc   240
caggctgagg acgaggctga ttattactgc agctcatata caagaagcag cactgaggta   300
ttcggcggag ggaccaagct gaccgtccta ggt                                333

SEQ ID NO: 41          moltype = AA   length = 113
FEATURE                Location/Qualifiers
REGION                 1..113
                       note = Description of Artificial Sequence: Synthetic
                       polypeptide
source                 1..113
                       mol_type = protein
                       organism = synthetic construct
SEQUENCE: 41
QMQLVQSGAE VKKPGASVKV SCKASEYTFT RHILHWVRQA PGQSLEWMGW INPGNGNTKY   60
SQKFQVRVTF TRDTSASTVY MELSSLRSED TAVYYCARLP DQWGQGTLVT VSS          113

SEQ ID NO: 42          moltype = AA   length = 110
FEATURE                Location/Qualifiers
REGION                 1..110
                       note = Description of Artificial Sequence: Synthetic
                       polypeptide
source                 1..110
                       mol_type = protein
                       organism = synthetic construct
SEQUENCE: 42
SYVLTQPPSA SGTPGQRVTI SCSGSSSNIG SNTVNWYQQL PGTAPKLLIY RNNQRPSGVP   60
DRFSGSKSGT SASLAISGLR SEDEADYYCA AWDDSLSGLF GTGTKVTVLG              110

SEQ ID NO: 43          moltype = DNA   length = 339
FEATURE                Location/Qualifiers
misc_feature           1..339
                       note = Description of Artificial Sequence: Synthetic
                       polynucleotide
source                 1..339
                       mol_type = other DNA
                       organism = synthetic construct
SEQUENCE: 43
cagatgcagc tggtgcagtc tgggggctgag gtgaagaagc ctggggcctc agtgaaggtt   60
tcctgcaagg cttctgaata caccttcact aggcatattc tacattgggt gcgccaggct   120
cccggacaaa gccttgagtg gatgggatgg atcaacccag gcaatggtaa tacaaaatat   180
tcacagaagt tccaggtcag agtcaccttt accaggggaca catccgcgag cacagtctat   240
atggagctga gcagcctgag atctgaagac acggccgtgt attactgtgc gcgcctgccg   300
gatcagtggg gtcaaggtac tctggtgacc gtctcctca                          339

SEQ ID NO: 44          moltype = DNA   length = 330
FEATURE                Location/Qualifiers
misc_feature           1..330
                       note = Description of Artificial Sequence: Synthetic
                       polynucleotide
source                 1..330
                       mol_type = other DNA
                       organism = synthetic construct
SEQUENCE: 44
tcctatgtgc tgactcagcc accctcagcg tctgggaccc ccgggcagag ggtcaccatc   60
tcttgttctg gaagcagctc caacatcgga agtaatactg taaactggta ccagcagctc   120
ccaggaacgg cccccaaact cctcatctat aggaataatc agcggccctc aggggtccct   180
gaccgattct ctggctccaa gtctggcacc tcagcctccc tggccatcag tgggctccgg   240
tccgaggatg aggctgatta ttactgtgca gcatgggatg acagcctgag tggtctcttc   300
ggaactggga ccaaggtcac cgtcctaggt                                    330

SEQ ID NO: 45          moltype = AA   length = 114
FEATURE                Location/Qualifiers
REGION                 1..114
                       note = Description of Artificial Sequence: Synthetic
                       polypeptide
source                 1..114
                       mol_type = protein
                       organism = synthetic construct
SEQUENCE: 45
EVQLVESGGG VVRPGGSLRL SCAASGFTFG DYGMSWVRQA PGKGLEWVSG INWNGGSTGY   60
ADSVKGRFTI SRDNAKNSLY LQMNSLRAED TAVYYCARSK QDYWGQGTLV TVSS         114

SEQ ID NO: 46          moltype = AA   length = 112
FEATURE                Location/Qualifiers
REGION                 1..112
                       note = Description of Artificial Sequence: Synthetic
                       polypeptide
source                 1..112
                       mol_type = protein
```

-continued

```
                        organism = synthetic construct
SEQUENCE: 46
QSALTQPPSA SGSPGQSVTI SCTGTSRDAG GYNYFSWYQQ HPGKAPKLLI YEVTKRPSGV   60
PDRFSGSKSG KTASLTVSGL QADDEAVYYC SSYGGSNNFR VFGGGTKLTV LG           112

SEQ ID NO: 47          moltype = DNA  length = 342
FEATURE                Location/Qualifiers
misc_feature           1..342
                        note = Description of Artificial Sequence: Synthetic
                         polynucleotide
source                 1..342
                        mol_type = other DNA
                        organism = synthetic construct
SEQUENCE: 47
gaggtgcagc tggtggagtc tggggggaggt gtggtacggc ctgggggggtc cctgagactc   60
tcctgtgcag cctctggatt cacctttggt gattatggca tgagctgggt ccgccaagct  120
ccagggaagg ggctggagtg ggtctctggt attaattgga atggtggtag cacaggttat  180
gcagactctg tgaagggccg attcaccatc tccagagaca cgccaagaa ctccctgtat   240
ctgcaaatga acagtctgag agccgaggac acggccgtat attactgtgc gcgctctaaa  300
caggattact ggggtcaagg tactctggtg accgtctcct ca                     342

SEQ ID NO: 48          moltype = DNA  length = 336
FEATURE                Location/Qualifiers
misc_feature           1..336
                        note = Description of Artificial Sequence: Synthetic
                         polynucleotide
source                 1..336
                        mol_type = other DNA
                        organism = synthetic construct
SEQUENCE: 48
cagtctgccc tgactcagcc tccctccgcg tccgggtctc ctggacagtc agtcaccatc   60
tcctgcactg gaaccagcag ggacgctggt ggttataatt atttctcctg gtaccaacaa  120
cacccaggca aagcccccaa actcctgatt tatgaggtca ctaagcggcc ctcagggggtc  180
cctgatcgct tctctggctc caagtctggc aagacggcct ccctgaccgt ctctgggctc  240
caggctgacg atgaggctgt atattactgc agctcatatg gaggcagcaa caactttcgg  300
gtgttcggcg gagggaccaa gctgaccgtc ctaggt                            336

SEQ ID NO: 49          moltype = AA  length = 114
FEATURE                Location/Qualifiers
REGION                 1..114
                        note = Description of Artificial Sequence: Synthetic
                         polypeptide
source                 1..114
                        mol_type = protein
                        organism = synthetic construct
SEQUENCE: 49
EVQLVETGGN LVQPGASLRL SCAASGFSFS GTAMHWVRQA PGKGLEWVST ISSTGRSTYY   60
RDSVKGRFTI SRDNSKNTLY LQMNSLRGED TAVYYCARVS FDYWGQGTLV TVSS         114

SEQ ID NO: 50          moltype = AA  length = 113
FEATURE                Location/Qualifiers
REGION                 1..113
                        note = Description of Artificial Sequence: Synthetic
                         polypeptide
source                 1..113
                        mol_type = protein
                        organism = synthetic construct
SEQUENCE: 50
QSVVTQPPSV SGAPGQRVTI SCTGSSSNIG AGYDVHWYQQ LPGTAPKLLI YGNSNRPSGV   60
PDRFSGSKSG TSASLAITGL QAEDEADYYC QSYDSSLSGS YVFGTGTKLT VLG          113

SEQ ID NO: 51          moltype = DNA  length = 342
FEATURE                Location/Qualifiers
misc_feature           1..342
                        note = Description of Artificial Sequence: Synthetic
                         polynucleotide
source                 1..342
                        mol_type = other DNA
                        organism = synthetic construct
SEQUENCE: 51
gaggtgcagc tggtggagac tggggggaaac ttggtacagc cggggggcgtc cctgagactc   60
tcctgtgcag cctctggatt cagctttagt ggcactgcca tgcactgggt ccgccaggct  120
ccagggaagg ggctggaatg ggtctcgact attagtagta ctgggcgtag cacatactac  180
agagactccg tgaagggccg gttcaccatc tccagagaca attccaagaa cacgctgtat  240
ctgcaaatga acagcctgag aggcgaggac acggccgtat attactgtgc gcgcgtttct  300
ttcgattact ggggtcaagg tactctggtg accgtctcct ca                     342

SEQ ID NO: 52          moltype = DNA  length = 339
FEATURE                Location/Qualifiers
```

```
misc_feature            1..339
                        note = Description of Artificial Sequence: Synthetic
                         polynucleotide
source                  1..339
                        mol_type = other DNA
                        organism = synthetic construct
SEQUENCE: 52
cagtctgtcg tgacgcagcc gccctcagtg tctggggccc cagggcagag ggtcaccatc   60
tcctgcactg ggagcagctc caacatcggg gcaggttatg atgtacactg gtaccagcag  120
cttccaggaa cagcccccaa actcctcatc tatggtaaca gcaatcggcc ctcaggggtc  180
cctgaccgat tctctggctc caagtctggc acctcagcct ccctggccat cactgggctc  240
caggctgagg atgaggctga ttattactgc cagtcctatg acagcagcct gagtggctcc  300
tacgtcttcg gaactgggac caagctgacc gtcctaggt                         339

SEQ ID NO: 53          moltype = AA   length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 53
EVQLVESGGA FVQPGGSLRL SCAASGFTFS SYAMTWVRQA PGKGLEWVST ISGRGRSTFY   60
ADSVKGRFTI SRDNSKNTLY LQMNSLRAED TAVYYCARYY HAGAFDLWGQ GTLVTVSS    118

SEQ ID NO: 54          moltype = AA   length = 111
FEATURE                Location/Qualifiers
REGION                 1..111
                       note = Description of Artificial Sequence: Synthetic
                        polypeptide
source                 1..111
                       mol_type = protein
                       organism = synthetic construct
SEQUENCE: 54
QSVVTQPASV SGSPGQSITI SCTGTSSDVG GYNYVSWYQQ HPGKAPKLMI YDVSKRPSGV   60
SNRFSGSKSG NTASLTISGL QAEDEADYYC SSYTSSSTLV FGGGTKLTVL G           111

SEQ ID NO: 55          moltype = DNA   length = 354
FEATURE                Location/Qualifiers
misc_feature           1..354
                       note = Description of Artificial Sequence: Synthetic
                        polynucleotide
source                 1..354
                       mol_type = other DNA
                       organism = synthetic construct
SEQUENCE: 55
gaggtgcagc tggtggagtc tggggggagcc tttgtacagc ctggggggtc cctgagactc   60
tcctgtgcag cctctggatt cacctttagc agctatgcca tgacctgggt ccgccaggct  120
ccagggaagg gcctggaatg ggtctcgact attagtggtc gtggtcgtag cacattctac  180
gcagactccg tgaagggccg gtttaccatc tccagagaca attccaagaa cacgctatat  240
ctgcaaatga acagtctgag agccgaggac acggccgtat attactgtgc gcgctactac  300
catgctggtg ctttcgatct gtggggtcaa ggtactctgg tgaccgtctc ctca        354

SEQ ID NO: 56          moltype = DNA   length = 333
FEATURE                Location/Qualifiers
misc_feature           1..333
                       note = Description of Artificial Sequence: Synthetic
                        polynucleotide
source                 1..333
                       mol_type = other DNA
                       organism = synthetic construct
SEQUENCE: 56
cagtctgtcg tgacgcagcc tgcctccgtg tctgggtctc ctggacagtc gatcaccatc   60
tcctgcactg gaaccagcag tgacgttggt ggttataact atgtctcctg gtaccaacag  120
cacccaggca aagcccccaa actcatgatt tatgatgtca gtaagcggcc ctcaggggtt  180
tctaatcgct tctctggctc caagtctggc aacacggcct ccctgaccat ctctgggctc  240
caggctgagg acgaggctga ttattactgc agctcatata caagcagcag cactttggta  300
ttcggcggag ggaccaagct gaccgtccta ggt                               333

SEQ ID NO: 57          moltype = AA   length = 114
FEATURE                Location/Qualifiers
REGION                 1..114
                       note = Description of Artificial Sequence: Synthetic
                        polypeptide
source                 1..114
                       mol_type = protein
                       organism = synthetic construct
SEQUENCE: 57
```

```
QMQLVQSGAE VKKPGASVKV SCKASGYTFN RYAITWVRQA PGQGLEWMGW ISAYNGNSHY  60
AQKLQGRVTM TTDTSTGTAY MELRRLRSDD TAVYYCARMA YDSWGQGTLV TVSS         114

SEQ ID NO: 58            moltype = AA  length = 111
FEATURE                  Location/Qualifiers
REGION                   1..111
                         note = Description of Artificial Sequence: Synthetic
                          polypeptide
source                   1..111
                         mol_type = protein
                         organism = synthetic construct
SEQUENCE: 58
QSVLTQPASV SGSPGQSLTI SCTGTSNDVG AYKYVSWYQQ YPGKAPKLIL YDVFKRPSGV  60
SNRFSGSKSD NTASLTISGL QAEDEADYYC FSLTSSNTYV FGTGTKVTVL G           111

SEQ ID NO: 59            moltype = DNA  length = 342
FEATURE                  Location/Qualifiers
misc_feature             1..342
                         note = Description of Artificial Sequence: Synthetic
                          polynucleotide
source                   1..342
                         mol_type = other DNA
                         organism = synthetic construct
SEQUENCE: 59
cagatgcagc tggtgcagtc tggagctgag gtgaagaagc ctggggcctc agtgaaggtc  60
tcctgcaagg cttctggtta cacctttaac agatatgcta tcacctgggt gcgacaggcc  120
cctggacaag gccttgagtg gatgggatgg atcagcgctt acaatggtaa ttcacactat  180
gcacagaagc tccagggcag agtcaccatg accacagaca catccacggg cacagcctat  240
atggagctga ggaggctgag atctgacgac acggccgtgt attactgtgc gcgcatggct  300
tacgattctt ggggtcaagg tactctggtg accgtctcct ca                     342

SEQ ID NO: 60            moltype = DNA  length = 333
FEATURE                  Location/Qualifiers
misc_feature             1..333
                         note = Description of Artificial Sequence: Synthetic
                          polynucleotide
source                   1..333
                         mol_type = other DNA
                         organism = synthetic construct
SEQUENCE: 60
cagtctgtgt tgacgcagcc tgcctccgtg tctgggtctc ctggacagtc gctcaccatc  60
tcctgcactg gaaccagcaa tgacgttggt gcttataagt atgtctcctg gtatcaacag  120
tacccaggca aagcccccaa actcatactt tatgatgtct ttaagcggcc ctcaggggtc  180
tctaatcgct tctctggctc caagtctgac aacacggcct ccctgaccat ctctgggctc  240
caggctgagg acgaggctga ttattactgc ttctcactta caagcagtaa cacttatgtc  300
ttcggaactg ggaccaaggt caccgtccta ggt                                333

SEQ ID NO: 61            moltype = AA  length = 117
FEATURE                  Location/Qualifiers
REGION                   1..117
                         note = Description of Artificial Sequence: Synthetic
                          polypeptide
source                   1..117
                         mol_type = protein
                         organism = synthetic construct
SEQUENCE: 61
EVQLVESGGG LVKPGGSLRL SCAASGFTFS DYYMSWIRQA PGKGLEWVSY ISSSGSTIYY  60
ADSVKGRFTI SRDNAKNSLY LQMNSLRAED TAVYYCARGY GKAYDQWGQG TLVTVSS      117

SEQ ID NO: 62            moltype = AA  length = 111
FEATURE                  Location/Qualifiers
REGION                   1..111
                         note = Description of Artificial Sequence: Synthetic
                          polypeptide
source                   1..111
                         mol_type = protein
                         organism = synthetic construct
SEQUENCE: 62
QSVLTQPPSA SGTPGQRVTI SCSGSRSNVG GNYVFWYQQV PGATPKLLIY RSNQRPSGVP  60
DRFAGSKSGS SASLAISGLR SEDEADYYCA TWDDSLSGFV FGTGTKVTVL G           111

SEQ ID NO: 63            moltype = DNA  length = 351
FEATURE                  Location/Qualifiers
misc_feature             1..351
                         note = Description of Artificial Sequence: Synthetic
                          polynucleotide
source                   1..351
                         mol_type = other DNA
                         organism = synthetic construct
```

-continued

```
SEQUENCE: 63
gaggtgcagc tggtggagtc tggggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac attagtagta gtggtagtac catatactac   180
gcagactctg tgaagggccg attcaccatc tccagggaca acgccaagaa ctcactgtat   240
ctgcaaatga acagcctgag agccgaggac acggccgtat attactgtgc gcgcggttac   300
ggtaaagctt acgatcagtg gggtcaaggt actctggtga ccgtctcctc a           351

SEQ ID NO: 64          moltype = DNA  length = 333
FEATURE                Location/Qualifiers
misc_feature           1..333
                       note = Description of Artificial Sequence: Synthetic
                        polynucleotide
source                 1..333
                       mol_type = other DNA
                       organism = synthetic construct
SEQUENCE: 64
cagtctgtgt tgactcagcc accctcagcg tctgggaccc ccggacagag ggtcaccatc    60
tcttgttctg gaagcaggtc caacgtagga ggtaattatg tattttggta ccagcaagtc   120
cccggagcga cccccaaact cctcatctat aggagtaatc agcggccctc gggggtccct   180
gaccgattgc ctggctccaa gtctggctcc tcagcctccc tggccatcag tggactccgg   240
tccgaggatg aggctgatta ttactgtgca acatgggatg acagcctgag tggtttttgtc   300
ttcggaactg ggaccaaggt caccgtccta ggt                                333

SEQ ID NO: 65          moltype = AA  length = 119
FEATURE                Location/Qualifiers
REGION                 1..119
                       note = Description of Artificial Sequence: Synthetic
                        polypeptide
source                 1..119
                       mol_type = protein
                       organism = synthetic construct
SEQUENCE: 65
QVQLVESGGG LVHPGGSLRL SCAASGFTFR SHSMNWVRQA PGKGLEWVSS ISSDSTYTYY    60
ADSVKGRFTI SRDNAKNSLY LQMNSLRAED TAVYYCARSG GQWKYYDYWG QGTLVTVSS    119

SEQ ID NO: 66          moltype = AA  length = 110
FEATURE                Location/Qualifiers
REGION                 1..110
                       note = Description of Artificial Sequence: Synthetic
                        polypeptide
source                 1..110
                       mol_type = protein
                       organism = synthetic construct
SEQUENCE: 66
SSELTQDPAV SVALGQTVRI TCQGDSLRSY YASWYQQKPG QAPVLVIYGK NNRPSGIPDR    60
FSGSSSGNTA SLTITGAQAE DEADYYCNSR DSSGNPPVVF GGGTKLTVLG              110

SEQ ID NO: 67          moltype = DNA  length = 357
FEATURE                Location/Qualifiers
misc_feature           1..357
                       note = Description of Artificial Sequence: Synthetic
                        polynucleotide
source                 1..357
                       mol_type = other DNA
                       organism = synthetic construct
SEQUENCE: 67
caggtgcagc tggtggagtc tggggggaggc ctggtccacc ctggggggtc cctgagactc    60
tcctgtgcag cctctggatt caccttcaga agccatagca gtaactgggt ccgccaggct   120
ccagggaagg ggctggagtg ggtctcatcc attagtagtg atagtactta cacatactac   180
gcagactcag tgaagggccg attcaccatc tccagagaca acgccaagaa ctcactgtat   240
ctgcaaatga acagcctgag agccgaggac acggccgtat attactgtgc gcgctctggt   300
ggtcagtgga aatactacga ttactgggggt caaggtactc tggtgaccgt ctcctca     357

SEQ ID NO: 68          moltype = DNA  length = 330
FEATURE                Location/Qualifiers
misc_feature           1..330
                       note = Description of Artificial Sequence: Synthetic
                        polynucleotide
source                 1..330
                       mol_type = other DNA
                       organism = synthetic construct
SEQUENCE: 68
tcttctgagc tgactcagga ccctgctgtg tctgtggcct gggacagac agtcaggatc    60
acatgccaag agacagcct cagaagctat tatgcaagct ggtaccagca gaagccagga   120
caggcccctg tacttgtcat ctatggtaaa aacaaccggc cctcagggat cccagaccga   180
ttctctggct ccagctcagg aaacacagct tccttgacca tcactggggc tcaggcgaa   240
gatgaggctg actattactg taactcccgg gacagcagtg taaccccccc tgtggtattc   300
ggcggaggga ccaagctgac cgtcctaggt                                    330
```

```
SEQ ID NO: 69             moltype = AA   length = 116
FEATURE                   Location/Qualifiers
REGION                    1..116
                          note = Description of Artificial Sequence: Synthetic
                           polypeptide
source                    1..116
                          mol_type = protein
                          organism = synthetic construct
SEQUENCE: 69
EVQLVESGGG LIQPGGSLRL SCAASGFTFS NYAMNWVRQA PGKGLEWVST INGRGSSTIY   60
ADSVKGRFTI SRDNSKNTLY LQMNSLRAED TATYYCARYI SRGLGDSWGQ GTLVTV      116

SEQ ID NO: 70             moltype = AA   length = 111
FEATURE                   Location/Qualifiers
REGION                    1..111
                          note = Description of Artificial Sequence: Synthetic
                           polypeptide
source                    1..111
                          mol_type = protein
                          organism = synthetic construct
SEQUENCE: 70
QSVVTQPPSM SAAPGQQVTI SCSGGNSNIE RNYVSWYLQL PGTAPKLVIF DNDRRPSGIP   60
DRFSGSKSGT SATLGITGLQ TGDEADYYCG TWDSSLRGWV FGGGTKLTVL G           111

SEQ ID NO: 71             moltype = DNA   length = 354
FEATURE                   Location/Qualifiers
misc_feature              1..354
                          note = Description of Artificial Sequence: Synthetic
                           polynucleotide
source                    1..354
                          mol_type = other DNA
                          organism = synthetic construct
SEQUENCE: 71
gaggtgcagc tggtggagtc cggggggaggc ttgatacagc ctggggggtc cctgagactc   60
tcctgtgcag cctctggatt caccttttagc aactatgcca tgaactgggt ccgccaggct  120
ccagggaagg ggctggagtg ggtctcaact attaatggtc gtggtagtag tacaatctac  180
gcagactccg tgaagggccg gttcaccatc tccagagaca attccaagaa cacgctgtat  240
ctgcaaatga acagcctgag agccgaggac acagccacgt attactgtgc gcgctacatc  300
tctcgtggtc tgggtgattc ttggggtcaa ggtactctgg tgaccgtctc ctca        354

SEQ ID NO: 72             moltype = DNA   length = 333
FEATURE                   Location/Qualifiers
misc_feature              1..333
                          note = Description of Artificial Sequence: Synthetic
                           polynucleotide
source                    1..333
                          mol_type = other DNA
                          organism = synthetic construct
SEQUENCE: 72
cagtctgtcg tgacgcagcc gccctcaatg tctgcggccc caggacagca agtcaccatc   60
tcctgctctg gaggcaactc caacattgag agaaattatg tatcctggta cctccagctc  120
cctggaacag ccccccaaact cgtcattttt gacaatgata ggcgaccctc agggattcct  180
gaccgattct ctggctccaa gtctggcacg tcagccaccc tgggcatcac cggactccag  240
actggggacg aggccgatta ttactgcgga acatgggata gcagcctgag aggttgggtg  300
ttcggcggag ggaccaagct gaccgtccta ggt                               333

SEQ ID NO: 73             moltype = AA   length = 116
FEATURE                   Location/Qualifiers
REGION                    1..116
                          note = Description of Artificial Sequence: Synthetic
                           polypeptide
source                    1..116
                          mol_type = protein
                          organism = synthetic construct
SEQUENCE: 73
QMQLVQSGAE VKKPGASVKV SCKASGYTFT SYYMHWVRQA PGQGLEWMGI INPSGGSTSY   60
AQKFQGRVTM TRDTSTSTVY MELSSLRSED TAVYYCARAG MGMDTWGQGT LVTVSS      116

SEQ ID NO: 74             moltype = AA   length = 111
FEATURE                   Location/Qualifiers
REGION                    1..111
                          note = Description of Artificial Sequence: Synthetic
                           polypeptide
source                    1..111
                          mol_type = protein
                          organism = synthetic construct
SEQUENCE: 74
QSALTQPPSA SGSPGQSVTI SCTGTSSDVG GYNYVSWYQQ HPGKAPKLMI YEVSKRPSGV   60
```

```
PDRFSGSKSG NTASLTVSGL QAEDEADYYC SSYAGSNTLV FGGGTKLTVL G          111

SEQ ID NO: 75           moltype = DNA   length = 348
FEATURE                 Location/Qualifiers
misc_feature            1..348
                        note = Description of Artificial Sequence: Synthetic
                        polynucleotide
source                  1..348
                        mol_type = other DNA
                        organism = synthetic construct
SEQUENCE: 75
cagatgcagc tggtgcagtc tggggctgag gtgaagaagc ctggggcctc agtgaaggtt   60
tcctgcaagg catctggata caccttcacc agctactata tgcactgggt gcgacaggcc  120
cctggacaag ggcttgagtg gatgggaata atcaacccta gtggtggtag cacaagctac  180
gcacagaagt tccagggcag agtcaccatg accagggaca cgtccacgag cacagtctac  240
atggagctga gcagcctgag atctgaggac acggccgtgt attactgtgc gcgcgctggt  300
atgggtatgg atacttgggg tcaaggtact ctggtgaccg tctcctca               348

SEQ ID NO: 76           moltype = DNA   length = 333
FEATURE                 Location/Qualifiers
misc_feature            1..333
                        note = Description of Artificial Sequence: Synthetic
                        polynucleotide
source                  1..333
                        mol_type = other DNA
                        organism = synthetic construct
SEQUENCE: 76
cagtctgccc tgactcagcc tccctccgcg tccgggtctc ctggacagtc agtcaccatc   60
tcctgcactg gaaccagcag tgacgttggt ggttataact atgtctcctg gtaccaacag  120
cacccaggca aagcccccaa actcatgatt tatgaggtca gtaagcggcc ctcaggggtc  180
cctgatcgct tctctggctc caagtctggc aacacggcct ccctgaccgt ctctgggctc  240
caggctgagg atgaggctga ttattactgc agctcatatg caggcagcaa caccttggtg  300
ttcggcggag ggaccaagct gaccgtccta ggt                                333

SEQ ID NO: 77           moltype = AA   length = 117
FEATURE                 Location/Qualifiers
REGION                  1..117
                        note = Description of Artificial Sequence: Synthetic
                        polypeptide
source                  1..117
                        mol_type = protein
                        organism = synthetic construct
SEQUENCE: 77
QVQLVQSGAE VKKPGASVKV SCRASGYTFT AYSLHWVRQA PGQGLEWMGW INPSSGGAVY   60
AQKFQGRVTM TRDTSISTAY MELSGLRSDD TAVYYCARNV GGQADDWGQG TLVTVSS      117

SEQ ID NO: 78           moltype = AA   length = 111
FEATURE                 Location/Qualifiers
REGION                  1..111
                        note = Description of Artificial Sequence: Synthetic
                        polypeptide
source                  1..111
                        mol_type = protein
                        organism = synthetic construct
SEQUENCE: 78
QSALTQPPSA SGSPGQSVTI SCTGTSSDIG GYNYVSWYQQ HPGKAPKLMI YEVNKRPSGV   60
PDRFSGSKSG NTASLTVSGL QAEDEADYYC ASFAGRKTLV FGGGTKLTVL G          111

SEQ ID NO: 79           moltype = DNA   length = 351
FEATURE                 Location/Qualifiers
misc_feature            1..351
                        note = Description of Artificial Sequence: Synthetic
                        polynucleotide
source                  1..351
                        mol_type = other DNA
                        organism = synthetic construct
SEQUENCE: 79
caggtgcagc tggtgcagtc tggggctgag gtgaagaagc ctggggcctc agtgaaggtc   60
tcctgcaggg cttctggata caccttcacc gcctactctt tacactgggt gcgacaggcc  120
cctggacaag ggcttgagtg gatgggatgg atcaaccccta gcagtggtgg cgcagtttat  180
gcacagaaat tccagggtag ggtcaccatg accagggaca cgtccatcag cacagcctac  240
atggagctga gtggcctgag atctgacgac acggccgtgt attactgtgc gcgcaacgtt  300
ggtggtcagg ctgatgactg gggtcaaggt actctggtga ccgtctcctc a          351

SEQ ID NO: 80           moltype = DNA   length = 333
FEATURE                 Location/Qualifiers
misc_feature            1..333
                        note = Description of Artificial Sequence: Synthetic
                        polynucleotide
```

```
source                  1..333
                        mol_type = other DNA
                        organism = synthetic construct
SEQUENCE: 80
caatctgccc tgactcagcc tccctccgcg tccgggtctc ctggacagtc agtcaccatc   60
tcctgcactg gaaccagcag tgacattggt ggttataact atgtctcctg gtaccaacag  120
cacccaggca aagcccccaa actcatgatt tatgaggtca ataagcggcc ctcaggggtc  180
cctgatcgct tctcgggctc caagtctggc aacacggcct ccctgaccgt ctctgggctc  240
caggctgagg atgaggctga ttattactgc gcctcatttg cgggcaggaa gacattggtc  300
ttcggcggag ggaccaagct gaccgtccta ggt                               333

SEQ ID NO: 81           moltype = AA  length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 81
QVQLVQSGAE VKKPGASVKV SCRASGYTFT AYSLHWVRQA PGQGLEWMGW INPSSGGAVY   60
AQKFQGRVTM TRDTSISTAY MELSGLRSDD TAVYYCARNV GGHADDWGQG TLVTVSS      117

SEQ ID NO: 82           moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 82
QSALTQPPSA SGSPGQSVTI SCTGTSTDIG GYNYVSWYQH HPSKAPKLMI YEVNKRPSGV   60
PDRFSGSKSG NTASLTVSGL QAEDEADYYC ASFAGRKTLV FGGGTKLTVL G            111

SEQ ID NO: 83           moltype = DNA  length = 351
FEATURE                 Location/Qualifiers
misc_feature            1..351
                        note = Description of Artificial Sequence: Synthetic
                         polynucleotide
source                  1..351
                        mol_type = other DNA
                        organism = synthetic construct
SEQUENCE: 83
caggtgcagc tggtgcagtc tggggctgag gtgaaaaagc ctggggcctc agtgaaagtc   60
tcctgcaggc cttctggata caccttcacc gcctactctt tacactgggt gcgacaggcc  120
cctggacaag ggcttgagtg gatgggatgg atcaacccta gcagtggtgg cgcagtttat  180
gcacagaaat ttcagggtag ggtcaccatg accagggaca cgtccatcag cacagcctac  240
atggagctga gtggcctgag atctgacgac acggccgtgt attactgtgc gcgcaacgtt  300
ggtggtcacg ctgatgactg gggtcaaggt actctggtga ccgtctcctc a           351

SEQ ID NO: 84           moltype = DNA  length = 333
FEATURE                 Location/Qualifiers
misc_feature            1..333
                        note = Description of Artificial Sequence: Synthetic
                         polynucleotide
source                  1..333
                        mol_type = other DNA
                        organism = synthetic construct
SEQUENCE: 84
caatctgccc tgactcagcc tccctccgcg tccgggtctc ctggacagtc agtcaccatc   60
tcctgcactg gaaccagcac tgacattggt ggttataact atgtctcctg gtaccaacac  120
cacccaagca aagcccccaa actcatgatt tatgaggtca ataagcggcc ctcaggggtc  180
cctgatcgct tctcgggctc caagtctggc aacacggcct ccctgaccgt ctctgggctc  240
caggctgagg atgaggctga ttattactgc gcctcatttg cgggcaggaa gacattggtc  300
ttcggcggag ggaccaagct gaccgtccta ggt                               333

SEQ ID NO: 85           moltype = AA  length = 129
FEATURE                 Location/Qualifiers
REGION                  1..129
                        note = Description of Artificial Sequence: Synthetic
                         polypeptide
source                  1..129
                        mol_type = protein
                        organism = synthetic construct
SEQUENCE: 85
QVQLVQSGGE VKKPGASVKV SCKASGFTFN TYGISWVRQA PGQGLEWMGW ISANNGHTKS   60
AQRFQDRVAM ATDTSTSTAY MELRSLKFDD TAVYYCARGG YHHQMQRYYK ATSVYSDYWG  120
QGTLVTVSS                                                           129
```

```
SEQ ID NO: 86              moltype = AA   length = 111
FEATURE                    Location/Qualifiers
REGION                     1..111
                           note = Description of Artificial Sequence: Synthetic
                            polypeptide
source                     1..111
                           mol_type = protein
                           organism = synthetic construct
SEQUENCE: 86
QSVVTQPPSV SAAPGQKVTI SCSGSSSNIG NNYVSWYQQL PGTAPKLLIY DNNKRPSGIP   60
DRFSGSKSGT SATLGITGLQ TGDEADYYCG TWDSSLSGVV FGGGTKLTVL G            111

SEQ ID NO: 87              moltype = DNA   length = 387
FEATURE                    Location/Qualifiers
misc_feature               1..387
                           note = Description of Artificial Sequence: Synthetic
                            polynucleotide
source                     1..387
                           mol_type = other DNA
                           organism = synthetic construct
SEQUENCE: 87
caggtccagc tggtgcagtc tggaggtgag gtgaagaagc ctggggcctc agtgaaggtc   60
tcctgcaagg cttctggttt cacctttaac acctatggca tcagttgggt gcgacaggcc   120
cctgacaag ggcttgagtg gatgggatgg atcagcgcta acaatggtca cacaaagtct    180
gcacagaggt tccaggacag agtcgccatg gccacagaca tccacgag cacggcctac      240
atggagctga ggagcctgaa atttgacgac acggccgtgt attactgtgc gcgcggtggt   300
taccatcatc agatgcagcg gtactacaaa gctacttctg tttactctga ttactggggt   360
caaggtactc tggtgaccgt ctcctca                                        387

SEQ ID NO: 88              moltype = DNA   length = 333
FEATURE                    Location/Qualifiers
misc_feature               1..333
                           note = Description of Artificial Sequence: Synthetic
                            polynucleotide
source                     1..333
                           mol_type = other DNA
                           organism = synthetic construct
SEQUENCE: 88
cagtctgtcg tgacgcagcc gccctcagtg tctgcggccc caggacagaa ggtcaccatc   60
tcctgctctg gaagcagctc caacattggg aataattatg tatcctggta ccagcaactc   120
ccaggaacag ccccccaaact cctcatttat gacaataata agcgaccctc agggattcct   180
gaccgattct ctggctccaa gtctggcacg tctgccaccc tgggcatcac cggactccag   240
actggggacg aggccgatta ttactgcgga acatgggata gcagcctgag tggtgtggta   300
ttcggcggag ggaccaagct gaccgtccta ggt                                333

SEQ ID NO: 89              moltype = AA   length = 116
FEATURE                    Location/Qualifiers
REGION                     1..116
                           note = Description of Artificial Sequence: Synthetic
                            polypeptide
source                     1..116
                           mol_type = protein
                           organism = synthetic construct
SEQUENCE: 89
QMQLVQSGAE VKKPGASVKV SCKASGYTFT SYYMHWVRQA PGQGLEWMGI INPSGGSSSY   60
AQKFQGRVTM TRDTSTSTVY MELSSLRSED TAVYYCARAG MGMDTWGQGT LVTVSS        116

SEQ ID NO: 90              moltype = AA   length = 111
FEATURE                    Location/Qualifiers
REGION                     1..111
                           note = Description of Artificial Sequence: Synthetic
                            polypeptide
source                     1..111
                           mol_type = protein
                           organism = synthetic construct
SEQUENCE: 90
QSALTQPPSA SGSPGQSVTI SCTGTSSDVG GYNYVSWYQQ HPGKAPKLMI YEVSKRPSGV   60
PDRFSGSKSG NTASLTVSGL QAEDEADYYC SSYAGSNTLV FGGGTKLTVL G            111

SEQ ID NO: 91              moltype = DNA   length = 348
FEATURE                    Location/Qualifiers
misc_feature               1..348
                           note = Description of Artificial Sequence: Synthetic
                            polynucleotide
source                     1..348
                           mol_type = other DNA
                           organism = synthetic construct
SEQUENCE: 91
```

-continued

```
cagatgcagc tggtgcagtc tggggctgag gtgaagaagc ctggggcctc agtgaaggtt   60
tcctgcaagg catctggata caccttcacc agctactata tgcactgggt gcgacaggcc  120
cctggacaag ggcttgagtg gatgggaata atcaaccata gtggtggtag ctcaagctac  180
gcacagaagt tccagggcag agtcaccatg accagggaca cgtccacgag cacagtctac  240
atggagctga gcagcctgag atctgaggac acggccgtgt attactgtgc gcgcgctggt  300
atgggtatgg atacttgggg tcaaggtact ctggtgaccg tctcctca              348
```

```
SEQ ID NO: 92           moltype = DNA   length = 333
FEATURE                 Location/Qualifiers
misc_feature            1..333
                        note = Description of Artificial Sequence: Synthetic
                         polynucleotide
source                  1..333
                        mol_type = other DNA
                        organism = synthetic construct
SEQUENCE: 92
cagtctgccc tgactcagcc tccctccgcg tccgggtctc ctggacagtc agtcaccatc   60
tcctgcactg gaaccagcag tgacgttggt ggttataact atgtctcctg gtaccaacag  120
cacccaggca aagcccccaa actcatgatt tatgaggtca gtaagcggcc ctcaggggtc  180
cctgatcgct tctctggctc caagtctggc aacacggcct ccctgaccgt ctctgggctc  240
caggctgagg atgaggctga ttattactgc agctcatatg caggcagcaa caccttggtg  300
ttcggcggag ggaccaagct gaccgtccta ggt                              333
```

```
SEQ ID NO: 93           moltype = AA   length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 93
QVQLVQSGAE VKKPGASVKV SCKASGYTFT SYYMHWVRQA PGQGLEWMGI INPSGGSTSY   60
AQKFQGRVTM TRDTSTSTVY MELSSLRSED TAVYYCARDV ISGFDSWGQG TLVTVSS     117
```

```
SEQ ID NO: 94           moltype = AA   length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 94
QSALTQPASV SGSPGQSITI SCTGTSSDVG GYNYVSWYQQ SPGKAPRLMI YGVSKRPSGV   60
PDRFSGSKSG NTASLTVSGL QAEDEADYYC SSYAGVNNLM FGGGTKLTVL G           111
```

```
SEQ ID NO: 95           moltype = DNA   length = 351
FEATURE                 Location/Qualifiers
misc_feature            1..351
                        note = Description of Artificial Sequence: Synthetic
                         polynucleotide
source                  1..351
                        mol_type = other DNA
                        organism = synthetic construct
SEQUENCE: 95
caggtgcagc tggtgcaatc tggggctgag gtgaagaagc ctggggcctc agtgaaggtt   60
tcctgcaagg catctggata caccttcacc agctactata tgcactgggt gcgacaggcc  120
cctggacaag ggcttgagtg gatgggaata atcaacccta gtggtggtag cacaagctac  180
gcacagaagt tccagggcag agtcaccatg accagggaca cgtccacgag cacagtctac  240
atggagctga gcagcctgag atctgaggac actgccgtgt attactgtgc gcgcgacgtt  300
atctctggtt tcgattcttg gggtcaaggt actctggtga ccgtctcctc a          351
```

```
SEQ ID NO: 96           moltype = DNA   length = 333
FEATURE                 Location/Qualifiers
misc_feature            1..333
                        note = Description of Artificial Sequence: Synthetic
                         polynucleotide
source                  1..333
                        mol_type = other DNA
                        organism = synthetic construct
SEQUENCE: 96
cagtctgccc tgactcagcc tgcctccgtg tctgggtctc ctggacagtc gatcaccatc   60
tcctgcactg gaaccagcag tgacgttggt ggttataact atgtctcctg gtaccaacaa  120
tccccaggca aagcccccag actcatgatt tatgggqtca gtaagcggcc ctctgggqtc  180
cctgatcgct tctctggctc caagtctggc aacacggcct ccctgaccgt ctctgggctc  240
caggctgaag atgaggctga ttattactgc agctcatatg caggcgtcaa caatttaatg  300
ttcggcggag ggaccaagct gaccgtccta ggt                              333
```

```
SEQ ID NO: 97            moltype = AA   length = 345
FEATURE                  Location/Qualifiers
source                   1..345
                         mol_type = protein
                         organism = Homo sapiens
SEQUENCE: 97
MYKDCIESTG DYFLLCDAEG PWGIILESLA ILGIVVTILL LLAFLFLMRK IQDCSQWNVL   60
PTQLLFLLSV LGLFGLAFAF IIELNQQTAP VRYFLFGVLF ALCFSCLLAH ASNLVKLVRG   120
CVSFSWTTIL CIAIGCSLLQ IIIATEYVTL IMTRGMMFVN MTPCQLNVDF VVLLVYVLFL   180
MALTFFVSKA TFCGPCENWK QHGRLIFITV LFSIIIWVVW ISMLLRGNPQ FQRQPQWDDP   240
VVCIALVTNA WVFLLLYIVP ELCILYRSCR QECPLQGNAC PVTAYQHSFQ VENQELSRAR   300
DSDGAEEDVA LTSYGTPIQP QTVDPTQECF IPQAKLSPQQ DAGGV                   345

SEQ ID NO: 98            moltype = AA   length = 21
FEATURE                  Location/Qualifiers
REGION                   1..21
                         note = Description of Artificial Sequence: Synthetic peptide
source                   1..21
                         mol_type = protein
                         organism = synthetic construct
SEQUENCE: 98
SRGGGGSGGG GSGGGGSLEM A                                             21

SEQ ID NO: 99            moltype = DNA   length = 63
FEATURE                  Location/Qualifiers
misc_feature             1..63
                         note = Description of Artificial Sequence: Synthetic
                         oligonucleotide
source                   1..63
                         mol_type = other DNA
                         organism = synthetic construct
SEQUENCE: 99
tctagaggtg gtggtggtag cggcggcggc ggctctggtg gtggtggatc cctcgagatg   60
gcc                                                                63

SEQ ID NO: 100           moltype = AA   length = 252
FEATURE                  Location/Qualifiers
REGION                   1..252
                         note = Description of Artificial Sequence: Synthetic
                         polypeptide
source                   1..252
                         mol_type = protein
                         organism = synthetic construct
SEQUENCE: 100
QSVLTQPPSV SAAPGQKVTI PCSGSRSNVG NYYVSWYQQL PGTAPKLLIY DNNKRPSGIP   60
DRFSGSKSGT SATLGITGLQ TGDEADYFCG TWDGSLSAHV FGTGTKVTVL GSRGGGGSGG   120
GGSGGGGSLE MAQVQLVQSG SELKKPGASV RVSCTASGYT FTSYYMHWVR QAPGQGLEWM   180
GVINPNAGST RYAQKFQGRV TMSTDTSTST AYMDLSSLRS EDTAVYYCAR GMYRSLLFYD   240
PWGQGTLVTV SS                                                       252

SEQ ID NO: 101           moltype = AA   length = 250
FEATURE                  Location/Qualifiers
REGION                   1..250
                         note = Description of Artificial Sequence: Synthetic
                         polypeptide
source                   1..250
                         mol_type = protein
                         organism = synthetic construct
SEQUENCE: 101
NFMLTQPHSV SESPGKTVSI SCTRTSGAIA GAYVQWFQQR PGSAPTTVIY DDNKRPSGVP   60
DRFSGSIDKS SNSASLTISG LKTEDEADYY CQSYDYDSSN VLFGGGTKLT VLGSRGGGGS   120
GGGGSGGGGS LEMAEVQLVE SGGGLVQPGG SLRLSCAASG FTFSNYAMSW VRQAPGKGLE   180
WVSAISGSGN TYYADSVKGR FTISRDNSKN TLYLQMNSLR AEDTAVYYCA RGSVRYTDIW   240
GQGTLVTVSS                                                          250

SEQ ID NO: 102           moltype = AA   length = 248
FEATURE                  Location/Qualifiers
REGION                   1..248
                         note = Description of Artificial Sequence: Synthetic
                         polypeptide
source                   1..248
                         mol_type = protein
                         organism = synthetic construct
SEQUENCE: 102
DIQLTQSPSS LSASVGDRVT ITCRASQSIS SYLNWYQQKP GKAPKLLIYA ASSLQSGVPS   60
RFSGSGSGTD FTLTISSLQP ADFATYYCQQ SYSVPYTFGQ GTKLEIKRSR GGGGSGGGGS   120
GGGGSLEMAE VQLVQSGGGL VQPGGSLRLS CATSGFTFNN YWMSWVRQAP GKGLEWVANI   180
KQDGSEKYYA DSVRGRFTIS RDNAKNSLSL QLNNLRAEDT AVYYCARSMS TAWGYDEWGQ   240
GTLVTVSS                                                            248
```

```
SEQ ID NO: 103            moltype = AA  length = 253
FEATURE                   Location/Qualifiers
REGION                    1..253
                          note = Description of Artificial Sequence: Synthetic
                           polypeptide
source                    1..253
                          mol_type = protein
                          organism = synthetic construct
SEQUENCE: 103
QSALTQPASV SGSPGQSITI SCTGTSSDVG GYNFVSWYQQ HPGKAPKVMI YDVSKRPSGI   60
SNRFSGSKSG NTASLTISGL QVEDEAEYYC SSYTSTRTVI FAGGTKVTVL GSRGGGGSGG  120
GGSGGGGSLE MAQVQLVQSG AEVKKPGASV KVSCKASGYT FTSYYMHWVR QAPGQGLEWM  180
GIINPSGGST RYAQKFQGRV TMTRDTSTST VYMELSSLRS EDTAVYYCAR GSSRWGGWTG  240
DYWGQGTLVT VSS                                                     253

SEQ ID NO: 104            moltype = AA  length = 249
FEATURE                   Location/Qualifiers
REGION                    1..249
                          note = Description of Artificial Sequence: Synthetic
                           polypeptide
MOD_RES                   37
                          note = Any amino acid
source                    1..249
                          mol_type = protein
                          organism = synthetic construct
SEQUENCE: 104
QSVLTQPPSL SGAPGQRVTI SCSGSRSNIG TNYVSWXQQL PGTAPKLLIY RNHQWPSGVP   60
DRFTGSKSGT SASLAISGLR SEDEADYYCA AWDDNLSGVV FGGGTKLTVL GSRGGGGSGG  120
GGSGGGGSLE MAEVQLVETG GGLVQPGGSL RLSCAASGST FSSYAMSWVR QAPGKGLEWV  180
SAISGRGRST YYADSVKGRF TISRDNSKNT LYLQMNSLRA EDTAVYYCAR YYKSSKDHWG  240
QGTLVTVSS                                                          249

SEQ ID NO: 105            moltype = AA  length = 253
FEATURE                   Location/Qualifiers
REGION                    1..253
                          note = Description of Artificial Sequence: Synthetic
                           polypeptide
source                    1..253
                          mol_type = protein
                          organism = synthetic construct
SEQUENCE: 105
QAVLTQPPSA SGTPGQRVTI SCSGSSSNIG SNYVYWYQQL PGTAPKLLIY RNNQRPSGVP   60
DRFSGSKSGT SASLAISGLR SEDEADYYCA AWDDSLSGYV FGTGTKVTVL GSRGGGGSGG  120
GGSGGGGSLE MAQVQLVQSG AEVQRPGASV RVSCKAIAYT FTDYYIHWVR QAPGQGPEWM  180
GWINPKSGRT QYAPKFQDRV TLARETPIST ASMELRGLTS DDTAVYYCAR VYGYSRWSGF  240
DLWGQGTLVT VSS                                                     253

SEQ ID NO: 106            moltype = AA  length = 256
FEATURE                   Location/Qualifiers
REGION                    1..256
                          note = Description of Artificial Sequence: Synthetic
                           polypeptide
source                    1..256
                          mol_type = protein
                          organism = synthetic construct
SEQUENCE: 106
QSALTQPASV SGSPGQSITI SCTGTSRDVG GYNYVSWYQQ YPGKAPKLMI YEVSKRPSGV   60
SNRFSGSKSG NTASLTISGL QAEDEADYYC SSYTSSSTLD FGTGTKVTVL GSRGGGGSGG  120
GGSGGGGSLE MAQVQLVQSG AEVKQPGASV KVSCQASGYT FTTYYMHWVR QAPGQGLEWM  180
GIINPNGGGT FYAQKFQDRV TMTRDTSTGT VYMELSSLRS DDTAVYYCAR GHKVYKSHPT  240
GGYDRWGQGT LVTVSS                                                  256

SEQ ID NO: 107            moltype = AA  length = 251
FEATURE                   Location/Qualifiers
REGION                    1..251
                          note = Description of Artificial Sequence: Synthetic
                           polypeptide
source                    1..251
                          mol_type = protein
                          organism = synthetic construct
SEQUENCE: 107
SYELTQPPSA SGTPGQRVTI SCSGSSSNIG SNYVSWYQQL PGTAPKLLIY RNNQRPSGVP   60
DRFSGSKSGT SASLAISGLR SEDEADYYCA AWDDSLSGVV FGGGTKLTVL GSRGGGGSGG  120
GGSGGGGSLE MAEVQLVQSG AEVKKPGSSV KVSCKASGGT FSSYAISWVR QAPGQGLEWM  180
GGIIPIFGTA KYAQKFQGRV TITADESTST AYMELSSLRS EDTAVYYCAR SHVAWSLLDY  240
WGQGTLVTVS S                                                       251

SEQ ID NO: 108            moltype = AA  length = 252
```

```
FEATURE           Location/Qualifiers
REGION            1..252
                  note = Description of Artificial Sequence: Synthetic
                   polypeptide
source            1..252
                  mol_type = protein
                  organism = synthetic construct
SEQUENCE: 108
QSVLTQPPSA SGTPGQRVTI SCSGSSSNIG SNYVYWYQQL PGTAPKLLIY RNNQRPSGVP  60
DRFSGSKSGT SASLAISGLR SEDEADYYCA AWDDSLSGWV FGGGTKLTVL GSRGGGGSGG  120
GGSGGGGSLE MAQVQLVQSG AEVKKPGSSV KVSCKASGGT FSSYAISWVR QAPGQGLEWM  180
GWMNPNSGNT GYAQKFQGRV TMTRNTSIST AYMELSSLRS EDTAVYYCAR YQSYKGSQSD  240
SWGQGTLVTV SS                                                      252

SEQ ID NO: 109        moltype = AA  length = 259
FEATURE           Location/Qualifiers
REGION            1..259
                  note = Description of Artificial Sequence: Synthetic
                   polypeptide
source            1..259
                  mol_type = protein
                  organism = synthetic construct
SEQUENCE: 109
QSALTQPASV SGSPGQSITI SCTGTSSDVG GYNYVSWYQQ HPGKAPKLMI YDVSKRPSGV  60
SNRFSGSKSG NTASLTISGL QAEDEADYYC SSYTRSSTEV FGGGTKLTVL GSRGGGGSGG  120
GGSGGGGSLE MAEVQLVQSG AEVKKPGASV KVSCKASGYT FTSYYMHWVR QAPGQGLEWM  180
GIINPSGGST SYAQKFQGRV TMTRDTSTST VYMELSSLRS EDTAVYYCAR GGSKKWSGEK  240
WRRENFDYWG QGTLVTVSS                                                259

SEQ ID NO: 110        moltype = AA  length = 244
FEATURE           Location/Qualifiers
REGION            1..244
                  note = Description of Artificial Sequence: Synthetic
                   polypeptide
source            1..244
                  mol_type = protein
                  organism = synthetic construct
SEQUENCE: 110
SYVLTQPPSA SGTPGQRVTI SCSGSSSNIG SNTVNWYQQL PGTAPKLLIY RNNQRPSGVP  60
DRFSGSKSGT SASLAISGLR SEDEADYYCA AWDDSLSGLF GTGTKVTVLG SRGGGGSGGG  120
GSGGGGSLEM AQMQLVQSGA EVKKPGASVK VSCKASEYTF TRHILHWVRQ APGQSLEWMG  180
WINPGNGNTK YSQKFQVRVT FTRDTSASTV YMELSSLRSE DTAVYYCARL PDQWGQGTLV  240
TVSS                                                              244

SEQ ID NO: 111        moltype = AA  length = 247
FEATURE           Location/Qualifiers
REGION            1..247
                  note = Description of Artificial Sequence: Synthetic
                   polypeptide
source            1..247
                  mol_type = protein
                  organism = synthetic construct
SEQUENCE: 111
QSALTQPPSA SGSPGQSVTI SCTGTSRDAG GYNYFSWYQQ HPGKAPKLLI YEVTKRPSGV  60
PDRFSGSKSG KTASLTVSGL QADDEAVYYC SSYGGSNNFR VFGGGTKLTV LGSRGGGGSG  120
GGGSGGGGSL EMAEVQLVES GGGVVRPGGS LRLSCAASGF TFGDYGMSWV RQAPGKGLEW  180
VSGINWNGGS TGYADSVKGR FTISRDNAKN SLYLQMNSLR AEDTAVYYCA RSKQDYWGQG  240
TLVTVSS                                                            247

SEQ ID NO: 112        moltype = AA  length = 248
FEATURE           Location/Qualifiers
REGION            1..248
                  note = Description of Artificial Sequence: Synthetic
                   polypeptide
source            1..248
                  mol_type = protein
                  organism = synthetic construct
SEQUENCE: 112
QSVVTQPPSV SGAPGQRVTI SCTGSSSNIG AGYDVHWYQQ LPGTAPKLLI YGNSNRPSGV  60
PDRFSGSKSG TSASLAITGL QAEDEADYYC QSYDSSLSGS YVFGTGTKLT VLGSRGGGGS  120
GGGGSGGGGS LEMAEVQLVE TGGNLVQPGA SLRLSCAASG FSFSGTAMHW VRQAPGKGLE  180
WVSTISSTGR STYYRDSVKG RFTISRDNSK NTLYLQMNSL RGEDTAVYYC ARVSFDYWGQ  240
GTLVTVSS                                                          248

SEQ ID NO: 113        moltype = AA  length = 250
FEATURE           Location/Qualifiers
REGION            1..250
                  note = Description of Artificial Sequence: Synthetic
                   polypeptide
```

-continued

```
source                    1..250
                          mol_type = protein
                          organism = synthetic construct
SEQUENCE: 113
QSVVTQPASV SGSPGQSITI SCTGTSSDVG GYNYVSWYQQ HPGKAPKLMI YDVSKRPSGV   60
SNRFSGSKSG NTASLTISGL QAEDEADYYC SSYTSSSTLV FGGGTKLTVL GSRGGGGSGG  120
GGSGGGGSLE MAEVQLVESG GAFVQPGGSL RLSCAASGFT FSSYAMTWVR QAPGKGLEWV  180
STISGRGRST FYADSVKGRF TISRDNSKNT LYLQMNSLRA EDTAVYYCAR YYHAGAFDLW  240
GQGTLVTVSS                                                         250

SEQ ID NO: 114            moltype = AA   length = 246
FEATURE                   Location/Qualifiers
REGION                    1..246
                          note = Description of Artificial Sequence: Synthetic
                           polypeptide
source                    1..246
                          mol_type = protein
                          organism = synthetic construct
SEQUENCE: 114
QSVLTQPASV SGSPGQSLTI SCTGTSNDVG AYKYVSWYQQ YPGKAPKLIL YDVFKRPSGV   60
SNRFSGSKSD NTASLTISGL QAEDEADYYC FSLTSSNTYV FGTGTKVTVL GSRGGGGSGG  120
GGSGGGGSLE MAQMQLVQSG AEVKKPGASV KVSCKASGYT FNRYAITWVR QAPGQGLEWM  180
GWISAYNGNS HYAQKLQGRV TMTTDTSTGT AYMELRRLRS DDTAVYYCAR MAYDSWGQGT  240
LVTVSS                                                             246

SEQ ID NO: 115            moltype = AA   length = 249
FEATURE                   Location/Qualifiers
REGION                    1..249
                          note = Description of Artificial Sequence: Synthetic
                           polypeptide
source                    1..249
                          mol_type = protein
                          organism = synthetic construct
SEQUENCE: 115
QSVLTQPPSA SGTPGQRVTI SCSGSRSNVG GNYVFWYQQV PGATPKLLIY RSNQRPSGVP   60
DRFAGSKSGS SASLAISGLR SEDEADYYCA TWDDSLSGFV FGTGTKVTVL GSRGGGGSGG  120
GGSGGGGSLE MAEVQLVESG GGLVKPGGSL RLSCAASGFT FSDYYMSWIR QAPGKGLEWV  180
SYISSSGSTI YYADSVKGRF TISRDNAKNS LYLQMNSLRA EDTAVYYCAR GYGKAYDQWG  240
QGTLVTVSS                                                          249

SEQ ID NO: 116            moltype = AA   length = 250
FEATURE                   Location/Qualifiers
REGION                    1..250
                          note = Description of Artificial Sequence: Synthetic
                           polypeptide
source                    1..250
                          mol_type = protein
                          organism = synthetic construct
SEQUENCE: 116
SSELTQDPAV SVALGQTVRI TCQGDSLRSY YASWYQQKPG QAPVLVIYGK NNRPSGIPDR   60
FSGSSSGNTA SLTITGAQAE DEADYYCNSR DSSGNPPVVF GGGTKLTVLG SRGGGGSGGG  120
GSGGGGSLEM AQVQLVESGG GLVHPGGSLR LSCAASGFTF RSHSMNWVRQ APGKGLEWVS  180
SISSDSTYTY YADSVKGRFT ISRDNAKNSL YLQMNSLRAE DTAVYYCARS GGQWKYYDYW  240
GQGTLVTVSS                                                         250

SEQ ID NO: 117            moltype = AA   length = 248
FEATURE                   Location/Qualifiers
REGION                    1..248
                          note = Description of Artificial Sequence: Synthetic
                           polypeptide
source                    1..248
                          mol_type = protein
                          organism = synthetic construct
SEQUENCE: 117
QSVVTQPPSM SAAPGQQVTI SCSGGNSNIE RNYVSWYLQL PGTAPKLVIF DNDRRPSGIP   60
DRFSGSKSGT SATLGITGLQ TGDEADYYCG TWDSSLRGWV FGGGTKLTVL GSRGGGGSGG  120
GGSGGGGSLE MAEVQLVESG GGLIQPGGSL RLSCAASGFT FSNYAMNWVR QAPGKGLEWV  180
STINGRGSST IYADSVKGRF TISRDNSKNT LYLQMNSLRA EDTATYYCAR YISRGLGDSW  240
GQGTLVTV                                                           248

SEQ ID NO: 118            moltype = AA   length = 248
FEATURE                   Location/Qualifiers
REGION                    1..248
                          note = Description of Artificial Sequence: Synthetic
                           polypeptide
source                    1..248
                          mol_type = protein
                          organism = synthetic construct
SEQUENCE: 118
```

```
QSALTQPPSA SGSPGQSVTI SCTGTSSDVG GYNYVSWYQQ HPGKAPKLMI YEVSKRPSGV   60
PDRFSGSKSG NTASLTVSGL QAEDEADYYC SSYAGSNTLV FGGGTKLTVL GSRGGGGSGG  120
GGSGGGGSLE MAQMQLVQSG AEVKKPGASV KVSCKASGYT FTSYYMHWVR QAPGQGLEWM  180
GIINPSGGST SYAQKFQGRV TMTRDTSTST VYMELSSLRS EDTAVYYCAR AGMGMDTWGQ  240
GTLVTVSS                                                           248

SEQ ID NO: 119           moltype = AA  length = 249
FEATURE                  Location/Qualifiers
REGION                   1..249
                         note = Description of Artificial Sequence: Synthetic
                          polypeptide
source                   1..249
                         mol_type = protein
                         organism = synthetic construct
SEQUENCE: 119
QSALTQPPSA SGSPGQSVTI SCTGTSSDIG GYNYVSWYQQ HPGKAPKLMI YEVNKRPSGV   60
PDRFSGSKSG NTASLTVSGL QAEDEADYYC ASFAGRKTLV FGGGTKLTVL GSRGGGGSGG  120
GGSGGGGSLE MAQVQLVQSG AEVKKPGASV KVSCRASGYT FTAYSLHWVR QAPGQGLEWM  180
GWINPSSGGA VYAQKFQGRV TMTRDTSIST AYMELSGLRS DDTAVYYCAR NVGGQADDWG  240
QGTLVTVSS                                                          249

SEQ ID NO: 120           moltype = AA  length = 249
FEATURE                  Location/Qualifiers
REGION                   1..249
                         note = Description of Artificial Sequence: Synthetic
                          polypeptide
source                   1..249
                         mol_type = protein
                         organism = synthetic construct
SEQUENCE: 120
QSALTQPPSA SGSPGQSVTI SCTGTSTDIG GYNYVSWYQH HPSKAPKLMI YEVNKRPSGV   60
PDRFSGSKSG NTASLTVSGL QAEDEADYYC ASFAGRKTLV FGGGTKLTVL GSRGGGGSGG  120
GGSGGGGSLE MAQVQLVQSG AEVKKPGASV KVSCRASGYT FTAYSLHWVR QAPGQGLEWM  180
GWINPSSGGA VYAQKFQGRV TMTRDTSIST AYMELSGLRS DDTAVYYCAR NVGGHADDWG  240
QGTLVTVSS                                                          249

SEQ ID NO: 121           moltype = AA  length = 261
FEATURE                  Location/Qualifiers
REGION                   1..261
                         note = Description of Artificial Sequence: Synthetic
                          polypeptide
source                   1..261
                         mol_type = protein
                         organism = synthetic construct
SEQUENCE: 121
QSVVTQPPSV SAAPGQKVTI SCSGSSSNIG NNYVSWYQQL PGTAPKLLIY DNNKRPSGIP   60
DRFSGSKSGT SATLGITGLQ TGDEADYYCG TWDSSLSGVV FGGGTKLTVL GSRGGGGSGG  120
GGSGGGGSLE MAQVQLVQSG GEVKKPGASV KVSCKASGFT FNTYGISWVR QAPGQGLEWM  180
GWISANNGHT KSAQRFQDRV AMATDTSTST AYMELRSLKF DDTAVYYCAR GGYHHQMQRY  240
YKATSVYSDY WGQGTLVTVS S                                            261

SEQ ID NO: 122           moltype = AA  length = 248
FEATURE                  Location/Qualifiers
REGION                   1..248
                         note = Description of Artificial Sequence: Synthetic
                          polypeptide
source                   1..248
                         mol_type = protein
                         organism = synthetic construct
SEQUENCE: 122
QSALTQPPSA SGSPGQSVTI SCTGTSSDVG GYNYVSWYQQ HPGKAPKLMI YEVSKRPSGV   60
PDRFSGSKSG NTASLTVSGL QAEDEADYYC SSYAGSNTLV FGGGTKLTVL GSRGGGGSGG  120
GGSGGGGSLE MAQMQLVQSG AEVKKPGASV KVSCKASGYT FTSYYMHWVR QAPGQGLEWM  180
GIINPSGGSS SYAQKFQGRV TMTRDTSTST VYMELSSLRS EDTAVYYCAR AGMGMDTWGQ  240
GTLVTVSS                                                           248

SEQ ID NO: 123           moltype = AA  length = 249
FEATURE                  Location/Qualifiers
REGION                   1..249
                         note = Description of Artificial Sequence: Synthetic
                          polypeptide
source                   1..249
                         mol_type = protein
                         organism = synthetic construct
SEQUENCE: 123
QSALTQPASV SGSPGQSITI SCTGTSSDVG GYNYVSWYQQ SPGKAPRLMI YGVSKRPSGV   60
PDRFSGSKSG NTASLTVSGL QAEDEADYYC SSYAGVNNLM FGGGTKLTVL GSRGGGGSGG  120
GGSGGGGSLE MAQVQLVQSG AEVKKPGASV KVSCKASGYT FTSYYMHWVR QAPGQGLEWM  180
GIINPSGGST SYAQKFQGRV TMTRDTSTST VYMELSSLRS EDTAVYYCAR DVISGFDSWG  240
```

-continued

```
QGTLVTVSS                                                            249

SEQ ID NO: 124        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 124
GYTFTSYY                                                             8

SEQ ID NO: 125        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 125
GYTFTSYY                                                             8

SEQ ID NO: 126        moltype = AA  length = 13
FEATURE               Location/Qualifiers
REGION                1..13
                      note = Description of Artificial Sequence: Synthetic peptide
source                1..13
                      mol_type = protein
                      organism = synthetic construct
SEQUENCE: 126
ARGMYRSLLF YDP                                                       13

SEQ ID NO: 127        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 127
RSNVGNYY                                                             8

SEQ ID NO: 128        moltype =   length =
SEQUENCE: 128
000

SEQ ID NO: 129        moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 129
GTWDGSLSAH V                                                         11

SEQ ID NO: 130        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 130
GFTFSNYA                                                             8

SEQ ID NO: 131        moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 131
ISGSGNT                                                             7

SEQ ID NO: 132        moltype = AA  length = 10
FEATURE               Location/Qualifiers
REGION                1..10
```

-continued

```
                        note = Description of Artificial Sequence: Synthetic peptide
source                  1..10
                        mol_type = protein
                        organism = synthetic construct
SEQUENCE: 132
ARGSVRYTDI                                                                10

SEQ ID NO: 133          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 133
SGAIAGAY                                                                  8

SEQ ID NO: 134          moltype =   length =
SEQUENCE: 134
000

SEQ ID NO: 135          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct SEQUENCE: 135
QSYDYDSSNV L                                                              11

SEQ ID NO: 136          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 136
GFTFNNYW                                                                  8

SEQ ID NO: 137          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 137
IKQDGSEK                                                                  8

SEQ ID NO: 138          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 138
ARSMSTAV                                                                  8

SEQ ID NO: 139          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 139
QSISSY                                                                    6

SEQ ID NO: 140          moltype =   length =
SEQUENCE: 140
000

SEQ ID NO: 141          moltype = AA  length = 9
FEATURE                 Location/Qualifiers
REGION                  1..9
                        note = Description of Artificial Sequence: Synthetic peptide
```

-continued

```
source                 1..9
                       mol_type = protein
                       organism = synthetic construct
SEQUENCE: 141
QQSYSVPYT                                                          9

SEQ ID NO: 142        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 142
GYTFTSYY                                                           8

SEQ ID NO: 143        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 143
INPSGGST                                                           8

SEQ ID NO: 144        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 144
ARGSSRWGGW TGDY                                                    14

SEQ ID NO: 145        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 145
SSDVGGYNF                                                          9

SEQ ID NO: 146        moltype =   length =
SEQUENCE: 146
000

SEQ ID NO: 147        moltype = AA  length = 20
FEATURE               Location/Qualifiers
REGION                1..20
                      note = Description of Artificial Sequence: Synthetic peptide
source                1..20
                      mol_type = protein
                      organism = synthetic construct
SEQUENCE: 147
SSYTSTRTVI FAGGTKVTVL                                              20

SEQ ID NO: 148        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 148
GSTFSSYA                                                           8

SEQ ID NO: 149        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 149
ISGRGRST                                                           8
```

```
SEQ ID NO: 150          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 150
ARYYKSKDH                                                             9

SEQ ID NO: 151          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 151
RSNIGTNY                                                              8

SEQ ID NO: 152          moltype =   length =
SEQUENCE: 152
000

SEQ ID NO: 153          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 153
AAWDDNLSGV V                                                          11

SEQ ID NO: 154          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 154
AYTFTDYY                                                              8

SEQ ID NO: 155          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 155
INPKSGRT                                                              8

SEQ ID NO: 156          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 156
ARVYGYSRWS GFDL                                                       14

SEQ ID NO: 157          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 157
SSNIGSNY                                                              8

SEQ ID NO: 158          moltype =   length =
SEQUENCE: 158
000
```

-continued

```
SEQ ID NO: 159          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct SEQUENCE: 159
AAWDDSLSGY V                                                        11

SEQ ID NO: 160          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct SEQUENCE: 160
GYTFTTYY                                                            8

SEQ ID NO: 161          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct SEQUENCE: 161
INPNGGGT                                                            8

SEQ ID NO: 162          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct SEQUENCE: 162
ARGHKVYKSH PTGGYDR                                                  17

SEQ ID NO: 163          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct SEQUENCE: 163
SRDVGGYNY                                                           9

SEQ ID NO: 164          moltype =    length =
SEQUENCE: 164
000

SEQ ID NO: 165          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct SEQUENCE: 165
SSYTSSSTLD                                                          10

SEQ ID NO: 166          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct SEQUENCE: 166
GGTFSSYA                                                            8

SEQ ID NO: 167          moltype = AA   length = 8
FEATURE                 Location/Qualifiers
REGION                  1..8
                        note = Description of Artificial Sequence: Synthetic peptide
source                  1..8
```

```
                          mol_type = protein
                          organism = synthetic construct
SEQUENCE: 167
IIPIFGTA                                                              8

SEQ ID NO: 168           moltype = AA  length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 168
ARSHVAWSLL DY                                                         12

SEQ ID NO: 169           moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 169
SSNIGSNY                                                              8

SEQ ID NO: 170           moltype =   length =
SEQUENCE: 170
000

SEQ ID NO: 171           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 171
AAWDDSLSGV V                                                          11

SEQ ID NO: 172           moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 172
GGTFSSYA                                                              8

SEQ ID NO: 173           moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 173
MNPNSGNT                                                              8

SEQ ID NO: 174           moltype = AA  length = 13
FEATURE                  Location/Qualifiers
REGION                   1..13
                         note = Description of Artificial Sequence: Synthetic peptide
source                   1..13
                         mol_type = protein
                         organism = synthetic construct
SEQUENCE: 174
ARYQSYKGSQ SDS                                                        13

SEQ ID NO: 175           moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 175
SSNIGSNY                                                              8
```

-continued

```
SEQ ID NO: 176          moltype =    length =
SEQUENCE: 176
000

SEQ ID NO: 177          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 177
AAWDDSLSGW V                                                     11

SEQ ID NO: 178          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 178
GYTFTSYY                                                         8

SEQ ID NO: 179          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 179
INPSGGST                                                         8

SEQ ID NO: 180          moltype = AA   length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 180
ARGGSKKWSG EKWRRENFDY                                            20

SEQ ID NO: 181          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 181
SSDVGGYNY                                                        9

SEQ ID NO: 182          moltype =    length =
SEQUENCE: 182
000

SEQ ID NO: 183          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 183
SSYTRSSTEV                                                       10

SEQ ID NO: 184          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 184
EYTFTRHI                                                         8

SEQ ID NO: 185          moltype = AA   length = 8
```

-continued

```
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 185
INPGNGNT                                                                    8

SEQ ID NO: 186          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 186
ARLPDQ                                                                      6

SEQ ID NO: 187          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 187
SSNIGSNT                                                                    8

SEQ ID NO: 188          moltype =    length =
SEQUENCE: 188
000

SEQ ID NO: 189          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 189
AAWDDSLSGL                                                                 10

SEQ ID NO: 190          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 190
GFTFGDYG                                                                    8

SEQ ID NO: 191          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 191
INWNGGST                                                                    8

SEQ ID NO: 192          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 192
ARSKQDY                                                                     7

SEQ ID NO: 193          moltype = AA   length = 9
FEATURE                 Location/Qualifiers
REGION                  1..9
                        note = Description of Artificial Sequence: Synthetic peptide
source                  1..9
                        mol_type = protein
```

```
SEQUENCE: 193                      organism = synthetic construct
SRDAGGYNY                                                                      9

SEQ ID NO: 194          moltype =   length =
SEQUENCE: 194
000

SEQ ID NO: 195          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct SEQUENCE: 195
SSYGGSNNFR V                                                        11

SEQ ID NO: 196          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct SEQUENCE: 196
GFSFSGTA                                                                       8

SEQ ID NO: 197          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct SEQUENCE: 197
ISSTGRST                                                                       8

SEQ ID NO: 198          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct SEQUENCE: 198
ARVSFDY                                                                        7

SEQ ID NO: 199          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct SEQUENCE: 199
SSNIGAGYD                                                                      9

SEQ ID NO: 200          moltype =   length =
SEQUENCE: 200
000

SEQ ID NO: 201          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct SEQUENCE: 201
QSYDSSLSGS YV                                                       12

SEQ ID NO: 202          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
```

-continued

```
SEQUENCE: 202
GFTFSSYA                                                              8

SEQ ID NO: 203        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 203
ISGRGRST                                                              8

SEQ ID NO: 204        moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 204
ARYYHAGAFD L                                                          11

SEQ ID NO: 205        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 205
SSDVGGYNY                                                             9

SEQ ID NO: 206        moltype =    length =
SEQUENCE: 206
000

SEQ ID NO: 207        moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 207
SSYTSSSTLV                                                            10

SEQ ID NO: 208        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 208
GYTFNRYA                                                              8

SEQ ID NO: 209        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 209
ISAYNGNS                                                              8

SEQ ID NO: 210        moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 210
ARMAYDS                                                               7

SEQ ID NO: 211        moltype = AA  length = 9
FEATURE               Location/Qualifiers
```

```
REGION                  1..9
                        note = Description of Artificial Sequence: Synthetic peptide
source                  1..9
                        mol_type = protein
                        organism = synthetic construct
SEQUENCE: 211
SNDVGAYKY                                                                9

SEQ ID NO: 212          moltype =   length =
SEQUENCE: 212
000

SEQ ID NO: 213          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 213
FSLTSSNTYV                                                               10

SEQ ID NO: 214          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 214
GFTFSDYY                                                                 8

SEQ ID NO: 215          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 215
ISSSGSTI                                                                 8

SEQ ID NO: 216          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 216
ARGYGKAYDQ                                                               10

SEQ ID NO: 217          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 217
RSNVGGNY                                                                 8

SEQ ID NO: 218          moltype =   length =
SEQUENCE: 218
000

SEQ ID NO: 219          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 219
ATWDDSLSGF V                                                             11

SEQ ID NO: 220          moltype = AA   length = 8
FEATURE                 Location/Qualifiers
REGION                  1..8
```

```
                           note = Description of Artificial Sequence: Synthetic peptide
source                     1..8
                           mol_type = protein
                           organism = synthetic construct
SEQUENCE: 220
GFTFRSHS                                                         8

SEQ ID NO: 221             moltype = AA  length = 8
FEATURE                    Location/Qualifiers
REGION                     1..8
                           note = Description of Artificial Sequence: Synthetic peptide
source                     1..8
                           mol_type = protein
                           organism = synthetic construct
SEQUENCE: 221
ISSDSTYT                                                         8

SEQ ID NO: 222             moltype = AA  length = 12
FEATURE                    Location/Qualifiers
REGION                     1..12
                           note = Description of Artificial Sequence: Synthetic peptide
source                     1..12
                           mol_type = protein
                           organism = synthetic construct
SEQUENCE: 222
ARSGGQWKYY DY                                                    12

SEQ ID NO: 223             moltype = AA  length = 6
FEATURE                    Location/Qualifiers
REGION                     1..6
                           note = Description of Artificial Sequence: Synthetic peptide
source                     1..6
                           mol_type = protein
                           organism = synthetic construct
SEQUENCE: 223
SLRSYY                                                           6

SEQ ID NO: 224             moltype =   length =
SEQUENCE: 224
000

SEQ ID NO: 225             moltype = AA  length = 12
FEATURE                    Location/Qualifiers
REGION                     1..12
                           note = Description of Artificial Sequence: Synthetic peptide
source                     1..12
                           mol_type = protein
                           organism = synthetic construct
SEQUENCE: 225
NSRDSSGNPP VV                                                    12

SEQ ID NO: 226             moltype = AA  length = 8
FEATURE                    Location/Qualifiers
REGION                     1..8
                           note = Description of Artificial Sequence: Synthetic peptide
source                     1..8
                           mol_type = protein
                           organism = synthetic construct
SEQUENCE: 226
GFTFSNYA                                                         8

SEQ ID NO: 227             moltype = AA  length = 8
FEATURE                    Location/Qualifiers
REGION                     1..8
                           note = Description of Artificial Sequence: Synthetic peptide
source                     1..8
                           mol_type = protein
                           organism = synthetic construct
SEQUENCE: 227
INGRGSST                                                         8

SEQ ID NO: 228             moltype = AA  length = 11
FEATURE                    Location/Qualifiers
REGION                     1..11
                           note = Description of Artificial Sequence: Synthetic peptide
source                     1..11
                           mol_type = protein
                           organism = synthetic construct
SEQUENCE: 228
```

-continued

```
ARYISRGLGD S                                                            11

SEQ ID NO: 229          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 229
NSNIERNY                                                                8

SEQ ID NO: 230          moltype =   length =
SEQUENCE: 230
000

SEQ ID NO: 231          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 231
GTWDSSLRGW V                                                            11

SEQ ID NO: 232          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 232
GYTFTSYY                                                                8

SEQ ID NO: 233          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 233
INPSGGST                                                                8

SEQ ID NO: 234          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 234
ARAGMGMDT                                                               9

SEQ ID NO: 235          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 235
SSDVGGYNY                                                               9

SEQ ID NO: 236          moltype =   length =
SEQUENCE: 236
000

SEQ ID NO: 237          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 237
SSYAGSNTLV                                                              10
```

```
SEQ ID NO: 238          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 238
GYTFTAYS                                                          8

SEQ ID NO: 239          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 239
INPSSGGA                                                          8

SEQ ID NO: 240          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 240
ARNVGGQADD                                                        10

SEQ ID NO: 241          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 241
SSDIGGYNY                                                         9

SEQ ID NO: 242          moltype =    length =
SEQUENCE: 242
000

SEQ ID NO: 243          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 243
ASFAGRKTLV                                                        10

SEQ ID NO: 244          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 244
GYTFTAYS                                                          8

SEQ ID NO: 245          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 245
INPSSGGA                                                          8

SEQ ID NO: 246          moltype = AA   length = 10
FEATURE                 Location/Qualifiers
REGION                  1..10
                        note = Description of Artificial Sequence: Synthetic peptide
```

```
source                      1..10
                            mol_type = protein
                            organism = synthetic construct
SEQUENCE: 246
ARNVGGHADD                                                                      10

SEQ ID NO: 247              moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 247
STDIGGYNY                                                                        9

SEQ ID NO: 248              moltype =   length =
SEQUENCE: 248
000

SEQ ID NO: 249              moltype = AA  length = 10
FEATURE                     Location/Qualifiers
REGION                      1..10
                            note = Description of Artificial Sequence: Synthetic peptide
source                      1..10
                            mol_type = protein
                            organism = synthetic construct
SEQUENCE: 249
ASFAGRKTLV                                                                      10

SEQ ID NO: 250              moltype = AA  length = 8
FEATURE                     Location/Qualifiers
REGION                      1..8
                            note = Description of Artificial Sequence: Synthetic peptide
source                      1..8
                            mol_type = protein
                            organism = synthetic construct
SEQUENCE: 250
GFTFNTYG                                                                         8

SEQ ID NO: 251              moltype = AA  length = 8
FEATURE                     Location/Qualifiers
REGION                      1..8
                            note = Description of Artificial Sequence: Synthetic peptide
source                      1..8
                            mol_type = protein
                            organism = synthetic construct
SEQUENCE: 251
ISANNGHT                                                                         8

SEQ ID NO: 252              moltype = AA  length = 22
FEATURE                     Location/Qualifiers
REGION                      1..22
                            note = Description of Artificial Sequence: Synthetic peptide
source                      1..22
                            mol_type = protein
                            organism = synthetic construct
SEQUENCE: 252
ARGGYHHQMQ RYYKATSVYS DY                                                        22

SEQ ID NO: 253              moltype = AA  length = 8
FEATURE                     Location/Qualifiers
REGION                      1..8
                            note = Description of Artificial Sequence: Synthetic peptide
source                      1..8
                            mol_type = protein
                            organism = synthetic construct
SEQUENCE: 253
SSNIGNNY                                                                         8

SEQ ID NO: 254              moltype =   length =
SEQUENCE: 254
000

SEQ ID NO: 255              moltype = AA  length = 11
FEATURE                     Location/Qualifiers
REGION                      1..11
                            note = Description of Artificial Sequence: Synthetic peptide
source                      1..11
```

```
                              mol_type = protein
                              organism = synthetic construct
SEQUENCE: 255
GTWDSSLSGV V                                                    11

SEQ ID NO: 256         moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 256
GYTFTSYY                                                        8

SEQ ID NO: 257         moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 257
INPSGGSS                                                        8

SEQ ID NO: 258         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 258
ARAGMGMDT                                                       9

SEQ ID NO: 259         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 259
SSDVGGYNY                                                       9

SEQ ID NO: 260         moltype =   length =
SEQUENCE: 260
000

SEQ ID NO: 261         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 261
SSYAGSNTLV                                                      10

SEQ ID NO: 262         moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 262
GYTFTSYY                                                        8

SEQ ID NO: 263         moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 263
INPSGGST                                                        8
```

```
SEQ ID NO: 264          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 264
ARDVISGFDS                                                        10

SEQ ID NO: 265          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 265
SSDVGGYNY                                                         9

SEQ ID NO: 266          moltype =   length =
SEQUENCE: 266
000

SEQ ID NO: 267          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 267
SSYAGVNNLM                                                        10

SEQ ID NO: 268          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 268
GFTFGDYG                                                          8

SEQ ID NO: 269          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 269
INWNGGST                                                          8

SEQ ID NO: 270          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 270
ARSKQGY                                                           7

SEQ ID NO: 271          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 271
SRDAGGYNY                                                         9

SEQ ID NO: 272          moltype =   length =
SEQUENCE: 272
000

SEQ ID NO: 273          moltype = AA   length = 11
```

```
FEATURE              Location/Qualifiers
REGION               1..11
                     note = Description of Artificial Sequence: Synthetic peptide
source               1..11
                     mol_type = protein
                     organism = synthetic construct
SEQUENCE: 273
SSYGGSNNFR V                                                                      11

SEQ ID NO: 274       moltype = AA   length = 114
FEATURE              Location/Qualifiers
REGION               1..114
                     note = Description of Artificial Sequence: Synthetic
                      polypeptide
source               1..114
                     mol_type = protein
                     organism = synthetic construct
SEQUENCE: 274
EVQLVESGGG VVRPGGSLRL SCAASGFTFG DYGMSWVRQA PGKGLEWVSG INWNGGSTGY  60
ADSVKGRFTI SRDNAKNSLY LQMNSLRAED TAVYYCARSK QDYWGQGTLV TVSS        114

SEQ ID NO: 275       moltype = AA   length = 136
FEATURE              Location/Qualifiers
REGION               1..136
                     note = Description of Artificial Sequence: Synthetic
                      polypeptide
source               1..136
                     mol_type = protein
                     organism = synthetic construct
SEQUENCE: 275
MKKTAIAIAV ALAGFATVAQ AAELQSALTQ PPSASGSPGQ SVTISCTGTS RDAGGYNYFS  60
WYQQHPGKAP KLLIYEVTKR PSGVPDRFSG SKSGKTASLT VSGLQADDEA VYYCSSYGGS  120
NNFRVFGGGT KLTVLG                                                  136

SEQ ID NO: 276       moltype = AA   length = 271
FEATURE              Location/Qualifiers
REGION               1..271
                     note = Description of Artificial Sequence: Synthetic
                      polypeptide
source               1..271
                     mol_type = protein
                     organism = synthetic construct
SEQUENCE: 276
MKKTAIAIAV ALAGFATVAQ AAELQSALTQ PPSASGSPGQ SVTISCTGTS RDAGGYNYFS  60
WYQQHPGKAP KLLIYEVTKR PSGVPDRFSG SKSGKTASLT VSGLQADDEA VYYCSSYGGS  120
NNFRVFGGGT KLTVLGSRGG GGSGGGGSGG GGSLEMAEVQ LVESGGGVVR PGGSLRLSCA  180
ASGFTFGDYG MSWVRQAPGK GLEWVSGINW NGGSTGYADS VKGRFTISRD NAKNSLYLQM  240
NSLRAEDTAV YYCARSKQDY WGQGTLVTVS S                                 271

SEQ ID NO: 277       moltype = DNA   length = 342
FEATURE              Location/Qualifiers
misc_feature         1..342
                     note = Description of Artificial Sequence: Synthetic
                      polynucleotide
source               1..342
                     mol_type = other DNA
                     organism = synthetic construct
SEQUENCE: 277
gaggtgcagc tggtggagtc tgggggaggt gtggtacggc ctggggggtc cctgagactc  60
tcctgtgcag cctctggatt cacctttggt gattatggca tgagctgggt ccgccaagct  120
ccagggaagg ggctggagtg ggtctctggt attaattgga atggtggtag cacaggttat  180
gcagactctg tgaagggccg attcaccatc tccagagaca cgccaagaa ctccctgtat  240
ctgcaaatga cagtctgag agccgaggac acggccgtat attactgtgc gcgctctaaa  300
caggattact ggggtcaagg tactctggtg accgtctcct ca                    342

SEQ ID NO: 278       moltype = DNA   length = 408
FEATURE              Location/Qualifiers
misc_feature         1..408
                     note = Description of Artificial Sequence: Synthetic
                      polynucleotide
source               1..408
                     mol_type = other DNA
                     organism = synthetic construct
SEQUENCE: 278
atgaaaaaga cagctatcgc gattgcagtg gcactggctg gtttcgctac cgtggccag   60
gcggccgagc tccagtctgc cctgactcag cctccctccg cgtccgggtc tcctggacag  120
tcagtcacca tctcctgcac tggaaccagc agggacgctg tggttataa ttatttctcc  180
tggtaccaac aacacccagg caaagccccc aaactcctga tttatgaggt cactaagcgg  240
ccctcagggg tccctgatcg cttctctggc tccaagtctg caagacggc ctccctgacc  300
```

```
gtctctgggc tccaggctga cgatgaggct gtatattact gcagctcata tggaggcagc  360
aacaactttc gggtgttcgg cggagggacc aagctgaccg tcctaggt                 408

SEQ ID NO: 279          moltype = DNA   length = 813
FEATURE                 Location/Qualifiers
misc_feature            1..813
                        note = Description of Artificial Sequence: Synthetic
                         polynucleotide
source                  1..813
                        mol_type = other DNA
                        organism = synthetic construct SEQUENCE: 279
atgaaaaaga cagctatcgc gattgcagtg gcactggctg gtttcgctac cgtggcccag  60
gcggccgagc tccagtctgc cctgactcag cctccctccg cgtccgggtc tcctggacag  120
tcagtcacca tctcctgcac tggaaccagc agggacgctg gtggttataa ttatttctcc  180
tggtaccaac aacacccagg caaagccccc aaactcctga tttatgaggt cactaagcgg  240
ccctcagggg tccctgatcg cttctctggc tccaagtctg gcaagacggc ctccctgacc  300
gtctctgggc tccaggctga cgatgaggct gtatattact gcagctcata tggaggcagc  360
aacaactttc gggtgttcgg cggagggacc aagctgaccg tcctaggttc tagaggtggt  420
ggtggtagcg gcggcggcgg ctctggtggt ggtggatccc tcgagatggc cgaggtgcag  480
ctggtggagt ctgggggagg tgtggtacgg cctgggGggt ccctgagact ctcctgtgca  540
gcctctggat tcaccttggg tgattatggc atgagctggg tccgccaagc tccagggaag  600
gggctggagt gggtctctgg tattaattgg aatggtggta gcacaggtta tgcagactct  660
gtgaagggcc gattcaccat ctccagagac aacgccaaga actccctgta tctgcaaatg  720
aacagtctga gagccgagga cacggccgta tattactgtg cgcgctctaa acaggattac  780
tggggtcaag gtactctggt gaccgtctcc tca                                813

SEQ ID NO: 280          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct SEQUENCE: 280
GFTFSNYA                                                             8

SEQ ID NO: 281          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct SEQUENCE: 281
ITNSGRST                                                             8

SEQ ID NO: 282          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct SEQUENCE: 282
ARVTHRRYGS TFDS                                                      14

SEQ ID NO: 283          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct SEQUENCE: 283
SSNIGSNT                                                             8

SEQ ID NO: 284          moltype =    length =
SEQUENCE: 284
000

SEQ ID NO: 285          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct

SEQUENCE: 285
```

-continued

```
AAWDDSVNGY V                                                             11

SEQ ID NO: 286          moltype = AA   length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 286
QLQLQESGGG SVQPGGSLRL SCAASGFTFS NYAMSWVRQA PGKGLEWVSA ITNSGRSTYY  60
ADSVKGRFTI SRDNSKNTLS LQMSSLRAED TAVYYCARVT HRRYGSTFDS RGQGTLVTVS  120
S                                                                   121

SEQ ID NO: 287          moltype = AA   length = 135
FEATURE                 Location/Qualifiers
REGION                  1..135
                        note = Description of Artificial Sequence: Synthetic
                         polypeptide
source                  1..135
                        mol_type = protein
                        organism = synthetic construct
SEQUENCE: 287
MKKTAIAIAV ALAGFATVAQ AAELSYELTQ PPSASGTPGQ RVSISCSGSS SNIGSNTVNW  60
YQQFPGTAPK LLIHSNNQRP SGVPDRFSGS KSGTSASLAI SGPQSEDEAD YYCAAWDDSV  120
NGYVFGTGTK VTVLG                                                    135

SEQ ID NO: 288          moltype = AA   length = 277
FEATURE                 Location/Qualifiers
REGION                  1..277
                        note = Description of Artificial Sequence: Synthetic
                         polypeptide
source                  1..277
                        mol_type = protein
                        organism = synthetic construct
SEQUENCE: 288
MKKTAIAIAV ALAGFATVAQ AAELSYELTQ PPSASGTPGQ RVSISCSGSS SNIGSNTVNW  60
YQQFPGTAPK LLIHSNNQRP SGVPDRFSGS KSGTSASLAI SGPQSEDEAD YYCAAWDDSV  120
NGYVFGTGTK VTVLGSRGGG GSGGGGSGGG GSLEMAQLQL QESGGGSVQP GGSLRLSCAA  180
SGFTFSNYAM SWVRQAPGKG LEWVSAITNS GRSTYYADSV KGRFTISRDN SKNTLSLQMS  240
SLRAEDTAVY YCARVTHRRY GSTFDSRGQG TLVTVSS                            277

SEQ ID NO: 289          moltype = DNA   length = 385
FEATURE                 Location/Qualifiers
misc_feature            1..385
                        note = Description of Artificial Sequence: Synthetic
                         polynucleotide
source                  1..385
                        mol_type = other DNA
                        organism = synthetic construct
SEQUENCE: 289
cagctgcagc tgcaggagtc ggggggaggc tcggtacagc cggggggggtc tctgagactg  60
tcctgtgcag cctctggatt caccttttagc aactatgcca tgagctgggt ccgccaggct  120
ccagggaagg ggctggagtg ggtctcagct atcactaata gtggtcgtag tacatactac  180
gcagactccg tgaagggccg gttcaccatc tccagagaca attccaagaa cacgctgtct  240
ttgcaaatga gcagcctgag agccgaagac acggccgtgt attactgtgc gcgcgttact  300
catcgtcgtt acggttctac tttcgattct cggggtcaag gtactctggt gaccgtctcc  360
tcaactagtg gccaggccgg ccagc                                         385

SEQ ID NO: 290          moltype = DNA   length = 405
FEATURE                 Location/Qualifiers
misc_feature            1..405
                        note = Description of Artificial Sequence: Synthetic
                         polynucleotide
source                  1..405
                        mol_type = other DNA
                        organism = synthetic construct
SEQUENCE: 290
atgaaaaaga cagctatcgc gattgcagtg gcactggctg gtttcgctac cgtggcccag  60
gcggccgagc tctcctatga gctgactcag ccaccctcag cgtctgggac ccccgggcag  120
agggtcagca tctcttgttc tggaagcagc tccaacatcg ggagtaatac tgtaaactgg  180
taccaacagt tccccggaac ggcccccaaa ctcctcatcc atagtaataa tcagcggccc  240
tcaggggtcc ctgaccgatt ctctggctcc aagtctggca cctcagcctc cctggccatc  300
agtgggcccc agtctgagga tgaggctgat tattactgtg cagcttggga tgacagtgtg  360
aatggttatg tcttcggaac tgggaccaag gtcaccgtcc taggt                   405

SEQ ID NO: 291          moltype = DNA   length = 831
FEATURE                 Location/Qualifiers
```

-continued

```
misc_feature            1..831
                        note = Description of Artificial Sequence: Synthetic
                         polynucleotide
source                  1..831
                        mol_type = other DNA
                        organism = synthetic construct
SEQUENCE: 291
atgaaaaaga cagctatcgc gattgcagtg gcactggctg gtttcgctac cgtggcccag    60
gcggccgagc tctcctatga gctgactcag ccaccctcag cgtcgtgggac ccccgggcag   120
agggtcagca tctcttgttc tggaagcagc tccaacatcg ggagtaatac tgtaaactgg   180
taccaacagt tccccggaac ggcccccaaa ctcctcatcc atagtaataa tcagcggccc   240
tcaggggtcc ctgaccgatt ctctggctcc aagtctggca cctcagcctc cctggccatc   300
agtgggcccc agtctgagga tgaggctgat tattactgtg cagcttggga tgacagtgtg   360
aatggttatg tcttcggaac tgggaccaag gtcaccgtcc taggttctag aggtggtggt   420
ggtagcggcg gcggcggctc tggtggtggt ggatccctcg agatggccca gctgcagctg   480
caggagtcgg ggggaggctc ggtacagccg ggggggtctc tgagactgtc ctgtgcagcc   540
tctggattca cctttagcaa ctatgccatg agctgggtcc gccaggctcc agggaagggg   600
ctggagtggg tctcagctat cactaatagt ggtcgtagta catactacgc agactccgtg   660
aagggccggt tcaccatctc cagagacaat tccaagaaca cgctgtcttt gcaaatgagc   720
agcctgagag ccgaagacac ggccgtgtat tactgtgcgc gcgttactca tcgtcgttac   780
ggttctactt tcgattctcg gggtcaaggt actctggtga ccgtctcctc a            831

SEQ ID NO: 292            moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 292
GGTFRSYA                                                               8

SEQ ID NO: 293            moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 293
IIPMLDIT                                                               8

SEQ ID NO: 294            moltype = AA   length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 294
ARTYSRSPFH MEDF                                                       14

SEQ ID NO: 295            moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 295
SSNIGGNT                                                               8

SEQ ID NO: 296            moltype =    length =
SEQUENCE: 296
000

SEQ ID NO: 297            moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 297
AAWDASRQGV                                                            10

SEQ ID NO: 298            moltype = AA   length = 121
FEATURE                  Location/Qualifiers
REGION                   1..121
```

-continued

```
                            note = Description of Artificial Sequence: Synthetic
                             polypeptide
source                      1..121
                            mol_type = protein
                            organism = synthetic construct
SEQUENCE: 298
QVQLVQSGAE VKKPGSSVKV SCKASGGTFR SYAITWVRQA PGQGLEWMGR IIPMLDITNY  60
AQKFQGRVTI TADKSTSTAY MELSSLRSED TAVYYCARTY SRSPFHMEDF WGQGTLVTVS  120
S                                                                   121

SEQ ID NO: 299             moltype = AA   length = 134
FEATURE                    Location/Qualifiers
REGION                     1..134
                           note = Description of Artificial Sequence: Synthetic
                            polypeptide
source                     1..134
                           mol_type = protein
                           organism = synthetic construct
SEQUENCE: 299
MKKTAIAIAV ALAGFATVAQ AAELQPVLTQ PPSASGTPGQ RVTISCSGSS SNIGGNTVSW  60
YQQVPGTAPR LLIFRNNQRP PGVPDRFSGS KSGTSASLAI SGLRSEDEAD YYCAAWDASR  120
QGVFGGGTKL TVLG                                                     134

SEQ ID NO: 300             moltype = AA   length = 276
FEATURE                    Location/Qualifiers
REGION                     1..276
                           note = Description of Artificial Sequence: Synthetic
                            polypeptide
source                     1..276
                           mol_type = protein
                           organism = synthetic construct
SEQUENCE: 300
MKKTAIAIAV ALAGFATVAQ AAELQPVLTQ PPSASGTPGQ RVTISCSGSS SNIGGNTVSW  60
YQQVPGTAPR LLIFRNNQRP PGVPDRFSGS KSGTSASLAI SGLRSEDEAD YYCAAWDASR  120
QGVFGGGTKL TVLGSRGGGG SGGGGSGGGG SLEMAQVQLV QSGAEVKKPG SSVKVSCKAS  180
GGTFRSYAIT WVRQAPGQGL EWMGRIIPML DITNYAQKFQ GRVTITADKS TSTAYMELSS  240
LRSEDTAVYY CARTYSRSPF HMEDFWGQGT LVTVSS                             276

SEQ ID NO: 301             moltype = DNA   length = 402
FEATURE                    Location/Qualifiers
misc_feature               1..402
                           note = Description of Artificial Sequence: Synthetic
                            polynucleotide
source                     1..402
                           mol_type = other DNA
                           organism = synthetic construct
SEQUENCE: 301
atgaaaaaga cagctatcgc gattgcagtg gcactggctg gtttcgctac cgtggcccag  60
gcggccgagc tccagcctgt gctgactcag ccaccctcag cgtctgggac ccccgggcag  120
agggtcacca tctcttgttc tggaagcagc tccaatatcg gaggtaacac tgtcagctgg  180
taccagcagg tcccaggaac ggcccccaga ctcctcattt ttaggaataa tcaacggccc  240
ccaggggtcc ctgaccgatt ctctggctcc aagtctggca cctcagcctc cctggccatc  300
agtgggctcc ggtctgagga tgaggctgat tattactgtg cagcatggga cgccagtcga  360
caaggggtgt tcggcggagg gaccaagctg accgtcctag gt                      402

SEQ ID NO: 302             moltype = DNA   length = 828
FEATURE                    Location/Qualifiers
misc_feature               1..828
                           note = Description of Artificial Sequence: Synthetic
                            polynucleotide
source                     1..828
                           mol_type = other DNA
                           organism = synthetic construct
SEQUENCE: 302
atgaaaaaga cagctatcgc gattgcagtg gcactggctg gtttcgctac cgtggcccag  60
gcggccgagc tccagcctgt gctgactcag ccaccctcag cgtctgggac ccccgggcag  120
agggtcacca tctcttgttc tggaagcagc tccaatatcg gaggtaacac tgtcagctgg  180
taccagcagg tcccaggaac ggcccccaga ctcctcattt ttaggaataa tcaacggccc  240
ccaggggtcc ctgaccgatt ctctggctcc aagtctggca cctcagcctc cctggccatc  300
agtgggctcc ggtctgagga tgaggctgat tattactgtg cagcatggga cgccagtcga  360
caaggggtgt tcggcggagg gaccaagctg accgtcctag gttctagagg tggtggtggt  420
agcggcggcg cgggctctgg tggtggtgga tccctcgaga tggcccaggt gcagctggtg  480
cagtctgggc ctgaggtgaa gaagcctggg tcctcggtga aggtctcctg caaggcttct  540
ggaggcacct tccgcagcta tgctatcacc tgggtgcgac aggcccctgg acaaggggctt  600
gagtggatgg gaaggatcat ccctatgctt gatataacaa actacgcaca gaagttccag  660
ggcagagtca cgattaccgc ggacaaatcc acgagcacag cctacatgga gctgagcagc  720
ctgagatctg aggacacggc cgtgtattac tgtgcgcgca cttactctcg ttctccgttc  780
catatggaag atttctgggg tcaaggtact ctggtgaccg tctcctca                828
```

-continued

```
SEQ ID NO: 303          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 303
GFTFSSYA                                                             8

SEQ ID NO: 304          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 304
ISGSGGST                                                             8

SEQ ID NO: 305          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 305
ARKYQDV                                                              7

SEQ ID NO: 306          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 306
SSNIGSNT                                                             8

SEQ ID NO: 307          moltype =    length =
SEQUENCE: 307
000

SEQ ID NO: 308          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 308
AAWDDSLSGR V                                                         11

SEQ ID NO: 309          moltype = AA   length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 309
GGGGSGGGGS GGGGS                                                     15

SEQ ID NO: 310          moltype = AA   length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 310
EVQLVESGGG LVQPGGSLRL SCAASGFTFS SYAMSWVRQA PGKGLEWVSA ISGSGGSTYY   60
ADSVKGRFTI SRDNAKNTLY LQMNSLRAED TAVYYCARKY QDVWGQGTLV TVSS          114

SEQ ID NO: 311          moltype = AA   length = 135
FEATURE                 Location/Qualifiers
REGION                  1..135
```

```
                         note = Description of Artificial Sequence: Synthetic
                          polypeptide
source                   1..135
                         mol_type = protein
                         organism = synthetic construct
SEQUENCE: 311
MKKTAIAIAV ALAGFATVAQ AAELQSVLTQ PPSASGTPGQ RVTISCSGSS SNIGSNTVNW   60
YQQLPGTAPK LLIYRNNQRP SGVPDRFSGS KSGTSASLAI SGLRSEDEAD YYCAAWDDSL  120
SGRVFGGGTK LTVLG                                                   135

SEQ ID NO: 312           moltype = AA   length = 270
FEATURE                  Location/Qualifiers
REGION                   1..270
                         note = Description of Artificial Sequence: Synthetic
                          polypeptide
source                   1..270
                         mol_type = protein
                         organism = synthetic construct
SEQUENCE: 312
MKKTAIAIAV ALAGFATVAQ AAELQSVLTQ PPSASGTPGQ RVTISCSGSS SNIGSNTVNW   60
YQQLPGTAPK LLIYRNNQRP SGVPDRFSGS KSGTSASLAI SGLRSEDEAD YYCAAWDDSL  120
SGRVFGGGTK LTVLGSRGGG GSGGGGSGGG GSLEMAEVQL VESGGGLVQP GGSLRLSCAA  180
SGFTFSSYAM SWVRQAPGKG LEWVSAISGS GGSTYYADSV KGRFTISRDN AKNTLYLQMN  240
SLRAEDTAVY YCARKYQDVW GQGTLVTVSS                                   270

SEQ ID NO: 313           moltype = DNA   length = 342
FEATURE                  Location/Qualifiers
misc_feature             1..342
                         note = Description of Artificial Sequence: Synthetic
                          polynucleotide
source                   1..342
                         mol_type = other DNA
                         organism = synthetic construct
SEQUENCE: 313
gaggtgcagc tggtggagtc tggggggaggc ttggtacagc ctggggggtc cctgagactc   60
tcctgtgcag cctctggatt cacctttagc agctatgcca tgagctgggt ccgccaggct  120
ccagggaagg ggctggagtg ggtctcagct attagtggta gtggtggtag cacatactac  180
gcagactccg tgaagggccg gttcaccatc tccagagaca atgccaagaa cacgctgtat  240
ctgcaaatga acagcctgag agccgaggac acggccgtat attactgtgc gcgcaaatac  300
caggatgttt ggggtcaagg tactctggtg accgtctcct ca                     342

SEQ ID NO: 314           moltype = DNA   length = 405
FEATURE                  Location/Qualifiers
misc_feature             1..405
                         note = Description of Artificial Sequence: Synthetic
                          polynucleotide
source                   1..405
                         mol_type = other DNA
                         organism = synthetic construct
SEQUENCE: 314
atgaaaaaga cagctatcgc gattgcagtg gcactggctg gtttcgctac cgtggcccag   60
gcggccgagc tccagtctgt gctgacgcag ccgccctcag cgtctgggac ccccgggcag  120
agggtcacca tctcttgttc tggaagcagc tccaacatcg gaagtaatac tgtaaactgg  180
taccagcagc tcccaggaac ggcccccaaa ctcctcatct ataggaataa tcagcggccc  240
tcaggggtcc ctgaccgatt ctctggctcc aagtctggca cctcagcctc cctggccatc  300
agtgggctcc ggtccgagga tgaggctgat tattactgtg cagcatggga tgacagcctg  360
agtggtaggg tgttcggcgg agggaccaag ctgaccgtcc taggt                  405

SEQ ID NO: 315           moltype = DNA   length = 810
FEATURE                  Location/Qualifiers
misc_feature             1..810
                         note = Description of Artificial Sequence: Synthetic
                          polynucleotide
source                   1..810
                         mol_type = other DNA
                         organism = synthetic construct
SEQUENCE: 315
atgaaaaaga cagctatcgc gattgcagtg gcactggctg gtttcgctac cgtggcccag   60
gcggccgagc tccagtctgt gctgacgcag ccgccctcag cgtctgggac ccccgggcag  120
agggtcacca tctcttgttc tggaagcagc tccaacatcg gaagtaatac tgtaaactgg  180
taccagcagc tcccaggaac ggcccccaaa ctcctcatct ataggaataa tcagcggccc  240
tcaggggtcc ctgaccgatt ctctggctcc aagtctggca cctcagcctc cctggccatc  300
agtgggctcc ggtccgagga tgaggctgat tattactgtg cagcatggga tgacagcctg  360
agtggtaggg tgttcggcgg agggaccaag ctgaccgtcc taggttctag aggtggtggt  420
ggtagcggcg cggcggctc tggtggtggt ggatccctcg agatggccga ggtgcagctg  480
gtggagtctg ggggaggctt ggtacagcct ggggggtccc tgagactctc ctgtgcagcc  540
tctggattca cctttagcag ctatgccatg agctgggtcc gccaggctcc agggaagggg  600
ctggagtggg tctcagctat tagtggtagt ggtggtagca catactacgc agactccgtg  660
aagggccggt tcaccatctc cagagacaat gccaagaaca cgctgtatct gcaaatgaac  720
```

-continued

```
agcctgagag ccgaggacac ggccgtatat tactgtgcgc gcaaatacca ggatgtttgg   780
ggtcaaggta ctctggtgac cgtctcctca                                    810

SEQ ID NO: 316          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 316
GFSFSGTA                                                              8

SEQ ID NO: 317          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 317
ISSTGRST                                                              8

SEQ ID NO: 318          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 318
ARPVSSMTLS IQSDG                                                      15

SEQ ID NO: 319          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 319
SSNIGAGYD                                                             9

SEQ ID NO: 320          moltype =    length =
SEQUENCE: 320
000

SEQ ID NO: 321          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 321
QSYDSSLRGY V                                                          11

SEQ ID NO: 322          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 322
QVQLVQSGGG VVQPGRSLRL SCAASGFSFS GTAMHWVRQA PGKGLEWVST ISSTGRSTYY    60
RDSVKGRFTI SRDNSKNTLY LQMNSLRGED TAVYYCARPV SSMTLSIQSD GWGQGTLVTV   120
SS                                                                   122

SEQ ID NO: 323          moltype = AA  length = 136
FEATURE                 Location/Qualifiers
REGION                  1..136
                        note = Description of Artificial Sequence: Synthetic
                         polypeptide
source                  1..136
                        mol_type = protein
                        organism = synthetic construct
SEQUENCE: 323
```

-continued

```
MKKTAIAIAV ALAGFATVAQ AAELQSVLTQ PPSVSGAPGQ RVTISCTGSS SNIGAGYDVH     60
WYQQLPGRAP KLLIYGNSNR PSGVPDRFSG SKSGTSASLA ITGLQAEDEA DYYCQSYDSS    120
LRGYVFGTGT KVTVLG                                                    136

SEQ ID NO: 324          moltype = AA   length = 279
FEATURE                 Location/Qualifiers
REGION                  1..279
                        note = Description of Artificial Sequence: Synthetic
                         polypeptide
source                  1..279
                        mol_type = protein
                        organism = synthetic construct
SEQUENCE: 324
MKKTAIAIAV ALAGFATVAQ AAELQSVLTQ PPSVSGAPGQ RVTISCTGSS SNIGAGYDVH     60
WYQQLPGRAP KLLIYGNSNR PSGVPDRFSG SKSGTSASLA ITGLQAEDEA DYYCQSYDSS    120
LRGYVFGTGT KVTVLGSRGG GGSGGGGSGG GGSLEMAQVQ LVQSGGGVVQ PGRSLRLSCA    180
ASGFSFSGTA MHWVRQAPGK GLEWVSTISS TGRSTYYRDS VKGRFTISRD NSKNTLYLQM    240
NSLRGEDTAV YYCARPVSSM TLSIQSDGWG QGTLVTVSS                           279

SEQ ID NO: 325          moltype = DNA   length = 366
FEATURE                 Location/Qualifiers
misc_feature            1..366
                        note = Description of Artificial Sequence: Synthetic
                         polynucleotide
source                  1..366
                        mol_type = other DNA
                        organism = synthetic construct
SEQUENCE: 325
caggtgcagc tggtgcagtc tgggggaggc gtggtccagc ctgggaggtc cctgagactc     60
tcctgtgcag cctctggatt cagctttagt ggcactggct tgcactgggt ccgccaggct    120
ccagggaagg ggctggaatg ggtctcgact attagtagta ctgggcgtag cacatactac    180
agagactccg tgaagggccg gttcaccatc tccagagaca attccaagaa cacgctgtat    240
ctgcaaatga acagcctgag aggcgaggac acggccgtat attactgtgc gcgcccggtt    300
tcttctatga ctctgtctat ccagtctgat ggttggggtc aaggtactct ggtgaccgtc    360
tcctca                                                              366

SEQ ID NO: 326          moltype = DNA   length = 408
FEATURE                 Location/Qualifiers
misc_feature            1..408
                        note = Description of Artificial Sequence: Synthetic
                         polynucleotide
source                  1..408
                        mol_type = other DNA
                        organism = synthetic construct
SEQUENCE: 326
atgaaaaaga cagctatcgc gattgcagtg gcactggctg gtttcgctac cgtggcccag     60
gcggccgagc tccagtctgt gttgacgcag ccgccctcag tgtctggggc cccagggcag    120
agggtcacca tctcctgcac tgggagcagc tccaacatcg gggcaggtta tgatgtacac    180
tggtaccagc agcttccagg aagagccccc aaactcctca tctatggtaa cagcaatcgg    240
ccctcagggg tccctgaccg attctctggc tccaagtctg gcacctcagc ctccctggcc    300
atcactgggc tccaggctga ggatgaggct gattattact gccagtccta tgacagcagc    360
ctgagaggtt atgtcttcgg aactgggacc aaggtcaccg tcctaggt                408

SEQ ID NO: 327          moltype = DNA   length = 837
FEATURE                 Location/Qualifiers
misc_feature            1..837
                        note = Description of Artificial Sequence: Synthetic
                         polynucleotide
source                  1..837
                        mol_type = other DNA
                        organism = synthetic construct
SEQUENCE: 327
atgaaaaaga cagctatcgc gattgcagtg gcactggctg gtttcgctac cgtggcccag     60
gcggccgagc tccagtctgt gttgacgcag ccgccctcag tgtctggggc cccagggcag    120
agggtcacca tctcctgcac tgggagcagc tccaacatcg gggcaggtta tgatgtacac    180
tggtaccagc agcttccagg aagagccccc aaactcctca tctatggtaa cagcaatcgg    240
ccctcagggg tccctgaccg attctctggc tccaagtctg gcacctcagc ctccctggcc    300
atcactgggc tccaggctga ggatgaggct gattattact gccagtccta tgacagcagc    360
ctgagaggtt atgtcttcgg aactgggacc aaggtcaccg tcctaggttc tagaggttcc    420
ggtggtagcg gcggcggcgg ctctggtggt ggtggatccc tcgagatggc ccaggtgcag    480
ctggtgcagt ctgggggagg cgtggtccag cctgggaggt ccctgagact ctcctgtgca    540
gcctctggat tcagctttag tggcactgcc atgcactggg tccgccaggc tccagggaag    600
gggctggaat gggtctcgac tattagtagt actgggcgta gcacatacta cagagactcc    660
gtgaagggcc ggttcaccat ctccagagac aattccaaga acacgctgta tctgcaaatg    720
aacagcctga gaggcgagga cacggccgta tattactgtg cgcgcccggt ttcttctatg    780
actctgtcta tccagtctga tggttggggt caaggtactc tggtgaccgt ctcctca       837

SEQ ID NO: 328          moltype = AA   length = 8
FEATURE                 Location/Qualifiers
```

-continued

```
REGION                1..8
                      note = Description of Artificial Sequence: Synthetic peptide
source                1..8
                      mol_type = protein
                      organism = synthetic construct
SEQUENCE: 328
GYTFTSYY                                                                 8

SEQ ID NO: 329        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 329
INPSGGST                                                                 8

SEQ ID NO: 330        moltype = AA  length = 23
FEATURE               Location/Qualifiers
REGION                1..23
                      note = Description of Artificial Sequence: Synthetic peptide
source                1..23
                      mol_type = protein
                      organism = synthetic construct
SEQUENCE: 330
ARGQKYHSQY SRGGTGGGMT QDM                                                23

SEQ ID NO: 331        moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 331
SSNIGNNY                                                                 8

SEQ ID NO: 332        moltype =   length =
SEQUENCE: 332
000

SEQ ID NO: 333        moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 333
GTWDSSLRNW V                                                             11

SEQ ID NO: 334        moltype = AA  length = 130
FEATURE               Location/Qualifiers
REGION                1..130
                      note = Description of Artificial Sequence: Synthetic
                       polypeptide
source                1..130
                      mol_type = protein
                      organism = synthetic construct
SEQUENCE: 334
QMQLVQSGAE VKKPGASVKV SCKASGYTFT SYYMHWVRQA PGQGLEWMGI INPSGGSTSY  60
AQKFQGRVTM TRDTSTSTVY MELSSLRSED TAVYYCARGQ KYHSQYSRGG TGGGMTQDMW  120
GQGTLVTVSS                                                         130

SEQ ID NO: 335        moltype = AA  length = 135
FEATURE               Location/Qualifiers
REGION                1..135
                      note = Description of Artificial Sequence: Synthetic
                       polypeptide
source                1..135
                      mol_type = protein
                      organism = synthetic construct
SEQUENCE: 335
MKKTAIAIAV ALAGFATVAQ AAELQSVVTQ PPSVSAAPGQ RVTISCSGGS SNIGNNYVSW  60
FQQLPRTAPK LLIYDNNKRP SGIPDRFSGS KSGTSAALDI TVLQTGDEAD YYCGTWDSSL  120
RNWVFGGGTK LTVLG                                                   135

SEQ ID NO: 336        moltype = AA  length = 286
```

-continued

```
FEATURE              Location/Qualifiers
REGION               1..286
                     note = Description of Artificial Sequence: Synthetic
                      polypeptide
source               1..286
                     mol_type = protein
                     organism = synthetic construct
SEQUENCE: 336
MKKTAIAIAV ALAGFATVAQ AAELQSVVTQ PPSVSAAPGQ RVTISCSGGS SNIGNNYVSW   60
FQQLPRTAPK LLIYDNNKRP SGIPDRFSGS KSGTSAALDI TVLQTGDEAD YYCGTWDSSL  120
RNWVFGGGTK LTVLGSRGGG GSGGGGSGGG GSLEMAQMQL VQSGAEVKKP GASVKVSCKA  180
SGYTFTSYYM HWVRQAPGQG LEWMGIINPS GGSTSYAQKF QGRVTMTRDT STSTVYMELS  240
SLRSEDTAVY YCARGQKYHS QYSRGGTGGG MTQDMWGQGT LVTVSS                 286

SEQ ID NO: 337       moltype = DNA  length = 390
FEATURE              Location/Qualifiers
misc_feature         1..390
                     note = Description of Artificial Sequence: Synthetic
                      polynucleotide
source               1..390
                     mol_type = other DNA
                     organism = synthetic construct
SEQUENCE: 337
cagatgcagc tggtgcagtc tggggctgag gtgaagaagc ctggggcctc agtgaaggtt   60
tcctgcaagg catctggata caccttcacc agctactata tgcactgggt gcgacaggcc  120
cctggacaag ggcttgagtg gatgggaata atcaaccota gtggtggtag cacaagctac  180
gcacaaaagt tccagggcag agtcaccatg accagggaca cgtccacgag cacagtctac  240
atggagctga gcagcctgag atctgaggac acggccgtgt attactgtgc gcgcggtcag  300
aaataccatt ctcagtactc tcgtggtggt actggtggtg gtatgactca ggatatgtgg  360
ggtcaaggta ctctggtgac cgtctcctca                                   390

SEQ ID NO: 338       moltype = DNA  length = 405
FEATURE              Location/Qualifiers
misc_feature         1..405
                     note = Description of Artificial Sequence: Synthetic
                      polynucleotide
source               1..405
                     mol_type = other DNA
                     organism = synthetic construct
SEQUENCE: 338
atgaaaaaga cagctatcgc gattgcagtg gcactggctg gtttcgctac cgtggcccag   60
gcggccgagc tccagtctgt cgtgacgcag ccgccctctg tgtctgcggc cccaggacag  120
agggtcacca tctcctgctc tggaggtagt tccaacattg ggaataatta tgtttcctgg  180
ttccaacaac tcccacgaac agcccccaaa ctcctcattt atgacaataa taagcgaccc  240
tcagggattc ctgaccgatt ctctggctcc aagtctggca cgtcagccgc cctggacatc  300
accgttctcc agactgggga cgaggccgat tattactgcg gaacttggga tagcagcctg  360
agaaattggg tgttcggcgg agggaccaag ctgaccgtcc taggt                  405

SEQ ID NO: 339       moltype = DNA  length = 858
FEATURE              Location/Qualifiers
misc_feature         1..858
                     note = Description of Artificial Sequence: Synthetic
                      polynucleotide
source               1..858
                     mol_type = other DNA
                     organism = synthetic construct
SEQUENCE: 339
atgaaaaaga cagctatcgc gattgcagtg gcactggctg gtttcgctac cgtggcccag   60
gcggccgagc tccagtctgt cgtgacgcag ccgccctctg tgtctgcggc cccaggacag  120
agggtcacca tctcctgctc tggaggtagt tccaacattg ggaataatta tgtttcctgg  180
ttccaacaac tcccacgaac agccccCaaa ctcctcattt atgacaataa taagcgaccc  240
tcagggattc ctgaccgatt ctctggctcc aagtctggca cgtcagccgc cctggacatc  300
accgttctcc agactgggga cgaggccgat tattactgcg gaacttggga tagcagcctg  360
agaaattggg tgttcggcgg agggaccaag ctgaccgtcc taggttctag aggtggtggt  420
ggtagcggcg gcggcggctc tggtggtggt ggatccctcg agatggccca gatgcagctg  480
gtgcagtctg gggctgaggt gaagaagcct ggggcctcag tgaaggtttc ctgcaaggca  540
tctggataca ccttcaccag ctactatatg cactgggtgc gacaggcccc tggacaaggg  600
cttgagtgga tgggaataat caaccctagt ggtggtagca caagctacgc acaaaagttc  660
cagggcagag tcaccatgac cagggacacg tccacgagca cagtctacat ggagctgagc  720
agcctgagat ctgaggacac ggccgtgtat tactgtgcgc gcggtcagaa ataccattct  780
cagtactctc gtggtggtac tggtggtggt atgactcagg atatgtgggg tcaaggtact  840
ctggtgaccg tctcctca                                                858

SEQ ID NO: 340       moltype = AA  length = 8
FEATURE              Location/Qualifiers
REGION               1..8
                     note = Description of Artificial Sequence: Synthetic peptide
source               1..8
                     mol_type = protein
```

SEQUENCE: 340
GYTFSRYY                                                               8

SEQ ID NO: 341          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 341
MNPNSGNT                                                               8

SEQ ID NO: 342          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 342
ARGRYHVIDY                                                            10

SEQ ID NO: 343          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 343
SSDVGGYNH                                                              9

SEQ ID NO: 344          moltype =    length =
SEQUENCE: 344
000

SEQ ID NO: 345          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 345
SSYAGSAHWV                                                            10

SEQ ID NO: 346          moltype = AA  length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 346
EVQLVQSGAE VKKPGASVKV SCKASGYTFS RYYIHWVRQA PGQGLEWMGW MNPNSGNTGY  60
AQKFQGRVTM TRNTSISTAY MELSSLRSED TAVYYCARGR YHVIDYWGQG TLVTVSS      117

SEQ ID NO: 347          moltype = AA  length = 135
FEATURE                 Location/Qualifiers
REGION                  1..135
                        note = Description of Artificial Sequence: Synthetic
                         polypeptide
source                  1..135
                        mol_type = protein
                        organism = synthetic construct
SEQUENCE: 347
MKKTAIAIAV ALAGFATVAQ AAELQSVLTQ PPSASGSPGQ SLTISCTGTS SDVGGYNHVS  60
WYQQYPGKAP KLMIYEVTKR PSGVPDRFSG SKSGNTASLT VSGLQAEDEA DYYCSSYAGS  120
AHWVFGGGTK LTVLG                                                     135

SEQ ID NO: 348          moltype = AA  length = 273
FEATURE                 Location/Qualifiers
REGION                  1..273
                        note = Description of Artificial Sequence: Synthetic
                         polypeptide
source                  1..273

```
                              mol_type = protein
                              organism = synthetic construct
SEQUENCE: 348
MKKTAIAIAV ALAGFATVAQ AAELQSVLTQ PPSASGSPGQ SLTISCTGTS SDVGGYNHVS    60
WYQQYPGKAP KLMIYEVTKR PSGVPDRFSG SKSGNTASLT VSGLQAEDEA DYYCSSYAGS   120
AHWVFGGGTK LTVLGSRGGG GSGGGGSGGG GSLEMAEVQL VQSGAEVKKP GASVKVSCKA   180
SGYTFSRYYI HWVRQAPGQG LEWMGWMNPN SGNTGYAQKF QGRVTMTRNT SISTAYMELS   240
SLRSEDTAVY YCARGRYHVI DYWGQGTLVT VSS                                273

SEQ ID NO: 349          moltype = DNA   length = 351
FEATURE                 Location/Qualifiers
misc_feature            1..351
                        note = Description of Artificial Sequence: Synthetic
                         polynucleotide
source                  1..351
                        mol_type = other DNA
                        organism = synthetic construct
SEQUENCE: 349
gaggtccagc tggtgcagtc tggggctgag gtgaagaagc ctggggcctc agtgaaggtt    60
tcctgcaagg catctggata caccttcagc aggtactata tacactgggt gcgacaggcc   120
cctggacaag ggcttgagtg gatgggatgg atgaacccta acagtggtaa cacaggctat   180
gcacagaagt tccagggcag agtcaccatg accaggaaca cctccataag cacagcctac   240
atggagctga gcagcctgag atctgaggac acggccgtgt attactgtgc gcgcggtcgt   300
taccatgtta tcgattactg gggtcaaggt actctggtga ccgtctcctc a             351

SEQ ID NO: 350          moltype = DNA   length = 405
FEATURE                 Location/Qualifiers
misc_feature            1..405
                        note = Description of Artificial Sequence: Synthetic
                         polynucleotide
source                  1..405
                        mol_type = other DNA
                        organism = synthetic construct
SEQUENCE: 350
atgaaaaaga cagctatcgc gattgcagtg gcactggctg gtttcgctac cgtggcccag    60
gcggccgagc tccagtctgt gttgactcag ccaccctccg cgtccgggtc tcctggacag   120
tcactcacca tctcctgcac tggaaccagc agtgacgttg gtggttataa ccatgtctcc   180
tggtaccaac agtacccagg caaagccccc aaactcatga tttatgaggt cactaagcgg   240
ccctcagggg tccctgatcg cttctctggc tccaagtctg gcaacacggc ctccctgacc   300
gtctctgggc tccaggctga ggatgaggct gattattact gcagctcata tgcaggcagc   360
gcccattggg tgttcggcgg agggaccaag ctgaccgtcc taggt                    405

SEQ ID NO: 351          moltype = DNA   length = 819
FEATURE                 Location/Qualifiers
misc_feature            1..819
                        note = Description of Artificial Sequence: Synthetic
                         polynucleotide
source                  1..819
                        mol_type = other DNA
                        organism = synthetic construct
SEQUENCE: 351
atgaaaaaga cagctatcgc gattgcagtg gcactggctg gtttcgctac cgtggcccag    60
gcggccgagc tccagtctgt gttgactcag ccaccctccg cgtccgggtc tcctggacag   120
tcactcacca tctcctgcac tggaaccagc agtgacgttg gtggttataa ccatgtctcc   180
tggtaccaac agtacccagg caaagccccc aaactcatga tttatgaggt cactaagcgg   240
ccctcagggg tccctgatcg cttctctggc tccaagtctg gcaacacggc ctccctgacc   300
gtctctgggc tccaggctga ggatgaggct gattattact gcagctcata tgcaggcagc   360
gcccattggg tgttcggcgg agggaccaag ctgaccgtcc taggttctag aggtggtggt   420
ggtagcggcg gcggcggctc tggtggtggt ggatccctcg agatggccga ggtccagctg   480
gtgcagtctg gggctgaggt gaagaagcct ggggcctcag tgaaggtttc ctgcaaggca   540
tctggataca ccttcagcag gtactatata cactgggtgc gacaggcccc tggacaaggg   600
cttgagtgga tgggatggat gaaccctaac agtggtaaca caggctatgc acagaagttc   660
cagggcagag tcaccatgac caggaacacc tccataagca gcctacat ggagctgagc      720
agcctgagat ctgaggacac ggccgtgtat tactgtgcgc gcggtcgtta ccatgttatc   780
gattactggg gtcaaggtac tctggtgacc gtctcctca                           819

SEQ ID NO: 352          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 352
GYTFNTYY                                                               8

SEQ ID NO: 353          moltype = AA   length = 8
FEATURE                 Location/Qualifiers
REGION                  1..8
```

```
                         note = Description of Artificial Sequence: Synthetic peptide
source                   1..8
                         mol_type = protein
                         organism = synthetic construct
SEQUENCE: 353
INPNNGGT                                                                 8

SEQ ID NO: 354           moltype = AA  length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 354
ARSYDY                                                                   6

SEQ ID NO: 355           moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 355
SSNIGSNY                                                                 8

SEQ ID NO: 356           moltype =    length =
SEQUENCE: 356
000

SEQ ID NO: 357           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 357
AAWDDSLSGR V                                                             11

SEQ ID NO: 358           moltype = AA  length = 113
FEATURE                  Location/Qualifiers
REGION                   1..113
                         note = Description of Artificial Sequence: Synthetic
                          polypeptide
source                   1..113
                         mol_type = protein
                         organism = synthetic construct
SEQUENCE: 358
QLQLVQSGAE VKKPGSSVKV SCKASGYTFN TYYLHWVRQA PGQGLEWMGR INPNNGGTNY  60
AQKFQGRVTM TRDTSINTAY MELSRLRSDD TAVYYCARSY DYWGQGTLVT VSS          113

SEQ ID NO: 359           moltype = AA  length = 135
FEATURE                  Location/Qualifiers
REGION                   1..135
                         note = Description of Artificial Sequence: Synthetic
                          polypeptide
source                   1..135
                         mol_type = protein
                         organism = synthetic construct
SEQUENCE: 359
MKKTAIAIAV ALAGFATVAQ AAELQAVLTQ PPSASGTPGQ RVTISCSGSS SNIGSNYVYW  60
YQQLPGTAPK LLIYRNNQRP SGVPDRFSGS KSGTSASLAI SGLRSEDEAD YYCAAWDDSL  120
SGRVFGTGTK VTVLG                                                    135

SEQ ID NO: 360           moltype = AA  length = 269
FEATURE                  Location/Qualifiers
REGION                   1..269
                         note = Description of Artificial Sequence: Synthetic
                          polypeptide
source                   1..269
                         mol_type = protein
                         organism = synthetic construct
SEQUENCE: 360
MKKTAIAIAV ALAGFATVAQ AAELQAVLTQ PPSASGTPGQ RVTISCSGSS SNIGSNYVYW  60
YQQLPGTAPK LLIYRNNQRP SGVPDRFSGS KSGTSASLAI SGLRSEDEAD YYCAAWDDSL  120
SGRVFGTGTK VTVLGSRGGG GSGGGGSGGG GSLEMAQLQL VQSGAEVKKP GSSVKVSCKA  180
SGYTFNTYYL HWVRQAPGQG LEWMGRINPN NGGTNYAQKF QGRVTMTRDT SINTAYMELS  240
```

-continued

```
RLRSDDTAVY YCARSYDYWG QGTLVTVSS                                   269

SEQ ID NO: 361          moltype = DNA   length = 339
FEATURE                 Location/Qualifiers
misc_feature            1..339
                        note = Description of Artificial Sequence: Synthetic
                         polynucleotide
source                  1..339
                        mol_type = other DNA
                        organism = synthetic construct
SEQUENCE: 361
cagctgcagc tggtgcaatc tggggctgag gtgaagaagc ctgggtcctc ggtgaaggtc   60
tcctgcaagg cttctggata caccttcaac acctactatc tgcactgggt acgacaggcc  120
cctggacaag ggcttgagtg gatgggacgg atcaacccta acaatggtgg cacaaactat  180
gcacagaagt tcagggcag ggtcaccatg accagggaca cgtccatcaa cacagcctac  240
atggagctga gcaggctgag atctgacgac acggccgtgt attactgtgc gcgctcttac  300
gattactggg gtcaaggtac tctggtgacc gtctcctca                        339

SEQ ID NO: 362          moltype = DNA   length = 405
FEATURE                 Location/Qualifiers
misc_feature            1..405
                        note = Description of Artificial Sequence: Synthetic
                         polynucleotide
source                  1..405
                        mol_type = other DNA
                        organism = synthetic construct
SEQUENCE: 362
atgaaaaaga cagctatcgc gattgcagtg gcactggctg gtttcgctac cgtggcccag   60
gcggccgagc tccaggctgt gctgactcag ccaccctcag cgtctgggac ccccgggcag  120
agggtcacca tctcttgttc tggaagcagc tccaacatcg gaagtaatta tgtatactgg  180
taccagcagc tcccaggaac ggcccccaaa ctcctcatct ataggaataa tcagcggccc  240
tcaggggtcc ctgaccgatt ctctggctcc aagtctggca cctcagcctc cctggccatc  300
agtgggctcc ggtccgagga tgaggctgat tattactgtg cagcatggga tgacagcctg  360
agtggtcggg tcttcggaac tgggaccaag gtcaccgtcc taggt                 405

SEQ ID NO: 363          moltype = DNA   length = 807
FEATURE                 Location/Qualifiers
misc_feature            1..807
                        note = Description of Artificial Sequence: Synthetic
                         polynucleotide
source                  1..807
                        mol_type = other DNA
                        organism = synthetic construct
SEQUENCE: 363
atgaaaaaga cagctatcgc gattgcagtg gcactggctg gtttcgctac cgtggcccag   60
gcggccgagc tccaggctgt gctgactcag ccaccctcag cgtctgggac ccccgggcag  120
agggtcacca tctcttgttc tggaagcagc tccaacatcg gaagtaatta tgtatactgg  180
taccagcagc tcccaggaac ggcccccaaa ctcctcatct ataggaataa tcagcggccc  240
tcaggggtcc ctgaccgatt ctctggctcc aagtctggca cctcagcctc cctggccatc  300
agtgggctcc ggtccgagga tgaggctgat tattactgtg cagcatggga tgacagcctg  360
agtggtcggg tcttcggaac tgggaccaag gtcaccgtcc taggttctag aggtggtggt  420
ggtagcggcg cgggcggctc tggtggtggt ggatccctcg agatggccca gctgcagctg  480
gtgcaatctg gggctgaggt gaagaagcct gggtcctcgg tgaaggtctc ctgcaaggct  540
tctggataca ccttcaacac ctactatctg cactgggtac gacaggcccc tggacaaggg  600
cttgagtgga tgggacggat caaccctaac aatggtggca caaactatgc acagaagttt  660
cagggcaggg tcaccatgac cagggacacg tccatcaaca cagcctacat ggagctgagc  720
aggctgagat ctgacgacac ggccgtgtat tactgtgcgc gctcttacga ttactggggt  780
caaggtactc tggtgaccgt ctcctca                                     807

SEQ ID NO: 364          moltype = DNA   length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 364
ggtggaggtg gatcaggtgg aggtggatct ggtggaggtg gatct                  45

SEQ ID NO: 365          moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 365
GGGGS                                                               5
```

```
SEQ ID NO: 366            moltype = AA   length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 366
SGGSGGS                                                                   7

SEQ ID NO: 367            moltype = AA   length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 367
GGGGSGGGS                                                                 9

SEQ ID NO: 368            moltype = AA   length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 368
GGGGSGGGGS                                                                10

SEQ ID NO: 369            moltype = AA   length = 18
FEATURE                   Location/Qualifiers
REGION                    1..18
                          note = Description of Artificial Sequence: Synthetic peptide
source                    1..18
                          mol_type = protein
                          organism = synthetic construct
SEQUENCE: 369
GGGGSGGGGS GGGGGGGS                                                       18

SEQ ID NO: 370            moltype = AA   length = 20
FEATURE                   Location/Qualifiers
REGION                    1..20
                          note = Description of Artificial Sequence: Synthetic peptide
source                    1..20
                          mol_type = protein
                          organism = synthetic construct
SEQUENCE: 370
GGGGSGGGGS GGGGSGGGGS                                                     20

SEQ ID NO: 371            moltype = AA   length = 25
FEATURE                   Location/Qualifiers
REGION                    1..25
                          note = Description of Artificial Sequence: Synthetic peptide
source                    1..25
                          mol_type = protein
                          organism = synthetic construct
SEQUENCE: 371
GGGGSGGGGS GGGGSGGGGS GGGGS                                               25

SEQ ID NO: 372            moltype = AA   length = 30
FEATURE                   Location/Qualifiers
REGION                    1..30
                          note = Description of Artificial Sequence: Synthetic
                           polypeptide
source                    1..30
                          mol_type = protein
                          organism = synthetic construct
SEQUENCE: 372
GGGGSGGGGS GGGGSGGGGS GGGGSGGGGS                                          30

SEQ ID NO: 373            moltype = AA   length = 35
FEATURE                   Location/Qualifiers
REGION                    1..35
                          note = Description of Artificial Sequence: Synthetic
                           polypeptide
source                    1..35
                          mol_type = protein
```

-continued

```
                         organism = synthetic construct
SEQUENCE: 373
GGGGSGGGGS GGGGSGGGGS GGGGSGGGGS GGGGS                                   35

SEQ ID NO: 374          moltype = AA   length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 374
EPKSCDKTHT CPPCP                                                         15

SEQ ID NO: 375          moltype = AA   length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 375
GGGGSGGGSE PKSCDKTHTC PPCP                                               24

SEQ ID NO: 376          moltype = AA   length = 62
FEATURE                 Location/Qualifiers
REGION                  1..62
                        note = Description of Artificial Sequence: Synthetic
                         polypeptide
source                  1..62
                        mol_type = protein
                        organism = synthetic construct
SEQUENCE: 376
ELKTPLGDTT HTCPRCPEPK SCDTPPPCPR CPEPKSCDTP PPCPRCPEPK SCDTPPPCPR   60
CP                                                                      62

SEQ ID NO: 377          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 377
GSGSGS                                                                   6

SEQ ID NO: 378          moltype =    length =
SEQUENCE: 378
000

SEQ ID NO: 379          moltype = AA   length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 379
TSGQAGQHHH HHHGAYPYDV PDYAS                                              25

SEQ ID NO: 380          moltype = DNA   length = 75
FEATURE                 Location/Qualifiers
misc_feature            1..75
                        note = Description of Artificial Sequence: Synthetic
                         oligonucleotide
source                  1..75
                        mol_type = other DNA
                        organism = synthetic construct
SEQUENCE: 380
actagtggcc aggccggcca gcaccatcac catcaccatg gcgcataccc gtacgacgtt   60
ccggactacg cttct                                                        75

SEQ ID NO: 381          moltype = DNA   length = 363
FEATURE                 Location/Qualifiers
misc_feature            1..363
                        note = Description of Artificial Sequence: Synthetic
                         polynucleotide
source                  1..363
                        mol_type = other DNA
```

-continued

```
                         organism = synthetic construct
SEQUENCE: 381
caggtgcagc tggtgcagtc tggggctgag gtgaagaagc ctgggtcctc ggtgaaggtc    60
tcctgcaagg cttctggagg caccttccgc agctatgcta tcacctgggt gcgacaggcc   120
cctggacaag ggcttgagtg gatgggaagg atcatcccta tgcttgatat aacaaactac   180
gcacagaagt tccagggcag agtcacgatt accgcggaca aatccacgag cacagcctac   240
atggagctga gcagcctgag atctgaggac acggccgtgt attactgtgc gcgcacttac   300
tctcgttctc cgttccatat ggaagatttc tggggtcaag gtactctggt gaccgtctcc   360
tca                                                                363

SEQ ID NO: 382          moltype = AA  length = 33
FEATURE                 Location/Qualifiers
REGION                  1..33
                        note = Description of Artificial Sequence: Synthetic
                         polypeptide
source                  1..33
                        mol_type = protein
                        organism = synthetic construct
SEQUENCE: 382
CLSSERERVE DLFEYECELL TSEPIFHCRQ EDC                                 33

SEQ ID NO: 383          moltype = AA  length = 10
FEATURE                 Location/Qualifiers
source                  1..10
                        mol_type = protein
                        organism = Homo sapiens
SEQUENCE: 383
CDAEGPWGII                                                          10

SEQ ID NO: 384          moltype = AA  length = 8
FEATURE                 Location/Qualifiers
source                  1..8
                        mol_type = protein
                        organism = Homo sapiens
SEQUENCE: 384
MFVNMTPC                                                             8

SEQ ID NO: 385          moltype = AA  length = 9
FEATURE                 Location/Qualifiers
source                  1..9
                        mol_type = protein
                        organism = Homo sapiens
SEQUENCE: 385
PQFQRQPQW                                                           9

SEQ ID NO: 386          moltype = AA  length = 13
FEATURE                 Location/Qualifiers
source                  1..13
                        mol_type = protein
                        organism = Homo sapiens
SEQUENCE: 386
CIESTGDYFL LCD                                                      13

SEQ ID NO: 387          moltype = AA  length = 11
FEATURE                 Location/Qualifiers
source                  1..11
                        mol_type = protein
                        organism = Homo sapiens
SEQUENCE: 387
NQQTAPVRYF L                                                        11

SEQ ID NO: 388          moltype = AA  length = 8
FEATURE                 Location/Qualifiers
source                  1..8
                        mol_type = protein
                        organism = Homo sapiens
SEQUENCE: 388
GDYFLLCD                                                             8

SEQ ID NO: 389          moltype = AA  length = 11
FEATURE                 Location/Qualifiers
source                  1..11
                        mol_type = protein
                        organism = Homo sapiens
SEQUENCE: 389
MFVNMTPCQL N                                                        11

SEQ ID NO: 390          moltype = AA  length = 11
FEATURE                 Location/Qualifiers
```

```
source                    1..11
                          mol_type = protein
                          organism = Homo sapiens
SEQUENCE: 390
GNPQFQRQPQ W                                                        11

SEQ ID NO: 391            moltype = AA   length = 9
FEATURE                   Location/Qualifiers
source                    1..9
                          mol_type = protein
                          organism = Homo sapiens
SEQUENCE: 391
LCDAEGPWG                                                           9

SEQ ID NO: 392            moltype = AA   length = 14
FEATURE                   Location/Qualifiers
source                    1..14
                          mol_type = protein
                          organism = Homo sapiens
SEQUENCE: 392
QFQRQPQWDD PVVC                                                     14

SEQ ID NO: 393            moltype = AA   length = 33
FEATURE                   Location/Qualifiers
REGION                    1..33
                          note = Description of Artificial Sequence: Synthetic
                           polypeptide
source                    1..33
                          mol_type = protein
                          organism = synthetic construct
SEQUENCE: 393
CMDYDFKVKL SSERERCWAI GCIFAELLTS EPC                                33

SEQ ID NO: 394            moltype = AA   length = 33
FEATURE                   Location/Qualifiers
REGION                    1..33
                          note = Description of Artificial Sequence: Synthetic
                           polypeptide
source                    1..33
                          mol_type = protein
                          organism = synthetic construct
SEQUENCE: 394
CMDYDFKVKL SSERERCCIF AELLTSEPIF HCC                                33

SEQ ID NO: 395            moltype = AA   length = 33
FEATURE                   Location/Qualifiers
REGION                    1..33
                          note = Description of Artificial Sequence: Synthetic
                           polypeptide
source                    1..33
                          mol_type = protein
                          organism = synthetic construct
SEQUENCE: 395
CMDYDFKVKL SSERERCELL TSEPIFHCRQ EDC                                33

SEQ ID NO: 396            moltype = AA   length = 33
FEATURE                   Location/Qualifiers
REGION                    1..33
                          note = Description of Artificial Sequence: Synthetic
                           polypeptide
source                    1..33
                          mol_type = protein
                          organism = synthetic construct
SEQUENCE: 396
CMDYDFKVKL SSERERCSEP IFHCRQEDIK TSC                                33

SEQ ID NO: 397            moltype = AA   length = 33
FEATURE                   Location/Qualifiers
REGION                    1..33
                          note = Description of Artificial Sequence: Synthetic
                           polypeptide
source                    1..33
                          mol_type = protein
                          organism = synthetic construct
SEQUENCE: 397
CFKVKLSSER ERVEDLCWAI GCIFAELLTS EPC                                33

SEQ ID NO: 398            moltype = AA   length = 33
FEATURE                   Location/Qualifiers
```

-continued

```
REGION                   1..33
                         note = Description of Artificial Sequence: Synthetic
                          polypeptide
source                   1..33
                         mol_type = protein
                         organism = synthetic construct
SEQUENCE: 398
CFKVKLSSER ERVEDLCCIF AELLTSEPIF HCC                                  33

SEQ ID NO: 399           moltype = AA   length = 33
FEATURE                  Location/Qualifiers
REGION                   1..33
                         note = Description of Artificial Sequence: Synthetic
                          polypeptide
source                   1..33
                         mol_type = protein
                         organism = synthetic construct
SEQUENCE: 399
CFKVKLSSER ERVEDLCELL TSEPIFHCRQ EDC                                  33

SEQ ID NO: 400           moltype = AA   length = 33
FEATURE                  Location/Qualifiers
REGION                   1..33
                         note = Description of Artificial Sequence: Synthetic
                          polypeptide
source                   1..33
                         mol_type = protein
                         organism = synthetic construct
SEQUENCE: 400
CFKVKLSSER ERVEDLCSEP IFHCRQEDIK TSC                                  33

SEQ ID NO: 401           moltype = AA   length = 33
FEATURE                  Location/Qualifiers
REGION                   1..33
                         note = Description of Artificial Sequence: Synthetic
                          polypeptide
source                   1..33
                         mol_type = protein
                         organism = synthetic construct
SEQUENCE: 401
CLSSERERVE DLFEYECWAI GCIFAELLTS EPC                                  33

SEQ ID NO: 402           moltype = AA   length = 33
FEATURE                  Location/Qualifiers
REGION                   1..33
                         note = Description of Artificial Sequence: Synthetic
                          polypeptide
source                   1..33
                         mol_type = protein
                         organism = synthetic construct
SEQUENCE: 402
CLSSERERVE DLFEYECCIF AELLTSEPIF HCC                                  33

SEQ ID NO: 403           moltype = AA   length = 33
FEATURE                  Location/Qualifiers
REGION                   1..33
                         note = Description of Artificial Sequence: Synthetic
                          polypeptide
source                   1..33
                         mol_type = protein
                         organism = synthetic construct
SEQUENCE: 403
CLSSERERVE DLFEYECSEP IFHCRQEDIK TSC                                  33

SEQ ID NO: 404           moltype = AA   length = 33
FEATURE                  Location/Qualifiers
REGION                   1..33
                         note = Description of Artificial Sequence: Synthetic
                          polypeptide
source                   1..33
                         mol_type = protein
                         organism = synthetic construct
SEQUENCE: 404
CRERVEDLFE YEGCKVCWAI GCIFAELLTS EPC                                  33

SEQ ID NO: 405           moltype = AA   length = 33
FEATURE                  Location/Qualifiers
REGION                   1..33
                         note = Description of Artificial Sequence: Synthetic
```

-continued

```
                          polypeptide
source                    1..33
                          mol_type = protein
                          organism = synthetic construct
SEQUENCE: 405
CRERVEDLFE YEGCKVCCIF AELLTSEPIF HCC                             33

SEQ ID NO: 406            moltype = AA  length = 33
FEATURE                   Location/Qualifiers
REGION                    1..33
                          note = Description of Artificial Sequence: Synthetic
                          polypeptide
source                    1..33
                          mol_type = protein
                          organism = synthetic construct
SEQUENCE: 406
CRERVEDLFE YEGCKVCELL TSEPIFHCRQ EDC                             33

SEQ ID NO: 407            moltype = AA  length = 33
FEATURE                   Location/Qualifiers
REGION                    1..33
                          note = Description of Artificial Sequence: Synthetic
                          polypeptide
source                    1..33
                          mol_type = protein
                          organism = synthetic construct
SEQUENCE: 407
CRERVEDLFE YEGCKVCSEP IFHCRQEDIK TSC                             33

SEQ ID NO: 408            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 408
MDYDFKVKLS SERER                                                 15

SEQ ID NO: 409            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 409
FKVKLSSERE RVEDL                                                 15

SEQ ID NO: 410            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 410
LSSERERVED LFEYE                                                 15

SEQ ID NO: 411            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 411
RERVEDLFEY EGCKV                                                 15

SEQ ID NO: 412            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 412
WAIGCIFAEL LTSEP                                                 15
```

-continued

```
SEQ ID NO: 413           moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 413
CIFAELLTSE PIFHC                                                15

SEQ ID NO: 414           moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 414
ELLTSEPIFH CRQED                                                15

SEQ ID NO: 415           moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 415
SEPIFHCRQE DIKTS                                                15
```

ANTIBODIES TARGETING G-PROTEIN COUPLED RECEPTOR AND METHODS OF USE

CROSS-REFERENCE TO RELATED APPLICATIONS

This application is a Continuation of U.S. patent application Ser. No. 16/732,022, filed Dec. 31, 2019, which is a Divisional of U.S. Pat. No. 10,590,196, filed Jun. 5, 2017, which is a Continuation of International Patent Application No. PCT/US2015/064122, filed Dec. 4, 2015, which claims priority to U.S. Provisional Application Ser. No. 62/088,228, filed Dec. 5, 2014, the contents of each of which are incorporated by reference in their entireties, and to each of which priority is claimed.

SEQUENCE LISTING

The specification further incorporates by reference the Sequence Listing submitted herewith on Dec. 22, 2022. Pursuant to 37 C.F.R. § 1.52(e)(5), the Sequence Listing file, identified as 089333.0491.xml, is 539,543 bytes and was created on Dec. 21, 2022. The Sequence Listing electronically filed herewith, does not extend beyond the scope of the specification and thus does not contain new matter.

FIELD OF THE INVENTION

The presently disclosed subject matter relates to human antibodies that bind to a G-protein coupled receptor (e.g., a G-protein coupled receptor family C group 5 member D (GPRC5D)), and methods of using the same.

BACKGROUND

G protein-coupled receptors, also known as seven-transmembrane domain receptors, 7TM receptors, heptahelical receptors, serpentine receptor, and G protein-linked receptors, constitute a large protein family of receptors that sense molecules outside the cell and activate inside signal transduction pathways and, ultimately, cellular responses. GPCRs can be categorized into six classes based on sequence homology and functional similarity: Class A (Rhodopsin-like), Class B (Secretin receptor family), Class C (Metabotropic glutamate/pheromone), Class D (Fungal mating pheromone receptors), Class E (Cyclic AMP receptors), and Class F (Frizzled/Smoothened).

G-protein coupled receptor family C group 5 member D (GPRC5D) is an orphan receptor with no known ligand or function in humans. It is a member of a family of retinoic acid-inducible G-protein-coupled receptors. It is overexpressed in multiple myeloma (MM) cells and is not expressed or expressed in a significantly lower level by any other cell type, benign or malignant, as shown in FIG. 1. Several groups have identified this gene as highly differentially expressed by gene expression profiling of primary MM cells when compared to normal tissue1 or other hematologic malignancies (Frigyesi, I., et al. Robust isolation of malignant plasma cells in multiple myeloma. Blood 123, 1336-1340 (2014); Cohen, Y., Gutwein, O., Garach-Jehoshua, O., Bar-Haim, A. & Kornberg, A. GPRC5D is a promising marker for monitoring the tumor load and to target multiple myeloma cells. Hematology (Amsterdam, Netherlands) 18, 348-351 (2013); Bam, R., et al. GPRC5D Is a Cell Surface Plasma Cell Marker Whose Expression Is High In Myeloma Cells and Reduced Following Coculture With Osteoclasts.

Blood 122, 3099 (2013)). It has been shown that higher mRNA expression correlates with worse overall survival (Atamaniuk, J., et al. Overexpression of G protein-coupled receptor 5D in the bone marrow is associated with poor prognosis in patients with multiple myeloma. European journal of clinical investigation 42, 953-960 (2012)). Surface staining of Bone marrow aspirates from patients with MM demonstrate plasma cell specific staining (Bam, R., et al. GPRC5D Is a Cell Surface Plasma Cell Marker Whose Expression Is High In Myeloma Cells and Reduced Following Coculture With Osteoclasts. Blood 122, 3099 (2013)). Given the significant role for GPRC5D in multiple myeloma, antibodies that recognize GPRC5D, and methods of using such agents, are desired.

SUMMARY

The presently disclosed subject matter provides human antibodies that bind to a G-protein coupled receptor (e.g., GPRC5D), and methods of using the same.

In certain embodiments, the presently disclosed subject matter provides an isolated antibody, or an antigen-binding fragment thereof, comprising a heavy chain variable region comprising an amino acid sequence that is at least about 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOS: 1, 5, 9, 13, 17, 21, 25, 29, 33, 37, 41, 45, 49, 53, 57, 61, 65, 69, 73, 77, 81, 85, 89, 93, 274, 286, 298, 310, 322, 334, 346 and 358, wherein the antibody or antigen-binding fragment thereof specifically binds to human GPRC5D.

In certain embodiments, the presently disclosed subject matter provides an isolated antibody, or an antigen-binding fragment thereof, comprising a light chain variable region comprising an amino acid sequence that is at least about 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, 94, 275, 287, 299, 311, 323, 335, 347 and 359, wherein the antibody or antigen-binding fragment thereof specifically binds to human GPRC5D.

In certain embodiments, the presently disclosed subject matter provides an isolated antibody, or an antigen-binding fragment thereof, comprising (a) a heavy chain variable region comprising an amino acid sequence that is at least about 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOS: 1, 5, 9, 13, 17, 21, 25, 29, 33, 37, 41, 45, 49, 53, 57, 61, 65, 69, 73, 77, 81, 85, 89, 93, 274, 286, 298, 310, 322, 334, 346 and 358; and (b) a light chain variable region comprising an amino acid sequence that is at least about 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, 94, 275, 287, 299, 311, 323, 335, 347 and 359, wherein the antibody or antigen-binding fragment thereof specifically binds to human GPRC5D.

In certain embodiments, the presently disclosed subject matter provides an isolated antibody, or an antigen-binding fragment thereof, comprising a heavy chain variable region and a light chain variable region, wherein the heavy chain variable region and the light chain variable region are selected from the group consisting of: (i) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:1, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:2; (ii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:5, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:6; (iii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:9, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:10; (iv) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:13, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:14; (v) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:17, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:18; (vi) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:21, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:22; (vii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:25, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:26; (viii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:29, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:30; (ix) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:33, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:34; (x) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:37, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:38; (xi) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:41, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:42; (xii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:45, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:46; (xiii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:49, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:50; (xiv) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:53, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:54; (xv) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:57, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:58; (xvi) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:61, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:62; (xvii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:65, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:66; (xviii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:69, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:70; (xix) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:73, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:74; (xx) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:77, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:78; (xxi) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:81, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:82; (xxii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:85, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:86; (xxiii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:89, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:90; (xxiv) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:93, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:94; (xxv) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:274, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:275; (xxvi) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:286, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:287; (xxvii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:298, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:299; (xxviii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:310, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:311; (xxix) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:322, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:323; (xxx) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:334, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:335; (xxxi) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:346, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:347; or (xxxii) a heavy chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:358, and a light chain variable region comprising amino acids having a sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the sequence set forth in SEQ ID NO:359, wherein the antibody or antigen-binding fragment thereof specifically binds to human GPRC5D.

In certain embodiments, the antibody or antigen-binding fragment comprises: (i) a heavy chain variable region comprising amino acids having a sequence set forth in SEQ ID NO:1, and a light chain variable region comprising amino acids having a sequence set forth in SEQ ID NO:2; (ii) a heavy chain variable region comprising amino acids having a sequence set forth in SEQ ID NO:5, and a light chain variable region comprising amino acids having a sequence set forth in SEQ ID NO:6; (iii) a heavy chain variable region comprising amino acids having a sequence set forth in SEQ ID NO:9, and a light chain variable region comprising amino acids having a sequence set forth in SEQ ID NO:10; (iv) a heavy chain variable region comprising amino acids having a sequence set forth in SEQ ID NO:13, and a light chain variable region comprising amino acids having a sequence set forth in SEQ ID NO:14; (v) a heavy chain variable region comprising amino acids having a sequence set forth in SEQ ID NO:17, and a light chain variable region comprising amino acids having a sequence set forth in SEQ ID NO:18; (vi) a heavy chain variable region comprising amino acids having a sequence set forth in SEQ ID NO:21, and a light chain variable region comprising amino acids having a sequence set forth in SEQ ID NO:22; (vii) a heavy chain variable region comprising amino acids having a sequence set forth in SEQ ID NO:25, and a light chain variable region comprising amino acids having a sequence set forth in SEQ ID NO:26; (viii) a heavy chain variable region comprising amino acids having a sequence set forth in SEQ ID NO:29, and a light chain variable region comprising amino acids having a sequence set forth in SEQ ID NO:30; (ix) a heavy chain variable region comprising amino acids having a sequence set forth in SEQ ID NO:33, and a light chain variable region comprising amino acids having a sequence set forth in SEQ ID NO:34; (x) a heavy chain variable region comprising amino acids having a sequence set forth in SEQ ID NO:37, and a light chain variable region comprising amino acids having a sequence set forth in SEQ ID NO:38; (xi) a heavy chain variable region comprising amino acids having a sequence set forth in SEQ ID NO:41, and a light chain variable region comprising amino acids having a sequence set forth in SEQ ID NO:42; (xii) a heavy chain variable region comprising amino acids having a sequence set forth in SEQ ID NO:45, and a light chain variable region comprising amino acids having a sequence set forth in SEQ ID NO:46; (xiii) a heavy chain variable region comprising amino acids having a sequence set forth in SEQ ID NO:49, and a light chain variable region comprising amino acids having a sequence set forth in SEQ ID NO:50; (xiv) a heavy chain variable region comprising amino acids having a sequence set forth in SEQ ID NO:53, and a light chain variable region comprising amino acids having a sequence set forth in SEQ ID NO:54; (xv) a heavy chain variable region comprising amino acids having a sequence set forth in SEQ ID NO:57, and a light chain variable region comprising amino acids having a sequence set forth in SEQ ID NO:58; (xvi) a heavy chain variable region comprising amino acids having a sequence set forth in SEQ ID NO:61, and a light chain variable region comprising amino acids having a sequence set forth in SEQ ID NO:62; (xvii) a heavy chain variable region comprising amino acids having a sequence set forth in SEQ ID NO:65, and a light chain variable region comprising amino acids having a sequence set forth in SEQ ID NO:66; (xviii) a heavy chain variable region comprising amino acids having a sequence set forth in SEQ ID NO:69, and a light chain variable region comprising amino acids having a sequence set forth in SEQ ID NO:70; (xix) a heavy chain variable region comprising amino acids having a sequence set forth in SEQ ID NO:73, and a light chain variable region comprising amino acids having a sequence set forth in SEQ ID NO:74; (xx) a heavy chain variable region comprising amino acids having a sequence set forth in SEQ ID NO:77, and a light chain variable region comprising amino acids having a sequence set forth in SEQ ID NO:78; (xxi) a heavy chain variable region comprising amino acids having a sequence set forth in SEQ ID NO:81, and a light chain variable region comprising amino acids having a sequence set forth in SEQ ID NO:82; (xxii) a heavy chain variable region comprising amino acids having a sequence set forth in SEQ ID NO:85, and a light chain variable region comprising amino acids having a sequence set forth in SEQ ID NO:86; (xxiii) a heavy chain variable region comprising amino acids having a sequence set forth in SEQ ID NO:89, and a light chain variable region comprising amino acids having a sequence set forth in SEQ ID NO:90; (xxiv) a heavy chain variable region comprising amino acids having a sequence set forth in SEQ ID NO:93, and a light chain variable region comprising amino acids having a sequence set forth in SEQ ID NO:94; (xxv) a heavy chain variable region comprising amino acids having a sequence set forth in SEQ ID NO:274, and a light chain variable region comprising amino acids having a set forth in SEQ ID NO:275; (xxvi) a heavy chain variable region comprising amino acids having a sequence set forth in SEQ ID NO:286, and a light chain variable region comprising amino acids having a sequence set forth in SEQ ID NO:287; (xxvii) a heavy chain variable region comprising amino acids having a sequence set forth in SEQ ID NO:298, and a light chain variable region comprising amino acids having a sequence set forth in SEQ ID NO:299; (xxviii) a heavy chain variable region comprising amino acids having a sequence set forth in SEQ ID NO:310, and a light chain variable region comprising amino acids having a sequence set forth in SEQ ID NO:311; (xxix) a heavy chain variable region comprising amino acids having a sequence set forth in SEQ ID NO:322, and a light chain variable region comprising amino acids having a sequence set forth in SEQ ID NO:323; (xxx) a heavy chain variable region comprising amino acids having a sequence set forth in SEQ ID NO:334, and a light chain variable region comprising amino acids having a sequence set forth in SEQ ID NO:335; (xxxi) a heavy chain variable region comprising amino acids having a sequence set forth in SEQ ID NO:346, and a light chain variable region comprising amino acids having a sequence set forth in SEQ ID NO:347; or (xxxii) a heavy chain variable region comprising amino acids having a sequence set forth in SEQ ID NO:358, and a light chain variable region comprising amino acids having a sequence set forth in SEQ ID NO:359.

In certain embodiments, the presently disclosed subject matter provides an isolated antibody, or an antigen-binding fragment thereof, comprising a heavy chain variable region comprising an amino acid sequence selected from the group consisting of SEQ ID NOS: 1, 5, 9, 13, 17, 21, 25, 29, 33, 37, 41, 45, 49, 53, 57, 61, 65, 69, 73, 77, 81, 85, 89, 93, 274, 286, 298, 310, 322, 334, 346 and 358, and conservative modifications thereof, wherein the antibody or antigen-binding fragment thereof specifically binds to human GPRC5D.

In certain embodiments, the presently disclosed subject matter provides an isolated antibody, or an antigen-binding fragment thereof, comprising a light chain variable region comprising an amino acid sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, 94, 275, 287, 299, 311, 323, 335, 347 and 359, and conservative modifications thereof, wherein the antibody or antigen-binding fragment thereof specifically binds to human GPRC5D.

In certain embodiments, the presently disclosed subject matter provides an isolated antibody, or an antigen-binding fragment thereof, comprising: a heavy chain variable region comprising an amino acid sequence selected from the group consisting of SEQ ID NOS: 1, 5, 9, 13, 17, 21, 25, 29, 33, 37, 41, 45, 49, 53, 57, 61, 65, 69, 73, 77, 81, 85, 89, 93, 274, 286, 298, 310, 322, 334, 346 and 358, and conservative modifications thereof; and a light chain variable region comprising an amino acid sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, 94, 275, 287, 299, 311, 323, 335, 347 and 359, and conservative modifications thereof, wherein the antibody or antigen-binding fragment thereof specifically binds to human GPRC5D.

The presently disclosed subject matter also provides an isolated antibody or antigen-binding fragment thereof comprising a heavy chain variable region that comprises CDR1, CDR2, and CDR3 domains; and a light chain variable region that comprises CDR1, CDR2, and CDR3 domains, wherein the heavy chain variable region and light chain variable region CDR3 domains are selected from the group consisting of:

(i) a heavy chain variable region CDR3 comprising amino acids having the sequence set forth in SEQ ID NO:126 and conservative modifications thereof; and a light chain variable region CDR3 comprising amino acids having the sequence set forth in SEQ ID NO: 129 and conservative modifications thereof;

(ii) a heavy chain variable region CDR3 comprising amino acids having the sequence set forth in SEQ ID NO: 132 and conservative modifications thereof; and a light chain variable region CDR3 comprising amino acids having the sequence set forth in SEQ ID NO: 135 and conservative modifications thereof;

(iii) a heavy chain variable region CDR3 comprising amino acids having the sequence set forth in SEQ ID NO: 138 and conservative modifications thereof; and a light chain variable region CDR3 comprising amino acids having the sequence set forth in SEQ ID NO:141 and conservative modifications thereof;

(iv) a heavy chain variable region CDR3 comprising amino acids having the sequence set forth in SEQ ID NO: 144 and conservative modifications thereof; and a light chain variable region CDR3 comprising amino acids having the sequence set forth in SEQ ID NO: 147 and conservative modifications thereof;

(v) a heavy chain variable region CDR3 comprising amino acids having the sequence set forth in SEQ ID NO:150 and conservative modifications thereof; and a light chain variable region CDR3 comprising amino acids having the sequence set forth in SEQ ID NO:153 and conservative modifications thereof;

(vi) a heavy chain variable region CDR3 comprising amino acids having the sequence set forth in SEQ ID NO: 156 and conservative modifications thereof; and a light chain variable region CDR3 comprising amino acids having the sequence set forth in SEQ ID NO: 159 and conservative modifications thereof;

(vii) a heavy chain variable region CDR3 comprising amino acids having the sequence set forth in SEQ ID NO: 162 and conservative modifications thereof; and a light chain variable region CDR3 comprising amino acids having the sequence set forth in SEQ ID NO: 165 and conservative modifications thereof;

(viii) a heavy chain variable region CDR3 comprising amino acids having the sequence set forth in SEQ ID NO: 168 and conservative modifications thereof; and a light chain variable region CDR3 comprising amino acids having the sequence set forth in SEQ ID NO:171 and conservative modifications thereof;

(ix) a heavy chain variable region CDR3 comprising amino acids having the sequence set forth in SEQ ID NO: 174 and conservative modifications thereof; and a light chain variable region CDR3 comprising amino acids having the sequence set forth in SEQ ID NO: 177 and conservative modifications thereof;

(x) a heavy chain variable region CDR3 comprising amino acids having the sequence set forth in SEQ ID NO:180 and conservative modifications thereof; and a light chain variable region CDR3 comprising amino acids having the sequence set forth in SEQ ID NO:183 and conservative modifications thereof;

(xi) a heavy chain variable region CDR3 comprising amino acids having the sequence set forth in SEQ ID NO: 186 and conservative modifications thereof; and a light chain variable region CDR3 comprising amino acids having the sequence set forth in SEQ ID NO: 189 and conservative modifications thereof;

(xii) a heavy chain variable region CDR3 comprising amino acids having the sequence set forth in SEQ ID NO: 192 and conservative modifications thereof; and a light chain variable region CDR3 comprising amino acids having the sequence set forth in SEQ ID NO:195 and conservative modifications thereof;

(xiii) a heavy chain variable region CDR3 comprising amino acids having the sequence set forth in SEQ ID NO: 198 and conservative modifications thereof; and a light chain variable region CDR3 comprising amino acids having the sequence set forth in SEQ ID NO: 201 and conservative modifications thereof;

(xiv) a heavy chain variable region CDR3 comprising amino acids having the sequence set forth in SEQ ID NO: 204 and conservative modifications thereof; and a light chain variable region CDR3 comprising amino acids having the sequence set forth in SEQ ID NO: 207 and conservative modifications thereof;

(xv) a heavy chain variable region CDR3 comprising amino acids having the sequence set forth in SEQ ID NO: 210 and conservative modifications thereof; and a light chain variable region CDR3 comprising amino acids having the sequence set forth in SEQ ID NO: 213 and conservative modifications thereof;

(xvi) a heavy chain variable region CDR3 comprising amino acids having the sequence set forth in SEQ ID NO: 216 and conservative modifications thereof; and a light chain variable region CDR3 comprising amino acids having the sequence set forth in SEQ ID NO: 219 and conservative modifications thereof;

(xvii) a heavy chain variable region CDR3 comprising amino acids having the sequence set forth in SEQ ID NO:222 and conservative modifications thereof; and a light chain variable region CDR3 comprising amino acids having the sequence set forth in SEQ ID NO:225 and conservative modifications thereof;

(xviii) a heavy chain variable region CDR3 comprising amino acids having the sequence set forth in SEQ ID NO: 228 and conservative modifications thereof; and a light chain variable region CDR3 comprising amino acids having the sequence set forth in SEQ ID NO: 231 and conservative modifications thereof;

(xix) a heavy chain variable region CDR3 comprising amino acids having the sequence set forth in SEQ ID NO: 234 and conservative modifications thereof; and a light chain variable region CDR3 comprising amino acids having the sequence set forth in SEQ ID NO:237 and conservative modifications thereof;

(xx) a heavy chain variable region CDR3 comprising amino acids having the sequence set forth in SEQ ID NO:240 and conservative modifications thereof; and a light chain variable region CDR3 comprising amino acids having the sequence set forth in SEQ ID NO: 243 and conservative modifications thereof;

(xxi) a heavy chain variable region CDR3 comprising amino acids having the sequence set forth in SEQ ID NO: 246 and conservative modifications thereof; and a light chain variable region CDR3 comprising amino acids having the sequence set forth in SEQ ID NO: 249 and conservative modifications thereof;

(xxii) a heavy chain variable region CDR3 comprising amino acids having the sequence set forth in SEQ ID NO: 252 and conservative modifications thereof; and a light chain variable region CDR3 comprising amino acids having the sequence set forth in SEQ ID NO: 255 and conservative modifications thereof;

(xxiii) a heavy chain variable region CDR3 comprising amino acids having the sequence set forth in SEQ ID NO: 258 and conservative modifications thereof; and a light chain variable region CDR3 comprising amino acids having the sequence set forth in SEQ ID NO: 261 and conservative modifications thereof;

(xxiv) a heavy chain variable region CDR3 comprising amino acids having the sequence set forth in SEQ ID NO: 264 and conservative modifications thereof; and a light chain variable region CDR3 comprising amino acids having the sequence set forth in SEQ ID NO: 267 and conservative modifications thereof;

(xxv) a heavy chain variable region CDR3 comprising amino acids having the sequence set forth in SEQ ID NO: 270 and conservative modifications thereof; and a light chain variable region CDR3 comprising amino acids having the sequence set forth in SEQ ID NO: 273 and conservative modifications thereof;

(xxvi) a heavy chain variable region CDR3 comprising amino acids having the sequence set forth in SEQ ID NO: 282 and conservative modifications thereof; and a light chain variable region CDR3 comprising amino acids having the sequence set forth in SEQ ID NO: 285 and conservative modifications thereof;

(xxvii) a heavy chain variable region CDR3 comprising amino acids having the sequence set forth in SEQ ID NO: 294 and conservative modifications thereof; and a light chain variable region CDR3 comprising amino acids having the sequence set forth in SEQ ID NO: 297 and conservative modifications thereof;

(xxviii) a heavy chain variable region CDR3 comprising amino acids having the sequence set forth in SEQ ID NO: 305 and conservative modifications thereof; and a light chain variable region CDR3 comprising amino acids having the sequence set forth in SEQ ID NO: 308 and conservative modifications thereof;

(xxix) a heavy chain variable region CDR3 comprising amino acids having the sequence set forth in SEQ ID NO: 318 and conservative modifications thereof; and a light chain variable region CDR3 comprising amino acids having the sequence set forth in SEQ ID NO: 321 and conservative modifications thereof;

(xxx) a heavy chain variable region CDR3 comprising amino acids having the sequence set forth in SEQ ID NO: 330 and conservative modifications thereof; and a light chain variable region CDR3 comprising amino acids having the sequence set forth in SEQ ID NO: 333 and conservative modifications thereof;

(xxxi) a heavy chain variable region CDR3 comprising amino acids having the sequence set forth in SEQ ID NO: 342 and conservative modifications thereof; and a light chain variable region CDR3 comprising amino acids having the sequence set forth in SEQ ID NO: 345 and conservative modifications thereof; and (xxxii) a heavy chain variable region CDR3 comprising amino acids having the sequence set forth in SEQ ID NO: 354 and conservative modifications thereof; and a light chain variable region CDR3 comprising amino acids having the sequence set forth in SEQ ID NO: 357 and conservative modifications thereof, wherein the antibody or antigen-binding portion thereof specifically binds to GPRC5D.

In certain embodiments, the heavy chain variable region and light chain variable region CDR2 domains the antibody or antigen-binding portion thereof are selected from the group consisting of:

(i) a heavy chain variable region CDR2 comprising amino acids having the sequence set forth in SEQ ID NO:125 and conservative modifications thereof; and a light chain variable region CDR2 comprising amino acids having the sequence set forth in SEQ ID NO: 128 and conservative modifications thereof;

(ii) a heavy chain variable region CDR2 comprising amino acids having the sequence set forth in SEQ ID NO: 131 and conservative modifications thereof; and a light chain variable region CDR2 comprising amino acids having the sequence set forth in SEQ ID NO: 134 and conservative modifications thereof;

(iii) a heavy chain variable region CDR2 comprising amino acids having the sequence set forth in SEQ ID NO: 137 and conservative modifications thereof; and a light chain variable region CDR2 comprising amino acids having the sequence set forth in SEQ ID NO: 140 and conservative modifications thereof;

(iv) a heavy chain variable region CDR2 comprising amino acids having the sequence set forth in SEQ ID NO: 143 and conservative modifications thereof; and a light chain variable region CDR2 comprising amino acids having the sequence set forth in SEQ ID NO: 146 and conservative modifications thereof;

(v) a heavy chain variable region CDR2 comprising amino acids having the sequence set forth in SEQ ID NO: 149 and conservative modifications thereof; and a light chain variable region CDR2 comprising amino acids having the sequence set forth in SEQ ID NO: 152 and conservative modifications thereof;

(vi) a heavy chain variable region CDR2 comprising amino acids having the sequence set forth in SEQ ID NO: 155 and conservative modifications thereof; and a light chain variable region CDR2 comprising amino acids having the sequence set forth in SEQ ID NO: 158 and conservative modifications thereof;

(vii) a heavy chain variable region CDR2 comprising amino acids having the sequence set forth in SEQ ID NO: 161 and conservative modifications thereof; and a light chain variable region CDR2 comprising amino acids having the sequence set forth in SEQ ID NO: 164 and conservative modifications thereof;

(viii) a heavy chain variable region CDR2 comprising amino acids having the sequence set forth in SEQ ID NO: 167 and conservative modifications thereof; and a light chain variable region CDR2 comprising amino acids having the sequence set forth in SEQ ID NO: 170 and conservative modifications thereof;

(ix) a heavy chain variable region CDR2 comprising amino acids having the sequence set forth in SEQ ID NO: 173 and conservative modifications thereof; and a light chain variable region CDR2 comprising amino acids having the sequence set forth in SEQ ID NO: 176 and conservative modifications thereof;

(x) a heavy chain variable region CDR2 comprising amino acids having the sequence set forth in SEQ ID NO:179 and conservative modifications thereof; and a light chain variable region CDR2 comprising amino acids having the sequence set forth in SEQ ID NO:182 and conservative modifications thereof;

(xi) a heavy chain variable region CDR2 comprising amino acids having the sequence set forth in SEQ ID NO: 185 and conservative modifications thereof; and a light chain variable region CDR2 comprising amino acids having the sequence set forth in SEQ ID NO: 188 and conservative modifications thereof;

(xii) a heavy chain variable region CDR2 comprising amino acids having the sequence set forth in SEQ ID NO:191 and conservative modifications thereof; and a light chain variable region CDR2 comprising amino acids having the sequence set forth in SEQ ID NO:194 and conservative modifications thereof;

(xiii) a heavy chain variable region CDR2 comprising amino acids having the sequence set forth in SEQ ID NO:197 and conservative modifications thereof; and a light chain variable region CDR2 comprising amino acids having the sequence set forth in SEQ ID NO:200 and conservative modifications thereof;

(xiv) a heavy chain variable region CDR2 comprising amino acids having the sequence set forth in SEQ ID NO: 203 and conservative modifications thereof; and a light chain variable region CDR2 comprising amino acids having the sequence set forth in SEQ ID NO: 206 and conservative modifications thereof;

(xv) a heavy chain variable region CDR2 comprising amino acids having the sequence set forth in SEQ ID NO: 209 and conservative modifications thereof; and a light chain variable region CDR2 comprising amino acids having the sequence set forth in SEQ ID NO: 212 and conservative modifications thereof;

(xvi) a heavy chain variable region CDR2 comprising amino acids having the sequence set forth in SEQ ID NO: 215 and conservative modifications thereof; and a light chain variable region CDR2 comprising amino acids having the sequence set forth in SEQ ID NO: 218 and conservative modifications thereof;

(xvii) a heavy chain variable region CDR2 comprising amino acids having the sequence set forth in SEQ ID NO: 221 and conservative modifications thereof; and a light chain variable region CDR2 comprising amino acids having the sequence set forth in SEQ ID NO: 224 and conservative modifications thereof;

(xviii) a heavy chain variable region CDR2 comprising amino acids having the sequence set forth in SEQ ID NO: 227 and conservative modifications thereof; and a light chain variable region CDR2 comprising amino acids having the sequence set forth in SEQ ID NO:230 and conservative modifications thereof;

(xix) a heavy chain variable region CDR2 comprising amino acids having the sequence set forth in SEQ ID NO:233 and conservative modifications thereof; and a light chain variable region CDR2 comprising amino acids having the sequence set forth in SEQ ID NO:236 and conservative modifications thereof;

(xx) a heavy chain variable region CDR2 comprising amino acids having the sequence set forth in SEQ ID NO:239 and conservative modifications thereof; and a light chain variable region CDR2 comprising amino acids having the sequence set forth in SEQ ID NO:242 and conservative modifications thereof;

(xxi) a heavy chain variable region CDR2 comprising amino acids having the sequence set forth in SEQ ID NO:245 and conservative modifications thereof; and a light chain variable region CDR2 comprising amino acids having the sequence set forth in SEQ ID NO:248 and conservative modifications thereof;

(xxii) a heavy chain variable region CDR2 comprising amino acids having the sequence set forth in SEQ ID NO:251 and conservative modifications thereof; and a light chain variable region CDR2 comprising amino acids having the sequence set forth in SEQ ID NO:254 and conservative modifications thereof;

(xxiii) a heavy chain variable region CDR2 comprising amino acids having the sequence set forth in SEQ ID NO:257 and conservative modifications thereof; and a light chain variable region CDR2 comprising amino acids having the sequence set forth in SEQ ID NO:260 and conservative modifications thereof;

(xxiv) a heavy chain variable region CDR2 comprising amino acids having the sequence set forth in SEQ ID NO:263 and conservative modifications thereof; and a light chain variable region CDR2 comprising amino acids having the sequence set forth in SEQ ID NO:266 and conservative modifications thereof;

(xxv) a heavy chain variable region CDR2 comprising amino acids having the sequence set forth in SEQ ID NO:269 and conservative modifications thereof; and a light chain variable region CDR2 comprising amino acids having the sequence set forth in SEQ ID NO:272 and conservative modifications thereof;

(xxvi) a heavy chain variable region CDR2 comprising amino acids having the sequence set forth in SEQ ID NO:281 and conservative modifications thereof; and a light chain variable region CDR2 comprising amino acids having the sequence set forth in SEQ ID NO:284 and conservative modifications thereof;

(xxvii) a heavy chain variable region CDR2 comprising amino acids having the sequence set forth in SEQ ID NO:293 and conservative modifications thereof; and a light chain variable region CDR2 comprising amino acids having the sequence set forth in SEQ ID NO:296 and conservative modifications thereof;

(xxviii) a heavy chain variable region CDR2 comprising amino acids having the sequence set forth in SEQ ID NO:304 and conservative modifications thereof; and a light chain variable region CDR2 comprising amino acids having the sequence set forth in SEQ ID NO:307 and conservative modifications thereof;

(xxix) a heavy chain variable region CDR2 comprising amino acids having the sequence set forth in SEQ ID NO:317 and conservative modifications thereof; and a light chain variable region CDR2 comprising amino acids having the sequence set forth in SEQ ID NO:320 and conservative modifications thereof;

(xxx) a heavy chain variable region CDR2 comprising amino acids having the sequence set forth in SEQ ID NO:329 and conservative modifications thereof; and a light chain variable region CDR2 comprising amino acids having the sequence set forth in SEQ ID NO:332 and conservative modifications thereof;

(xxxi) a heavy chain variable region CDR2 comprising amino acids having the sequence set forth in SEQ ID NO:341 and conservative modifications thereof; and a light chain variable region CDR2 comprising amino acids having the sequence set forth in SEQ ID NO:344 and conservative modifications thereof; and (xxxii) a heavy chain variable region CDR2 comprising amino acids having the sequence set forth in SEQ ID NO:353 and conservative modifications thereof; and a light chain variable region CDR2 comprising amino acids having the sequence set forth in SEQ ID NO:356 and conservative modifications thereof, wherein the antibody or antigen-binding portion thereof specifically binds to GPRC5D.

In certain embodiments, the heavy chain variable region and light chain variable region CDR1 domains of the antibody or antigen-binding portion thereof are selected from the group consisting of:

(i) a heavy chain variable region CDR1 comprising amino acids having the sequence set forth in SEQ ID NO:124 and conservative modifications thereof; and a light chain variable region CDR1 comprising amino acids having the sequence set forth in SEQ ID NO: 127 and conservative modifications thereof;

(ii) a heavy chain variable region CDR1 comprising amino acids having the sequence set forth in SEQ ID NO:130 and conservative modifications thereof; and a light chain variable region CDR1 comprising amino acids having the sequence set forth in SEQ ID NO:133 and conservative modifications thereof;

(iii) a heavy chain variable region CDR1 comprising amino acids having the sequence set forth in SEQ ID NO:136 and conservative modifications thereof; and a light chain variable region CDR1 comprising amino acids having the sequence set forth in SEQ ID NO:139 and conservative modifications thereof;

(iv) a heavy chain variable region CDR1 comprising amino acids having the sequence set forth in SEQ ID NO:142 and conservative modifications thereof; and a light chain variable region CDR1 comprising amino acids having the sequence set forth in SEQ ID NO:145 and conservative modifications thereof;

(v) a heavy chain variable region CDR1 comprising amino acids having the sequence set forth in SEQ ID NO:148 and conservative modifications thereof; and a light chain variable region CDR1 comprising amino acids having the sequence set forth in SEQ ID NO:151 and conservative modifications thereof;

(vi) a heavy chain variable region CDR1 comprising amino acids having the sequence set forth in SEQ ID NO:154 and conservative modifications thereof; and a light chain variable region CDR1 comprising amino acids having the sequence set forth in SEQ ID NO:157 and conservative modifications thereof;

(vii) a heavy chain variable region CDR1 comprising amino acids having the sequence set forth in SEQ ID NO:160 and conservative modifications thereof; and a light chain variable region CDR1 comprising amino acids having the sequence set forth in SEQ ID NO:163 and conservative modifications thereof;

(viii) a heavy chain variable region CDR1 comprising amino acids having the sequence set forth in SEQ ID NO:166 and conservative modifications thereof; and a light chain variable region CDR1 comprising amino acids having the sequence set forth in SEQ ID NO:169 and conservative modifications thereof;

(ix) a heavy chain variable region CDR1 comprising amino acids having the sequence set forth in SEQ ID NO:172 and conservative modifications thereof; and a light chain variable region CDR1 comprising amino acids having the sequence set forth in SEQ ID NO:175 and conservative modifications thereof;

(x) a heavy chain variable region CDR1 comprising amino acids having the sequence set forth in SEQ ID NO:178 and conservative modifications thereof; and a light chain variable region CDR1 comprising amino acids having the sequence set forth in SEQ ID NO:181 and conservative modifications thereof;

(xi) a heavy chain variable region CDR1 comprising amino acids having the sequence set forth in SEQ ID NO:184 and conservative modifications thereof; and a light chain variable region CDR1 comprising amino acids having the sequence set forth in SEQ ID NO:187 and conservative modifications thereof;

(xii) a heavy chain variable region CDR1 comprising amino acids having the sequence set forth in SEQ ID NO:190 and conservative modifications thereof; and a light chain variable region CDR1 comprising amino acids having the sequence set forth in SEQ ID NO:193 and conservative modifications thereof;

(xiii) a heavy chain variable region CDR1 comprising amino acids having the sequence set forth in SEQ ID NO:196 and conservative modifications thereof; and a light chain variable region CDR1 comprising amino acids having the sequence set forth in SEQ ID NO:199 and conservative modifications thereof;

(xiv) a heavy chain variable region CDR1 comprising amino acids having the sequence set forth in SEQ ID NO:202 and conservative modifications thereof; and a light chain variable region CDR1 comprising amino acids having the sequence set forth in SEQ ID NO:205 and conservative modifications thereof;

(xv) a heavy chain variable region CDR1 comprising amino acids having the sequence set forth in SEQ ID NO:208 and conservative modifications thereof; and a light chain variable region CDR1 comprising amino acids having the sequence set forth in SEQ ID NO:211 and conservative modifications thereof;

(xvi) a heavy chain variable region CDR1 comprising amino acids having the sequence set forth in SEQ ID NO:214 and conservative modifications thereof; and a light chain variable region CDR1 comprising amino acids having the sequence set forth in SEQ ID NO:217 and conservative modifications thereof;

(xvii) a heavy chain variable region CDR1 comprising amino acids having the sequence set forth in SEQ ID NO:220 and conservative modifications thereof; and a light chain variable region CDR1 comprising amino acids having the sequence set forth in SEQ ID NO:223 and conservative modifications thereof;

(xviii) a heavy chain variable region CDR1 comprising amino acids having the sequence set forth in SEQ ID NO:226 and conservative modifications thereof; and a light chain variable region CDR1 comprising amino acids having the sequence set forth in SEQ ID NO:229 and conservative modifications thereof;

(xix) a heavy chain variable region CDR1 comprising amino acids having the sequence set forth in SEQ ID NO:232 and conservative modifications thereof; and a light chain variable region CDR1 comprising amino acids having the sequence set forth in SEQ ID NO:235 and conservative modifications thereof;

(xx) a heavy chain variable region CDR1 comprising amino acids having the sequence set forth in SEQ ID NO:238 and conservative modifications thereof; and a light chain variable region CDR1 comprising amino acids having the sequence set forth in SEQ ID NO:241 and conservative modifications thereof;

(xxi) a heavy chain variable region CDR1 comprising amino acids having the sequence set forth in SEQ ID NO:244 and conservative modifications thereof; and a light chain variable region CDR1 comprising amino acids having the sequence set forth in SEQ ID NO:247 and conservative modifications thereof;

(xxii) a heavy chain variable region CDR1 comprising amino acids having the sequence set forth in SEQ ID NO:250 and conservative modifications thereof; and a light chain variable region CDR1 comprising amino acids having the sequence set forth in SEQ ID NO:253 and conservative modifications thereof;

(xxiii) a heavy chain variable region CDR1 comprising amino acids having the sequence set forth in SEQ ID NO:256 and conservative modifications thereof; and a light chain variable region CDR1 comprising amino acids having the sequence set forth in SEQ ID NO:259 and conservative modifications thereof;

(xxiv) a heavy chain variable region CDR1 comprising amino acids having the sequence set forth in SEQ ID NO:262 and conservative modifications thereof; and a light chain variable region CDR1 comprising amino acids having the sequence set forth in SEQ ID NO:265 and conservative modifications thereof;

(xxv) a heavy chain variable region CDR1 comprising amino acids having the sequence set forth in SEQ ID NO:268 and conservative modifications thereof; and a light chain variable region CDR1 comprising amino acids having the sequence set forth in SEQ ID NO:271 and conservative modifications thereof;

(xxvi) a heavy chain variable region CDR1 comprising amino acids having the sequence set forth in SEQ ID NO:280 and conservative modifications thereof; and a light chain variable region CDR1 comprising amino acids having the sequence set forth in SEQ ID NO:283 and conservative modifications thereof;

(xxvii) a heavy chain variable region CDR1 comprising amino acids having the sequence set forth in SEQ ID NO:292 and conservative modifications thereof; and a light chain variable region CDR1 comprising amino acids having the sequence set forth in SEQ ID NO:295 and conservative modifications thereof;

(xxviii) a heavy chain variable region CDR1 comprising amino acids having the sequence set forth in SEQ ID NO:303 and conservative modifications thereof; and a light chain variable region CDR1 comprising amino acids having the sequence set forth in SEQ ID NO:306 and conservative modifications thereof;

(xxix) a heavy chain variable region CDR1 comprising amino acids having the sequence set forth in SEQ ID NO:316 and conservative modifications thereof; and a light chain variable region CDR1 comprising amino acids having the sequence set forth in SEQ ID NO:319 and conservative modifications thereof;

(xxx) a heavy chain variable region CDR1 comprising amino acids having the sequence set forth in SEQ ID NO:328 and conservative modifications thereof; and a light chain variable region CDR1 comprising amino acids having the sequence set forth in SEQ ID NO:331 and conservative modifications thereof;

(xxxi) a heavy chain variable region CDR1 comprising amino acids having the sequence set forth in SEQ ID NO:340 and conservative modifications thereof; and a light chain variable region CDR1 comprising amino acids having the sequence set forth in SEQ ID NO:343 and conservative modifications thereof; and (xxxii) a heavy chain variable region CDR1 comprising amino acids having the sequence set forth in SEQ ID NO:352 and conservative modifications thereof; and a light chain variable region CDR1 comprising amino acids having the sequence set forth in SEQ ID NO:355 and conservative modifications thereof, wherein the antibody or antigen-binding portion thereof specifically binds to GPRC5D.

Furthermore, the presently disclosed subject matter provides an isolated antibody, or an antigen-binding portion thereof, comprising:

(i) a heavy chain variable region CDR1 comprising amino acids having the sequence set forth in SEQ ID NO: 124; a heavy chain variable region CDR2 comprising amino acids having the sequence set forth in SEQ ID NO: 125; and a heavy chain variable region CDR3 comprising amino acids having the sequence set forth in SEQ ID NO: 126;

(ii) a heavy chain variable region CDR1 comprising amino acids having the sequence set forth in SEQ ID NO: 130; a heavy chain variable region CDR2 comprising amino acids having the sequence set forth in SEQ ID NO: 131; and a heavy chain variable region CDR3 comprising amino acids having the sequence set forth in SEQ ID NO: 132;

(iii) a heavy chain variable region CDR1 comprising amino acids having the sequence set forth in SEQ ID NO: 136; a heavy chain variable region CDR2 comprising amino acids having the sequence set forth in SEQ ID NO: 137; and a heavy chain variable region CDR3 comprising amino acids having the sequence set forth in SEQ ID NO: 138;

(iv) a heavy chain variable region CDR1 comprising amino acids having the sequence set forth in SEQ ID NO: 142; a heavy chain variable region CDR2 comprising amino acids having the sequence set forth in SEQ ID NO: 143; and a heavy chain variable region CDR3 comprising amino acids having the sequence set forth in SEQ ID NO: 144;

(v) a heavy chain variable region CDR1 comprising amino acids having the sequence set forth in SEQ ID NO: 148; a heavy chain variable region CDR2 comprising amino acids having the sequence set forth in SEQ ID NO: 149; and a heavy chain variable region CDR3 comprising amino acids having the sequence set forth in SEQ ID NO: 150;

(vi) a heavy chain variable region CDR1 comprising amino acids having the sequence set forth in SEQ ID NO: 154; a heavy chain variable region CDR2 comprising amino acids having the sequence set forth in SEQ ID NO: 155; and a heavy chain variable region CDR3 comprising amino acids having the sequence set forth in SEQ ID NO: 156;

(vii) a heavy chain variable region CDR1 comprising amino acids having the sequence set forth in SEQ ID NO: 160; a heavy chain variable region CDR2 comprising amino acids having the sequence set forth in SEQ ID NO: 161; and a heavy chain variable region CDR3 comprising amino acids having the sequence set forth in SEQ ID NO: 162;

(viii) a heavy chain variable region CDR1 comprising amino acids having the sequence set forth in SEQ ID NO: 166; a heavy chain variable region CDR2 comprising amino acids having the sequence set forth in SEQ ID NO: 167; and a heavy chain variable region CDR3 comprising amino acids having the sequence set forth in SEQ ID NO: 168;

(ix) a heavy chain variable region CDR1 comprising amino acids having the sequence set forth in SEQ ID NO: 172; a heavy chain variable region CDR2 comprising amino acids having the sequence set forth in SEQ ID NO: 173; and a heavy chain variable region CDR3 comprising amino acids having the sequence set forth in SEQ ID NO: 174;

(x) a heavy chain variable region CDR1 comprising amino acids having the sequence set forth in SEQ ID NO: 178; a heavy chain variable region CDR2 comprising amino acids having the sequence set forth in SEQ ID NO: 179; and a heavy chain variable region CDR3 comprising amino acids having the sequence set forth in SEQ ID NO: 180;

(xi) a heavy chain variable region CDR1 comprising amino acids having the sequence set forth in SEQ ID NO: 184; a heavy chain variable region CDR2 comprising amino acids having the sequence set forth in SEQ ID NO: 185; and a heavy chain variable region CDR3 comprising amino acids having the sequence set forth in SEQ ID NO: 186;

(xii) a heavy chain variable region CDR1 comprising amino acids having the sequence set forth in SEQ ID NO: 190 a heavy chain variable region CDR2 comprising amino acids having the sequence set forth in SEQ ID NO: 191; and a heavy chain variable region CDR3 comprising amino acids having the sequence set forth in SEQ ID NO: 192;

(xiii) a heavy chain variable region CDR1 comprising amino acids having the sequence set forth in SEQ ID NO: 196; a heavy chain variable region CDR2 comprising amino acids having the sequence set forth in SEQ ID NO: 197; and a heavy chain variable region CDR3 comprising amino acids having the sequence set forth in SEQ ID NO: 198;

(xiv) a heavy chain variable region CDR1 comprising amino acids having the sequence set forth in SEQ ID NO: 202; a heavy chain variable region CDR2 comprising amino acids having the sequence set forth in SEQ ID NO: 203; and a heavy chain variable region CDR3 comprising amino acids having the sequence set forth in SEQ ID NO: 204;

(xv) a heavy chain variable region CDR1 comprising amino acids having the sequence set forth in SEQ ID NO: 208; a heavy chain variable region CDR2 comprising amino acids having the sequence set forth in SEQ ID NO: 209; and a heavy chain variable region CDR3 comprising amino acids having the sequence set forth in SEQ ID NO: 210;

(xvi) a heavy chain variable region CDR1 comprising amino acids having the sequence set forth in SEQ ID NO: 214; a heavy chain variable region CDR2 comprising amino acids having the sequence set forth in SEQ ID NO: 215; and a heavy chain variable region CDR3 comprising amino acids having the sequence set forth in SEQ ID NO: 216;

(xvii) a heavy chain variable region CDR1 comprising amino acids having the sequence set forth in SEQ ID NO: 220; a heavy chain variable region CDR2 comprising amino acids having the sequence set forth in SEQ ID NO: 221; and a heavy chain variable region CDR3 comprising amino acids having the sequence set forth in SEQ ID NO: 222;

(xviii) a heavy chain variable region CDR1 comprising amino acids having the sequence set forth in SEQ ID NO: 226; a heavy chain variable region CDR2 comprising amino acids having the sequence set forth in SEQ ID NO: 227; and a heavy chain variable region CDR3 comprising amino acids having the sequence set forth in SEQ ID NO: 228;

(xix) a heavy chain variable region CDR1 comprising amino acids having the sequence set forth in SEQ ID NO: 232; a heavy chain variable region CDR2 comprising amino acids having the sequence set forth in SEQ ID NO: 233; and a heavy chain variable region CDR3 comprising amino acids having the sequence set forth in SEQ ID NO: 234;

(xx) a heavy chain variable region CDR1 comprising amino acids having the sequence set forth in SEQ ID NO: 238; a heavy chain variable region CDR2 comprising amino acids having the sequence set forth in SEQ ID NO: 239; and a heavy chain variable region CDR3 comprising amino acids having the sequence set forth in SEQ ID NO: 240;

(xxi) a heavy chain variable region CDR1 comprising amino acids having the sequence set forth in SEQ ID NO: 244; a heavy chain variable region CDR2 comprising amino acids having the sequence set forth in SEQ ID NO: 245; and a heavy chain variable region CDR3 comprising amino acids having the sequence set forth in SEQ ID NO: 246;

(xxii) a heavy chain variable region CDR1 comprising amino acids having the sequence set forth in SEQ ID NO: 250; a heavy chain variable region CDR2 comprising amino acids having the sequence set forth in SEQ ID NO: 251; and a heavy chain variable region CDR3 comprising amino acids having the sequence set forth in SEQ ID NO: 252; and (xxiii) a heavy chain variable region CDR1 comprising amino acids having the sequence set forth in SEQ ID NO: 256; a heavy chain variable region CDR2 comprising amino acids having the sequence set forth in SEQ ID NO: 257; and a heavy chain variable region CDR3 comprising amino acids having the sequence set forth in SEQ ID NO: 258;

(xxiv) a heavy chain variable region CDR1 comprising amino acids having the sequence set forth in SEQ ID NO: 262; a heavy chain variable region CDR2 comprising amino acids having the sequence set forth in SEQ ID NO: 263; and a heavy chain variable region CDR3 comprising amino acids having the sequence set forth in SEQ ID NO: 264;

(xxv) a heavy chain variable region CDR1 comprising amino acids having the sequence set forth in SEQ ID NO: 268; a heavy chain variable region CDR2 comprising amino acids having the sequence set forth in SEQ ID NO: 269; and a heavy chain variable region CDR3 comprising amino acids having the sequence set forth in SEQ ID NO: 270;

(xxvi) a heavy chain variable region CDR1 comprising amino acids having the sequence set forth in SEQ ID NO: 280; a heavy chain variable region CDR2 comprising amino acids having the sequence set forth in SEQ ID NO: 281; and a heavy chain variable region CDR3 comprising amino acids having the sequence set forth in SEQ ID NO: 282;

(xxvii) a heavy chain variable region CDR1 comprising amino acids having the sequence set forth in SEQ ID NO: 292; a heavy chain variable region CDR2 comprising amino acids having the sequence set forth in SEQ ID NO: 293; and a heavy chain variable region CDR3 comprising amino acids having the sequence set forth in SEQ ID NO: 294;

(xxviii) a heavy chain variable region CDR1 comprising amino acids having the sequence set forth in SEQ ID NO: 303; a heavy chain variable region CDR2 comprising amino acids having the sequence set forth in SEQ ID NO: 304; and a heavy chain variable region CDR3 comprising amino acids having the sequence set forth in SEQ ID NO: 305;

(xxix) a heavy chain variable region CDR1 comprising amino acids having the sequence set forth in SEQ ID NO: 316; a heavy chain variable region CDR2 comprising amino acids having the sequence set forth in SEQ ID NO: 317; and a heavy chain variable region CDR3 comprising amino acids having the sequence set forth in SEQ ID NO: 318;

(xxx) a heavy chain variable region CDR1 comprising amino acids having the sequence set forth in SEQ ID NO: 328; a heavy chain variable region CDR2 comprising amino acids having the sequence set forth in SEQ ID NO: 329; and a heavy chain variable region CDR3 comprising amino acids having the sequence set forth in SEQ ID NO: 330;

(xxxi) a heavy chain variable region CDR1 comprising amino acids having the sequence set forth in SEQ ID NO: 340; a heavy chain variable region CDR2 comprising amino acids having the sequence set forth in SEQ ID NO: 341; and a heavy chain variable region CDR3 comprising amino acids having the sequence set forth in SEQ ID NO: 342; or (xxxii) a heavy chain variable region CDR1 comprising amino acids having the sequence set forth in SEQ ID NO: 352; a heavy chain variable region CDR2 comprising amino acids having the sequence set forth in SEQ ID NO: 353; and a heavy chain variable region CDR3 comprising amino acids having the sequence set forth in SEQ ID NO: 354;

wherein the antibody or antigen-binding portion thereof specifically binds to GPRC5D.

Additionally, the presently disclosed subject matter provides an isolated antibody, or an antigen-binding portion thereof, comprising:

(i) a light chain variable region CDR1 comprising amino acids having the sequence set forth in SEQ ID NO: 127; a light chain variable region CDR2 comprising amino acids having the sequence set forth in SEQ ID NO:129; and a light chain variable region CDR3 comprising amino acids having the sequence set forth in SEQ ID NO: 130;

(ii) a light chain variable region CDR1 comprising amino acids having the sequence set forth in SEQ ID NO: 133; a light chain variable region CDR2 comprising amino acids having the sequence set forth in SEQ ID NO:134; and a light chain variable region CDR3 comprising SEQ ID NO: 135;

(iii) a light chain variable region CDR1 comprising amino acids having the sequence set forth in SEQ ID NO: 139; a light chain variable region CDR2 comprising amino acids having the sequence set forth in SEQ ID NO:140; and a light chain variable region CDR3 comprising amino acids having the sequence set forth in SEQ ID NO: 141;

(iv) a light chain variable region CDR1 comprising amino acids having the sequence set forth in SEQ ID NO: 145; a light chain variable region CDR2 comprising SEQ ID NO:146; and a light chain variable region CDR3 comprising amino acids having the sequence set forth in SEQ ID NO: 147;

(v) a light chain variable region CDR1 comprising amino acids having the sequence set forth in SEQ ID NO: 151; a light chain variable region CDR2 comprising amino acids having the sequence set forth in SEQ ID NO:152; and a light chain variable region CDR3 comprising amino acids having the sequence set forth in SEQ ID NO: 153;

(vi) a light chain variable region CDR1 comprising amino acids having the sequence set forth in SEQ ID NO: 157; a light chain variable region CDR2 comprising amino acids having the sequence set forth in SEQ ID NO:158; and a light chain variable region CDR3 comprising amino acids having the sequence set forth in SEQ ID NO: 159;

(vii) a light chain variable region CDR1 comprising amino acids having the sequence set forth in SEQ ID NO: 163; a light chain variable region CDR2 comprising amino acids having the sequence set forth in SEQ ID NO:164; and a light chain variable region CDR3 comprising amino acids having the sequence set forth in SEQ ID NO: 165;

(viii) a light chain variable region CDR1 comprising amino acids having the sequence set forth in SEQ ID NO: 169; a light chain variable region CDR2 comprising amino acids having the sequence set forth in SEQ ID NO:170; and a light chain variable region CDR3 comprising SEQ ID NO: 171;

(ix) a light chain variable region CDR1 comprising amino acids having the sequence set forth in SEQ ID NO: 175; a light chain variable region CDR2 comprising amino acids having the sequence set forth in SEQ ID NO:176; and a light chain variable region CDR3 comprising amino acids having the sequence set forth in SEQ ID NO: 177;

(x) a light chain variable region CDR1 comprising amino acids having the sequence set forth in SEQ ID NO: 181; a light chain variable region CDR2 comprising amino acids having the sequence set forth in SEQ ID NO:182; and a light chain variable region CDR3 comprising amino acids having the sequence set forth in SEQ ID NO: 183;

(xi) a light chain variable region CDR1 comprising amino acids having the sequence set forth in SEQ ID NO: 187; a light chain variable region CDR2 comprising amino acids having the sequence set forth in SEQ ID NO:188; and a light chain variable region CDR3 comprising amino acids having the sequence set forth in SEQ ID NO: 189;

(xii) a light chain variable region CDR1 comprising amino acids having the sequence set forth in SEQ ID NO: 193; a light chain variable region CDR2 comprising amino acids having the sequence set forth in SEQ ID NO:194; and a light chain variable region CDR3 comprising amino acids having the sequence set forth in SEQ ID NO: 195;

(xiii) a light chain variable region CDR1 comprising amino acids having the sequence set forth in SEQ ID NO: 199; a light chain variable region CDR2 comprising amino acids having the sequence set forth in SEQ ID NO:200; and a light chain variable region CDR3 comprising amino acids having the sequence set forth in SEQ ID NO: 201;

(xiv) a light chain variable region CDR1 comprising amino acids having the sequence set forth in SEQ ID NO: 205; a light chain variable region CDR2 comprising amino acids having the sequence set forth in SEQ ID NO:206; and a light chain variable region CDR3 comprising amino acids having the sequence set forth in SEQ ID NO: 207;

(xv) a light chain variable region CDR1 comprising amino acids having the sequence set forth in SEQ ID NO: 211; a light chain variable region CDR2 comprising amino acids having the sequence set forth in SEQ ID NO:212; and a light chain variable region CDR3 comprising amino acids having the sequence set forth in SEQ ID NO: 213;

(xvi) a light chain variable region CDR1 comprising amino acids having the sequence set forth in SEQ ID NO: 217; a light chain variable region CDR2 comprising amino acids having the sequence set forth in SEQ ID NO:218; and a light chain variable region CDR3 comprising amino acids having the sequence set forth in SEQ ID NO: 219;

(xvii) a light chain variable region CDR1 comprising amino acids having the sequence set forth in SEQ ID NO: 223; a light chain variable region CDR2 comprising amino acids having the sequence set forth in SEQ ID NO:224; and a light chain variable region CDR3 comprising amino acids having the sequence set forth in SEQ ID NO: 225;

(xviii) a light chain variable region CDR1 comprising amino acids having the sequence set forth in SEQ ID NO: 229; a light chain variable region CDR2 comprising amino acids having the sequence set forth in SEQ ID NO:230; and a light chain variable region CDR3 comprising amino acids having the sequence set forth in SEQ ID NO: 231;

(xix) a light chain variable region CDR1 comprising amino acids having the sequence set forth in SEQ ID NO: 235; a light chain variable region CDR2 comprising amino acids having the sequence set forth in SEQ ID NO:236; and a light chain variable region CDR3 comprising amino acids having the sequence set forth in SEQ ID NO: 237;

(xx) a light chain variable region CDR1 comprising amino acids having the sequence set forth in SEQ ID NO: 241; a light chain variable region CDR2 comprising amino acids having the sequence set forth in SEQ ID NO:242; and a light chain variable region CDR3 comprising amino acids having the sequence set forth in SEQ ID NO: 243;

(xxi) a light chain variable region CDR1 comprising amino acids having the sequence set forth in SEQ ID NO: 247; a light chain variable region CDR2 comprising amino acids having the sequence set forth in SEQ ID NO:248; and a light chain variable region CDR3 comprising amino acids having the sequence set forth in SEQ ID NO: 249;

(xxii) a light chain variable region CDR1 comprising amino acids having the sequence set forth in SEQ ID NO: 253; a light chain variable region CDR2 comprising amino acids having the sequence set forth in SEQ ID NO:254; and a light chain variable region CDR3 comprising amino acids having the sequence set forth in SEQ ID NO: 255;

(xxiii) a light chain variable region CDR1 comprising amino acids having the sequence set forth in SEQ ID NO: 259; a light chain variable region CDR2 comprising amino acids having the sequence set forth in SEQ ID NO:250; and a light chain variable region CDR3 comprising amino acids having the sequence set forth in SEQ ID NO: 261; or (xxiv) a light chain variable region CDR1 comprising amino acids having the sequence set forth in SEQ ID NO: 265; a light chain variable region CDR2 comprising amino acids having the sequence set forth in SEQ ID NO:266; and a light chain variable region CDR3 comprising amino acids having the sequence set forth in SEQ ID NO: 267;

(xxv) a light chain variable region CDR1 comprising amino acids having the sequence set forth in SEQ ID NO: 271; a light chain variable region CDR2 comprising amino acids having the sequence set forth in SEQ ID NO:272; and a light chain variable region CDR3 comprising amino acids having the sequence set forth in SEQ ID NO: 273;

(xxvi) a light chain variable region CDR1 comprising amino acids having the sequence set forth in SEQ ID NO: 283; a light chain variable region CDR2 comprising amino acids having the sequence set forth in SEQ ID NO:284; and a light chain variable region CDR3 comprising amino acids having the sequence set forth in SEQ ID NO: 285;

(xxvii) a light chain variable region CDR1 comprising amino acids having the sequence set forth in SEQ ID NO: 295; a light chain variable region CDR2 comprising amino acids having the sequence set forth in SEQ ID NO:296; and a light chain variable region CDR3 comprising amino acids having the sequence set forth in SEQ ID NO: 297;

(xxviii) a light chain variable region CDR1 comprising amino acids having the sequence set forth in SEQ ID NO: 306; a light chain variable region CDR2 comprising amino acids having the sequence set forth in SEQ ID NO:307; and a light chain variable region CDR3 comprising amino acids having the sequence set forth in SEQ ID NO: 308;

(xxix) a light chain variable region CDR1 comprising amino acids having the sequence set forth in SEQ ID NO: 319; a light chain variable region CDR2 comprising amino acids having the sequence set forth in SEQ ID NO:320; and a light chain variable region CDR3 comprising amino acids having the sequence set forth in SEQ ID NO: 321;

(xxx) a light chain variable region CDR1 comprising amino acids having the sequence set forth in SEQ ID NO: 331; a light chain variable region CDR2 comprising amino acids having the sequence set forth in SEQ ID NO:332; and a light chain variable region CDR3 comprising amino acids having the sequence set forth in SEQ ID NO: 333;

(xxxi) a light chain variable region CDR1 comprising amino acids having the sequence set forth in SEQ ID NO: 343; a light chain variable region CDR2 comprising amino acids having the sequence set forth in SEQ ID NO:344; and a light chain variable region CDR3 comprising amino acids having the sequence set forth in SEQ ID NO: 345; or (xxxii) a light chain variable region CDR1 comprising amino acids having the sequence set forth in SEQ ID NO: 355; a light chain variable region CDR2 comprising amino acids having the sequence set forth in SEQ ID NO:356; and a light chain variable region CDR3 comprising amino acids having the sequence set forth in SEQ ID NO: 357, wherein the antibody or antigen-binding portion thereof specifically binds to GPRC5D.

The presently disclosed subject matter also provides an isolated antibody, or an antigen-binding portion thereof, comprising:

(i) a heavy chain variable region CDR1 comprising amino acids having the sequence set forth in SEQ ID NO: 124; a heavy chain variable region CDR2 comprising amino acids having the sequence set forth in SEQ ID NO: 125; a heavy chain variable region CDR3 comprising amino acids having the sequence set forth in SEQ ID NO: 126; a light chain variable region CDR1 comprising amino acids having the sequence set forth in SEQ ID NO: 127; a light chain variable region CDR2 comprising amino acids having the sequence set forth in SEQ ID NO:128; and a light chain variable region CDR3 comprising amino acids having the sequence set forth in SEQ ID NO: 129;

(ii) a heavy chain variable region CDR1 comprising amino acids having the sequence set forth in SEQ ID NO: 130; a heavy chain variable region CDR2 comprising amino acids having the sequence set forth in SEQ ID NO: 131; a heavy chain variable region CDR3 comprising amino acids having the sequence set forth in SEQ ID NO: 132; a light chain variable region CDR1 comprising amino acids having the sequence set forth in SEQ ID NO: 133; a light chain variable region CDR2 comprising amino acids having the sequence set forth in SEQ ID NO:134; and a light chain variable region CDR3 comprising amino acids having the sequence set forth in SEQ ID NO: 135;

(iii) a heavy chain variable region CDR1 comprising amino acids having the sequence set forth in SEQ ID NO: 136; a heavy chain variable region CDR2 comprising amino acids having the sequence set forth in SEQ ID NO: 137; a heavy chain variable region CDR3 comprising amino acids having the sequence set forth in SEQ ID NO: 138; a light chain variable region CDR1 comprising amino acids having the sequence set forth in SEQ ID NO: 139; a light chain variable region CDR2 comprising amino acids having the sequence set forth in SEQ ID NO:140; and a light chain variable region CDR3 comprising amino acids having the sequence set forth in SEQ ID NO: 141;

(iv) a heavy chain variable region CDR1 comprising amino acids having the sequence set forth in SEQ ID NO: 142; a heavy chain variable region CDR2 comprising amino acids having the sequence set forth in SEQ ID NO: 143; a heavy chain variable region CDR3 comprising amino acids having the sequence set forth in SEQ ID NO: 144; a light chain variable region CDR1 comprising amino acids having the sequence set forth in SEQ ID NO: 145; a light chain variable region CDR2 comprising amino acids having the sequence set forth in SEQ ID NO:146; and a light chain variable region CDR3 comprising amino acids having the sequence set forth in SEQ ID NO: 147;

(v) a heavy chain variable region CDR1 comprising amino acids having the sequence set forth in SEQ ID NO: 148; a heavy chain variable region CDR2 comprising amino acids having the sequence set forth in SEQ ID NO: 149; a heavy chain variable region CDR3 comprising amino acids having the sequence set forth in SEQ ID NO: 150; a light chain variable region CDR1 comprising amino acids having the sequence set forth in SEQ ID NO: 151; a light chain variable region CDR2 comprising amino acids having the sequence set forth in SEQ ID NO:152; and a light chain variable region CDR3 comprising amino acids having the sequence set forth in SEQ ID NO: 153;

(vi) a heavy chain variable region CDR1 comprising amino acids having the sequence set forth in SEQ ID NO: 154; a heavy chain variable region CDR2 comprising amino acids having the sequence set forth in SEQ ID NO: 155; a heavy chain variable region CDR3 comprising amino acids having the sequence set forth in SEQ ID NO: 156; a light chain variable region CDR1 comprising amino acids having the sequence set forth in SEQ ID NO: 157; a light chain variable region CDR2 comprising amino acids having the sequence set forth in SEQ ID NO:158; and a light chain variable region CDR3 comprising amino acids having the sequence set forth in SEQ ID NO: 159;

(vii) a heavy chain variable region CDR1 comprising amino acids having the sequence set forth in SEQ ID NO: 160; a heavy chain variable region CDR2 comprising amino acids having the sequence set forth in SEQ ID NO: 161; a heavy chain variable region CDR3 comprising amino acids having the sequence set forth in SEQ ID NO: 162; a light chain variable region CDR1 comprising amino acids having the sequence set forth in SEQ ID NO: 163; a light chain variable region CDR2 comprising amino acids having the sequence set forth in SEQ ID NO:164; and a light chain variable region CDR3 comprising amino acids having the sequence set forth in SEQ ID NO: 165;

(viii) a heavy chain variable region CDR1 comprising amino acids having the sequence set forth in SEQ ID NO: 166; a heavy chain variable region CDR2 comprising amino acids having the sequence set forth in SEQ ID NO: 167; a heavy chain variable region CDR3 comprising amino acids having the sequence set forth in SEQ ID NO: 168; a light chain variable region CDR1 comprising amino acids having the sequence set forth in SEQ ID NO: 169; a light chain variable region CDR2 comprising amino acids having the sequence set forth in SEQ ID NO:170; and a light chain variable region CDR3 comprising amino acids having the sequence set forth in SEQ ID NO: 171;

(ix) a heavy chain variable region CDR1 comprising amino acids having the sequence set forth in SEQ ID NO: 172; a heavy chain variable region CDR2 comprising amino acids having the sequence set forth in SEQ ID NO: 173; a heavy chain variable region CDR3 comprising amino acids having the sequence set forth in SEQ ID NO: 174; a light chain variable region CDR1 comprising amino acids having the sequence set forth in SEQ ID NO: 175; a light chain variable region CDR2 comprising amino acids having the sequence set forth in SEQ ID NO:176; and a light chain variable region CDR3 comprising amino acids having the sequence set forth in SEQ ID NO: 177;

(x) a heavy chain variable region CDR1 comprising amino acids having the sequence set forth in SEQ ID NO: 178; a heavy chain variable region CDR2 comprising amino acids having the sequence set forth in SEQ ID NO: 179; a heavy chain variable region CDR3 comprising amino acids having the sequence set forth in SEQ ID NO: 180; a light chain variable region CDR1 comprising amino acids having the sequence set forth in SEQ ID NO: 181; a light chain variable region CDR2 comprising amino acids having the sequence set forth in SEQ ID NO:182; and a light chain variable region CDR3 comprising amino acids having the sequence set forth in SEQ ID NO: 183;

(xi) a heavy chain variable region CDR1 comprising amino acids having the sequence set forth in SEQ ID NO: 184; a heavy chain variable region CDR2 comprising amino acids having the sequence set forth in SEQ ID NO: 185; a heavy chain variable region CDR3 comprising amino acids having the sequence set forth in SEQ ID NO: 186; a light chain variable region CDR1 comprising amino acids having the sequence set forth in SEQ ID NO: 187; a light chain variable region CDR2 comprising amino acids having the sequence set forth in SEQ ID NO:188; and a light chain variable region CDR3 comprising amino acids having the sequence set forth in SEQ ID NO: 189;

(xii) a heavy chain variable region CDR1 comprising amino acids having the sequence set forth in SEQ ID NO: 190; a heavy chain variable region CDR2 comprising amino acids having the sequence set forth in SEQ ID NO: 191; a heavy chain variable region CDR3 comprising amino acids having the sequence set forth in SEQ ID NO: 192; a light chain variable region CDR1 comprising amino acids having the sequence set forth in SEQ ID NO: 193; a light chain variable region CDR2 comprising amino acids having the sequence set forth in SEQ ID NO:194; and a light chain variable region CDR3 comprising amino acids having the sequence set forth in SEQ ID NO: 195;

(xiii) a heavy chain variable region CDR1 comprising amino acids having the sequence set forth in SEQ ID NO: 196; a heavy chain variable region CDR2 comprising amino acids having the sequence set forth in SEQ ID NO: 197; a heavy chain variable region CDR3 comprising amino acids having the sequence set forth in SEQ ID NO: 198; a light chain variable region CDR1 comprising amino acids having the sequence set forth in SEQ ID NO: 199; a light chain variable region CDR2 comprising amino acids having the sequence set forth in SEQ ID NO:200; and a light chain variable region CDR3 comprising amino acids having the sequence set forth in SEQ ID NO: 201;

(xiv) a heavy chain variable region CDR1 comprising amino acids having the sequence set forth in SEQ ID NO: 202; a heavy chain variable region CDR2 comprising amino acids having the sequence set forth in SEQ ID NO: 203; a heavy chain variable region CDR3 comprising amino acids having the sequence set forth in SEQ ID NO: 204; a light chain variable region CDR1 comprising amino acids having the sequence set forth in SEQ ID NO: 205; a light chain variable region CDR2 comprising amino acids having the sequence set forth in SEQ ID NO:206; and a light chain variable region CDR3 comprising amino acids having the sequence set forth in SEQ ID NO: 207;

(xv) a heavy chain variable region CDR1 comprising amino acids having the sequence set forth in SEQ ID NO: 208; a heavy chain variable region CDR2 comprising amino acids having the sequence set forth in SEQ ID NO: 209; a heavy chain variable region CDR3 comprising amino acids having the sequence set forth in SEQ ID NO: 210; a light chain variable region CDR1 comprising amino acids having the sequence set forth in SEQ ID NO: 211; a light chain variable region CDR2 comprising amino acids having the sequence set forth in SEQ ID NO:212; and a light chain variable region CDR3 comprising amino acids having the sequence set forth in SEQ ID NO: 213;

(xvi) a heavy chain variable region CDR1 comprising amino acids having the sequence set forth in SEQ ID NO: 214; a heavy chain variable region CDR2 comprising amino acids having the sequence set forth in SEQ ID NO: 215; a heavy chain variable region CDR3 comprising amino acids having the sequence set forth in SEQ ID NO: 216; a light chain variable region CDR1 comprising amino acids having the sequence set forth in SEQ ID NO: 217; a light chain variable region CDR2 comprising amino acids having the sequence set forth in SEQ ID NO:218; and a light chain variable region CDR3 comprising amino acids having the sequence set forth in SEQ ID NO: 219;

(xvii) a heavy chain variable region CDR1 comprising amino acids having the sequence set forth in SEQ ID NO: 220; a heavy chain variable region CDR2 comprising amino acids having the sequence set forth in SEQ ID NO: 221; a heavy chain variable region CDR3 comprising amino acids having the sequence set forth in SEQ ID NO: 222; a light chain variable region CDR1 comprising amino acids having the sequence set forth in SEQ ID NO: 223; a light chain variable region CDR2 comprising amino acids having the sequence set forth in SEQ ID NO:224; and a light chain variable region CDR3 comprising amino acids having the sequence set forth in SEQ ID NO: 225;

(xviii) a heavy chain variable region CDR1 comprising amino acids having the sequence set forth in SEQ ID NO: 226; a heavy chain variable region CDR2 comprising amino acids having the sequence set forth in SEQ ID NO: 227; a heavy chain variable region CDR3 comprising amino acids having the sequence set forth in SEQ ID NO: 228; a light chain variable region CDR1 comprising amino acids having the sequence set forth in SEQ ID NO: 229; a light chain variable region CDR2 comprising amino acids having the sequence set forth in SEQ ID NO:230; and a light chain variable region CDR3 comprising amino acids having the sequence set forth in SEQ ID NO: 231;

(xix) a heavy chain variable region CDR1 comprising amino acids having the sequence set forth in SEQ ID NO: 232; a heavy chain variable region CDR2 comprising amino acids having the sequence set forth in SEQ ID NO: 233; a heavy chain variable region CDR3 comprising amino acids having the sequence set forth in SEQ ID NO: 234; a light chain variable region CDR1 comprising amino acids having the sequence set forth in SEQ ID NO: 235; a light chain variable region CDR2 comprising amino acids having the sequence set forth in SEQ ID NO:236; and a light chain variable region CDR3 comprising amino acids having the sequence set forth in SEQ ID NO: 237;

(xx) a heavy chain variable region CDR1 comprising amino acids having the sequence set forth in SEQ ID NO: 238; a heavy chain variable region CDR2 comprising amino acids having the sequence set forth in SEQ ID NO: 239; a heavy chain variable region CDR3 comprising amino acids having the sequence set forth in SEQ ID NO: 240; a light chain variable region CDR1 comprising amino acids having the sequence set forth in SEQ ID NO: 241; a light chain variable region CDR2 comprising amino acids having the sequence set forth in SEQ ID NO:242; and a light chain variable region CDR3 comprising amino acids having the sequence set forth in SEQ ID NO: 243;

(xxi) a heavy chain variable region CDR1 comprising amino acids having the sequence set forth in SEQ ID NO: 244; a heavy chain variable region CDR2 comprising amino acids having the sequence set forth in SEQ ID NO: 245; a heavy chain variable region CDR3 comprising amino acids having the sequence set forth in SEQ ID NO: 246; a light chain variable region CDR1 comprising amino acids having the sequence set forth in SEQ ID NO: 247; a light chain variable region CDR2 comprising amino acids having the sequence set forth in SEQ ID NO:248; and a light chain variable region CDR3 comprising amino acids having the sequence set forth in SEQ ID NO: 249;

(xxii) a heavy chain variable region CDR1 comprising amino acids having the sequence set forth in SEQ ID NO: 250; a heavy chain variable region CDR2 comprising amino acids having the sequence set forth in SEQ ID NO: 251; a heavy chain variable region CDR3 comprising amino acids having the sequence set forth in SEQ ID NO: 252; a light chain variable region CDR1 comprising amino acids having the sequence set forth in SEQ ID NO: 253; a light chain variable region CDR2 comprising amino acids having the sequence set forth in SEQ ID NO:254; and a light chain variable region CDR3 comprising amino acids having the sequence set forth in SEQ ID NO: 255;

(xxiii) a heavy chain variable region CDR1 comprising amino acids having the sequence set forth in SEQ ID NO: 256; a heavy chain variable region CDR2 comprising amino acids having the sequence set forth in SEQ ID NO: 257; a heavy chain variable region CDR3 comprising amino acids having the sequence set forth in SEQ ID NO: 258; a light chain variable region CDR1 comprising amino acids having the sequence set forth in SEQ ID NO: 259; a light chain variable region CDR2 comprising amino acids having the sequence set forth in SEQ ID NO:260; and a light chain variable region CDR3 comprising amino acids having the sequence set forth in SEQ ID NO: 261;

(xxiv) a heavy chain variable region CDR1 comprising amino acids having the sequence set forth in SEQ ID NO: 262; a heavy chain variable region CDR2 comprising amino acids having the sequence set forth in SEQ ID NO: 263; a heavy chain variable region CDR3 comprising amino acids having the sequence set forth in SEQ ID NO: 264; a light chain variable region CDR1 comprising amino acids having the sequence set forth in SEQ ID NO: 265; a light chain variable region CDR2 comprising amino acids having the sequence set forth in SEQ ID NO:266; and a light chain variable region CDR3 comprising amino acids having the sequence set forth in SEQ ID NO: 267;

(xxv) a heavy chain variable region CDR1 comprising amino acids having the sequence set forth in SEQ ID NO: 268; a heavy chain variable region CDR2 comprising amino acids having the sequence set forth in SEQ ID NO: 269; a heavy chain variable region CDR3 comprising amino acids having the sequence set forth in SEQ ID NO: 270; a light chain variable region CDR1 comprising amino acids having the sequence set forth in SEQ ID NO: 271; a light chain variable region CDR2 comprising amino acids having the sequence set forth in SEQ ID NO:272; and (vi) a light chain variable region CDR3 comprising amino acids having the sequence set forth in SEQ ID NO: 273;

(xxvi) a heavy chain variable region CDR1 comprising amino acids having the sequence set forth in SEQ ID NO: 280; a heavy chain variable region CDR2 comprising amino acids having the sequence set forth in SEQ ID NO: 281; a heavy chain variable region CDR3 comprising amino acids having the sequence set forth in SEQ ID NO: 282; a light chain variable region CDR1 comprising amino acids having the sequence set forth in SEQ ID NO: 283; a light chain variable region CDR2 comprising amino acids having the sequence set forth in SEQ ID NO:284; and a light chain variable region CDR3 comprising amino acids having the sequence set forth in SEQ ID NO: 285;

(xxvii) a heavy chain variable region CDR1 comprising amino acids having the sequence set forth in SEQ ID NO: 292; a heavy chain variable region CDR2 comprising amino acids having the sequence set forth in SEQ ID NO: 293; a heavy chain variable region CDR3 comprising amino acids having the sequence set forth in SEQ ID NO: 294; a light chain variable region CDR1 comprising amino acids having the sequence set forth in SEQ ID NO: 295; a light chain variable region CDR2 comprising amino acids having the sequence set forth in SEQ ID NO:296; and a light chain variable region CDR3 comprising amino acids having the sequence set forth in SEQ ID NO: 297;

(xxviii) a heavy chain variable region CDR1 comprising amino acids having the sequence set forth in SEQ ID NO: 303; a heavy chain variable region CDR2 comprising amino acids having the sequence set forth in SEQ ID NO: 304; a heavy chain variable region CDR3 comprising amino acids having the sequence set forth in SEQ ID NO: 305; a light chain variable region CDR1 comprising amino acids having the sequence set forth in SEQ ID NO: 306; a light chain variable region CDR2 comprising amino acids having the sequence set forth in SEQ ID NO: 307; and a light chain variable region CDR3 comprising amino acids having the sequence set forth in SEQ ID NO: 308;

(xxix) a heavy chain variable region CDR1 comprising amino acids having the sequence set forth in SEQ ID NO: 316; a heavy chain variable region CDR2 comprising amino acids having the sequence set forth in SEQ ID NO: 317; a heavy chain variable region CDR3 comprising amino acids having the sequence set forth in SEQ ID NO: 318; a light chain variable region CDR1 comprising amino acids having the sequence set forth in SEQ ID NO: 319; a light chain variable region CDR2 comprising amino acids having the sequence set forth in SEQ ID NO: 320; and a light chain variable region CDR3 comprising amino acids having the sequence set forth in SEQ ID NO: 321;

(xxx) a heavy chain variable region CDR1 comprising amino acids having the sequence set forth in SEQ ID NO: 328; a heavy chain variable region CDR2 comprising amino acids having the sequence set forth in SEQ ID NO: 329; a heavy chain variable region CDR3 comprising amino acids having the sequence set forth in SEQ ID NO: 330; a light chain variable region CDR1 comprising amino acids having the sequence set forth in SEQ ID NO: 331; a light chain variable region CDR2 comprising amino acids having the sequence set forth in SEQ ID NO: 332; and a light chain variable region CDR3 comprising amino acids having the sequence set forth in SEQ ID NO: 333;

(xxxi) a heavy chain variable region CDR1 comprising amino acids having the sequence set forth in SEQ ID NO: 340; a heavy chain variable region CDR2 comprising amino acids having the sequence set forth in SEQ ID NO: 341; a heavy chain variable region CDR3 comprising amino acids having the sequence set forth in SEQ ID NO: 342; a light chain variable region CDR1 comprising amino acids having the sequence set forth in SEQ ID NO: 343; a light chain variable region CDR2 comprising amino acids having the sequence set forth in SEQ ID NO: 344; and a light chain variable region CDR3 comprising amino acids having the sequence set forth in SEQ ID NO: 345; or (xxxii) a heavy chain variable region CDR1 comprising amino acids having the sequence set forth in SEQ ID NO: 352; a heavy chain variable region CDR2 comprising amino acids having the sequence set forth in SEQ ID NO: 353; a heavy chain variable region CDR3 comprising amino acids having the sequence set forth in SEQ ID NO: 354; a light chain variable region CDR1 comprising amino acids having the sequence set forth in SEQ ID NO: 355; a light chain variable region CDR2 comprising amino acids having the sequence set forth in SEQ ID NO: 356; and a light chain variable region CDR3 comprising amino acids having the sequence set forth in SEQ ID NO: 357.

Furthermore, the presently disclosed subject matter provides an isolated antibody, or an antigen-binding portion thereof, which cross-competes for binding to human GPRC5D with any of the disclosed antibodies. In certain embodiments, the presently disclosed subject matter provides an isolated antibody, or an antigen-binding portion thereof, which binds to the same epitope on human GPRC5D with an isolated antibody, or an antigen-binding portion thereof of any of the antibodies disclosed herein.

In certain embodiments, the presently disclosed subject matter provides an isolated antibody, or an antigen-binding portion thereof, which cross-competes for binding to human GPRC5D with a reference antibody or reference antigen-binding portion thereof comprising: (i) a heavy chain variable region comprising amino acids having a sequence set forth in SEQ ID NO:1, and a light chain variable region comprising amino acids having a sequence set forth in SEQ ID NO:2; (ii) a heavy chain variable region comprising amino acids having a sequence set forth in SEQ ID NO:5, and a light chain variable region comprising amino acids having a sequence set forth in SEQ ID NO:6; (iii) a heavy chain variable region comprising amino acids having a sequence set forth in SEQ ID NO:9, and a light chain variable region comprising amino acids having a sequence set forth in SEQ ID NO:10; (iv) a heavy chain variable region comprising amino acids having a sequence set forth in SEQ ID NO:13, and a light chain variable region comprising amino acids having a sequence set forth in SEQ ID NO:14; (v) a heavy chain variable region comprising amino acids having a sequence set forth in SEQ ID NO:17, and a light chain variable region comprising amino acids having a sequence set forth in SEQ ID NO:18; (vi) a heavy chain variable region comprising amino acids having a sequence set forth in SEQ ID NO:21, and a light chain variable region comprising amino acids having a sequence set forth in SEQ ID NO:22; (vii) a heavy chain variable region comprising amino acids having a sequence set forth in SEQ ID NO:25, and a light chain variable region comprising amino acids having a sequence set forth in SEQ ID NO:26; (viii) a heavy chain variable region comprising amino acids having a sequence set forth in SEQ ID NO:29, and a light chain variable region comprising amino acids having a sequence set forth in SEQ ID NO:30; (ix) a heavy chain variable region comprising amino acids having a sequence set forth in SEQ ID NO:33, and a light chain variable region comprising amino acids having a sequence set forth in SEQ ID NO:34; (x) a heavy chain variable region comprising amino acids having a sequence set forth in SEQ ID NO:37, and a light chain variable region comprising amino acids having a sequence set forth in SEQ ID NO:38; (xi) a heavy chain variable region comprising amino acids having a sequence set forth in SEQ ID NO:41, and a light chain variable region comprising amino acids having a sequence set forth in SEQ ID NO:42; (xii) a heavy chain variable region comprising amino acids having a sequence set forth in SEQ ID NO:45, and a light chain variable region comprising amino acids having a sequence set forth in SEQ ID NO:46; (xiii) a heavy chain variable region comprising amino acids having a sequence set forth in SEQ ID NO:49, and a light chain variable region comprising amino acids having a sequence set forth in SEQ ID NO:50; (xiv) a heavy chain variable region comprising amino acids having a sequence set forth in SEQ ID NO:53, and a light chain variable region comprising amino acids having a sequence set forth in SEQ ID NO:54; (xv) a heavy chain variable region comprising amino acids having a sequence set forth in SEQ ID NO:57, and a light chain variable region comprising amino acids having a sequence set forth in SEQ ID NO:58; (xvi) a heavy chain variable region comprising amino acids having a sequence set forth in SEQ ID NO:61, and a light chain variable region comprising amino acids having a sequence set forth in SEQ ID NO:62; (xvii) a heavy chain variable region comprising amino acids having a sequence set forth in SEQ ID NO:65, and a light chain variable region comprising amino acids having a sequence set forth in SEQ ID NO:66; (xviii) a heavy chain variable region comprising amino acids having a sequence set forth in SEQ ID NO:69, and a light chain variable region comprising amino acids having a sequence set forth in SEQ ID NO:70; (xix) a heavy chain variable region comprising amino acids having a sequence set forth in SEQ ID NO:73, and a light chain variable region comprising amino acids having a sequence set forth in SEQ ID NO:74; (xx) a heavy chain variable region comprising amino acids having a sequence set forth in SEQ ID NO:77, and a light chain variable region comprising amino acids having a sequence set forth in SEQ ID NO:78; (xxi) a heavy chain variable region comprising amino acids having a sequence set forth in SEQ ID NO:81, and a light chain variable region comprising amino acids having a sequence set forth in SEQ ID NO:82; (xxii) a heavy chain variable region comprising amino acids having a sequence set forth in SEQ ID NO:85, and a light chain variable region comprising amino acids having a sequence set forth in SEQ ID NO:86; (xxiii) a heavy chain variable region comprising amino acids having a sequence set forth in SEQ ID NO:89, and a light chain variable region comprising amino acids having a sequence set forth in SEQ ID NO:90; (xxiv) a heavy chain variable region comprising amino acids having a sequence set forth in SEQ ID NO:93, and a light chain variable region comprising amino acids having a sequence set forth in SEQ ID NO:94; (xxv) a heavy chain variable region comprising amino acids having a sequence set forth in SEQ ID NO:274, and a light chain variable region comprising amino acids having a sequence set forth in SEQ ID NO:275; (xxvi) a heavy chain variable region comprising amino acids having a sequence set forth in SEQ ID NO:286, and a light chain variable region comprising amino acids having a sequence set forth in SEQ ID NO:287; (xxvii) a heavy chain variable region comprising amino acids having a sequence set forth in SEQ ID NO:298, and a light chain variable region comprising amino acids having a sequence set forth in SEQ ID NO:299; (xviii) a heavy chain variable region comprising amino acids having a sequence set forth in SEQ ID NO:310, and a light chain variable region comprising amino acids having a sequence set forth in SEQ ID NO:311; (xxi) a heavy chain variable region comprising amino acids having a sequence set forth in SEQ ID NO:322, and a light chain variable region comprising amino acids having a sequence set forth in SEQ ID NO:323; (xx) a heavy chain variable region comprising amino acids having a sequence set forth in SEQ ID NO:334, and a light chain variable region comprising amino acids having a sequence set forth in SEQ ID NO:335; (xxi) a heavy chain variable region comprising amino acids having a sequence set forth in SEQ ID NO:346, and a light chain variable region comprising amino acids having a sequence set forth in SEQ ID NO:347; or (xxii) a heavy chain variable region comprising amino acids having a sequence set forth in SEQ ID NO:358, and a light chain variable region comprising amino acids having a sequence set forth in SEQ ID NO:359.

In addition, the presently disclosed subject matter provides an isolated antibody, or an antigen-binding portion thereof, which binds to the same epitope on human GPRC5D as a reference antibody or reference antigen-binding portion thereof comprising: (i) a heavy chain variable region comprising amino acids having a sequence set forth in SEQ ID NO:1, and a light chain variable region comprising amino acids having a sequence set forth in SEQ ID NO:2; (ii) a heavy chain variable region comprising amino acids having a sequence set forth in SEQ ID NO:5, and a light chain variable region comprising amino acids having a sequence set forth in SEQ ID NO:6; (iii) a heavy chain variable region comprising amino acids having a sequence set forth in SEQ ID NO:9, and a light chain variable region comprising amino acids having a sequence set forth in SEQ ID NO:10; (iv) a heavy chain variable region comprising amino acids having a sequence set forth in SEQ ID NO:13, and a light chain variable region comprising amino acids having a sequence set forth in SEQ ID NO:14; (v) a heavy chain variable region comprising amino acids having a sequence set forth in SEQ ID NO:17, and a light chain variable region comprising amino acids having a sequence set forth in SEQ ID NO:18; (vi) a heavy chain variable region comprising amino acids having a sequence set forth in SEQ ID NO:21, and a light chain variable region comprising amino acids having a sequence set forth in SEQ ID NO:22; (vii) a heavy chain variable region comprising amino acids having a sequence set forth in SEQ ID NO:25, and a light chain variable region comprising amino acids having a sequence set forth in SEQ ID NO:26; (viii) a heavy chain variable region comprising amino acids having a sequence set forth in SEQ ID NO:29, and a light chain variable region comprising amino acids having a sequence set forth in SEQ ID NO:30; (ix) a heavy chain variable region comprising amino acids having a sequence set forth in SEQ ID NO:33, and a light chain variable region comprising amino acids having a sequence set forth in SEQ ID NO:34; (x) a heavy chain variable region comprising amino acids having a sequence set forth in SEQ ID NO:37, and a light chain variable region comprising amino acids having a sequence set forth in SEQ ID NO:38; (xi) a heavy chain variable region comprising amino acids having a sequence set forth in SEQ ID NO:41, and a light chain variable region comprising amino acids having a sequence set forth in SEQ ID NO:42; (xii) a heavy chain variable region comprising amino acids having a sequence set forth in SEQ ID NO:45, and a light chain variable region comprising amino acids having a sequence set forth in SEQ ID NO:46; (xiii) a heavy chain variable region comprising amino acids having a sequence set forth in SEQ ID NO:49, and a light chain variable region comprising amino acids having a sequence set forth in SEQ ID NO:50; (xiv) a heavy chain variable region comprising amino acids having a sequence set forth in SEQ ID NO:53, and a light chain variable region comprising amino acids having a sequence set forth in SEQ ID NO:54; (xv) a heavy chain variable region comprising amino acids having a sequence set forth in SEQ ID NO:57, and a light chain variable region comprising amino acids having a sequence set forth in SEQ ID NO:58; (xvi) a heavy chain variable region comprising amino acids having a sequence set forth in SEQ ID NO:61, and a light chain variable region comprising amino acids having a sequence set forth in SEQ ID NO:62; (xvii) a heavy chain variable region comprising amino acids having a sequence set forth in SEQ ID NO:65, and a light chain variable region comprising amino acids having a sequence set forth in SEQ ID NO:66; (xviii) a heavy chain variable region comprising amino acids having a sequence set forth in SEQ ID NO:69, and a light chain variable region comprising amino acids having a sequence set forth in SEQ ID NO:70; (xix) a heavy chain variable region comprising amino acids having a sequence set forth in SEQ ID NO:73, and a light chain variable region comprising amino acids having a sequence set forth in SEQ ID NO:74; (xx) a heavy chain variable region comprising amino acids having a sequence set forth in SEQ ID NO:77, and a light chain variable region comprising amino acids having a sequence set forth in SEQ ID NO:78; (xxi) a heavy chain variable region comprising amino acids having a sequence set forth in SEQ ID NO:81, and a light chain variable region comprising amino acids having a sequence set forth in SEQ ID NO:82; (xxii) a heavy chain variable region comprising amino acids having a sequence set forth in SEQ ID NO:85, and a light chain variable region comprising amino acids having a sequence set forth in SEQ ID NO:86; (xxiii) a heavy chain variable region comprising amino acids having a sequence set forth in SEQ ID NO:89, and a light chain variable region comprising amino acids having a sequence set forth in SEQ ID NO:90; (xxiv) a heavy chain variable region comprising amino acids having a sequence set forth in SEQ ID NO:93, and a light chain variable region comprising amino acids having a sequence set forth in SEQ ID NO:94; (xxv) a heavy chain variable region comprising amino acids having a sequence set forth in SEQ ID NO:274, and a light chain variable region comprising amino acids having a sequence set forth in SEQ ID NO:275; (xxvi) a heavy chain variable region comprising amino acids having a sequence set forth in SEQ ID NO:286, and a light chain variable region comprising amino acids having a sequence set forth in SEQ ID NO:287; (xxvii) a heavy chain variable region comprising amino acids having a sequence set forth in SEQ ID NO:298, and a light chain variable region comprising amino acids having a sequence set forth in SEQ ID NO:299; (xviii) a heavy chain variable region comprising amino acids having a sequence set forth in SEQ ID NO:310, and a light chain variable region comprising amino acids having a sequence set forth in SEQ ID NO:311; (xxi) a heavy chain variable region comprising amino acids having a sequence set forth in SEQ ID NO:322, and a light chain variable region comprising amino acids having a sequence set forth in SEQ ID NO:323; (xx) a heavy chain variable region comprising amino acids having a sequence set forth in SEQ ID NO:334, and a light chain variable region comprising amino acids having a sequence set forth in SEQ ID NO:335; (xxi) a heavy chain variable region comprising amino acids having a sequence set forth in SEQ ID NO:346, and a light chain variable region comprising amino acids having a sequence set forth in SEQ ID NO:347; or (xxii) a heavy chain variable region comprising amino acids having a sequence set forth in SEQ ID NO:358, and a light chain variable region comprising amino acids having a sequence set forth in SEQ ID NO:359.

In certain embodiments, the antibodies of the present disclosure bind to GPRC5D comprising the amino acid sequence set forth in SEQ ID NO:97. In certain embodiments, the antibodies of the present disclosure binds to human GPRC5D with a binding affinity ($K_d$) of from about $1 \times 10^{-9}$ M to about $1 \times 10^{-8}$ M.

In certain embodiments, the antibodies of the present disclosure binds to one, two, three or four epitope region selected from the group consisting of an epitope region in N-terminal region comprising amino acids 1-27 of SEQ ID NO:97, an epitope region in ECL1 region comprising amino acids 85-93 of SEQ ID NO:97, an epitope region in ECL2 region comprising amino acids 145-167 of SEQ ID NO:97, and an epitope region in ECL3 region comprising amino acids 226-239 of SEQ ID NO:97. In certain embodiments, the antibodies of the present disclosure bind to an epitope region comprising amino acids 16-23 of SEQ ID NO:97. In certain embodiments, the antibodies of the present disclosure bind to an epitope region comprising amino acids 15-23 of SEQ ID NO:97. In certain embodiments, the antibodies of the present disclosure bind to an epitope region comprising amino acids 16-25 of SEQ ID NO:97. In certain embodiments, the antibodies of the present disclosure bind to an epitope region comprising amino acids 10-17 of SEQ ID NO:97. In certain embodiments, the antibodies of the present disclosure bind to an epitope region comprising amino acids 5-17 of SEQ ID NO:97. In certain embodiments, the antibodies of the present disclosure bind to an epitope region comprising amino acids 85-95 of SEQ ID NO:97. In certain embodiments, the antibodies of the present disclosure bind to an epitope region comprising amino acids 157-164 of SEQ ID NO:97. In certain embodiments, the antibodies of the present disclosure bind to an epitope region comprising amino acids 157-167 of SEQ ID NO:97. In certain embodiments, the antibodies of the present disclosure bind to an epitope region comprising amino acids 230-237 of SEQ ID NO:97. In certain embodiments, the antibodies of the present disclosure bind to an epitope region comprising amino acids 229-237 of SEQ ID NO:97. In certain embodiments, the antibodies of the present disclosure bind to an epitope region comprising amino acids 230-243 of SEQ ID NO:97. In certain embodiments, the antibodies of the present disclosure bind to an epitope region comprising amino acids 227-237 of SEQ ID NO:97.

The presently disclosed subject matter also provides an isolated antibody, or antigen-binding fragment thereof, comprising an amino acid sequence selected from the group consisting of SEQ ID NOS: 100-123, 276, 288, 300, 312, 324, 336, 348 and 360.

In certain embodiments, the antibody or antigen-binding fragment thereof comprises a human variable region framework region. In certain embodiments, the antibody or antigen-binding fragment thereof is fully human or an antigen-binding fragment thereof. In certain embodiments, the antibody or antigen-binding fragment thereof is a chimeric antibody or an antigen-binding fragment thereof. In certain embodiments, the antibody or antigen-binding portion thereof is a humanized antibody or an antigen-binding fragment thereof. In certain embodiments, the antigen-binding fragment of the antibody is an Fab, Fab', F(ab')$_2$, Fv or single chain Fv (scFv).

The presently disclosed subject matter also provides a composition comprising the antibody or antigen-binding fragment thereof disclosed herein, and a pharmaceutically acceptable carrier.

In addition, the presently disclosed subject matter provides an immunoconjugate comprising the antibody or antigen-binding fragment thereof disclosed herein, linked to a therapeutic agent. In certain embodiments, the therapeutic agent is a drug, cytotoxin, or a radioactive isotope. The presently disclosed subject matter also provides a composition comprising such immunoconjugate and a pharmaceutically acceptable carrier.

Furthermore, the presently disclosed subject matter provides a bispecific molecule comprising the antibody or antigen-binding fragment thereof disclosed herein, linked to a second functional moiety. In certain embodiments, the second functional moiety has a different binding specificity than the antibody or antigen binding fragment thereof. In certain embodiments, the second functional moiety has a binding specificity for an immune cell. In certain embodiments, the second functional moiety has a binding specificity for CD3.

The presently disclosed subject matter also provides a composition comprising such bispecific molecule and a pharmaceutically acceptable carrier.

In addition, the presently disclosed subject matter provides an isolated nucleic acid that encodes the antibody or antigen-binding fragment thereof disclosed herein, an expression vector comprising such nucleic acid molecule, and a host cell comprising such expression vector.

Furthermore, the presently disclosed subject matter provides a method for detecting GPRC5D in a whole cell or tissue. In certain embodiments, the method comprises: contacting a cell or tissue with the antibody or antigen-binding fragment thereof disclosed herein, wherein said antibody or antigen-binding fragment thereof comprises a detectable label; and determining the amount of the labeled antibody or antigen-binding fragment thereof bound to said cell or tissue by measuring the amount of detectable label associated with said cell or tissue, wherein the amount of bound antibody or antigen-binding fragment thereof indicates the amount of GPRC5D in said cell or tissue.

Furthermore, the presently disclosed subject matter provides a method of treating a tumor in a subject. In certain embodiments, the method comprises: administering an effective amount of the antibody or antigen-binding fragment thereof disclosed herein to the subject, thereby inducing death of a tumor cell in the subject. In certain embodiments, the method reduces the number of the tumor cells. In certain embodiments, the method reduces the tumor size. In certain embodiments, the method eradicates the tumor in the subject. In certain embodiments, the subject is a human.

In addition, the presently disclosed subject matter provides use of the antibody or antigen-binding fragment disclosed herein for the treatment of a tumor, and the antibody or antigen-binding fragment thereof disclosed herein for use in treating a tumor in a subject.

Furthermore, the presently disclosed subject matter provides a kit for treating a tumor, comprising the antibody or antigen-binding fragment thereof disclosed herein. In certain embodiments, the kit further comprises written instructions for using the antibody or antigen-binding fragment thereof for treating a subject having a tumor.

In certain embodiments, the tumor is multiple myeloma or Waldenstrom's Macroglobulinemia. In certain embodiments, the tumor is multiple myeloma.

BRIEF DESCRIPTION OF THE FIGURES

The following Detailed Description, given by way of example, but not intended to limit the invention to specific embodiments described, may be understood in conjunction with the accompanying drawings.

FIGS. 5A-5D illustrates heat map technology. (i) Table of combined peptides, with two sub-sequences indicated as "Loop 1" and "Loop 2". (ii) Data from A displayed as a matrix. (iii) Color bar indication of the heat map representation. (iv) Heat map visualization of data from A.

FIG. 12 depicts FACS analysis of anti-GPRC5D antibodies.

DETAILED DESCRIPTION OF EMBODIMENTS OF THE INVENTION

Figure 1:
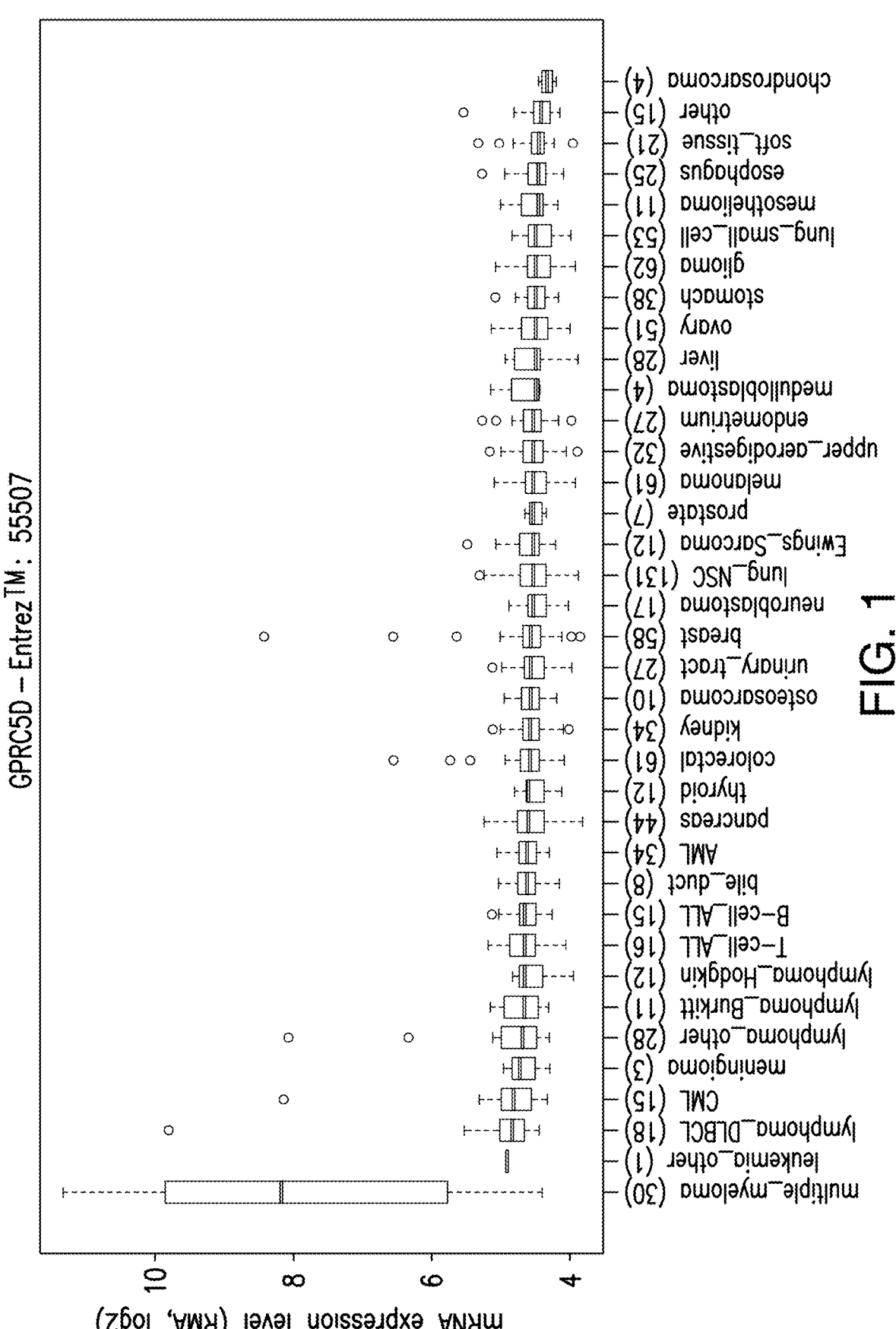
FIG. 1 depicts the human GPRC5D expression in various tissues.
Figure 1:
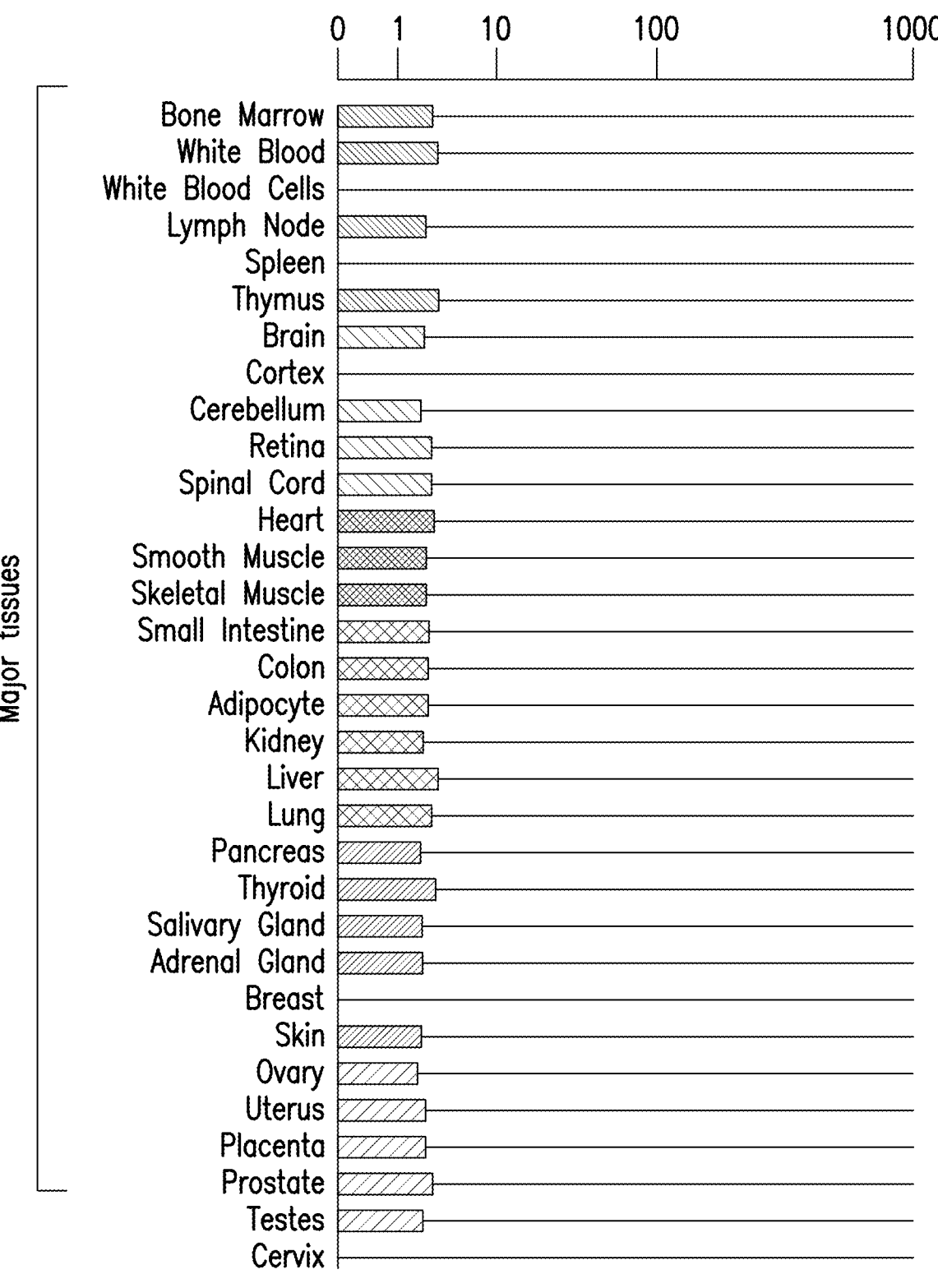
Figure 1:
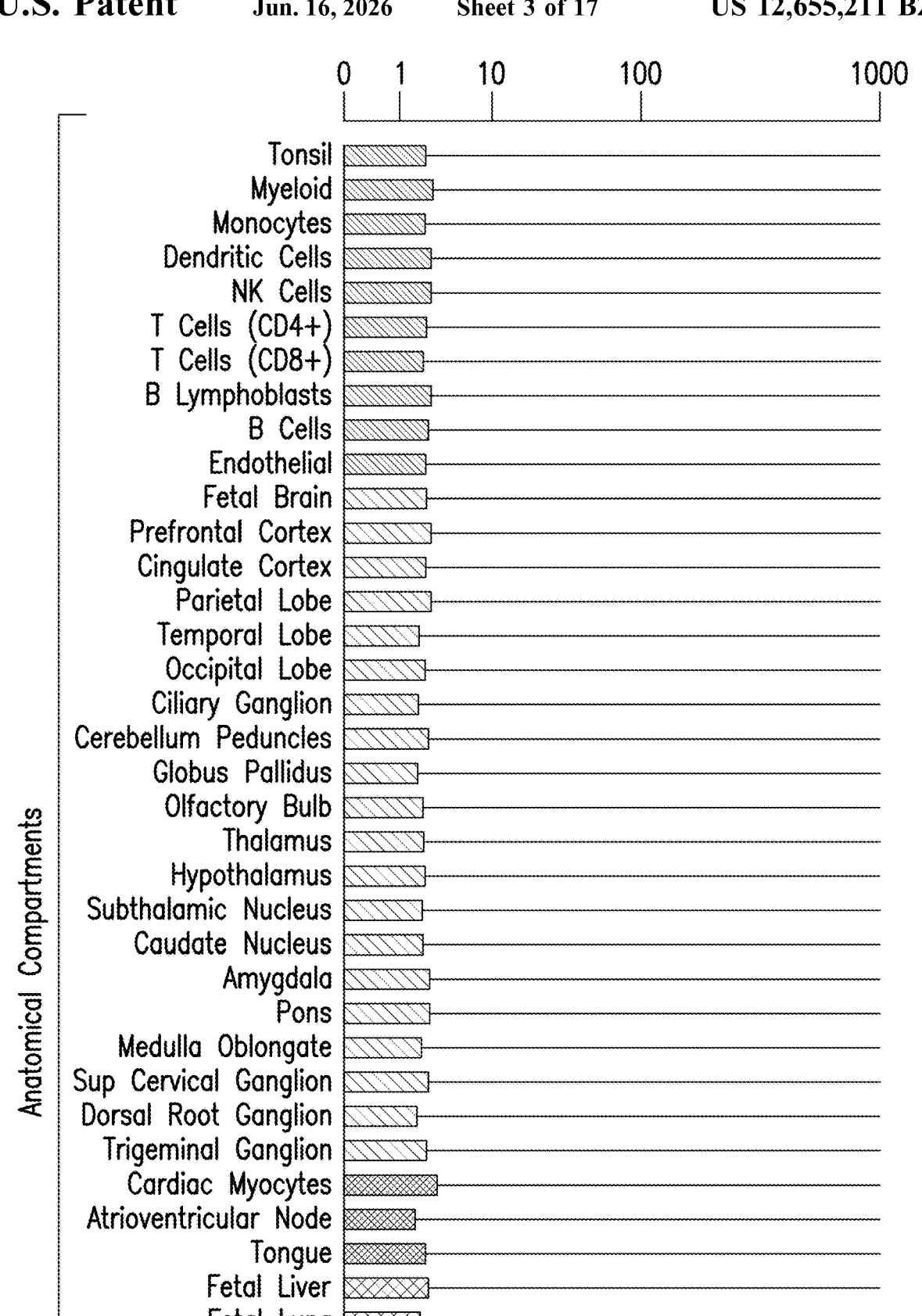
Figure 1:
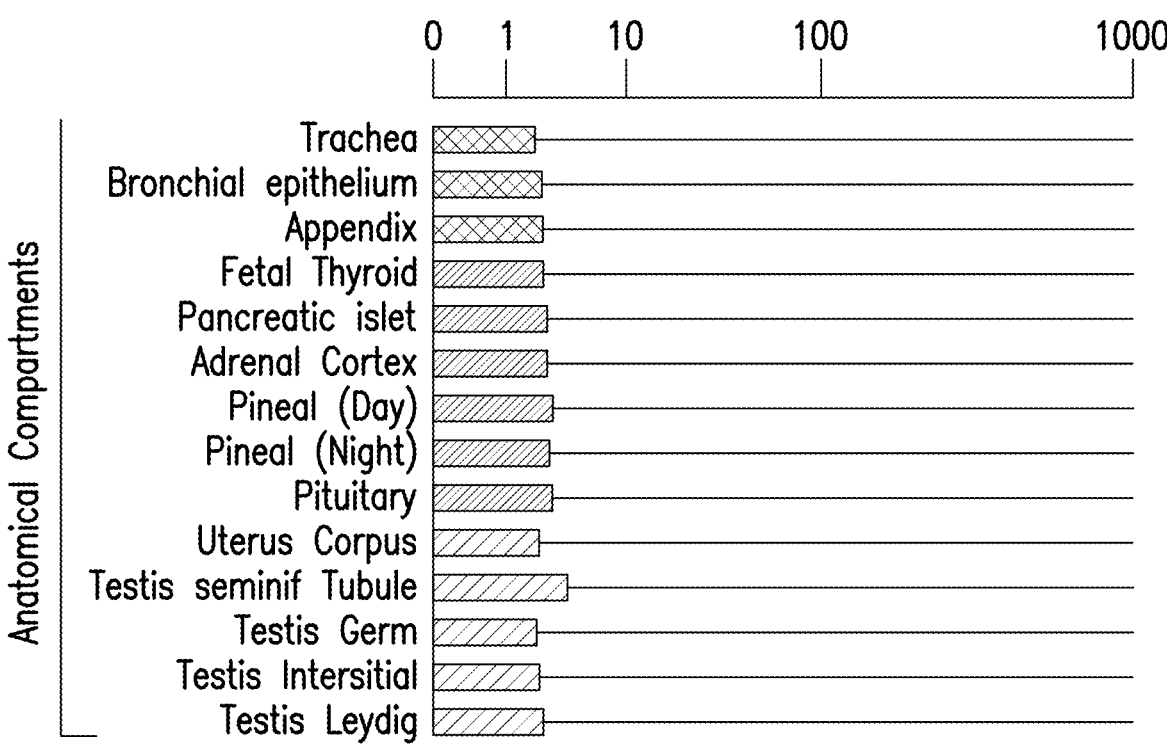

All publications, patents and other references cited herein are incorporated by reference in their entirety into the present disclosure.

In practicing the presently disclosed subject matter, many conventional techniques in molecular biology, microbiology, cell biology, biochemistry, and immunology are used, which are within the skill of the art. These techniques are described in greater detail in, for example, Molecular Cloning: a Laboratory Manual 3rd edition, J. F. Sambrook and D. W. Russell, ed. Cold Spring Harbor Laboratory Press 2001; Recombinant Antibodies for Immunotherapy, Melvyn Little, ed. Cambridge University Press 2009; Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions are hereby incorporated by reference as part of the present disclosure.

Definitions

In the description that follows, certain conventions will be followed as regards the usage of terminology. Generally, terms used herein are intended to be interpreted consistently with the meaning of those terms as they are known to those of skill in the art.

An "antigen-binding protein" is a protein or polypeptide that comprises an antigen-binding region or antigen-binding portion, that is, has a strong affinity to another molecule to which it binds. Antigen-binding proteins encompass antibodies, chimeric antigen receptors (CARs) and fusion proteins.

"Antibody" and "antibodies" as those terms are known in the art refer to antigen binding proteins of the immune system. The term "antibody" as referred to herein includes whole, full length antibodies having an antigen-binding region, and any fragment thereof in which the "antigen-binding portion" or "antigen-binding region" is retained, or single chains, for example, single chain variable fragment (scFv), thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant (CH) region. The heavy chain constant region is comprised of three domains, CH1, CH2 and CH3. Each light chain is comprised of a light chain variable region (abbreviated herein as $V_L$) and a light chain constant CL region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1 q) of the classical complement system.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the presently disclosed subject matter may include amino acid residues not encoded by human germline immunoglobulin sequences (e.g., mutations introduced by random or site-specific mutagenesis in vitro or by somatic mutation in vivo).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the presently disclosed subject matter may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline $V_H$ and $V_L$ sequences, may not naturally exist within the human antibody germline repertoire in vivo.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human GPRC5D" is intended to refer to an antibody that binds to human GPRC5D with a $K_D$ of $5\times10^{-7}$ M or less, $1\times10^{-7}$ M or less, $5\times10^{-8}$ M or less, $1\times10^{-8}$ M or less, $5\times10^{-9}$ M or less, $1\times10^{-9}$ M or less, $5\times10^{-10}$ M or less, or $1\times10^{-10}$ M or less.

An "antibody that competes for binding" or "antibody that cross-competes for binding" with a reference antibody for binding to an antigen, e.g., GPRC5D, refers to an antibody that blocks binding of the reference antibody to the antigen (e.g., GPRC5D) in a competition assay by 50% or more, and conversely, the reference antibody blocks binding of the antibody to the antigen (e.g., GPRC5D) in a competition assay by 50% or more. An exemplary competition assay is described in "Antibodies", Harlow and Lane (Cold Spring Harbor Press, Cold Spring Harbor, NY).

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen (e.g., a GPRC5D polypeptide)."

The term "antigen-binding portion" or "antigen-binding region" of an antibody, as used herein, refers to that region or portion of the antibody that binds to the antigen and which confers antigen specificity to the antibody; fragments of antigen-binding proteins, for example, antibodies includes one or more fragments of an antibody that retain the ability to specifically bind to an antigen (e.g., a GPRC5D polypeptide). It has been shown that the antigen-binding function of an antibody can be performed by fragments of a full-length antibody. Examples of antigen-binding fragments encompassed within the term "antibody fragments" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules. These are known as single chain Fv (scFv); see e.g., Bird et al., 1988 Science 242:423-426; and Huston et al., 1988 Proc. Natl. Acad. Sci. 85:5879-5883. These antibody fragments are obtained using conventional techniques known to those of skill in the art, and the fragments are screened for utility in the same manner as are intact antibodies.

An "isolated antibody" or "isolated antigen-binding protein" is one which has been identified and separated and/or recovered from a component of its natural environment. "Synthetic antibodies" or "recombinant antibodies" are generally generated using recombinant technology or using peptide synthetic techniques known to those of skill in the art.

The terms "GPRC5D" and "G-protein coupled receptor family C group 5 member D" are used interchangeably, and include variants, isoforms, species homologs of human GPRC5D, and analogs having at least one common epitope with GPRC5D (e.g., human GPRC5D). An exemplary human GPRC5D sequence can be found under GenBank™ Protein Accession No: NP_061124.1.

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker (e.g., 10, 15, 20, 25 amino acids), which connects the N-terminus of the VH with the C-terminus of the VL, or the C-terminus of the VH with the N-terminus of the VL. The linker is usually rich in glycine for flexibility, as well as serine or threonine for solubility. The linker can link the heavy chain variable region and the light chain variable region of the antibody or an antigen-binding fragment thereof. Non-limiting examples of linkers are disclosed in Shen et al., Anal. Chem. 80(6):1910-1917 (2008) and WO 2014/087010, the contents of which are hereby incorporated by reference in their entireties. In certain embodiments, the linker is a G4S linker (SEQ ID NO: 365).

In certain embodiments, the linker comprises amino acids having the sequence set forth in SEQ ID NO:309 as provided below:

```
                                    [SEQ ID NO: 309]
          GGGGSGGGGSGGGGS.
```

In certain embodiments, the nucleic acid sequence encoding the amino acid sequence of SEQ ID NO:309 is set forth in SEQ ID NO:364, which is provided below:

```
                                    [SEQ ID NO: 364]
   GGTGGAGGTGGATCAGGTGGAGGTGGATCTGGTGGAGGTGGATCT.
```

In one non-limiting example, the linker comprises amino acids having the sequence set forth in SEQ ID NO:98 as provided below.

```
                                    [SEQ ID NO: 98]
          SRGGGGSGGGGSGGGGSLEMA
```

In certain embodiments, the nucleic acid sequence encoding the amino acid sequence of SEQ ID NO:98 is set forth in SEQ ID NO:99, which is provided below:

```
                                    [SEQ ID NO: 99]
tctagaggtggtggtggtagcggcggcggcggctctggtggtggtgga tccctcgagatggcc
```

In certain embodiments, the linker comprises amino acids having the following sequence

```
                                    [SEQ ID NO: 365]
          GGGGS.
```

In certain embodiments, the linker comprises amino acids having the following sequence

```
                                    [SEQ ID NO: 366]
          SGGSGGS.
```

In certain embodiments, the linker comprises amino acids having the following sequence

```
                                    [SEQ ID NO: 367]
          GGGGSGGGS.
```

In certain embodiments, the linker comprises amino acids having the following sequence

```
                                    [SEQ ID NO: 368]
          GGGGSGGGGS.
```

In certain embodiments, the linker comprises amino acids having the following sequence

```
                                    [SEQ ID NO: 369]
          GGGGSGGGGSGGGGGGS.
```

In certain embodiments, the linker comprises amino acids having the following sequence

```
                                           [SEQ ID NO: 370]
        GGGGSGGGGSGGGGSGGGGS.
```

In certain embodiments, the linker comprises amino acids having the following sequence

```
                                           [SEQ ID NO: 371]
        GGGGSGGGGSGGGGSGGGGSGGGGS.
```

In certain embodiments, the linker comprises amino acids having the following sequence

```
                                           [SEQ ID NO: 372]
        GGGGSGGGGSGGGGSGGGGSGGGGSGGGGS.
```

In certain embodiments, the linker comprises amino acids having the following sequence

```
                                           [SEQ ID NO: 373]
        GGGGSGGGGSGGGGSGGGGGGGGSGGGGSGGGGS.
```

In certain embodiments, the linker comprises amino acids having the following sequence

```
                                           [SEQ ID NO: 374]
        EPKSCDKTHTCPPCP.
```

In certain embodiments, the linker comprises amino acids having the following sequence

```
                                           [SEQ ID NO: 375]
        GGGGSGGGSEPKSCDKTHTCPPCP.
```

In certain embodiments, the linker comprises amino acids having the following sequence

```
                                           [SEQ ID NO: 376]
ELKTPLGDTTHTCPRCPEPKSCDTPPPCPRCPEPKSCDTPPPCPRCPEPK

SCDTPPPCPRCP.
```

In certain embodiments, the linker comprises amino acids having the following sequence

```
                                           [SEQ ID NO: 377]
        GSGSGS.
```

In certain embodiments, the linker comprises amino acids having the following sequence

```
                                           [SEQ ID NO: 378]
        AAA.
```

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife et al., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Biol Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "F(ab')₂" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')₂" fragment can be split into two individual Fab' fragments.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

"CDRs" are defined as the complementarity determining region amino acid sequences of an antibody which are the hypervariable regions of immunoglobulin heavy and light chains. See, e. g., Kabat et al., Sequences of Proteins of Immunological Interest, 4th U. S. Department of Health and Human Services, National Institutes of Health (1987). The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise three heavy chain and three light chain CDRs or CDR regions in the variable region. CDRs provide the majority of contact residues for the binding of the antibody to the antigen or epitope.

An "isolated antibody" is one which has been separated from a component of its natural environment. In certain embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

An "isolated nucleic acid encoding an antibody" (including references to a specific antibody, e.g. an anti-KLB antibody) refers to one or more nucleic acid molecules encoding antibody heavy and light chains (or fragments thereof), including such nucleic acid molecule(s) in a single vector separate vectors, and such nucleic acid molecule(s) present at one or more locations in a host cell.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

An "immunoconjugate" is an antibody conjugated to one or more heterologous molecule(s), including, but not limited to, a cytotoxic agent.

An "effective amount" of an agent, e.g., an anti-GPRC5D antibody or an antigen-binding fragment thereof, a pharmaceutical comprision comprising thereof, refers to an amount effective, at dosages and for periods of time necessary, to achieve the desired therapeutic or prophylactic result, e.g., treating a tumor (e.g., multiple myeloma).

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In certain embodiments, antibodies of the presently disclosed subject matter are used to delay development of a disease or to slow the progression of a disease, e.g., a tumor (multiple myeloma).

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As described herein, any concentration range, percentage range, ratio range or integer range is to be understood to include the value of any integer within the recited range and, when appropriate, fractions thereof (such as one tenth and one hundredth of an integer), unless otherwise indicated.

Anti-GPRC5D Antibodies

The antibodies of the presently disclosed subject matter are characterized by particular functional features or properties of the antibodies. For example, the antibodies bind specifically to GPRC5D (e.g., bind to human GPRC5D and may cross-react with GPRC5D from other species, such as mouse). In certain embodiments, an antibody of the presently disclosed subject matter binds to GPRC5D with high affinity, for example with a $K_d$ of $1\times10^{-7}$ M or less, e.g., about $1\times10^{8}$ M or less, about $1\times10^{-9}$ M or less, or about $1\times10^{-10}$ M or less. In certain embodiments, a presently disclosed anti-GPRC5D antibody binds to GPRC5D (e.g., human GPRC5D) with a $K_d$ of from about $1\times10^{-10}$ M to about $1\times10^{-7}$ M, e.g., about from about $1\times10^{-10}$ M to about $1\times10^{-9}$ M, from $1\times10^{-9}$ M to about $1\times10^{-8}$ M, or from about $1\times10^{-8}$ M to about $1\times10^{-7}$ M. In certain embodiments, a presently disclosed anti-GPRC5D antibody binds to GPRC5D (e.g., human GPRC5D) with a $K_d$ of about $1\times10^{-8}$ M or less. In certain embodiments, a presently disclosed anti-GPRC5D antibody binds to GPRC5D (e.g., human GPRC5D) with a $K_d$ of from about $1\times10^{-9}$ M to about $1\times10^{-8}$ M. In certain embodiments, a presently disclosed anti-GPRC5D antibody binds to GPRC5D (e.g., human GPRC5D) with a $K_d$ of from about $1\times10^{-9}$ M to about $1.5\times10^{-9}$ M. In certain embodiments, a presently disclosed anti-GPRC5D antibody binds to GPRC5D (e.g., human GPRC5D) with a $K_d$ of about $1.2\times10^{-9}$ M. In certain embodiments, a presently disclosed anti-GPRC5D antibody binds to GPRC5D (e.g., human GPRC5D) with a $K_d$ of from about $4\times10^{-9}$ M to about $5\times10^{-9}$ M. In certain embodiments, a presently disclosed anti-GPRC5D antibody binds to GPRC5D (e.g., human GPRC5D) with a $K_d$ of about $5\times10^{-9}$ M. In certain embodiments, a presently disclosed anti-GPRC5D antibody binds to GPRC5D (e.g., human GPRC5D) with a $K_d$ of about $4.8\times10^{-9}$ M. In certain embodiments, a presently disclosed anti-GPRC5D antibody binds to GPRC5D (e.g., human GPRC5D) with a $K_d$ of from about $8\times10^{-9}$ M to about $9\times10^{-9}$ M. In certain embodiments, a presently disclosed anti-GPRC5D antibody binds to GPRC5D (e.g., human GPRC5D) with a $K_d$ of about $8\times10^{-9}$ M. In certain embodiments, a presently disclosed anti-GPRC5D antibody binds to GPRC5D (e.g., human GPRC5D) with a $K_d$ of about $8.1\times10^{-9}$ M.

The heavy and light chains of an antibody of the presently disclosed subject matter can be full-length (e.g., an antibody can include at least one (e.g., one or two) complete heavy chains, and at least one (e.g., one or two) complete light chains) or can include an antigen-binding portion (a Fab, F(ab')$_2$, Fv or a single chain Fv fragment ("scFv")). In certain embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

1. Single-Chain Variable Fragments (scFvs)

In certain embodiments, the presently disclosed subject matter includes antibodies that have the scFv sequence fused to one or more constant domains to form an antibody with an Fc region of a human immunoglobulin to yield a bivalent protein, increasing the overall avidity and stability of the antibody. In addition, the Fc portion allows the direct conjugation of other molecules, including but not limited to fluorescent dyes, cytotoxins, radioisotopes etc. to the antibody for example, for use in antigen quantitation studies, to immobilize the antibody for affinity measurements, for targeted delivery of a therapeutic agent, to test for Fc-mediated cytotoxicity using immune effector cells and many other applications.

The results presented here highlight the specificity, sensitivity and utility of the antibodies of the invention in targeting a GPRC5D polypeptide.

The molecules of the invention are based on the identification and selection of single chain variable fragments (scFvs) using phage display, the amino acid sequence of which confers the molecules' specificity for a GPRC5D polypeptide of interest and forms the basis of all antigen binding proteins of the disclosure. The scFv, therefore, can be used to design a diverse array of "antibody" molecules, including, for example, full length antibodies, fragments thereof, such as Fab and F(ab')$_2$, minibodies, fusion proteins, including scFv-Fc fusions, multivalent antibodies, that is, antibodies that have more than one specificity for the same antigen or different antigens, for example, bispecific antibodies, tribodies, etc. (see Cuesta et al., Multivalent antibodies: when design surpasses evolution. Trends in Biotechnology 28:355-362 2010).

In certain embodiments, the antigen-binding protein is a full length antibody, the heavy and light chains of an antibody of the presently disclosed subject matter can be full-length (e.g., an antibody can include at least one, and preferably two, complete heavy chains, and at least one, and preferably two, complete light chains) or can include an antigen-binding portion (a Fab, F(ab')$_2$, Fv or a single chain Fv fragment ("scFv")). In certain embodiments, the antibody heavy chain constant region is chosen from, e.g., IgG1, IgG2, IgG3, IgG4, IgM, IgA1, IgA2, IgD, and IgE. In certain embodiments, the immunoglobulin isotype is selected from IgG1, IgG2, IgG3, and IgG4, more particularly, IgG1 (e.g., human IgG1). The choice of antibody isotype can depend on the immune effector function that the antibody is designed to elicit.

In constructing a recombinant immunoglobulin, appropriate amino acid sequences for constant regions of various immunoglobulin isotypes and methods for the production of a wide array of antibodies are known to those of skill in the art.

In certain embodiments, the antibody or other antigen binding protein is an anti-GPRC5D scFv or an antigen-binding fragment thereof having an antigen-binding region that comprises the amino acid sequence of SEQ ID NO: 100 and specifically binds to a GPRC5D polypeptide (e.g., a GPRC5D polypeptide having the amino acid sequence SEQ ID NO:97 which is provided below, or fragments thereof).

[SEQ ID NO: 97]

```
MYKDCIESTGDYFLLCDAEGPWGIILESLAILGIVVTILLLLAFLFLMR

KIQDCSQWNVLPTQLLFLLSVLGLFGLAFAFIIELNQQTAPVRYFLFGV

LFALCFSCLLAHASNLVKLVRGCVSFSWTTILCIAIGCSLLQIIIATEY

VTLIMTRGMMFVNMTPCQLNVDFVVLLVYVLFLMALTFFVSKATFCGPC

ENWKQHGRLIFITVLFSIIIWVVWISMLLRGNPQFORQPQWDDPVVCIA

LVTNAWVFLLLYIVPELCILYRSCRQECPLQGNACPVTAYQHSFQVENQ

ELSRARDSDGAEEDVALTSYGTPIQPQTVDPTQECFIPQAKLSPQQDAG

GV
```

The N-terminal region of human GPRC5D has amino acids 1-27 of SEQ ID NO:97. The extracellular loop 1 (ECL1) region of human GPRC5D has amino acids 85-93 of SEQ ID NO:97. The extracellular loop 2 (ECL2) region of human GPRC5D has amino acids 145-167 of SEQ ID NO:97. The extracellular loop 3 (ECL3) region of human GPRC5D has amino acids 226-239 of SEQ ID NO:97.

In certain embodiments, the antibody or other antigen binding protein is an anti-GPRC5D scFv or an antigen-binding fragment thereof having an antigen-binding region that comprises the amino acid sequence of SEQ ID NO:100 and specifically binds to a GPRC5D polypeptide (e.g., a GPRC5D polypeptide having the amino acid sequence SEQ ID NO:97, or fragments thereof), which is designated as ET150-153 scFv (also referred to as "ET150-3 scFv").

In certain embodiments, the anti-GPRC5D scFv antibody comprises a heavy chain variable region comprising amino acids having the sequence set forth in SEQ ID NO:1 and a light chain variable region comprising amino acids having the sequence set forth in SEQ ID NO:2, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 1. In certain embodiments, the anti-GPRC5D scFv comprises a $V_H$ comprising amino acids having the sequence set forth in SEQ ID NO:1, as shown in Table 1. In certain embodiments, the anti-GPRC5D scFv comprises a $V_L$ comprising amino acids having the sequence set forth in SEQ ID NO:2, as shown in Table 1. In certain embodiments, the anti-GPRC5D scFv comprises a $V_H$ comprising amino acids having the sequence set forth in SEQ ID NO:1 and a $V_L$ comprising amino acids having the sequence set forth in SEQ ID NO:2, as shown in Table 1. In certain embodiments, the anti-GPRC5D scFv comprises a $V_H$ CDR1 comprising amino acids having the sequence set forth in SEQ ID NO:124 or conservative modifications thereof, a $V_H$ CDR2 comprising amino acids having the sequence set forth in SEQ ID NO:125 or conservative modifications thereof, and a $V_H$ CDR3 comprising amino acids having the sequence set forth in SEQ ID NO:126 or conservative modifications thereof, as shown in Table 1. In certain embodiments, the anti-GPRC5D scFv comprises a $V_L$ CDR1 comprising amino acids having the sequence set forth in SEQ ID NO:127 or conservative modifications thereof, a $V_L$ CDR2 comprising amino acids having the sequence set forth in SEQ ID NO:128 or conservative modifications thereof, and a $V_L$ CDR3 comprising amino acids having the sequence set forth in SEQ ID NO:129 or conservative modifications thereof, as shown in Table 1. In certain embodiments, the anti-GPRC5D scFv comprises a $V_H$ CDR1 comprising amino acids having the sequence set forth in SEQ ID NO:124 or conservative modifications thereof, a $V_H$ CDR2 comprising amino acids having the sequence set forth in SEQ ID NO:125 or conservative modifications thereof, a $V_H$ CDR3 comprising amino acids having the sequence set forth in SEQ ID NO:126 or conservative modifications thereof, a $V_L$ CDR1 comprising amino acids having the sequence set forth in SEQ ID NO:127 or conservative modifications thereof, a $V_L$ CDR2 comprising amino acids having the sequence set forth in SEQ ID NO:128 or conservative modifications thereof, and a $V_L$ CDR3 comprising amino acids having the sequence set forth in SEQ ID NO:129 or conservative modifications thereof, as shown in Table 1. In certain embodiments, the anti-GPRC5D scFv comprises a $V_H$ CDR1 comprising amino acids having the sequence set forth in SEQ ID NO:124, a $V_H$ CDR2 comprising amino acids having the sequence set forth in SEQ ID NO:125, a $V_H$ CDR3 comprising amino acids having the sequence set forth in SEQ ID NO: 126, a $V_L$ CDR1 comprising amino acids having the sequence set forth in SEQ ID NO: 127, a $V_L$ CDR2 comprising amino acids having the sequence set forth in SEQ ID NO: 128, and a $V_L$ CDR3 comprising amino acids having the sequence set forth in SEQ ID NO: 129.

Table 2. In certain embodiments, the anti-GPRC5D scFv comprises a $V_H$ CDR1 comprising amino acids having the sequence set forth in SEQ ID NO:130 or conservative modifications thereof, a $V_H$ CDR2 comprising amino acids having the sequence set forth in SEQ ID NO:131 or con-

TABLE 1

| Antigen | A GPRC5D polypeptide having the amino acid sequence of SEQ ID NO: 97 | | |
| --- | --- | --- | --- |
| CDRs | 1 | 2 | 3 |
| $V_H$ | GYTFTSYY [SEQ ID NO: 124] | GYTFTSYY [SEQ ID NO: 125] | ARGMYRSLLFYDP [SEQ ID NO: 126] |
| $V_L$ | RSNVGNYY [SEQ ID NO: 127] | DNN [SEQ ID NO: 128] | GTWDGSLSAHV [SEQ ID NO: 129] |
| Full $V_H$ | QVQLVQSGSELKKPGASVRVSCTASGYTFTSYYMEIWVRQAPGQGLEW MGVINPNAGSTRYAQKFQGRVTMSTDTSTSTAYMDLSSLRSEDTAVYY CARGMYRSLLFYDPWGQGTLVTVSS [SEQ ID NO: 1] | | |
| DNA | Caggtgcagctggtgcagtctgggtctgagttgaagaagcctgggcctcagtcagagtctcctgcacggcttctg gatacacccttcaccagttactatatgcactgggtgcgacaggcccctggacaagggcttgagtggatgggagtaat caaccctaatgctggcagcacaagatacgcacagaaattccagggcagagtcaccatgagcactgacacgtcca cgagcacagcctacatggacctgagcagtctgagatctgaggacacggccgtgtattactgtgcgcgcggtatgta ccgttctctgctgttctacgatccgtggggtcaaggtactctggtgaccgtctcctca [SEQ ID NO: 3] | | |
| Full $V_L$ | QSVLTQPPSVSAAPGQKVTIPCSGSRSNVGNYYVSWYQQLPGTAPKLLI YDNNKRPSGIPDRFSGSKSGTSATLGITGLQTGDEADYFCGTWDGSLSA HVFGTGTKVTVLG [SEQ ID NO: 2] | | |
| DNA | Cagtctgtgttgacgcagccgccctcagtgtctgcggccccaggacagaaggtcaccatcccctgctctggaagc cgttccaacgttgggaattattatgtgtcctggtaccagcaactcccaggaacagcccccaaactcctcatttatgac aataataagcgaccctcagggattcctgaccgattctctggctccaagtctggcacgtcagccaccctgggcatcac cggactccagactggggacgaggccgattatttctgcggaacatgggatggcagcctgagtgcccatgtatcgga actgggaccaaggtcaccgtcctaggt [SEQ ID NO: 4] | | |
| scFv | QSVLTQPPSVSAAPGQKVTIPCSGSRSNVGNYYVSWYQQLPGTAPKLLI YDNNKRPSGIPDRFSGSKSGTSATLGITGLQTGDEADYFCGTWDGSLSA HVFGTGTKVTVLGSRGGGGSGGGGSGGGGSLEMAQVQLVQSGSELKK PGASVRVSCTASGYTFTSYYMHWVRQAPGQGLEWMGVINPNAGSTRY AQKFQGRVTMSTDTSTSTAYIVIDLSSLRSEDTAVYYCARGMYRSLLFYD PWGQGTLVTVSS [SEQ ID NO: 100] | | |

In certain embodiments, the antibody or other antigen binding protein is an anti-GPRC5D scFv or an antigen-binding fragment thereof having an antigen-binding region that comprises the amino acid sequence of SEQ ID NO: 101 and specifically binds to a GPRC5D polypeptide (e.g., a GPRC5D polypeptide having the amino acid sequence SEQ ID NO:97, or fragments thereof), which is designated as ET150-166 scFv (also referred to as "ET150-16 scFv"). In certain embodiments, the anti-GPRC5D scFv antibody comprises a heavy chain variable region comprising amino acids having the sequence set forth in SEQ ID NO:5 and a light chain variable region comprising amino acids having the sequence set forth in SEQ ID NO:6, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 2. In certain embodiments, the anti-GPRC5D scFv comprises a $V_H$ comprising amino acids having the sequence set forth in SEQ ID NO:5, as shown in Table 2. In certain embodiments, the anti-GPRC5D scFv comprises a $V_L$ comprising amino acids having the sequence set forth in SEQ ID NO:6, as shown in Table 2. In certain embodiments, the anti-GPRC5D scFv comprises a $V_H$ comprising amino acids having the sequence set forth in SEQ ID NO:5 and a $V_L$ Comprising amino acids having the sequence set forth in SEQ ID NO:6, as shown in servative modifications thereof, and a $V_H$ CDR3 comprising amino acids having the sequence set forth in SEQ ID NO:132 or conservative modifications thereof, as shown in Table 2. In certain embodiments, the anti-GPRC5D scFv comprises a $V_L$ CDR1 comprising amino acids having the sequence set forth in SEQ ID NO:133 or conservative modifications thereof, a $V_L$ CDR2 comprising amino acids having the sequence set forth in SEQ ID NO:134 or conservative modifications thereof, and a $V_L$ CDR3 comprising amino acids having the sequence set forth in SEQ ID NO:135 or conservative modifications thereof, as shown in Table 2. In certain embodiments, the anti-GPRC5D scFv comprises a $V_H$ CDR1 comprising amino acids having the sequence set forth in SEQ ID NO:130 or conservative modifications thereof, a $V_H$ CDR2 comprising amino acids having the sequence set forth in SEQ ID NO: 131 or conservative modifications thereof, a $V_H$ CDR3 comprising amino acids having the sequence set forth in SEQ ID NO: 132 or conservative modifications thereof, a $V_L$ CDR1 comprising amino acids having the sequence set forth in SEQ ID NO: 133 or conservative modifications thereof, a $V_L$ CDR2 comprising amino acids having the sequence set forth in SEQ ID NO: 134 or conservative modifications thereof, and a $V_L$ CDR3 comprising amino acids having the sequence set forth in SEQ ID NO:135 or conservative modifications thereof, as shown in Table 2. In certain embodiments, the anti-GPRC5D scFv comprises a $V_H$ CDR1 comprising amino acids having the sequence set forth in SEQ ID NO:130, a $V_H$ CDR2 comprising amino acids having the sequence set forth in SEQ ID NO:131, a V_H CDR3 comprising amino acids having the sequence set forth in SEQ ID NO:132, a VE CDR1 comprising amino acids having the sequence set forth in SEQ ID NO: 133, a V_L CDR2 comprising amino acids having the sequence set forth in SEQ ID NO: 134, and a V_L CDR3 comprising amino acids having the sequence set forth in SEQ ID NO: 135.

set forth in SEQ ID NO:9 and a V_L comprising amino acids having the sequence set forth in SEQ ID NO:10, as shown in Table 3. In certain embodiments, the anti-GPRC5D scFv comprises a V_H CDR1 comprising amino acids having the sequence set forth in SEQ ID NO:136 or conservative modifications thereof, a V_H CDR2 comprising amino acids having the sequence set forth in SEQ ID NO:137 or con-

TABLE 2

Antigen  A GPRC5D polypeptide having the amino acid sequence of SEQ ID NO: 97

| CDRs | 1 | 2 | 3 |
|---|---|---|---|
| V_H | GFTFSNYA [SEQ ID NO: 130] | ISGSGNT [SEQ ID NO: 131] | ARGSVRYTDI [SEQ ID NO: 132] |
| V_L | SGAIAGAY [SEQ ID NO: 133] | DDN [SEQ ID NO: 134] | QSYDYDSSNVL [SEQ ID NO: 135] |

Full V_H  EVQLVESGGGLVQPGGSLRLSCAASGFTFSNYAMSWVRQAPGKGLE
          WVSAISGSGNTYYADSVKGRFTISRDNSKNTLYLQMNSLRAEDTAVY
          YCARGSVRYTDIWGQGTLVTVSS [SEQ ID NO: 5]

DNA  Gaggtgcagctggtggagtctggggggaggcttggtacagcctgggggtccctgagactctcctgtgcagc
     ctctggattcacctttagcaactatgccatgagttgggtccgccaggctccagggaagggactggagtgggtct
     cagctattagtggtagtggtaacacatactacgcagactccgtgaagggccggttcaccatctccagagacaat
     tccaagaacacgctgtatctgcaaatgaacagcctgagagccgaggacacggccgtatattactgtgcgcgcg
     gttctgttcgttacactgatatctggggtcaaggtactctggtgaccgtctcctca [SEQ ID NO: 7]

Full V_L  NFMLTQPHSVSESPGKTVSISCTRTSGAIAGAYVQWFQQRPGSAPTTV
          IYDDNKRPSGVPDRFSGSIDKSSNSASLTISGLKTEDEADYYCQSYDY
          DSSNVLFGGGTKLTVLG [SEQ ID NO: 6]

DNA  Aattttatgctgactcagccccactcagtgtcggagtctccggggaagacggtaagcatctcctgcacccgca
     ccagtggcgccattgccggcgcctatgtgcagtggttccagcagcgcccgggcagtgcccccaccactgtga
     tctatgacgataacaaaagaccctctggggtccctgatcggttctctgggtccatcgacaagtcctccaactctg
     cctccctcaccatctctggactgaagactgaggacgaggctgactattattgtcagtatatgattatgatagcag
     caatgtgctattcggcggagggaccaagctgaccgtcctaggt [SEQ ID NO: 8]

scFv  NFMLTQPHSVSESPGKTVSISCTRTSGAIAGAYVQWFQQRPGSAPTTV
      IYDDNKRPSGVPDRFSGSIDKSSNSASLTISGLKTEDEADYYCQSYDY
      DSSNVLFGGGTKLTVLGSRGGGGSGGGGSGGGGSLEMAEVQLVESG
      GGLVQPGGSLRLSCAASGFTFSNYAMSWVRQAPGKGLEWVSAISGS
      GNTYYADSVKGRFTISRDNSKNTLYLQMNSLRAEDTAVYYCARGSV
      RYTDIWGQGTLVTVSS [SEQ ID NO: 101]

In certain embodiments, the antibody or other antigen binding protein is an anti-GPRC5D scFv or an antigen-binding fragment thereof having an antigen-binding region that comprises the amino acid sequence of SEQ ID NO:102 and specifically binds to a GPRC5D polypeptide (e.g., a GPRC5D polypeptide having the amino acid sequence SEQ ID NO:97, or fragments thereof), which is designated as ET150-170 scFv (also referred to as "ET150-20 scFv").

In certain embodiments, the anti-GPRC5D scFv antibody comprises a heavy chain variable region comprising amino acids having the sequence set forth in SEQ ID NO:9 and a light chain variable region comprising amino acids having the sequence set forth in SEQ ID NO:10, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with V_H and V_L regions or CDRs selected from Table 3. In certain embodiments, the anti-GPRC5D scFv comprises a V_H comprising amino acids having the sequence set forth in SEQ ID NO:9, as shown in Table 3. In certain embodiments, the anti-GPRC5D scFv comprises a V_L comprising amino acids having the sequence set forth in SEQ ID NO:10, as shown in Table 3. In certain embodiments, the anti-GPRC5D scFv comprises a V_H comprising amino acids having the sequence servative modifications thereof, and a V_H CDR3 comprising amino acids having the sequence set forth in SEQ ID NO:138 or conservative modifications thereof, as shown in Table 3. In certain embodiments, the anti-GPRC5D scFv comprises a V_L CDR1 comprising amino acids having the sequence set forth in SEQ ID NO:139 or conservative modifications thereof, a V_L CDR2 comprising amino acids having the sequence set forth in SEQ ID NO:140 or conservative modifications thereof, and a V_L CDR3 comprising amino acids having the sequence set forth in SEQ ID NO:141 or conservative modifications thereof, as shown in Table 3. In certain embodiments, the anti-GPRC5D scFv comprises a V_H CDR1 comprising amino acids having the sequence set forth in SEQ ID NO:136 or conservative modifications thereof, a V_H CDR2 comprising amino acids having the sequence set forth in SEQ ID NO:137 or conservative modifications thereof, a V_H CDR3 comprising amino acids having the sequence set forth in SEQ ID NO:138 or conservative modifications thereof, a V_L CDR1 comprising amino acids having the sequence set forth in SEQ ID NO:139 or conservative modifications thereof, a V_L CDR2 comprising amino acids having the sequence set forth in SEQ ID NO:140 or conservative modifications thereof, and a V_L CDR3 comprising amino acids having the sequence set forth in SEQ ID NO:141 or conservative modifications thereof, as shown in Table 3. In certain embodiments, the anti-GPRC5D scFv comprises a V_H CDR1 comprising amino acids having the sequence set forth in SEQ ID NO:136, a $V_H$ CDR2 comprising amino acids having the sequence set forth in SEQ ID NO:137, a $V_H$ CDR3 comprising amino acids having the sequence set forth in SEQ ID NO:138, a $V_L$ CDR1 comprising amino acids having the sequence set forth in SEQ ID NO:139, a $V_L$ CDR2 comprising amino acids having the sequence set forth in SEQ ID NO:140, and a $V_L$ CDR3 comprising amino acids having the sequence set forth in SEQ ID NO:141.

having the sequence set forth in SEQ ID NO:14, as shown in Table 4. In certain embodiments, the anti-GPRC5D scFv comprises a $V_H$ comprising amino acids having the sequence set forth in SEQ ID NO:13 and a $V_L$ comprising amino acids having the sequence set forth in SEQ ID NO:14, as shown in Table 4. In certain embodiments, the anti-GPRC5D scFv comprises a $V_H$ CDR1 comprising amino acids having the sequence set forth in SEQ ID NO:142 or conservative modifications thereof, a $V_H$ CDR2 comprising amino acids

TABLE 3

Antigen A GPRC5D polypeptide having the amino acid sequence of SEQ ID NO: 97

| CDRs | 1 | 2 | 3 |
|---|---|---|---|
| $V_H$ | GFTFNNYW [SEQ ID NO: 136] | IKQDGSEK [SEQ ID NO: 137] | ARSMSTAV [SEQ ID NO: 138] |
| $V_L$ | QSISSY [SEQ ID NO: 139] | AAS [SEQ ID NO: 140] | QQSYSVPYT [SEQ ID NO: 141] |
| Full $V_H$ | EVQLVQSGGGLVQPGGSLRLSCATSGFTFNNYWMSWVRQAPGKGLE WVANIKQDGSEKYYADSVRGRFTISRDNAKNSLSLQLNNLRAEDTAV YYCARSMSTAWGYDEWGQGTLVTVSS [SEQ ID NO: 9] | | |
| DNA | Gaggtgcagctggtgcagtctggggggaggcttggtccagcctggggggtccctgagactctcctgtgcaacct ctggattcacctttaataactattggatgagttgggtccgccaggctccagggaaggggctggagtgggtggcc aacataaagcaagatggaagtgagaaatactacgcggactctgtgaggggccgattcaccatctccagagaca acgccaagaactcactgtctctgcaattgaacaacctgagagccgaggacacggccgtgtattactgtgcgcgc tctatgtctactgatggggttacgatgaatggggtcaaggtactctggtgaccgtctcctca [SEQ ID NO: 11] | | |
| Full $V_L$ | DIQLTQSPSSLSASVGDRVTITCRASQSISSYLNWYQQKPGKAPKLLIY AASSLQSGVPSRFSGSGSGTDFTLTISSLQPADFATYYCQQSYSVPYTF GQGTKLEIKR [SEQ ID NO: 10] | | |
| DNA | Gacatccagttgacccagtctccatcctccctgtctgcatctgtcggagacagagtcaccatcacttgccgggca agtcagagcattagcagctatttaaattggtatcaacagaaaccagggaaagcccctaagctcctgatctatgctg catccagtttgcaaagtggggtcccatcaaggttcagtggcagtggatctgggacagatttcactctcaccatcag cagtctgcaacctgcagattttgcaacttactactgtcaacagagttacagtgtcccgtacacttttggccagggga ccaagctggagatcaaacgt [SEQ ID NO: 12] | | |
| scFv | DIQLTQSPSSLSASVGDRVTITCRASQSISSYLNWYQQKPGKAPKLLIY AASSLQSGVPSRFSGSGSGTDFTLTISSLQPADFATYYCQQSYSVPYTF GQGTKLEIKRSRGGGGSGGGGSGGGGSLEMAEVQLVQSGGGLVQPG GSLRLSCATSGFTFNNYWMSWVRQAPGKGLEWVANIKQDGSEKYYA DSVRGRFTISRDNAKNSLSLQLNNLRAEDTAVYYCARSMSTAWGYDE WGQGTLVTVSS [SEQ ID NO: 102] | | |

In certain embodiments, the antibody or other antigen binding protein is an anti-GPRC5D scFv or an antigen-binding fragment thereof having an antigen-binding region that comprises the amino acid sequence of SEQ ID NO: 103 and specifically binds to a GPRC5D polypeptide (e.g., a GPRC5D polypeptide having the amino acid sequence SEQ ID NO:97, or fragments thereof), which is designated as ET150-171 scFv (also referred to as "ET150-21 scFv").

In certain embodiments, the anti-GPRC5D scFv antibody comprises a heavy chain variable region comprising amino acids having the sequence set forth in SEQ ID NO: 13 and a light chain variable region comprising amino acids having the sequence set forth in SEQ ID NO: 14, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 4. In certain embodiments, the anti-GPRC5D scFv comprises a $V_H$ comprising amino acids having the sequence set forth in SEQ ID NO:13, as shown in Table 4. In certain embodiments, the anti-GPRC5D scFv comprises a $V_L$ comprising amino acids having the sequence set forth in SEQ ID NO:143 or conservative modifications thereof, and a $V_H$ CDR3 comprising amino acids having the sequence set forth in SEQ ID NO:144 or conservative modifications thereof, as shown in Table 4. In certain embodiments, the anti-GPRC5D scFv comprises a $V_L$ CDR1 comprising amino acids having the sequence set forth in SEQ ID NO:145 or conservative modifications thereof, a $V_L$ CDR2 comprising amino acids having the sequence set forth in SEQ ID NO:146 or conservative modifications thereof, and a $V_L$ CDR3 comprising amino acids having the sequence set forth in SEQ ID NO:147 or conservative modifications thereof, as shown in Table 4. In certain embodiments, the anti-GPRC5D scFv comprises a $V_H$ CDR1 comprising amino acids having the sequence set forth in SEQ ID NO:142 or conservative modifications thereof, a $V_H$ CDR2 comprising amino acids having the sequence set forth in SEQ ID NO:143 or conservative modifications thereof, a $V_H$ CDR3 comprising amino acids having the sequence set forth in SEQ ID NO:144 or conservative modifications thereof, a $V_L$ CDR1 comprising amino acids having the sequence set forth in SEQ ID NO:145 or conservative modifications thereof, a $V_L$ CDR2 comprising amino acids having the sequence set forth in SEQ ID NO:146 or conservative modifications thereof, and a V_L CDR3 comprising amino acids having the sequence set forth in SEQ ID NO:147 or conservative modifications thereof, as shown in Table 4. In certain embodiments, the anti-GPRC5D scFv comprises a V_H CDR1 comprising amino acids having the sequence set forth in SEQ ID NO:142, a V_H CDR2 comprising amino acids having the sequence set forth in SEQ ID NO:143, a V_H CDR3 comprising amino acids having the sequence set forth in SEQ ID NO:144, a V_L CDR1 comprising amino acids having the sequence set forth in SEQ ID NO:145, a V_L CDR2 comprising amino acids having the sequence set forth in SEQ ID NO:146, and a V_L CDR3 comprising amino acids having the sequence set forth in SEQ ID NO: 147.

embodiments, the anti-GPRC5D scFv comprises a V_H comprising amino acids having the sequence set forth in SEQ ID NO:17, as shown in Table 5. In certain embodiments, the anti-GPRC5D scFv comprises a V_L comprising amino acids having the sequence set forth in SEQ ID NO:18, as shown in Table 5. In certain embodiments, the anti-GPRC5D scFv comprises a V_H comprising amino acids having the sequence set forth in SEQ ID NO:17 and a V_L comprising amino acids having the sequence set forth in SEQ ID NO:18, as shown in Table 5. In certain embodiments, the anti-GPRC5D scFv comprises a V_H CDR1 comprising amino acids having the sequence set forth in SEQ ID NO:148 or conservative modifications thereof, a V_H CDR2 comprising amino acids

TABLE 4

```
Antigen  A GPRC5D polypeptide having the amino acid sequence of SEQ ID NO: 97

CDRs     1                      2                    3
V_H      GYTFTSYY [SEQ          INPSGGST [SEQ ID     ARGSSRWGGWTGDY
         ID NO: 142]            NO: 143]             [SEQ ID NO: 144]

V_L      SSDVGGYNF [SEQ         DVS [SEQ ID NO: 146] SSYTSTRTVIFAGGTKVTV
         ID NO: 145]                                 L [SEQ ID NO: 147]

Full V_H QVQLVQSGAEVKKPGASVKVSCKASGYTFTSYYMHWVRQAPGQGLEW
         MGIINPSGGSTRYAQKFQGRVTMTRDTSTSTVYMELSSLRSEDTAVYYC
         ARGSSRWGGWTGDYWGQGTLVTVSS [SEQ ID NO: 13]

DNA      Caggtgcagctggtgcagtctgggggctgaggtgaagaagcctgggggcctcagtgaaggtttcctgcaaggcatct
         ggatacacctttaccagctactatatgcactgggtgcgacaggcccctggacaagggcttgagtggatgggaataat
         caaccctagtggtggtagcacaaggtacgcacagaagttccagggcagagtcaccatgaccagggacacgtcaac
         gagcacagtctacatggagctgagcagcctgagatctgaggacacgccgtgtattactgtgcgcgcggttcttctc
         gctggggtggttggactggtgattactggggtcaaggtactctggtgaccgtctcctca [SEQ ID NO: 15]

Full V_L QSALTQPASVSGSPGQSITISCTGTSSDVGGYNFVSWYQQHPGKAPKVMI
         YDVSKRPSGISNRFSGSKSGNTASLTISGLQVEDEAEYYCSSYTSTRTVIF
         AGGTKVTVLG [SEQ ID NO: 14]

DNA      Caatctgccctgactcagcctgcctccgtgtctgggtctcctggacagtcgatcaccatctcctgcactggaaccagc
         agtgacgttggtggttataactttgtctcctggtaccaacagcacccaggcaaagcccccaaagtcatgatttatgatg
         tcagtaagcggccctcagggattcttaatcgcttctctggctccaagtctggcaacacggcctccctgaccatctctgg
         gctccaggttgaggacgaggctgaatattactgcagctcatatacaagcactagaactgtgatattcgccggaggga
         ccaaggtcaccgtcctaggt [SEQ ID NO: 16]

scFv     QSALTQPASVSGSPGQSITISCTGTSSDVGGYNFVSWYQQHPGKAPKVMI
         YDVSKRPSGISNRFSGSKSGNTASLTISGLQVEDEAEYYCSSYTSTRTVIF
         AGGTKVTVLG
         SRGGGGSGGGGSGGGGSLEMAQVQLVQSGAEVKKPGASVKVSCKASG
         YTFTSYYMEIWVRQAPGQGLEWMGIINPSGGSTRYAQKFQGRVTMTRDT
         STSTVYMELSSLRSEDTAVYYCARGSSRWGGWTGDYWGQGTLVTVSS
         [SEQ ID NO: 103]
```

In certain embodiments, the antibody or other antigen binding protein is an anti-GPRC5D scFv or an antigen-binding fragment thereof having an antigen-binding region that comprises the amino acid sequence of SEQ ID NO: 104 and specifically binds to a GPRC5D polypeptide (e.g., a GPRC5D polypeptide having the amino acid sequence SEQ ID NO:97, or fragments thereof), which is designated as ET150-175 scFv (also referred to as "ET150-25 scFv").

In certain embodiments, the anti-GPRC5D scFv antibody comprises a heavy chain variable region comprising amino acids having the sequence set forth in SEQ ID NO:17 and a light chain variable region comprising amino acids having the sequence set forth in SEQ ID NO:18, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with V_H and V_L regions or CDRs selected from Table 5. In certain having the sequence set forth in SEQ ID NO:149 or conservative modifications thereof, and a V_H CDR3 comprising amino acids having the sequence set forth in SEQ ID NO:150 or conservative modifications thereof, as shown in Table 5. In certain embodiments, the anti-GPRC5D scFv comprises a V_L CDR1 comprising amino acids having the sequence set forth in SEQ ID NO:151 or conservative modifications thereof, a V_L CDR2 comprising amino acids having the sequence set forth in SEQ ID NO:152 or conservative modifications thereof, and a V_L CDR3 comprising amino acids having the sequence set forth in SEQ ID NO:153 or conservative modifications thereof, as shown in Table 5. In certain embodiments, the anti-GPRC5D scFv comprises a V_H CDR1 comprising amino acids having the sequence set forth in SEQ ID NO:148 or conservative modifications thereof, a V_H CDR2 comprising amino acids having the sequence set forth in SEQ ID NO:149 or conservative modifications thereof, a V_H CDR3 comprising amino acids having the sequence set forth in SEQ ID NO: 150 or conservative modifications thereof, a V_L CDR1 comprising amino acids having the sequence set forth in SEQ ID NO:151 or conservative modifications thereof, a V$_L$ CDR2 comprising amino acids having the sequence set forth in SEQ ID NO:152 or conservative modifications thereof, and a V$_L$ CDR3 comprising amino acids having the sequence set forth in SEQ ID NO:153 or conservative modifications thereof, as shown in Table 5. In certain embodiments, the anti-GPRC5D scFv comprises a V$_H$ CDR1 comprising amino acids having the sequence set forth in SEQ ID NO: 148, a V$_H$ CDR2 comprising amino acids having the sequence set forth in SEQ ID NO: 149, a V$_H$ CDR3 comprising amino acids having the sequence set forth in SEQ ID NO: 150, a V$_L$ CDR1 comprising amino acids having the sequence set forth in SEQ ID NO:151, a V$_L$ CDR2 comprising amino acids having the sequence set forth in SEQ ID NO: 152, and a V$_L$ CDR3 comprising amino acids having the sequence set forth in SEQ ID NO: 153.

certain embodiments, the anti-GPRC5D scFv antibody is an scFv-Fc fusion protein or full length human IgG with V$_H$ and V$_L$ regions or CDRs selected from Table 6. In certain embodiments, the anti-GPRC5D scFv comprises a V$_H$ comprising amino acids having the sequence set forth in SEQ ID NO:21, as shown in Table 6. In certain embodiments, the anti-GPRC5D scFv comprises a V$_L$ comprising amino acids having the sequence set forth in SEQ ID NO:22, as shown in Table 6. In certain embodiments, the anti-GPRC5D scFv comprises a V$_H$ comprising amino acids having the sequence set forth in SEQ ID NO:21 and a V$_L$ comprising amino acids having the sequence set forth in SEQ ID NO:22, as shown in Table 6. In certain embodiments, the anti-GPRC5D scFv comprises a V$_H$ CDR1 comprising amino acids having the sequence set forth in SEQ ID NO: 154 or conservative modifications thereof, a V$_H$ CDR2 comprising amino acids having the sequence set forth in SEQ ID NO:155 or con-

TABLE 5

Antigen A GPRC5D polypeptide having the amino acid sequence of SEQ ID NO: 97

| CDRs | 1 | 2 | 3 |
|---|---|---|---|
| V$_H$ | GSTFSSYA [SEQ ID NO: 148] | ISGRGRST [SEQ ID NO: 149] | ARYYKSKDH [SEQ ID NO: 150] |
| V$_L$ | RSNIGTNY [SEQ ID NO: 151] | RNH [SEQ ID NO: 152] | AAWDDNLSGVV [SEQ ID NO: 153] |
| Full V$_H$ | EVQLVETGGGLVQPGGSLRLSCAASGSTFSSYAMSWVRQAPGKGLE WVSAISGRGRSTYYADSVKGRFTISRDNSKNTLYLQMNSLRAEDTAV YYCARYYKSSKDHWGQGTLVTVSS [SEQ ID NO: 17] | | |
| DNA | Gaggtgcagctggtggagactgggggaggcttggtacagcctggggggtccctgagactctcctgtgcagcc tctggatccaccttagcagctatgccatgagctgggtccgccaggctccagggaagggggctggagtgggtctc agctattagtggtcgtggtcgtagcacatactacgcagactccgtgaagggccggttcaccatctccagagaca attccaagaacacgctgtatctgcaaatgaacagcctgagagccgaggacacggccgtatattactgtgcgcgc tactacaaatcttctaaagatcattggggtcaaggtactctggtgaccgtctcctca [SEQ ID NO: 19] | | |
| Full V$_L$ | QSVLTQPPSLSGAPGQRVTISCSGSRSNIGTNYVSWXQQLPGTAPKLLI YRNHQWPSGVPDRFTGSKSGTSASLAISGLRSEDEADYYCAAWDDNL SGVVFGGGTKLTVLG [SEQ ID NO: 18] | | |
| DNA | Cagtctgtgttgacgcagccgccctcactgtctggggcccccagggcagagggtcaccatctcttgttccggaag caggtccaacatcggaactaattatgtatcctggnaccagcaactcccaggaacggccccaaactcctcatcta taggaatcatcagtggccctcaggggtccctgaccgattcactggctccaagtctggcacctcagcctccctggc catcagtgggctccggtccgaggatgaggctgattactactgtgcagcatgggatgacaatttgagtggtgtggt gttcggcggagggaccaagctgaccgtcctaggt [SEQ ID NO: 20] | | |
| scFv | QSVLTQPPSLSGAPGQRVTISCSGSRSNIGTNYVSWXQQLPGTAPKLLI YRNHQWPSGVPDRFTGSKSGTSASLAISGLRSEDEADYYCAAWDDNL SGVVFGGGTKLTVLGSRGGGGSGGGGSGGGGSLEMAEVQLVETGGG LVQPGGSLRLSCAASGSTFSSYAMSWVRQAPGKGLEWVSAISGRGRS TYYADSVKGRFTISRDNSKNTLYLQMNSLRAEDTAVYYCARYYKSSK DHWGQGTLVTVSS [SEQ ID NO: 104] | | |

In certain embodiments, the antibody or other antigen binding protein is an anti-GPRC5D scFv or an antigen-binding fragment thereof having an antigen-binding region that comprises the amino acid sequence of SEQ ID NO: 105 and specifically binds to a GPRC5D polypeptide (e.g., a GPRC5D polypeptide having the amino acid sequence SEQ ID NO:97, or fragments thereof), which is designated as ET150-154 scFv (also referred to as "ET150-4 scFv").

In certain embodiments, the anti-GPRC5D scFv antibody comprises a heavy chain variable region comprising amino acids having the sequence set forth in SEQ ID NO:21 and a light chain variable region comprising amino acids having the sequence set forth in SEQ ID NO:22, optionally with (iii) a linker sequence, for example a linker peptide, between the heavy chain variable region and the light chain variable region. In certain embodiments, the linker comprises amino acids having the sequence set forth in SEQ ID NO:98. In servative modifications thereof, and a V$_H$ CDR3 comprising amino acids having the sequence set forth in SEQ ID NO:156 or conservative modifications thereof, as shown in Table 6. In certain embodiments, the anti-GPRC5D scFv comprises a V$_L$ CDR1 comprising amino acids having the sequence set forth in SEQ ID NO:157 or conservative modifications thereof, a V$_L$ CDR2 comprising amino acids having the sequence set forth in SEQ ID NO:158 or conservative modifications thereof, and a V$_L$ CDR3 comprising amino acids having the sequence set forth in SEQ ID NO:159 or conservative modifications thereof, as shown in Table 6. In certain embodiments, the anti-GPRC5D scFv comprises a V$_H$ CDR1 comprising amino acids having the sequence set forth in SEQ ID NO:154 or conservative modifications thereof, a V$_H$ CDR2 comprising amino acids having the sequence set forth in SEQ ID NO:155 or conservative modifications thereof, a V$_H$ CDR3 comprising amino acids having the sequence set forth in SEQ ID NO:156 or conservative modifications thereof, a $V_L$ CDR1 comprising amino acids having the sequence set forth in SEQ ID NO:157 or conservative modifications thereof, a $V_L$ CDR2 comprising amino acids having the sequence set forth in SEQ ID NO:158 or conservative modifications thereof, and a $V_L$ CDR3 comprising amino acids having the sequence set forth in SEQ ID NO:159 or conservative modifications thereof, as shown in Table 6. In certain embodiments, the anti-GPRC5D scFv comprises a $V_H$ CDR1 comprising amino acids having the sequence set forth in SEQ ID NO:154, a $V_H$ CDR2 comprising amino acids having the sequence set forth in SEQ ID NO:155, a $V_H$ CDR3 comprising amino acids having the sequence set forth in SEQ ID NO:156, a $V_L$ CDR1 comprising amino acids having the sequence set forth in SEQ ID NO:157, a $V_L$ CDR2 comprising amino acids having the sequence set forth in SEQ ID NO:158, and a $V_L$ CDR3 comprising amino acids having the sequence set forth in SEQ ID NO:159.

heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 7. In certain embodiments, the anti-GPRC5D scFv comprises a $V_H$ comprising amino acids having the sequence set forth in SEQ ID NO:25, as shown in Table 7. In certain embodiments, the anti-GPRC5D scFv comprises a $V_L$ comprising amino acids having the sequence set forth in SEQ ID NO:26, as shown in Table 7. In certain embodiments, the anti-GPRC5D scFv comprises a $V_H$ comprising amino acids having the sequence set forth in SEQ ID NO:25 and a $V_L$ comprising amino acids having the sequence set forth in SEQ ID NO:26, as shown in Table 7. In certain embodiments, the anti-GPRC5D scFv comprises a $V_H$ CDR1 comprising amino acids having the sequence set forth in SEQ ID NO:160 or conservative modifications thereof, a $V_H$ CDR2 comprising amino acids

TABLE 6

Antigen A GPRC5D polypeptide having the amino acid sequence of SEQ ID NO: 97

| CDRs | 1 | 2 | 3 |
|---|---|---|---|
| $V_H$ | AYTFTDYY [SEQ ID NO: 154] | INPKSGRT [SEQ ID NO: 155] | ARVYGYSRWSGFDL [SEQ ID NO: 156] |
| $V_L$ | SSNIGSNY [SEQ ID NO: 157] | RNN [SEQ ID NO: 158] | AAWDDSLSGYV [SEQ ID NO: 159] |

Full $V_H$ QVQLVQSGAEVQRPGASVRVSCKAIAYTFTDYYIEIWVRQAPGQGP
EWMGWINPKSGRTQYAPKFQDRVTLARETPISTASMELRGLTSDDT
AVYYCARVYGYSRWSGFDLWGQGTLVTVSS [SEQ ID NO: 21]

DNA Caggtccagctggtgcagtctggggctgaggtgcagaggcctgggcctcagtgagggtctcctgcaag
gctattgcgtacaccttcaccgactactatatccactgggtgcagcggcccctggacaagggcctgagtgg
atggggtggatcaaccctaaaagtggtcgcacacagtatgcaccgaagtttcaagacagggtcaccctggc
cagggagacgcccatcagcacagcctccatggagctgcgcggactgacatctgacgacacggccgtgtat
tactgtgcgcgcgtttacggttactctcgttggtctggtttcgatctgtggggtcaaggtactctggtgaccgtc
tcctca [SEQ ID NO: 23]

Full $V_L$ QAVLTQPPSASGTPGQRVTISCSGSSSNIGSNYVYWYQQLPGTAPKL
LIYRNNQRPSGVPDRFSGSKSGTSASLATSGLRSEDEADYYCAAWD
DSLSGYVFGTGTKVTVLG [SEQ ID NO: 22]

DNA Caggctgtgctgactcagccaccctcagcgtctgggacccccgggcagagggtcaccatctcttgttctgg
aagcagctccaacatcggaagtaattatgtatactggtaccagcagctcccaggaacggcccccaaactcct
catctataggaataatcagcggccctcaggggtccctgaccgattctctggctccaagtctggcacctcagc
ctccctggccatcagtgggctccggtccgaggatgaggctgattattactgtgcagcatgggatgacagcct
gagtggttatgtcttcggaactgggaccaaggtcaccgtcctaggt [SEQ ID NO: 24]

scFv QAVLTQPPSASGTPGQRVTISCSGSSSNIGSNYVYWYQQLPGTAPKL
LIYRNNQRPSGVPDRFSGSKSGTSASLATSGLRSEDEADYYCAAWD
DSLSGYVFGTGTKVTVLGSRGGGGSGGGGSGGGGSLEMAQVQLV
QSGAEVQRPGASVRVSCKAIAYTFTDYYIEWVRQAPGQGPEWMG
WINPKSGRTQYAPKFQDRVTLARETPISTASMELRGLTSDDTAVYY
CARVYGYSRWSGFDLWGQGTLVTVSS [SEQ ID NO: 105]

In certain embodiments, the antibody or other antigen binding protein is an anti-GPRC5D scFv or an antigen-binding fragment thereof having an antigen-binding region that comprises the amino acid sequence of SEQ ID NO: 106 and specifically binds to a GPRC5D polypeptide (e.g., a GPRC5D polypeptide having the amino acid sequence SEQ ID NO:97, or fragments thereof), which is designated as ET150-156 scFv (also referred to as "ET150-6 scFv").

In certain embodiments, the anti-GPRC5D scFv antibody comprises a heavy chain variable region comprising amino acids having the sequence set forth in SEQ ID NO:25 and a light chain variable region comprising amino acids having the sequence set forth in SEQ ID NO:26, optionally with (iii) a linker sequence, for example a linker peptide, between the having the sequence set forth in SEQ ID NO:161 or conservative modifications thereof, and a $V_H$ CDR3 comprising amino acids having the sequence set forth in SEQ ID NO:162 or conservative modifications thereof, as shown in Table 7. In certain embodiments, the anti-GPRC5D scFv comprises a $V_L$ CDR1 comprising amino acids having the sequence set forth in SEQ ID NO:163 or conservative modifications thereof, a $V_L$ CDR2 comprising amino acids having the sequence set forth in SEQ ID NO:164 or conservative modifications thereof, and a $V_L$ CDR3 comprising amino acids having the sequence set forth in SEQ ID NO:165 or conservative modifications thereof, as shown in Table 7. In certain embodiments, the anti-GPRC5D scFv comprises a $V_H$ CDR1 comprising amino acids having the sequence set forth in SEQ ID NO:160 or conservative modifications thereof, a $V_H$ CDR2 comprising amino acids having the sequence set forth in SEQ ID NO:161 or conservative modifications thereof, a $V_H$ CDR3 comprising amino acids having the sequence set forth in SEQ ID NO:162 or conservative modifications thereof, a $V_L$ CDR1 comprising amino acids having the sequence set forth in SEQ ID NO:163 or conservative modifications thereof, a $V_L$ CDR2 comprising amino acids having the sequence set forth in SEQ ID NO:164 or conservative modifications thereof, and a $V_L$ CDR3 comprising amino acids having the sequence set forth in SEQ ID NO:165 or conservative modifications thereof, as shown in Table 7. In certain embodiments, the anti-GPRC5D scFv comprises a $V_H$ CDR1 comprising amino acids having the sequence set forth in SEQ ID NO:160, a $V_H$ CDR2 comprising amino acids having the sequence set forth in SEQ ID NO:161, a $V_H$ CDR3 comprising amino acids having the sequence set forth in SEQ ID NO:162, a $V_L$ CDR1 comprising amino acids having the sequence set forth in SEQ ID NO:163, a $V_L$ CDR2 comprising amino acids having the sequence set forth in SEQ ID NO:164, and a $V_L$ CDR3 comprising amino acids having the sequence set forth in SEQ ID NO:165.

light chain variable region comprising amino acids having the sequence set forth in SEQ ID NO:30, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 8. In certain embodiments, the anti-GPRC5D scFv comprises a $V_H$ comprising amino acids having the sequence set forth in SEQ ID NO:29, as shown in Table 8. In certain embodiments, the anti-GPRC5D scFv comprises a $V_L$ comprising amino acids having the sequence set forth in SEQ ID NO:30, as shown in Table 8. In certain embodiments, the anti-GPRC5D scFv comprises a $V_H$ comprising amino acids having the sequence set forth in SEQ ID NO:29 and a $V_L$ comprising amino acids having the sequence set forth in SEQ ID NO:30, as shown in Table 8. In certain embodiments, the anti-GPRC5D scFv comprises a $V_H$ CDR1 comprising amino acids having the sequence set forth in SEQ ID NO:166 or conservative modifications thereof, a $V_H$ CDR2 comprising amino acids having the sequence set forth in SEQ ID NO:167 or con-

TABLE 7

Antigen A GPRC5D polypeptide having the amino acid sequence of SEQ ID NO: 97

| CDRs | 1 | 2 | 3 |
|---|---|---|---|
| $V_H$ | GYTFTTYY [SEQ ID NO: 160] | INPNGGGT [SEQ ID NO: 161] | ARGHKVYKSHPTGGYDR [SEQ ID NO: 162] |
| $V_L$ | SRDVGGYNY [SEQ ID NO: 163] | EVS [SEQ ID NO: 164] | SSYTSSSTLD [SEQ ID NO: 165] |

Full $V_H$  QVQLVQSGAEVKQPGASVKVSCQASGYTFTTYYMEIWVRQAPGQGLE
WMGIINPNGGGTFYAQKFQDRVTMTRDTSTGTVYMELSSLRSDDTAVY
YCARGHKVYKSHPTGGYDRWGQGTLVTVSS [SEQ ID NO: 25]

DNA  Caggtgcagctggtgcaatctgggggctgaggtgaagcagcctgggggcctcagtgaaggtttcctgccaggcatct
ggatacaccttcaccacttattatatgcactgggtgcgacaggcccctggacaagggcttgagtggatgggaataat
caaccctaatggtggtggcacattctacgcacagaagttccaggacagagtcaccatgaccagggacacgtccac
gggcacagtctacatggaactgagcagcctgagatctgacgacactgccgtgtattactgtgcgcgcggtcataaa
gtttacaaatctcatccgactggtggttacgatcgttggggtcaaggtactctggtgaccgtctcctca [SEQ ID
NO: 27]

Full $V_L$  QSALTQPASVSGSPGQSITISCTGTSRDVGGYNYVSWYQQYPGKAPKLM
IYEVSKRPSGVSNRFSGSKSGNTASLTISGLQAEDEADYYCSSYTSSSTLD
FGTGTKVTVLG [SEQ ID NO: 26]

DNA  Caatctgccctgactcagcctgcctccgtgtctgggtctcctggacagtcgatcaccatctcctgcactggaaccag
ccgtgacgttggtggttataactatgtctcctggtaccaacagtacccaggcaaagcccccaaactcatgatttatga
ggtcagtaagcggccctcaggggtttctaatcgcttctctggctccaagtctggcaacacggcctccctgaccatct
ctgggctccaggctgaggacgaggctgattattactgcagctcatataccagtagcagcactttagacttcggaact
gggaccaaggtcaccgtcctaggt [SEQ ID NO: 28]

scFv  QSALTQPASVSGSPGQSITISCTGTSRDVGGYNYVSWYQQYPGKAPKLM
IYEVSKRPSGVSNRFSGSKSGNTASLTISGLQAEDEADYYCSSYTSSSTLD
FGTGTKVTVLGSRGGGGSGGGGSGGGGSLEMAQVQLVQSGAEVKQPG
ASVKVSCQASGYTFTTYYMHWVRQAPGQGLEWMGIINPNGGGTFYAQ
KFQDRVTMTRDTSTGTVYMELSSLRSDDTAVYYCARGHKVYKSHPTG
GYDRWGQGTLVTVSS [SEQ ID NO: 106]

In certain embodiments, the antibody or other antigen binding protein is an anti-GPRC5D scFv or an antigen-binding fragment thereof having an antigen-binding region that comprises the amino acid sequence of SEQ ID NO: 107 and specifically binds to a GPRC5D polypeptide (e.g., a GPRC5D polypeptide having the amino acid sequence SEQ ID NO:97, or fragments thereof), which is designated as ET150-157 scFv (also referred to as "ET150-7 scFv").

In certain embodiments, the anti-GPRC5D scFv antibody comprises a heavy chain variable region comprising amino acids having the sequence set forth in SEQ ID NO:29 and a servative modifications thereof, and a $V_H$ CDR3 comprising amino acids having the sequence set forth in SEQ ID NO:168 or conservative modifications thereof, as shown in Table 8. In certain embodiments, the anti-GPRC5D scFv comprises a $V_L$ CDR1 comprising amino acids having the sequence set forth in SEQ ID NO:169 or conservative modifications thereof, a $V_L$ CDR2 comprising amino acids having the sequence set forth in SEQ ID NO:170 or conservative modifications thereof, and a $V_L$ CDR3 comprising amino acids having the sequence set forth in SEQ ID NO:171 or conservative modifications thereof, as shown in Table 8. In certain embodiments, the anti-GPRC5D scFv comprises a V$_H$ CDR1 comprising amino acids having the sequence set forth in SEQ ID NO:166 or conservative modifications thereof, a V$_H$ CDR2 comprising amino acids having the sequence set forth in SEQ ID NO:167 or conservative modifications thereof, a V$_H$ CDR3 comprising amino acids having the sequence set forth in SEQ ID NO:168 or conservative modifications thereof, a V$_L$ CDR1 comprising amino acids having the sequence set forth in SEQ ID NO:169 or conservative modifications thereof, a V$_L$ CDR2 comprising amino acids having the sequence set forth in SEQ ID NO:170 or conservative modifications thereof, and a V$_L$ CDR3 comprising amino acids having the sequence set forth in SEQ ID NO:171 or conservative modifications thereof, as shown in Table 8. In certain embodiments, the anti-GPRC5D scFv comprises a V$_H$ CDR1 comprising amino acids having the sequence set forth in SEQ ID NO:166, a V$_H$ CDR2 comprising amino acids having the sequence set forth in SEQ ID NO: 167, a V$_H$ CDR3 comprising amino acids having the sequence set forth in SEQ ID NO: 168, a V$_L$ CDR1 comprising amino acids having the sequence set forth in SEQ ID NO: 169, a V$_L$ CDR2 comprising amino acids having the sequence set forth in SEQ ID NO: 170, and a V$_L$ CDR3 comprising amino acids having the sequence set forth in SEQ ID NO:171.

In certain embodiments, the anti-GPRC5D scFv antibody comprises a heavy chain variable region comprising amino acids having the sequence set forth in SEQ ID NO:33 and a light chain variable region comprising amino acids having the sequence set forth in SEQ ID NO:34, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with V$_H$ and V$_L$ regions or CDRs selected from Table 9. In certain embodiments, the anti-GPRC5D scFv comprises a V$_H$ comprising amino acids having the sequence set forth in SEQ ID NO:33, as shown in Table 9. In certain embodiments, the anti-GPRC5D scFv comprises a V$_L$ comprising amino acids having the sequence set forth in SEQ ID NO:34, as shown in Table 9. In certain embodiments, the anti-GPRC5D scFv comprises a V$_H$ comprising amino acids having the sequence set forth in SEQ ID NO:33 and a V$_L$ comprising amino acids having the sequence set forth in SEQ ID NO:34, as shown in Table 9. In certain embodiments, the anti-GPRC5D scFv comprises a V$_H$ CDR1 comprising amino acids having the sequence set forth in SEQ ID NO:172 or conservative modifications thereof, a V$_H$ CDR2 comprising amino acids

TABLE 8

Antigen A GPRC5D polypeptide having the amino acid sequence of SEQ ID NO: 97

| CDRs | 1 | 2 | 3 |
|---|---|---|---|
| V$_H$ | GGTFSSYA [SEQ ID NO: 166] | IIPIFGTA [SEQ ID NO: 167] | ARSHVAWSLLDY [SEQ ID NO: 168] |
| V$_L$ | SSNIGSNY [SEQ ID NO: 169] | RNN [SEQ ID NO: 170] | AAWDDSLSGVV [SEQ ID NO: 171] |

Full V$_H$  EVQLVQSGAEVKKPGSSVKVSCKASGGTFSSYAISWVRQAPGQGLEW
MGGIIPIFGTAKYAQKFQGRVTITADESTSTAYMELSSLRSEDTAVYYC
ARSHVAWSLLDYWGQGTLVTVSS [SEQ ID NO: 29]

DNA  Gaggtccagctggtgcagtctggggctgaggtgaagaagcctgggtcctcggtgaaggtctcctgcaaggctt
ctggaggcaccttcagcagctatgctatcagctgggtgcgacaggcccctggacaagggcttgagtggatggg
agggattatccctatctttggtacagcaaaatatgcacagaagttccagggcagagtcacgattaccgcggacga
atccacgagcacagcctacatggagctgagcagcctgagatctgaggacacggccgtgtattactgtgcgcgct
ctcatgttgcttggtctctgctgattactggggtcaaggtactctggtgaccgtctcctca [SEQ ID NO: 31]

Full V$_L$  SYELTQPPSASGTPGQRVTISCSGSSSNIGSNYVSWYQQLPGTAPKLLIY
RNNQRPSGVPDRFSGSKSGTSASLATSGLRSEDEADYYCAAWDDSLSG
VVFGGGTKLTVLG [SEQ ID NO: 30]

DNA  Tcctatgagctgactcagccaccctcagcgtctgggacccccgggcagagggtcaccatctcttgttctggaag
cagctccaacatcggaagtaattatgtatcctggtaccagcagctcccaggaacggcccccaaactcctcatcta
taggaataatcagcggcccctcaggggtccctgaccgattctctggctccaagtctggcacctcagcctccctggc
catcagtgggctccggtccgaggatgaggctgattattactgtgcagcatgggatgacagcctgagtggtgtggt
attcggcggagggaccaagctgaccgtcctaggt [SEQ ID NO: 32]

scFv  SYELTQPPSASGTPGQRVTISCSGSSSNIGSNYVSWYQQLPGTAPKLLIY
RNNQRPSGVPDRFSGSKSGTSASLATSGLRSEDEADYYCAAWDDSLSG
VVFGGGTKLTVLGSRGGGGSGGGGSGGGGSLEMAEVQLVQSGAEVK
KPGSSVKVSCKASGGTFSSYAISWVRQAPGQGLEWMGGIIPIFGTAKY
AQKFQGRVTITADESTSTAYMELSSLRSEDTAVYYCARSHVAWSLLD
YWGQGTLVTVSS [SEQ ID NO: 107]

In certain embodiments, the antibody or other antigen binding protein is an anti-GPRC5D scFv or an antigen-binding fragment thereof having an antigen-binding region that comprises the amino acid sequence of SEQ ID NO: 108 and specifically binds to a GPRC5D polypeptide (e.g., a GPRC5D polypeptide having the amino acid sequence SEQ ID NO:97, or fragments thereof), which is designated as ET150-159 scFv (also referred to as "ET150-9 scFv").

having the sequence set forth in SEQ ID NO:173 or conservative modifications thereof, and a V$_H$ CDR3 comprising amino acids having the sequence set forth in SEQ ID NO:174 or conservative modifications thereof, as shown in Table 9. In certain embodiments, the anti-GPRC5D scFv comprises a V$_L$ CDR1 comprising amino acids having the sequence set forth in SEQ ID NO:175 or conservative modifications thereof, a V$_L$ CDR2 comprising amino acids having the sequence set forth in SEQ ID NO:176 or conservative modifications thereof, and a $V_L$ CDR3 comprising amino acids having the sequence set forth in SEQ ID NO:177 or conservative modifications thereof, as shown in Table 9. In certain embodiments, the anti-GPRC5D scFv comprises a $V_H$ CDR1 comprising amino acids having the sequence set forth in SEQ ID NO:172 or conservative modifications thereof, a $V_H$ CDR2 comprising amino acids having the sequence set forth in SEQ ID NO:173 or conservative modifications thereof, a $V_H$ CDR3 comprising amino acids having the sequence set forth in SEQ ID NO:174 or conservative modifications thereof, a $V_L$ CDR1 comprising amino acids having the sequence set forth in SEQ ID NO:175 or conservative modifications thereof, a $V_L$ CDR2 comprising amino acids having the sequence set forth in SEQ ID NO:176 or conservative modifications thereof, and a $V_L$ CDR3 comprising amino acids having the sequence set forth in SEQ ID NO:177 or conservative modifications thereof, as shown in Table 9. In certain embodiments, the anti-GPRC5D scFv comprises a $V_H$ CDR1 comprising amino acids having the sequence set forth in SEQ ID NO: 172, a $V_H$ CDR2 comprising amino acids having the sequence set forth in SEQ ID NO: 173, a $V_H$ CDR3 comprising amino acids having the sequence set forth in SEQ ID NO:174, a $V_L$ CDR1 comprising amino acids having the sequence set forth in SEQ ID NO:175, a $V_L$ CDR2 comprising amino acids having the sequence set forth in SEQ ID NO:176, and a $V_L$ CDR3 comprising amino acids having the sequence set forth in SEQ ID NO: 177.

and specifically binds to a GPRC5D polypeptide (e.g., a GPRC5D polypeptide having the amino acid sequence SEQ ID NO:97, or fragments thereof), which is designated as ET150-160 scFv (also referred to as "ET150-10 scFv").

In certain embodiments, the anti-GPRC5D scFv antibody comprises a heavy chain variable region comprising amino acids having the sequence set forth in SEQ ID NO:37 and a light chain variable region comprising amino acids having the sequence set forth in SEQ ID NO:38, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 10. In certain embodiments, the anti-GPRC5D scFv comprises a $V_H$ comprising amino acids having the sequence set forth in SEQ ID NO:37, as shown in Table 10. In certain embodiments, the anti-GPRC5D scFv comprises a $V_L$ comprising amino acids having the sequence set forth in SEQ ID NO:38, as shown in Table 10. In certain embodiments, the anti-GPRC5D scFv comprises a $V_H$ comprising amino acids having the sequence set forth in SEQ ID NO:37 and a $V_L$ comprising amino acids having the sequence set forth in SEQ ID NO:38, as shown in Table 10. In certain embodiments, the anti-GPRC5D scFv comprises a $V_H$ CDR1 comprising amino acids having the sequence set forth in SEQ ID NO:178 or conservative modifications thereof, a $V_H$ CDR2 comprising amino acids

TABLE 9

Antigen A GPRC5D polypeptide having the amino acid sequence of SEQ ID NO: 97

| CDRs | 1 | 2 | 3 |
|---|---|---|---|
| $V_H$ | GGTFSSYA [SEQ ID NO: 172] | MNPNSGNT [SEQ ID NO: 173] | ARYQSYKGSQSD S [SEQ ID NO: 174] |
| $V_L$ | SSNIGSNY[SEQ ID NO: 175] | RNN [SEQ ID NO: 176] | AAWDDSLSGWV [SEQ ID NO: 177] |

```
Full V_H    QVQLVQSGAEVKKPGSSVKVSCKASGGTFSSYAISWVRQAPGQGL
            EWMGWMNPNSGNTGYAQKFQGRVTMTRNTSISTAYMELSSLRSE
            DTAVYYCARYQSYKGSQSDSWGQGTLVTVSS [SEQ ID NO: 33]

DNA         Caggtgcagctggtgcagtctgggggctgaggtgaagaagcctgggtcctcagtgaaggtctcctgcaag
            gcttctggaggcaccttcagcagctatgctatcagctgggtgcgacaggcccctggacaagggcttgagt
            ggatgggatggatgaaccctaacagtggtaacacaggctatgcacagaagttccagggcagagtcaccat
            gaccaggaacacctccataagcacagcctacatggagctgagcagcctgagatctgaggacacggccgt
            gtattactgtgcgcgctaccagtatacaaaggttctcagtctgattcttggggtcaaggtactctggtgaccg
            tctcctca [SEQ ID NO: 35]

Full V_L    QSVLTQPPSASGTPGQRVTISCSGSSSNIGSNYVYWYQQLPGTAPK
            LLIYRNNQRPSGVPDRFSGSKSGTSASLAISGLRSEDEADYYCAAW
            DDSLSGWVFGGGTKLTVLG [SEQ ID NO: 34]

DNA         Cagtctgtgttgacgcagccaccctcagcgtctgggacccccgggcagagggtcaccatctcttgttctg
            gaagcagctccaacatcggaagtaattatgtatactggtaccagcagctcccaggaacggcccccaaact
            cctcatctataggaataatcageggccctcaggggtccctgaccgattctctggctccaagtctggcacctc
            agcctccctggccatcagtgggctccggtccgaggatgaggctgattattactgtgcagcatgggatgaca
            gcctgagtggttgggtgttcggcggagggaccaagctgaccgtcctaggt [SEQ ID NO: 36]

scFv        QSVLTQPPSASGTPGQRVTISCSGSSSNIGSNYVYWYQQLPGTAPK
            LLIYRNNQRPSGVPDRFSGSKSGTSASLAISGLRSEDEADYYCAAW
            DDSLSGWVFGGGTKLTVLGSRGGGGSGGGGSGGGGSLEMAQVQL
            VQSGAEVKKPGSSVKVSCKASGGTFSSYAISWVRQAPGQGLEWM
            GWMNPNSGNTGYAQKFQGRVTMTRNTSISTAYMELSSLRSEDTA
            VYYCARYQSYKGSQSDSWGQGTLVTVSS [SEQ ID NO: 108]
```

In certain embodiments, the antibody or other antigen binding protein is an anti-GPRC5D scFv or an antigen-binding fragment thereof having an antigen-binding region that comprises the amino acid sequence of SEQ ID NO: 109 having the sequence set forth in SEQ ID NO:179 or conservative modifications thereof, and a $V_H$ CDR3 comprising amino acids having the sequence set forth in SEQ ID NO:180 or conservative modifications thereof, as shown in Table 10. In certain embodiments, the anti-GPRC5D scFv comprises a $V_L$ CDR1 comprising amino acids having the NO:182, and a $V_L$ CDR3 comprising amino acids having the sequence set forth in SEQ ID NO:183.

TABLE 10

Antigen A GPRC5D polypeptide having the amino acid sequence of SEQ ID NO: 97

| CDRs | 1 | 2 | 3 |
|---|---|---|---|
| $V_H$ | GYTFTSYY[SEQ ID NO: 178] | INPSGGST [SEQ ID NO: 179] | ARGGSKKWSGEKW RRENFDY [SEQ ID NO: 180] |
| $V_L$ | SSDVGGYNY [SEQ ID NO: 181] | DVS [SEQ ID NO: 182] | SSYTRSSTEV [SEQ ID NO: 183] |

Full $V_H$ EVQLVQSGAEVKKPGASVKVSCKASGYTFTSYYMEIWVRQAPGQG
LEWMGIINPSGGSTSYAQKFQGRVTMTRDTSTSTVYMELSSLRSED
TAVYYCARGGSKKWSGEKWRRENFDYWGQGTLVTVSS [SEQ ID
NO: 37]

DNA Gaggtccagctggtacagtctggggctgaggtgaagaagcctggggcctcagtgaaggtttcctgcaagg
catctggatacaccttcaccagctactatatgcactgggtgcgacaggcccctggacaagggcttgagtgga
tgggaataatcaaccctagtggtggtagcacaagctacgcacagaagttccagggcagagtcaccatgacc
agggacacgtccacgagcacagtctacatggagctgagcagcctgagatctgaggacacggccgtgtatt
actgtgcgcgcggtggttctaaaaaatggtctggtgaaaaatggcgtcgtgaaaacttcgattactggggtca
aggtactctggtgaccgtctcctca [SEQ ID NO: 39]

Full $V_L$ QSALTQPASVSGSPGQSITISCTGTSSDVGGYNYVSWYQQHPGKAP
KLMIYDVSKRPSGVSNRFSGSKSGNTASLTISGLQAEDEADYYCSSY
TRSSTEVFGGGTKLTVLG [SEQ ID NO: 38]

DNA Caatctgccctgactcagcctgcctccgtgtctgggtctcctggacagtcgatcaccatctcctgcactggaa
ccagcagtgacgttggtggttataactatgtctcctggtaccaacagcacccaggcaaagcccccaaactca
tgatttatgatgtcagtaageggcctcaggggtttctaatcgcttctctggctccaagtctggcaacacggcc
tccctgaccatctctgggctccaggctgaggacgaggctgattattactgcagctcatatacaagaagcagc
actgaggtattcggcggagggaccaagctgaccgtcctaggt [SEQ ID NO: 40]

scFv QSALTQPASVSGSPGQSITISCTGTSSDVGGYNYVSWYQQHPGKAP
KLMIYDVSKRPSGVSNRFSGSKSGNTASLTISGLQAEDEADYYCSSY
TRSSTEVFGGGTKLTVLGSRGGGGSGGGGSGGGGSLEMAEVQLVQ
SGAEVKKPGASVKVSCKASGYTFTSYYMEIWVRQAPGQGLEWMGI
INPSGGSTSYAQKFQGRVTMTRDTSTSTVYMELSSLRSEDTAVYYC
ARGGSKKWSGEKWRRENFDYWGQGTLVTVSS [SEQ ID NO: 109]

sequence set forth in SEQ ID NO:181 or conservative modifications thereof, a $V_L$ CDR2 comprising amino acids having the sequence set forth in SEQ ID NO:182 or conservative modifications thereof, and a $V_L$ CDR3 comprising amino acids having the sequence set forth in SEQ ID NO:183 or conservative modifications thereof, as shown in Table 10. In certain embodiments, the anti-GPRC5D scFv comprises a $V_H$ CDR1 comprising amino acids having the sequence set forth in SEQ ID NO:178 or conservative modifications thereof, a $V_H$ CDR2 comprising amino acids having the sequence set forth in SEQ ID NO:179 or conservative modifications thereof, a $V_H$ CDR3 comprising amino acids having the sequence set forth in SEQ ID NO:180 or conservative modifications thereof, a $V_L$ CDR1 comprising amino acids having the sequence set forth in SEQ ID NO:181 or conservative modifications thereof, a $V_L$ CDR2 comprising amino acids having the sequence set forth in SEQ ID NO:182 or conservative modifications thereof, and a $V_L$ CDR3 comprising amino acids having the sequence set forth in SEQ ID NO:183 or conservative modifications thereof, as shown in Table 10. In certain embodiments, the anti-GPRC5D scFv comprises a $V_H$ CDR1 comprising amino acids having the sequence set forth in SEQ ID NO:178, a $V_H$ CDR2 comprising amino acids having the sequence set forth in SEQ ID NO:179, a $V_H$ CDR3 comprising amino acids having the sequence set forth in SEQ ID NO:180, a $V_L$ CDR1 comprising amino acids having the sequence set forth in SEQ ID NO:181, a $V_L$ CDR2 comprising amino acids having the sequence set forth in SEQ ID In certain embodiments, the antibody or other antigen binding protein is an anti-GPRC5D scFv or an antigen-binding fragment thereof having an antigen-binding region that comprises the amino acid sequence of SEQ ID NO: 110 and specifically binds to a GPRC5D polypeptide (e.g., a GPRC5D polypeptide having the amino acid sequence SEQ ID NO:97, or fragments thereof), which is designated as ET150-161 scFv (also referred to as "ET 150-11 scFv").

In certain embodiments, the anti-GPRC5D scFv antibody comprises a heavy chain variable region comprising amino acids having the sequence set forth in SEQ ID NO:41 and a light chain variable region comprising amino acids having the sequence set forth in SEQ ID NO:42, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 11. In certain embodiments, the anti-GPRC5D scFv comprises a $V_H$ comprising amino acids having the sequence set forth in SEQ ID NO:41, as shown in Table 11. In certain embodiments, the anti-GPRC5D scFv comprises a $V_L$ comprising amino acids having the sequence set forth in SEQ ID NO:42, as shown in Table 11. In certain embodiments, the anti-GPRC5D scFv comprises a $V_H$ comprising amino acids having the sequence set forth in SEQ ID NO:41 and a $V_L$ comprising amino acids having the sequence set forth in SEQ ID NO:42, as shown in Table 11. In certain embodiments, the anti-GPRC5D scFv comprises a V_H CDR1 comprising amino acids having the sequence set forth in SEQ ID NO:184 or conservative modifications thereof, a V_H CDR2 comprising amino acids having the sequence set forth in SEQ ID NO: 185 or conservative modifications thereof, and a V_H CDR3 comprising amino acids having the sequence set forth in SEQ ID NO: 186 or conservative modifications thereof, as shown in sequence set forth in SEQ ID NO: 185, a V_H CDR3 comprising amino acids having the sequence set forth in SEQ ID NO: 186, a V_L CDR1 comprising amino acids having the sequence set forth in SEQ ID NO: 187, a V_L CDR2 comprising amino acids having the sequence set forth in SEQ ID NO: 188, and a V_L CDR3 comprising amino acids having the sequence set forth in SEQ ID NO: 189.

TABLE 11

| Antigen | A GPRC5D polypeptide having the amino acid sequence of SEQ ID NO: 97 | | |
|---|---|---|---|
| CDRs | 1 | 2 | 3 |
| V_H | EYTFTRHI [SEQ ID NO: 184] | INPGNGNT [SEQ ID NO: 185] | ARLPDQ [SEQ ID NO: 186] |
| V_L | SSNIGSNT [SEQ ID NO: 187] | RNN [SEQ ID NO: 188] | AAWDDSLSGL [SEQ ID NO: 189] |
| Full V_H | QMQLVQSGAEVKKPGASVKVSCKASEYTFTRHILHWVRQAPGQSL EWMGWINPGNGNTKYSQKFQVRVTFTRDTSASTVYMELSSLRSED TAVYYCARLPDQWGQGTLVTVSS [SEQ ID NO: 41] | | |
| DNA | Cagatgcagctggtgcagtctgggggctgaggtgaagaagcctggggcctcagtgaaggtttcctgcaagg cttctgaatacaccttcactaggcatattctacattgggtgcgccaggctcccggacaaagccttgagtggat gggatggatcaacccaggcaatggtaatacaaaatattcacagaagttccaggtcagagtcacctttaccag ggacacatccgcgagcacagtctatatggagctgagcagcctgagatctgaagacacggccgtgtattact gtgcgcgcctgccggatcagtggggtcaaggtactctggtgaccgtctcctca [SEQ ID NO: 43] | | |
| Full V_L | SYVLTQPPSASGTPGQRVTISCSGSSSNIGSNTVNWYQQLPGTAPKL LIYRNNQRPSGVPDRFSGSKSGTSASLAISGLRSEDEADYYCAAWD DSLSGLFGTGTKVTVLG [SEQ ID NO: 42] | | |
| DNA | Tcctatgtgctgactcagccaccctcagcgtctgggacccccgggcagagggtcaccatctcttgttctgga agcagctccaacatcggaagtaatactgtaaactggtaccagcagctcccaggaacggcccccaaactcct catctataggaataatcageggccctcaggggtccctgaccgattctctggctccaagtctggcacctcagc ctccctggccatcagtgggctccggtccgaggatgaggctgattattactgtgcagcatgggatgacagcct gagtggtctcttcggaactgggaccaaggtcaccgtcctaggt [SEQ ID NO: 44] | | |
| scFv | SYVLTQPPSASGTPGQRVTISCSGSSSNIGSNTVNWYQQLPGTAPKL LIYRNNQRPSGVPDRFSGSKSGTSASLAISGLRSEDEADYYCAAWD DSLSGLFGTGTKVTVLGSRGGGGSGGGGSGGGGSLEMAQMQLVQ SGAEVKKPGASVKVSCKASEYTFTRHILHWVRQAPGQSLEWMGWI NPGNGNTKYSQKFQVRVTFTRDTSASTVYMELSSLRSEDTAVYYC ARLPDQWGQGTLVTVSS [SEQ ID NO: 110] | | |

Table 11. In certain embodiments, the anti-GPRC5D scFv comprises a V_L CDR1 comprising amino acids having the sequence set forth in SEQ ID NO: 187 or conservative modifications thereof, a V_L CDR2 comprising amino acids having the sequence set forth in SEQ ID NO: 188 or conservative modifications thereof, and a V_L CDR3 comprising amino acids having the sequence set forth in SEQ ID NO: 189 or conservative modifications thereof, as shown in Table 11. In certain embodiments, the anti-GPRC5D scFv comprises a V_H CDR1 comprising amino acids having the sequence set forth in SEQ ID NO: 184 or conservative modifications thereof, a V_H CDR2 comprising amino acids having the sequence set forth in SEQ ID NO: 185 or conservative modifications thereof, a V_H CDR3 comprising amino acids having the sequence set forth in SEQ ID NO: 186 or conservative modifications thereof, a V_L CDR1 comprising amino acids having the sequence set forth in SEQ ID NO: 187 or conservative modifications thereof, a V_L CDR2 comprising amino acids having the sequence set forth in SEQ ID NO: 188 or conservative modifications thereof, and a V_L CDR3 comprising amino acids having the sequence set forth in SEQ ID NO: 189 or conservative modifications thereof, as shown in Table 11. In certain embodiments, the anti-GPRC5D scFv comprises a V_H CDR1 comprising amino acids having the sequence set forth in SEQ ID NO: 184, a V_H CDR2 comprising amino acids having the In certain embodiments, the antibody or other antigen binding protein is an anti-GPRC5D scFv or an antigen-binding fragment thereof having an antigen-binding region that comprises the amino acid sequence of SEQ ID NO: 111 and specifically binds to a GPRC5D polypeptide (e.g., a GPRC5D polypeptide having the amino acid sequence SEQ ID NO:97, or fragments thereof), which is designated as ET150-162 scFv (also referred to as "ET 150-12 scFv").

In certain embodiments, the anti-GPRC5D scFv antibody comprises a heavy chain variable region comprising amino acids having the sequence set forth in SEQ ID NO:45 and a light chain variable region comprising amino acids having the sequence set forth in SEQ ID NO:46, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with V_H and V_L regions or CDRs selected from Table 12. In certain embodiments, the anti-GPRC5D scFv comprises a V_H comprising amino acids having the sequence set forth in SEQ ID NO:45, as shown in Table 12. In certain embodiments, the anti-GPRC5D scFv comprises a V_L comprising amino acids having the sequence set forth in SEQ ID NO:46, as shown in Table 12. In certain embodiments, the anti-GPRC5D scFv comprises a $V_H$ comprising amino acids having the sequence set forth in SEQ ID NO:45 and a $V_L$ comprising amino acids having the sequence set forth in SEQ ID NO:46, as shown in Table 12. In certain embodiments, the anti-GPRC5D scFv comprises a $V_H$ CDR1 comprising amino acids having the sequence set forth in SEQ ID NO:190 or conservative modifications thereof, a $V_H$ CDR2 comprising amino acids having the sequence set forth in SEQ ID NO: 191 or conservative modifications thereof, and a $V_H$ CDR3 comprising amino acids having the sequence set forth in SEQ ID NO: 192 or conservative modifications thereof, as shown in Table 12. In certain embodiments, the anti-GPRC5D scFv thereof, as shown in Table 12. In certain embodiments, the anti-GPRC5D scFv comprises a $V_H$ CDR1 comprising amino acids having the sequence set forth in SEQ ID NO: 190, a $V_H$ CDR2 comprising amino acids having the sequence set forth in SEQ ID NO: 191, a $V_H$ CDR3 comprising amino acids having the sequence set forth in SEQ ID NO: 192, a $V_L$ CDR1 comprising amino acids having the sequence set forth in SEQ ID NO: 193, a $V_L$ CDR2 comprising amino acids having the sequence set forth in SEQ ID NO: 194, and a $V_L$ CDR3 comprising amino acids having the sequence set forth in SEQ ID NO: 195.

TABLE 12

Antigen A GPRC5D polypeptide having the amino acid sequence of SEQ ID NO: 97

| CDRs | 1 | 2 | 3 |
|---|---|---|---|
| $V_H$ | GFTFGDYG [SEQ ID NO: 190] | INWNGGST [SEQ ID NO: 191] | ARSKQDY [SEQ ID NO: 192] |
| $V_L$ | SRDAGGYNY [SEQ ID NO: 193] | EVT [SEQ ID NO: 194] | SSYGGSNNFRV [SEQ ID NO: 195] |

Full $V_H$    EVQLVESGGGVVRPGGSLRLSCAASGFTFGDYGMSWVRQAPGKG
LEWVSGINWNGGSTGYADSVKGRFTISRDNAKNSLYLQMNSLRA
EDTAVYYCARSKQDYWGQGTLVTVSS [SEQ ID NO: 45]

DNA    Gaggtgcagctggtggagtctggggggaggtgtggtacggcctggggggtccctgagactctcctgtgca
gcctctggattcacctttggtgattatggcatgagctgggtccgccaagctccagggaaggggctggagtg
ggtctctggtattaattggaatggtggtagcacaggttatgcagactctgtgaaggggcgattcaccatctcc
agagacaacgccaagaactccctgtatctgcaaatgaacagtctgagagccgaggacacggccgtatatt
actgtgcgcgctctaaacaggattactggggtcaaggtactctggtgaccgtctcctca [SEQ ID NO: 47]

Full $V_L$    QSALTQPPSASGSPGQSVTISCTGTSRDAGGYNYFSWYQQHPGKA
PKLLIYEVTKRPSGVPDRFSGSKSGKTASLTVSGLQADDEAVYYCS
SYGGSNNFRVFGGGTKLTVLG [SEQ ID NO: 46]

DNA    Cagtctgccctgactcagcctcctccgcgtccgggtctcctggacagtcagtcaccatctcctgcactgg
aaccagcagggacgctggtggttataattatttctcctggtaccaacaacacccaggcaaagcccccaaac
tcctgatttatgaggtcactaageggccctcaggggtccctgatcgcttctctggctccaagtctggcaaga
cggcctccctgaccgtctctgggctccaggctgacgatgaggctgtatattactgcagctcatatggaggc
agcaacaactttcgggtgttcggcggagggaccaagctgaccgtcctaggt [SEQ ID NO: 48]

scFv    QSALTQPPSASGSPGQSVTISCTGTSRDAGGYNYFSWYQQHPGKA
PKLLIYEVTKRPSGVPDRFSGSKSGKTASLTVSGLQADDEAVYYCS
SYGGSNNFRVFGGGTKLTVLGSRGGGGSGGGGSGGGGSLEMAEV
QLVESGGGVVRPGGSLRLSCAASGFTFGDYGMSWVRQAPGKGLE
WVSGINWNGGSTGYADSVKGRFTISRDNAKNSLYLQMNSLRAED
TAVYYCARSKQDYWGQGTLVTVSS [SEQ ID NO: 111]

comprises a $V_L$ CDR1 comprising amino acids having the sequence set forth in SEQ ID NO: 193 or conservative modifications thereof, a $V_L$ CDR2 comprising amino acids having the sequence set forth in SEQ ID NO: 194 or conservative modifications thereof, and a $V_L$ CDR3 comprising amino acids having the sequence set forth in SEQ ID NO: 195 or conservative modifications thereof, as shown in Table 12. In certain embodiments, the anti-GPRC5D scFv comprises a $V_H$ CDR1 comprising amino acids having the sequence set forth in SEQ ID NO: 190 or conservative modifications thereof, a $V_H$ CDR2 comprising amino acids having the sequence set forth in SEQ ID NO: 191 or conservative modifications thereof, a $V_H$ CDR3 comprising amino acids having the sequence set forth in SEQ ID NO: 192 or conservative modifications thereof, a $V_L$ CDR1 comprising amino acids having the sequence set forth in SEQ ID NO: 193 or conservative modifications thereof, a $V_L$ CDR2 comprising amino acids having the sequence set forth in SEQ ID NO: 194 or conservative modifications thereof, and a $V_L$ CDR3 comprising amino acids having the sequence set forth in SEQ ID NO: 195 or conservative modifications In certain embodiments, the antibody or other antigen binding protein is an anti-GPRC5D scFv or an antigen-binding fragment thereof having an antigen-binding region that comprises the amino acid sequence of SEQ ID NO: 112 and specifically binds to a GPRC5D polypeptide (e.g., a GPRC5D polypeptide having the amino acid sequence SEQ ID NO:97, or fragments thereof), which is designated as ET150-163 scFv (also referred to as "ET150-13 scFv").

In certain embodiments, the anti-GPRC5D scFv antibody comprises a heavy chain variable region comprising amino acids having the sequence set forth in SEQ ID NO:49 and a light chain variable region comprising amino acids having the sequence set forth in SEQ ID NO:50, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 13. In certain embodiments, the anti-GPRC5D scFv comprises a $V_H$ comprising amino acids having the sequence set forth in SEQ ID NO:49, as shown in Table 13. In certain embodiments, the anti-GPRC5D scFv comprises a $V_L$ comprising amino acids having the sequence set forth in SEQ ID NO:50, as shown in Table 13. In certain embodiments, the anti-GPRC5D scFv comprises a $V_H$ comprising amino acids having the sequence set forth in SEQ ID NO:49 and a $V_L$ comprising amino acids having the sequence set forth in SEQ ID NO:50, as shown in Table 13. In certain embodiments, the anti-GPRC5D scFv comprises a $V_H$ CDR1 comprising amino acids having the sequence set forth in SEQ ID NO:196 or conservative modifications thereof, a $V_H$ CDR2 comprising amino acids having the sequence set forth in SEQ ID NO: 197 or conservative modifications thereof, and a $V_H$ CDR3 comprising amino acids having the sequence set forth in SEQ ID NO: 198 or conservative modifications thereof, as shown in CDR2 comprising amino acids having the sequence set forth in SEQ ID NO:200 or conservative modifications thereof, and a $V_L$ CDR3 comprising amino acids having the sequence set forth in SEQ ID NO:201 or conservative modifications thereof, as shown in Table 13. In certain embodiments, the anti-GPRC5D scFv comprises a $V_H$ CDR1 comprising amino acids having the sequence set forth in SEQ ID NO: 196, a $V_H$ CDR2 comprising amino acids having the sequence set forth in SEQ ID NO: 197, a $V_H$ CDR3 comprising amino acids having the sequence set forth in SEQ ID NO: 198, a $V_L$ CDR1 comprising amino acids having the sequence set forth in SEQ ID NO: 199, a $V_L$ CDR2 comprising amino acids having the sequence set forth in SEQ ID NO:200, and a $V_L$ CDR3 comprising amino acids having the sequence set forth in SEQ ID NO:201.

TABLE 13

Antigen A GPRC5D polypeptide having the amino acid sequence of SEQ ID NO: 97

| CDRs | 1 | 2 | 3 |
|---|---|---|---|
| $V_H$ | GFSFSGTA[SEQ ID NO: 196] | ISSTGRST [SEQ ID NO: 197] | ARVSFDY [SEQ ID NO: 198] |
| $V_L$ | SSNIGAGYD [SEQ ID NO: 199] | GNS [SEQ ID NO: 200] | QSYDSSLSGSYV [SEQ ID NO: 201] |

Full $V_H$ EVQLVETGGNLVQPGASLRLSCAASGFSFSGTAMHWVRQAPGKGLE
WVSTISSTGRSTYYRDSVKGRFTISRDNSKNTLYLQMNSLRGEDTAV
YYCARVSFDYWGQGTLVTVSS [SEQ ID NO: 49]

DNA Gaggtgcagctggtggagactggggggaaacttggtacagccggggcgtccctgagactctcctgtgcagc
ctctggattcagattagtggcactgccatgcactgggtccgccaggctccagggaaggggctggaatgggtc
tcgactattagtagtactgggcgtagcacatactacagagactccgtgaagggccggttcaccatctccagaga
caattccaagaacacgctgtatctgcaaatgaacagcctgagaggcgaggacacggccgtatattactgtgcg
cgcgtttctttcgattactggggtcaaggtactctggtgaccgtctcctca [SEQ ID NO: 51]

Full $V_L$ QSVVTQPPSVSGAPGQRVTISCTGSSSNIGAGYDVHWYQQLPGTAPK
LLIYGNSNRPSGVPDRFSGSKSGTSASLAITGLQAEDEADYYCQSYDS
SLSGSYVFGTGTKLTVLG [SEQ ID NO: 50]

DNA Cagtctgtcgtgacgcagccgccctcagtgtctggggcccccagggcagagggtcaccatctcctgcactggg
agcagctccaacatcggggcaggttatgatgtacactggtaccagcagcttccaggaacagcccccaaactcc
tcatctatggtaacagcaatcggccctcaggggtccctgaccgattctctggctccaagtctggcacctcagcct
ccctggccatcactgggctccaggctgaggatgaggctgattattactgccagtcctatgacagcagcctgagt
ggctcctacgtcttcggaactgggaccaagctgaccgtcctaggt [SEQ ID NO: 52]

scFv QSVVTQPPSVSGAPGQRVTISCTGSSSNIGAGYDVHWYQQLPGTAPK
LLIYGNSNRPSGVPDRFSGSKSGTSASLAITGLQAEDEADYYCQSYDS
SLSGSYVFGTGTKLTVLGSRGGGGSGGGGSGGGGSLEMAEVQLVET
GGNLVQPGASLRLSCAASGFSFSGTAMHWVRQAPGKGLEWVSTISST
GRSTYYRDSVKGRFTISRDNSKNTLYLQMNSLRGEDTAVYYCARVSF
DYWGQGTLVTVSS [SEQ ID NO: 112]

Table 13. In certain embodiments, the anti-GPRC5D scFv comprises a $V_L$ CDR1 comprising amino acids having the sequence set forth in SEQ ID NO: 199 or conservative modifications thereof, a $V_L$ CDR2 comprising amino acids having the sequence set forth in SEQ ID NO:200 or conservative modifications thereof, and a $V_L$ CDR3 comprising amino acids having the sequence set forth in SEQ ID NO:201 or conservative modifications thereof, as shown in Table 13. In certain embodiments, the anti-GPRC5D scFv comprises a $V_H$ CDR1 comprising amino acids having the sequence set forth in SEQ ID NO: 196 or conservative modifications thereof, a $V_H$ CDR2 comprising amino acids having the sequence set forth in SEQ ID NO: 197 or conservative modifications thereof, a $V_H$ CDR3 comprising amino acids having the sequence set forth in SEQ ID NO: 198 or conservative modifications thereof, a $V_L$ CDR1 comprising amino acids having the sequence set forth in SEQ ID NO: 199 or conservative modifications thereof, a $V_L$ In certain embodiments, the antibody or other antigen binding protein is an anti-GPRC5D scFv or an antigen-binding fragment thereof having an antigen-binding region that comprises the amino acid sequence of SEQ ID NO: 113 and specifically binds to a GPRC5D polypeptide (e.g., a GPRC5D polypeptide having the amino acid sequence SEQ ID NO:97, or fragments thereof), which is designated as ET150-151 scFv (also referred to as "ET150-1 scFv").

In certain embodiments, the anti-GPRC5D scFv antibody comprises a heavy chain variable region comprising amino acids having the sequence set forth in SEQ ID NO:53 and a light chain variable region comprising amino acids having the sequence set forth in SEQ ID NO:54, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 14. In certain embodiments, the anti-GPRC5D scFv comprises a $V_H$ comprising amino acids having the sequence set forth in SEQ ID NO:53, as shown in Table 14. In certain embodiments, the anti-GPRC5D scFv comprises a $V_L$ comprising amino acids having the sequence set forth in SEQ ID NO:54, as shown in Table 14. In certain embodiments, the anti-GPRC5D scFv comprises a $V_H$ comprising amino acids having the sequence set forth in SEQ ID NO:53 and a $V_L$ comprising amino acids having the sequence set forth in SEQ ID NO:54, as shown in Table 14. In certain embodiments, the anti-GPRC5D scFv comprises a $V_H$ CDR1 comprising amino acids having the sequence set forth in SEQ ID NO:202 or conservative modifications thereof, a $V_H$ CDR2 comprising amino acids having the sequence set forth in SEQ ID NO:203 or conservative modifications thereof, and a $V_H$ CDR3 comprising amino acids having the sequence set forth in SEQ ID NO: 204 or conservative modifications thereof, as shown in Table amino acids having the sequence set forth in SEQ ID NO: 204 or conservative modifications thereof, a $V_L$ CDR1 comprising amino acids having the sequence set forth in SEQ ID NO: 205 or conservative modifications thereof, a $V_L$ CDR2 comprising amino acids having the sequence set forth in SEQ ID NO: 206 or conservative modifications thereof, and a $V_L$ CDR3 comprising amino acids having the sequence set forth in SEQ ID NO: 207 or conservative modifications thereof, as shown in Table 14. In certain embodiments, the anti-GPRC5D scFv comprises a $V_H$ CDR1 comprising amino acids having the sequence set forth in SEQ ID NO: 202, a $V_H$ CDR2 comprising amino acids having the sequence set forth in SEQ ID NO: 203, a $V_H$ CDR3 comprising amino acids having the sequence set forth in SEQ ID NO: 204, a $V_L$ CDR1 comprising amino acids having the sequence set forth in SEQ ID NO: 205, a $V_L$ CDR2 comprising amino acids having the sequence set forth in SEQ ID NO: 206, and a $V_L$ CDR3 comprising amino acids having the sequence set forth in SEQ ID NO: 207.

TABLE 14

Antigen A GPRC5D polypeptide having the amino acid sequence of SEQ ID NO: 97

| CDRs | 1 | 2 | 3 |
|---|---|---|---|
| $V_H$ | GFTFSSYA [SEQ ID NO: 202] | ISGRGRST [SEQ ID NO: 203] | ARYYHAGAFDL [SEQ ID NO: 204] |
| $V_L$ | SSDVGGYNY [SEQ ID NO: 205] | DVS [SEQ ID NO: 206] | SSYTSSSTLV [SEQ ID NO: 207] |

Full $V_H$    EVQLVESGGAFVQPGGSLRLSCAASGFTFSSYAMTWVRQAPGKGL
EWVSTISGRGRSTFYADSVKGRFTISRDNSKNTLYLQMNSLRAEDT
AVYYCARYYHAGAFDLWGQGTLVTVSS [SEQ ID NO: 53]

DNA       Gaggtgcagctggtggagtctgggggaggcctttgtacagcctggggggtccctgagactctcctgtgcag
cctctggattcacctttagcagctatgccatgacctgggtccgccaggctccagggaagggcctggaatg
ggtctcgactattagtggtcgtggtcgtagcacattctacgcagactccgtgaagggccggtttaccatctcc
agagacaattccaagaacacgctatatctgcaaatgaacagtctgagagccgaggacacggccgtatatt
actgtgcgcgctactaccatgctggtgctttcgatctgtggggtcaaggtactctggtgaccgtctcctca
[SEQ ID NO: 55]

Full $V_L$    QSVVTQPASVSGSPGQSITISCTGTSSDVGGYNYVSWYQQHPGKA
PKLMIYDVSKRPSGVSNRFSGSKSGNTASLTISGLQAEDEADYYCS
YTSSSTLVFGGGTKLTVLG [SEQ ID NO: 54]

DNA       Cagtctgtcgtgacgcagcctgcctccgtgtctgggtctcctggacagtcgatcaccatctcctgcactgg
aaccagcagtgacgttggtggttataactatgtctcctggtaccaacagcacccaggcaaagcccccaaac
tcatgatttatgatgtcagtaagcggccctcaggggtttctaatcgcttctctggctccaagtctggcaacac
ggcctccctgaccatctctgggctccaggctgaggacgaggctgattattactgcagctcatatacaagca
gcagcactttggtattcggcggagggaccaagctgaccgtcctaggt [SEQ ID NO: 56]

scFv      QSVVTQPASVSGSPGQSITISCTGTSSDVGGYNYVSWYQQHPGKA
PKLMIYDVSKRPSGVSNRFSGSKSGNTASLTISGLQAEDEADYYCS
YTSSSTLVFGGGTKLTVLGSRGGGGSGGGGSGGGGSLEMAEVQL
VESGGAFVQPGGSLRLSCAASGFTFSSYAMTWVRQAPGKGLEWV
STISGRGRSTFYADSVKGRFTISRDNSKNTLYLQMNSLRAEDTAVY
YCARYYHAGAFDLWGQGTLVTVSS [SEQ ID NO: 113]

14. In certain embodiments, the anti-GPRC5D scFv comprises a $V_L$ CDR1 comprising amino acids having the sequence set forth in SEQ ID NO: 205 or conservative modifications thereof, a $V_L$ CDR2 comprising amino acids having the sequence set forth in SEQ ID NO: 206 or conservative modifications thereof, and a $V_L$ CDR3 comprising amino acids having the sequence set forth in SEQ ID NO: 207 or conservative modifications thereof, as shown in Table 14. In certain embodiments, the anti-GPRC5D scFv comprises a $V_H$ CDR1 comprising amino acids having the sequence set forth in SEQ ID NO: 202 or conservative modifications thereof, a $V_H$ CDR2 comprising amino acids having the sequence set forth in SEQ ID NO: 203 or conservative modifications thereof, a $V_H$ CDR3 comprising In certain embodiments, the antibody or other antigen binding protein is an anti-GPRC5D scFv or an antigen-binding fragment thereof having an antigen-binding region that comprises the amino acid sequence of SEQ ID NO: 114 and specifically binds to a GPRC5D polypeptide (e.g., a GPRC5D polypeptide having the amino acid sequence SEQ ID NO:97, or fragments thereof), which is designated as ET150-152 scFv (also referred to as "ET150-2 scFv").

In certain embodiments, the anti-GPRC5D scFv antibody comprises a heavy chain variable region comprising amino acids having the sequence set forth in SEQ ID NO:57 and a light chain variable region comprising amino acids having the sequence set forth in SEQ ID NO:58, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 15. In certain embodiments, the anti-GPRC5D scFv comprises a $V_H$ comprising amino acids having the sequence set forth in SEQ ID NO:57, as shown in Table 15. In certain embodiments, the anti-GPRC5D scFv comprises a $V_L$ comprising amino acids having the sequence set forth in SEQ ID NO:58, as shown in Table 15. In certain embodiments, the anti-GPRC5D scFv comprises a $V_H$ comprising amino acids having the sequence set forth in SEQ ID NO:57 and a $V_L$ comprising amino acids having the sequence set forth in SEQ ID NO:58, as shown in Table 15. In certain embodiments, the anti-GPRC5D scFv comprises a $V_H$ CDR1 comprising amino acids having the sequence set forth in SEQ ID NO:208 or conservative modifications thereof, a $V_H$ CDR2 comprising amino acids having the sequence set forth in SEQ ID NO: 209 or conservative modifications thereof, and a $V_H$ CDR3 comprising amino acids having the sequence set forth in SEQ ID NO: 210 or conservative modifications thereof, as shown in modifications thereof, a $V_H$ CDR2 comprising amino acids having the sequence set forth in SEQ ID NO: 209 or conservative modifications thereof, a $V_H$ CDR3 comprising amino acids having the sequence set forth in SEQ ID NO: 210 or conservative modifications thereof, a $V_L$ CDR1 comprising amino acids having the sequence set forth in SEQ ID NO: 211 or conservative modifications thereof, a $V_L$ CDR2 comprising amino acids having the sequence set forth in SEQ ID NO: 212 or conservative modifications thereof, and a $V_L$ CDR3 comprising amino acids having the sequence set forth in SEQ ID NO: 213 or conservative modifications thereof, as shown in Table 15. In certain embodiments, the anti-GPRC5D scFv comprises a $V_H$ CDR1 comprising amino acids having the sequence set forth in SEQ ID NO: 208, a $V_H$ CDR2 comprising amino acids having the sequence set forth in SEQ ID NO: 209, a $V_H$ CDR3 comprising amino acids having the sequence set forth in SEQ ID NO: 210, a $V_L$ CDR1 comprising amino acids having the sequence set forth in SEQ ID NO: 211, a $V_L$ CDR2 comprising amino acids having the sequence set forth in SEQ ID NO: 212, and a $V_L$ CDR3 comprising amino acids having the sequence set forth in SEQ ID NO: 213.

TABLE 15

| Antigen | A GPRC5D polypeptide having the amino acid sequence of SEQ ID NO: 97 | | |
|---|---|---|---|
| CDRs | 1 | 2 | 3 |
| $V_H$ | GYTFNRYA [SEQ ID NO: 208] | ISAYNGNS [SEQ ID NO: 209] | ARMAYDS [SEQ ID NO: 210] |
| $V_L$ | SNDVGAYKY [SEQ ID NO: 211] | DVF [SEQ ID NO: 212] | FSLTSSNTYV [SEQ ID NO: 213] |
| Full $V_H$ | QMQLVQSGAEVKKPGASVKVSCKASGYTFNRYAITWVRQAPGQGLE WMGWISAYNGNSHYAQKLQGRVTMTTDTSTGTAYMELRRLRSDDT AVYYCARMAYDSWGQGTLVTVSS [SEQ ID NO: 57] | | |
| DNA | Cagatgcagctggtgcagtctggagctgaggtgaagaagcctggggcctcagtgaaggtctcctgcaaggctt ctggttacacctttaacagatatgctatcacctgggtgcgacaggcccctggacaaggccttgagtggatgggat ggatcagcgcttacaatggtaattcacactatgcacagaagctccagggcagagtcaccatgaccacagacac atccacgggcacagcctatatggagctgaggaggctgagatctgacgacacggccgtgtattactgtgcgcgc atggettacgattatggggtcaaggtactctggtgaccgtctcctca [SEQ ID NO: 59] | | |
| Full $V_L$ | QSVLTQPASVSGSPGQSLTISCTGTSNDVGAYKYVSWYQQYPGKAPK LILYDVFKRPSGVSNRFSGSKSDNTASLTISGLQAEDEADYYCFSLTSS NTYVFGTGTKVTVLG [SEQ ID NO: 58] | | |
| DNA | Cagtctgtgttgacgcagcctgcctccgtgtctgggtctcctggacagtcgctcaccatctcctgcactggaacc agcaatgacgttggtgcttataagtatgtctcctggtatcaacagtacccaggcaaagcccccaaactcatacttta tgatgtattaagcggccctcagggggtctctaatcgcttctctggctccaagtctgacaacacggcctccctgacc atctctgggctccaggctgaggacgaggctgattattactgcttctcactt
acaagcagtaacacttatgtcttcgg aactgggaccaaggtcaccgtcctaggt [SEQ ID NO: 60] | | |
| scFv | QSVLTQPASVSGSPGQSLTISCTGTSNDVGAYKYVSWYQQYPGKAPK LILYDVFKRPSGVSNRFSGSKSDNTASLTISGLQAEDEADYYCFSLTSS NTYVFGTGTKVTVLGSRGGGGSGGGGSGGGGSLEMAQMQLVQSGAE VKKPGASVKVSCKASGYTFNRYAITWVRQAPGQGLEWMGWISAYNG NSHYAQKLQGRVTMTTDTSTGTAYMELRRLRSDDTAVYYCARMAY DSWGQGTLVTVSS [SEQ ID NO: 114] | | |

Table 15. In certain embodiments, the anti-GPRC5D scFv comprises a $V_L$ CDR1 comprising amino acids having the sequence set forth in SEQ ID NO: 211 or conservative modifications thereof, a $V_L$ CDR2 comprising amino acids having the sequence set forth in SEQ ID NO: 212 or conservative modifications thereof, and a $V_L$ CDR3 comprising amino acids having the sequence set forth in SEQ ID NO: 213 or conservative modifications thereof, as shown in Table 15. In certain embodiments, the anti-GPRC5D scFv comprises a $V_H$ CDR1 comprising amino acids having the sequence set forth in SEQ ID NO: 208 or conservative In certain embodiments, the antibody or other antigen binding protein is an anti-GPRC5D scFv or an antigen-binding fragment thereof having an antigen-binding region that comprises the amino acid sequence of SEQ ID NO: 115 and specifically binds to a GPRC5D polypeptide (e.g., a GPRC5D polypeptide having the amino acid sequence SEQ ID NO:97, or fragments thereof), which is designated as ET150-155 scFv (also referred to as "ET150-5 scFv").

In certain embodiments, the anti-GPRC5D scFv antibody comprises a heavy chain variable region comprising amino acids having the sequence set forth in SEQ ID NO:61 and a light chain variable region comprising amino acids having the sequence set forth in SEQ ID NO:62, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 16. In certain embodiments, the anti-GPRC5D scFv comprises a $V_H$ comprising amino acids having the sequence set forth in SEQ ID NO:61, as shown in Table 16. In certain embodiments, the anti-GPRC5D scFv comprises a $V_L$ comprising amino acids having the sequence set forth in SEQ ID NO:62, as shown in Table 16. In certain embodiments, the anti-GPRC5D scFv comprises a $V_H$ comprising amino acids having the sequence set forth in SEQ ID NO:61 and a $V_L$ comprising amino acids having the sequence set forth in SEQ ID NO:62, as shown in Table 16. In certain embodiments, the anti-GPRC5D scFv comprises a $V_H$ CDR1 comprising amino acids having the sequence set forth in SEQ ID NO:214 or conservative modifications thereof, a $V_H$ CDR2 comprising amino acids having the sequence set forth in SEQ ID NO: 215 or conservative modifications thereof, and a $V_H$ CDR3 comprising amino acids having the sequence set forth in SEQ ID NO: 216 or conservative modifications thereof, as shown in Table 16. In certain embodiments, the anti-GPRC5D scFv comprises a $V_H$ CDR1 comprising amino acids having the sequence set forth in SEQ ID NO: 214 or conservative modifications thereof, a $V_H$ CDR2 comprising amino acids having the sequence set forth in SEQ ID NO: 215 or conservative modifications thereof, a $V_H$ CDR3 comprising amino acids having the sequence set forth in SEQ ID NO: 216 or conservative modifications thereof, a $V_L$ CDR1 comprising amino acids having the sequence set forth in SEQ ID NO: 217 or conservative modifications thereof, a $V_L$ CDR2 comprising amino acids having the sequence set forth in SEQ ID NO: 218 or conservative modifications thereof, and a $V_L$ CDR3 comprising amino acids having the sequence set forth in SEQ ID NO: 219 or conservative modifications thereof, as shown in Table 16. In certain embodiments, the anti-GPRC5D scFv comprises a $V_H$ CDR1 comprising amino acids having the sequence set forth in SEQ ID NO: 214, a $V_H$ CDR2 comprising amino acids having the sequence set forth in SEQ ID NO: 215, a $V_H$ CDR3 comprising amino acids having the sequence set forth in SEQ ID NO: 216, a $V_L$ CDR1 comprising amino acids having the sequence set forth in SEQ ID NO: 217, a $V_L$ CDR2 comprising amino acids having the sequence set forth in SEQ ID NO: 218, and a $V_L$ CDR3 comprising amino acids having the sequence set forth in SEQ ID NO: 219.

TABLE 16

Antigen A GPRC5D polypeptide having the amino acid sequence of SEQ ID NO: 97

| CDRs | 1 | 2 | 3 |
|------|---|---|---|
| $V_H$ | GFTFSDYY [SEQ ID NO: 214] | ISSSGSTI [SEQ ID NO: 215] | ARGYGKAYDQ [SEQ ID NO: 216] |
| $V_L$ | RSNVGGNY [SEQ ID NO: 217] | RSN [SEQ ID NO: 218] | ATWDDSLSGFV [SEQ ID NO: 219] |

Full $V_H$    EVQLVESGGGLVKPGGSLRLSCAASGFTFSDYYMSWIRQAPGKGLEW
VSYISSSGSTIYYADSVKGRFTISRDNAKNSLYLQMNSLRAEDTAVYY
CARGYGKAYDQWGQGTLVTVSS [SEQ ID NO: 61]

DNA    Gaggtgcagctggtggagtctggggaggcttggtcaagcctggagggtccctgagactctcctgtgcagcct
ctggattcaccttcagtgactactacatgagctggatccgccaggctccagggaaggggctggagtgggtttcat
acattagtagtagtggtagtaccatatactacgcagactctgtgaaggggccgattcaccatctccagggacaacg
ccaagaactcactgtatctgcaaatgaacagcctgagagccgaggacacggccgtatattactgtgcgcgcggt
tacggtaaagcttacgatcagtggggtcaaggtactctggtgaccgtctcctca [SEQ ID NO: 63]

Full $V_L$    QSVLTQPPSASGTPGQRVTISCSGSRSNVGGNYVFWYQQVPGATPKLL
IYRSNQRPSGVPDRFAGSKSGSSASLATSGLRSEDEADYYCATWDDSL
SGFVFGTGTKVTVLG [SEQ ID NO: 62]

DNA    Cagtctgtgttgactcagccaccctcagcgtctgggacccccggacagagggtcaccatctcttgttctggaag
caggtccaacgtaggaggtaattatgtattttggtaccagcaagtccccggagcgaccccaaactcctcatctat
aggagtaatcageggccctcgggggtccctgaccgattcgctggctccaagtctggctcctcagcctccctggc
catcagtggactccggtccgaggatgaggctgattattactgtgcaacatgggatgacagcctgagtggttttgtc
ttcggaactgggaccaaggtcaccgtcctaggt [SEQ ID NO: 64]

scFv    QSVLTQPPSASGTPGQRVTISCSGSRSNVGGNYVFWYQQVPGATPKLL
IYRSNQRPSGVPDRFAGSKSGSSASLATSGLRSEDEADYYCATWDDSL
SGFVFGTGTKVTVLGSRGGGGSGGGGSGGGGSLEMAEVQLVESGGG
LVKPGGSLRLSCAASGFTFSDYYMSWIRQAPGKGLEWVSYISSSGSTIY
YADSVKGRFTISRDNAKNSLYLQMNSLRAEDTAVYYCARGYGKAYD
QWGQGTLVTVSS [SEQ ID NO: 115]

Table 16. In certain embodiments, the anti-GPRC5D scFv comprises a $V_L$ CDR1 comprising amino acids having the sequence set forth in SEQ ID NO: 217 or conservative modifications thereof, a $V_L$ CDR2 comprising amino acids having the sequence set forth in SEQ ID NO: 218 or conservative modifications thereof, and a $V_L$ CDR3 comprising amino acids having the sequence set forth in SEQ ID NO: 219 or conservative modifications thereof, as shown in In certain embodiments, the antibody or other antigen binding protein is an anti-GPRC5D scFv or an antigen-binding fragment thereof having an antigen-binding region that comprises the amino acid sequence of SEQ ID NO: 116 and specifically binds to a GPRC5D polypeptide (e.g., a GPRC5D polypeptide having the amino acid sequence SEQ ID NO:97, or fragments thereof), which is designated as ET150-158 scFv (also referred to as "ET150-8 scFv").

In certain embodiments, the anti-GPRC5D scFv antibody comprises a heavy chain variable region comprising amino acids having the sequence set forth in SEQ ID NO:65 and a light chain variable region comprising amino acids having the sequence set forth in SEQ ID NO:66, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 17. In certain embodiments, the anti-GPRC5D scFv comprises a $V_H$ comprising amino acids having the sequence set forth in SEQ ID NO:65, as shown in Table 17. In certain embodiments, the anti-GPRC5D scFv comprises a $V_L$ comprising amino acids having the sequence set forth in SEQ ID NO:66, as shown in Table 17. In certain embodiments, the anti-GPRC5D scFv comprises a $V_H$ comprising amino acids having the sequence set forth in SEQ ID NO:65 and a $V_L$ comprising amino acids having the sequence set forth in SEQ ID NO:66, as shown in Table 17. In certain embodiments, the anti-GPRC5D scFv comprises a $V_H$ CDR1 comprising amino acids having the sequence set forth in SEQ ID NO:220 or conservative modifications thereof, a $V_H$ CDR2 comprising amino acids having the sequence set forth in SEQ ID NO: 221 or conservative modifications thereof, and a $V_H$ CDR3 comprising amino acids having the sequence set forth in SEQ ID NO: 222 or conservative modifications thereof, as shown in modifications thereof, a $V_L$ CDR2 comprising amino acids having the sequence set forth in SEQ ID NO: 224 or conservative modifications thereof, and a $V_L$ CDR3 comprising amino acids having the sequence set forth in SEQ ID NO: 225 or conservative modifications thereof, as shown in Table 17. In certain embodiments, the anti-GPRC5D scFv comprises a $V_H$ CDR1 comprising amino acids having the sequence set forth in SEQ ID NO: 220 or conservative modifications thereof, a $V_H$ CDR2 comprising amino acids having the sequence set forth in SEQ ID NO: 221 or conservative modifications thereof, a $V_H$ CDR3 comprising amino acids having the sequence set forth in SEQ ID NO: 222 or conservative modifications thereof, a $V_L$ CDR1 comprising amino acids having the sequence set forth in SEQ ID NO: 223 or conservative modifications thereof, a $V_L$ CDR2 comprising amino acids having the sequence set forth in SEQ ID NO: 224 or conservative modifications thereof, and a $V_L$ CDR3 comprising amino acids having the sequence set forth in SEQ ID NO: 225 or conservative modifications thereof, as shown in Table 17. In certain embodiments, the anti-GPRC5D scFv comprises a $V_H$ CDR1 comprising amino acids having the sequence set forth in SEQ ID NO: 220, a $V_H$ CDR2 comprising amino acids having the sequence set forth in SEQ ID NO: 221, a $V_H$ CDR3 comprising amino acids having the sequence set forth in SEQ ID NO: 222, a $V_L$ CDR1 comprising amino acids having the sequence set forth in SEQ ID NO: 223, a $V_L$ CDR2 comprising amino acids having the sequence set forth in SEQ ID NO: 224, and a $V_L$ CDR3 comprising amino acids having the sequence set forth in SEQ ID NO: 225.

TABLE 17

Antigen A GPRC5D polypeptide having the amino acid sequence of SEQ ID NO: 97

| CDRs | 1 | 2 | 3 |
|---|---|---|---|
| $V_H$ | GFTFRSHS [SEQ ID NO: 220] | ISSDSTYT [SEQ ID NO: 221] | ARSGGQWKYYDY [SEQ ID NO: 222] |
| $V_L$ | SLRSYY [SEQ ID NO: 223] | GKN [SEQ ID NO: 224] | NSRDSSGNPPVV [SEQ ID NO: 225] |

Full $V_H$ QVQLVESGGGLVHPGGSLRLSCAASGFTFRSHSMNWVRQAPGKGLE
WVSSISSDSTYTYYADSVKGRFTISRDNAKNSLYLQMNSLRAEDTAV
YYCARSGGQWKYYDYWGQGTLVTVSS [SEQ ID NO: 65]

DNA Caggtgcagctggtggagtctggggggaggcctggtccaccctggggggtccctgagactctcctgtgcagcct
ctggattcaccttcagaagccatagcatgaactgggtccgccaggctccagggaaggggctggagtgggtctc
atccattagtagtgatagtacttacacatactacgcagactcagtgaagggccgattcaccatctccagagacaac
gccaagaactcactgtatctgcaaatgaacagcctgagagccgaggacacggccgtatattactgtgcgcgctc
tggtggtcagtggaaatactacgattactggggtcaaggtactctggtgaccgtctcctca [SEQ ID NO: 67]

Full $V_L$ SSELTQDPAVSVALGQTVRITCQGDSLRSYYASWYQQKPGQAPVLVIY
GKNNRPSGIPDRFSGSSSGNTASLTITGAQAEDEADYYCNSRDSSGNPP
VVFGGGTKLTVLG [SEQ ID NO: 66]

DNA Tcttctgagctgactcaggaccctgctgtgtctgtggccttgggacagacagtcaggatcacatgccaaggaga
cagcctcagaagctattatgcaagctggtaccagcagaagccaggacaggccctgtacttgtcatctatggtaa
aaacaaccggccctcagggatcccagaccgattctctggctccagctcaggaaacacagcttccttgaccatca
ctggggctcaggcggaagatgaggctgactattactgtaactcccgggacagcagtggtaacccccctgtggta
ttcggcggagggaccaagctgaccgtcctaggt [SEQ ID NO: 68]

scFv SSELTQDPAVSVALGQTVRITCQGDSLRSYYASWYQQKPGQAPVLVIY
GKNNRPSGIPDRFSGSSSGNTASLTITGAQAEDEADYYCNSRDSSGNPP
VVFGGGTKLTVLGSRGGGGSGGGGSGGGGSLEMAQVQLVESGGGLV
HPGGSLRLSCAASGFTFRSHSMNWVRQAPGKGLEWVSSISSDSTYTY
YADSVKGRFTISRDNAKNSLYLQMNSLRAEDTAVYYCARSGGQWKY
YDYWGQGTLVTVSS [SEQ ID NO: 116]

Table 17. In certain embodiments, the anti-GPRC5D scFv comprises a $V_L$ CDR1 comprising amino acids having the sequence set forth in SEQ ID NO: 223 or conservative In certain embodiments, the antibody or other antigen binding protein is an anti-GPRC5D scFv or an antigen-binding fragment thereof having an antigen-binding region that comprises the amino acid sequence of SEQ ID NO: 117 and specifically binds to a GPRC5D polypeptide (e.g., a GPRC5D polypeptide having the amino acid sequence SEQ ID NO:97, or fragments thereof), which is designated as ET150-168 scFv (also referred to as "ET150-18 scFv").

In certain embodiments, the anti-GPRC5D scFv antibody comprises a heavy chain variable region comprising amino acids having the sequence set forth in SEQ ID NO:69 and a light chain variable region comprising amino acids having the sequence set forth in SEQ ID NO:70, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 18. In certain embodiments, the anti-GPRC5D scFv comprises a $V_H$ comprising amino acids having the sequence set forth in SEQ ID NO:69, as shown in Table 18. In certain embodiments, the anti-GPRC5D scFv comprises a $V_L$ comprising amino acids having the sequence set forth in SEQ ID NO:70, as shown in Table 18. In certain embodiments, the anti-GPRC5D scFv comprises a $V_H$ comprising amino acids having the sequence set forth in SEQ ID NO:69 and a $V_L$ comprising amino acids having the sequence set forth in SEQ ID NO:70, as shown in Table 18. In certain embodiments, the anti-GPRC5D scFv comprises a $V_H$ CDR1 comprising amino acids having the sequence set forth in SEQ ID NO:226 or conservative modifications thereof, a $V_H$ CDR2 comprising amino acids having the sequence set forth in SEQ ID NO: 227 or conservative modifications thereof, and a $V_H$ CDR3 comprising amino acids having the sequence set forth in SEQ ID NO: 228 or conservative modifications thereof, as shown in Table 18. In certain embodiments, the anti-GPRC5D scFv comprises a $V_L$ CDR1 comprising amino acids having the sequence set forth in SEQ ID NO: 229 or conservative modifications thereof, a $V_L$ CDR2 comprising amino acids having the sequence set forth in SEQ ID NO: 230 or conservative modifications thereof, and a $V_L$ CDR3 comprising amino acids having the sequence set forth in SEQ ID NO: 231 or conservative modifications thereof, as shown in Table 18. In certain embodiments, the anti-GPRC5D scFv comprises a $V_H$ CDR1 comprising amino acids having the sequence set forth in SEQ ID NO: 226 or conservative modifications thereof, a $V_H$ CDR2 comprising amino acids having the sequence set forth in SEQ ID NO: 227 or conservative modifications thereof, a $V_H$ CDR3 comprising amino acids having the sequence set forth in SEQ ID NO: 228 or conservative modifications thereof, a $V_L$ CDR1 comprising amino acids having the sequence set forth in SEQ ID NO: 229 or conservative modifications thereof, a $V_L$ CDR2 comprising amino acids having the sequence set forth in SEQ ID NO: 230 or conservative modifications thereof, and a $V_L$ CDR3 comprising amino acids having the sequence set forth in SEQ ID NO: 231 or conservative modifications thereof, as shown in Table 18. In certain embodiments, the anti-GPRC5D scFv comprises a $V_H$ CDR1 comprising amino acids having the sequence set forth in SEQ ID NO: 226, a $V_H$ CDR2 comprising amino acids having the sequence set forth in SEQ ID NO: 227, a $V_H$ CDR3 comprising amino acids having the sequence set forth in SEQ ID NO: 228, a $V_L$ CDR1 comprising amino acids having the sequence set forth in SEQ ID NO: 229, a $V_L$ CDR2 comprising amino acids having the sequence set forth in SEQ ID NO: 230, and a $V_L$ CDR3 comprising amino acids having the sequence set forth in SEQ ID NO: 231.

TABLE 18

Antigen A GPRC5D polypeptide having the amino acid sequence of SEQ ID NO: 97

| CDRs | 1 | 2 | 3 |
|---|---|---|---|
| $V_H$ | GFTFSNYA [SEQ ID NO: 226] | INGRGSST [SEQ ID NO: 227] | ARYISRGLGDS [SEQ ID NO: 228] |
| $V_L$ | NSNIERNY[SEQ ID NO: 229] | DND [SEQ ID NO: 230] | GTWDSSLRGWV [SEQ ID NO: 231] |

Full $V_H$   EVQLVESGGGLIQPGGSLRLSCAASGFTFSNYAMNWVRQAPGKGLEW
VSTINGRGSSTIYADSVKGRFTISRDNSKNTLYLQMNSLRAEDTATYY
CARYISRGLGDSWGQGTLVTV [SEQ ID NO: 69]

DNA   Gaggtgcagctggtggagtccggggggaggcttgatacagcctggggggtccctgagactctcctgtgcagcc
tctggattcacctttagcaactatgccatgaactgggtccgccaggctccagggaaggggctggagtgggtctc
aactattaatggtcgtggtagtagtacaatctacgcagactccgtgaagggccggttcaccatctccagagacaa
ttccaagaacacgctgtatctgcaaatgaacagcctgagagccgaggacacagccacgtattactgtgcgcgct
acatctctcgtggtctgggtgattcttggggtcaaggtactctggtgaccgtctcctca [SEQ ID NO: 71]

Full $V_L$   QSVVTQPPPSMSAAPGQQVTISCSGGNSNIERNYVSWYLQLPGTAPKLV
IFDNDRRPSGIPDRFSGSKSGTSATLGITGLQTGDEADYYCGTWDSSLR
GWVFGGGTKLTVLG [SEQ ID NO: 70]

DNA   Cagtctgtcgtgacgcagccgccctcaatgtctgcggccccaggacagcaagtcaccatctcctgctctggag
gcaactccaacattgagagaaattatgtatcctggtacctccagctccctggaacagcccccaaactcgtcattttt
gacaatgataggcgaccctcagggattcctgaccgattctctggctccaagtctggcacgtcagccaccctggg
catcaccggactccagactggggacgaggccgattattactgcggaacatgggatagcagcctgagaggttgg
gtgttcggcggagggaccaagctgaccgtcctaggt [SEQ ID NO: 72]

scFv   QSVVTQPPPSMSAAPGQQVTISCSGGNSNIERNYVSWYLQLPGTAPKLV
IFDNDRRPSGIPDRFSGSKSGTSATLGITGLQTGDEADYYCGTWDSSLR
GWVFGGGTKLTVLGSRGGGGSGGGGSGGGGSLEMAEVQLVESGGGL
IQPGGSLRLSCAASGFTFSNYAMNWVRQAPGKGLEWVSTINGRGSSTI
YADSVKGRFTISRDNSKNTLYLQMNSLRAEDTATYYCARYISRGLGDS
WGQGTLVTV [SEQ ID NO: 117]

In certain embodiments, the antibody or other antigen binding protein is an anti-GPRC5D scFv or an antigen-binding fragment thereof having an antigen-binding region that comprises the amino acid sequence of SEQ ID NO: 118 and specifically binds to a GPRC5D polypeptide (e.g., a GPRC5D polypeptide having the amino acid sequence SEQ ID NO:97, or fragments thereof), which is designated as ET150-164 scFv (also referred to as "ET150-14 scFv").

In certain embodiments, the anti-GPRC5D scFv antibody comprises a heavy chain variable region comprising amino acids having the sequence set forth in SEQ ID NO:73 and a light chain variable region comprising amino acids having the sequence set forth in SEQ ID NO:74, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 19. In certain embodiments, the anti-GPRC5D scFv comprises a $V_H$ comprising amino acids having the sequence set forth in SEQ ID NO:73, as shown in Table 19. In certain embodiments, the anti-GPRC5D scFv comprises a $V_L$ comprising amino acids having the sequence set forth in SEQ ID NO:74, as shown in Table 19. In certain embodiments, the anti-GPRC5D scFv comprises a $V_H$ comprising amino acids having the sequence set forth in SEQ ID NO:73 and a $V_L$ comprising amino acids having the sequence set forth in SEQ ID NO:74, as shown in Table 19. In certain embodiments, the anti-GPRC5D scFv comprises a $V_H$ CDR1 comprising amino acids having the sequence set forth in SEQ ID NO:232 or conservative modifications thereof, a $V_H$ CDR2 comprising amino acids having the sequence set forth in SEQ ID NO: 233 or conservative modifications thereof, and a $V_H$ CDR3 comprising amino acids having the sequence set forth in SEQ ID NO: 234 or conservative modifications thereof, as shown in Table 19. In certain embodiments, the anti-GPRC5D scFv comprises a $V_L$ CDR1 comprising amino acids having the sequence set forth in SEQ ID NO: 235 or conservative modifications thereof, a $V_L$ CDR2 comprising amino acids having the sequence set forth in SEQ ID NO: 236 or conservative modifications thereof, and a $V_L$ CDR3 comprising amino acids having the sequence set forth in SEQ ID NO: 237 or conservative modifications thereof, as shown in Table 19. In certain embodiments, the anti-GPRC5D scFv comprises a $V_H$ CDR1 comprising amino acids having the sequence set forth in SEQ ID NO: 232 or conservative modifications thereof, a $V_H$ CDR2 comprising amino acids having the sequence set forth in SEQ ID NO: 233 or conservative modifications thereof, a $V_H$ CDR3 comprising amino acids having the sequence set forth in SEQ ID NO: 234 or conservative modifications thereof, a $V_L$ CDR1 comprising amino acids having the sequence set forth in SEQ ID NO: 235 or conservative modifications thereof, a $V_L$ CDR2 comprising amino acids having the sequence set forth in SEQ ID NO: 236 or conservative modifications thereof, and a $V_L$ CDR3 comprising amino acids having the sequence set forth in SEQ ID NO: 237 or conservative modifications thereof, as shown in Table 19. In certain embodiments, the anti-GPRC5D scFv comprises a $V_H$ CDR1 comprising amino acids having the sequence set forth in SEQ ID NO: 232, a $V_H$ CDR2 comprising amino acids having the sequence set forth in SEQ ID NO: 233, a $V_H$ CDR3 comprising amino acids having the sequence set forth in SEQ ID NO: 234, a $V_L$ CDR1 comprising amino acids having the sequence set forth in SEQ ID NO: 235, a $V_L$ CDR2 comprising amino acids having the sequence set forth in SEQ ID NO: 236, and a $V_L$ CDR3 comprising amino acids having the sequence set forth in SEQ ID NO: 237.

TABLE 19

Antigen A GPRC5D polypeptide having the amino acid sequence of SEQ ID NO: 97

| CDRs | 1 | 2 | 3 |
|---|---|---|---|
| $V_H$ | GYTFTSYY [SEQ ID NO: 232] | INPSGGST [SEQ ID NO: 233 | ARAGMGMDT [SEQ ID NO: 234] |
| $V_L$ | SSDVGGYNY [SEQ ID NO: 235] | EVS [SEQ ID NO: 236] | SSYAGSNTLV [SEQ ID NO: 237] |

Full $V_H$ QMQLVQSGAEVKKPGASVKVSCKASGYTFTSYYMEIWVRQAPGQGL
EWMGIINPSGGSTSYAQKFQGRVTMRDTSTSTVYMELSSLRSEDTAV
YYCARAGMGMDTWGQGTLVTVSS [SEQ ID NO: 73]

DNA Cagatgcagctggtgcagtctggggctgaggtgaagaagcctggggcctcagtgaaggtttcctgcaaggcat
ctggatacaccttcaccagctactatatgcactgggtgcgacaggcccctggacaagggcttgagtggatggga
ataatcaaccctagtggtggtagcacaagctacgcacagaagttccagggcagagtcaccatgaccagggaca
cgtccacgagcacagtctacatggagctgagcagcctgagatctgaggacacggccgtgtattactgtgcgcg
cgctggtatgggtatggatacttggggtcaaggtactctggtgaccgtctcctca [SEQ ID NO: 75]

Full $V_L$ QSALTQPPSASGSPGQSVTISCTGTSSDVGGYNYVSWYQQHPGKAPKL
MIYEVSKRPSGVPDRFSGSKSGNTASLTVSGLQAEDEADYYCSSYAGS
NTLVFGGGTKLTVLG [SEQ ID NO: 74]

DNA Cagtctgccctgactcagcctccctccgcgtccgggtctcctggacagtcagtcaccatctcctgcactggaac
cagcagtgacgttggtggttataaactatgtctcctggtaccaacagcacccaggcaaagcccccaaactcatgat
ttatgaggtcagtaageggccctcaggggtccctgatcgcttctctggctccaagtctggcaacacggcctccct
gaccgtctctgggctccaggctgaggatgaggctgattattactgcagctcatatgcaggcagcaacaccttggt
gttcggcggagggaccaagctgaccgtcctaggt [SEQ ID NO: 76]

scFv QSALTQPPSASGSPGQSVTISCTGTSSDVGGYNYVSWYQQHPGKAPKL
MIYEVSKRPSGVPDRFSGSKSGNTASLTVSGLQAEDEADYYCSSYAGS
NTLVFGGGTKLTVLGSRGGGGSGGGGSGGGGSLEMAQMQLVQSGAE
VKKPGASVKVSCKASGYTFTSYYMHWVRQAPGQGLEWMGIINPSGG
STSYAQKFQGRVTMRDTSTSTVYMELSSLRSEDTAVYYCARAGMG
MDTWGQGTLVTVSS [SEQ ID NO: 118]

In certain embodiments, the antibody or other antigen binding protein is an anti-GPRC5D scFv or an antigen-binding fragment thereof having an antigen-binding region that comprises the amino acid sequence of SEQ ID NO: 119 and specifically binds to a GPRC5D polypeptide (e.g., a GPRC5D polypeptide having the amino acid sequence SEQ ID NO:97, or fragments thereof), which is designated as ET150-165 scFv (also referred to as "ET150-15 scFv").

In certain embodiments, the anti-GPRC5D scFv antibody comprises a heavy chain variable region comprising amino acids having the sequence set forth in SEQ ID NO:77 and a light chain variable region comprising amino acids having the sequence set forth in SEQ ID NO:78, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 20. In certain embodiments, the anti-GPRC5D scFv comprises a $V_H$ comprising amino acids having the sequence set forth in SEQ ID NO:77, as shown in Table 20. In certain embodiments, the anti-GPRC5D scFv comprises a $V_L$ comprising amino acids having the sequence set forth in SEQ ID NO:78, as shown in Table 20. In certain embodiments, the anti-GPRC5D scFv comprises a $V_H$ comprising amino acids having the sequence set forth in SEQ ID NO:77 and a $V_L$ comprising amino acids having the sequence set forth in SEQ ID NO:78, as shown in Table 20. In certain embodiments, the anti-GPRC5D scFv comprises a $V_H$ CDR1 comprising amino acids having the sequence set forth in SEQ ID NO:238 or conservative modifications thereof, a $V_H$ CDR2 comprising amino acids having the sequence set forth in SEQ ID NO: 239 or conservative modifications thereof, and a $V_H$ CDR3 comprising amino acids having the sequence set forth in SEQ ID NO: 240 or conservative modifications thereof, as shown in Table 20. In certain embodiments, the anti-GPRC5D scFv comprises a $V_L$ CDR1 comprising amino acids having the sequence set forth in SEQ ID NO: 241 or conservative modifications thereof, a $V_L$ CDR2 comprising amino acids having the sequence set forth in SEQ ID NO: 242 or conservative modifications thereof, and a $V_L$ CDR3 comprising amino acids having the sequence set forth in SEQ ID NO: 243 or conservative modifications thereof, as shown in Table 20. In certain embodiments, the anti-GPRC5D scFv comprises a $V_H$ CDR1 comprising amino acids having the sequence set forth in SEQ ID NO: 238 or conservative modifications thereof, a VA CDR2 comprising amino acids having the sequence set forth in SEQ ID NO: 239 or conservative modifications thereof, a $V_H$ CDR3 comprising amino acids having the sequence set forth in SEQ ID NO: 240 or conservative modifications thereof, a $V_L$ CDR1 comprising amino acids having the sequence set forth in SEQ ID NO: 241 or conservative modifications thereof, a $V_L$ CDR2 comprising amino acids having the sequence set forth in SEQ ID NO: 242 or conservative modifications thereof, and a $V_L$ CDR3 comprising amino acids having the sequence set forth in SEQ ID NO: 243 or conservative modifications thereof, as shown in Table 20. In certain embodiments, the anti-GPRC5D scFv comprises a $V_H$ CDR1 comprising amino acids having the sequence set forth in SEQ ID NO: 238, a $V_H$ CDR2 comprising amino acids having the sequence set forth in SEQ ID NO: 239, a $V_H$ CDR3 comprising amino acids having the sequence set forth in SEQ ID NO: 240, a $V_L$ CDR1 comprising amino acids having the sequence set forth in SEQ ID NO: 241, a $V_L$ CDR2 comprising amino acids having the sequence set forth in SEQ ID NO: 242, and a $V_L$ CDR3 comprising amino acids having the sequence set forth in SEQ ID NO: 243.

TABLE 20

Antigen A GPRC5D polypeptide having the amino acid sequence of SEQ ID NO: 97

| CDRs | 1 | 2 | 3 |
|---|---|---|---|
| $V_H$ | GYTFTAYS [SEQ ID NO: 238] | INPSSGGA [SEQ ID NO: 239] | ARNVGGQADD [SEQ ID NO: 240] |
| $V_L$ | SSDIGGYNY [SEQ ID NO: 241] | EVN [SEQ ID NO: 242] | ASFAGRKTLV [SEQ ID NO: 243] |

Full $V_H$   QVQLVQSGAEVKKPGASVKVSCRASGYTFTAYSLHWVRQAPGQGLE
WMGWINPSSGGAVYAQKFQGRVTMTRDTSISTAYMELSGLRSDDTA
VYYCARNVGGQADDWGQGTLVTVSS [SEQ ID NO: 77]

DNA   Caggtgcagctggtgcagtctggggctgaggtgaagaagcctggggcctcagtgaaggtctcctgcagggct
tctggatacaccttcaccgcctactattacactgggtgcgacaggcccctggacaagggcttgagtggatggga
tggatcaaccctagcagtggtggcgcagtttatgcacagaaatttcagggtagggtcaccatgaccagggacac
gtccatcagcacagcctacatggagctgagtggcctgagatctgacgacacggccgtgtattactgtgcgcgca
acgttggtggtcaggctgatgactggggtcaaggtactctggtgaccgtctcctca [SEQ ID NO: 79]

Full $V_L$   QSALTQPPSASGSPGQSVTISCTGTSSDIGGYNYVSWYQQHPGKAPKL
MIYEVNKRPSGVPDRFSGSKSGNTASLTVSGLQAEDEADYYCASFAG
RKTLVFGGGTKLTVLG [SEQ ID NO: 78]

DNA   Caatctgccctgactcagcctccctccgcgtccgggtctcctggacagtcagtcaccatctcctgcactggaacc
agcagtgacattggtggttataactatgtctcctggtaccaacagcacccaggcaaagcccccaaactcatgattt
atgaggtcaataageggccctcaggggtccctgatcgcttctcgggctccaagtctggcaacacggcctccctg
accgtctctgggctccaggctgaggatgaggctgattattactgcgcctcatttgggggcaggaagacattggtc
ttcggcggagggaccaagctgaccgtcctaggt [SEQ ID NO: 80]

scFv   QSALTQPPSASGSPGQSVTISCTGTSSDIGGYNYVSWYQQHPGKAPKL
MIYEVNKRPSGVPDRFSGSKSGNTASLTVSGLQAEDEADYYCASFAG
RKTLVFGGGTKLTVLGSRGGGGSGGGGSGGGGSLEMAQVQLVQSGA
EVKKPGASVKVSCRASGYTFTAYSLHWVRQAPGQGLEWMGWINPSS
GGAVYAQKFQGRVTMTRDTSISTAYMELSGLRSDDTAVYYCARNVG
GQADDWGQGTLVTVSS [SEQ ID NO: 119]

In certain embodiments, the antibody or other antigen binding protein is an anti-GPRC5D scFv or an antigen-binding fragment thereof having an antigen-binding region that comprises the amino acid sequence of SEQ ID NO: 120 and specifically binds to a GPRC5D polypeptide (e.g., a GPRC5D polypeptide having the amino acid sequence SEQ ID NO:97, or fragments thereof), which is designated as ET150-167 scFv (also referred to as "ET150-17 scFv").

In certain embodiments, the anti-GPRC5D scFv antibody comprises a heavy chain variable region comprising amino acids having the sequence set forth in SEQ ID NO:81 and a light chain variable region comprising amino acids having the sequence set forth in SEQ ID NO:82, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 21. In certain embodiments, the anti-GPRC5D scFv comprises a $V_H$ comprising amino acids having the sequence set forth in SEQ ID NO:81, as shown in Table 21. In certain embodiments, the anti-GPRC5D scFv comprises a $V_L$ comprising amino acids having the sequence set forth in SEQ ID NO:82, as shown in Table 21. In certain embodiments, the anti-GPRC5D scFv comprises a $V_H$ comprising amino acids having the sequence set forth in SEQ ID NO:81 and a $V_L$ comprising amino acids having the sequence set forth in SEQ ID NO:82, as shown in Table 21. In certain embodiments, the anti-GPRC5D scFv comprises a $V_H$ CDR1 comprising amino acids having the sequence set forth in SEQ ID NO:244 or conservative modifications thereof, a $V_H$ CDR2 comprising amino acids having the sequence set forth in SEQ ID NO: 245 or conservative modifications thereof, and a $V_H$ CDR3 comprising amino acids having the sequence set forth in SEQ ID NO: 246 or conservative modifications thereof, as shown in Table 21. In certain embodiments, the anti-GPRC5D scFv comprises a $V_L$ CDR1 comprising amino acids having the sequence set forth in SEQ ID NO: 247 or conservative modifications thereof, a $V_L$ CDR2 comprising amino acids having the sequence set forth in SEQ ID NO: 248 or conservative modifications thereof, and a $V_L$ CDR3 comprising amino acids having the sequence set forth in SEQ ID NO: 249 or conservative modifications thereof, as shown in Table 21. In certain embodiments, the anti-GPRC5D scFv comprises a $V_H$ CDR1 comprising amino acids having the sequence set forth in SEQ ID NO: 244 or conservative modifications thereof, a $V_H$ CDR2 comprising amino acids having the sequence set forth in SEQ ID NO: 245 or conservative modifications thereof, a $V_H$ CDR3 comprising amino acids having the sequence set forth in SEQ ID NO: 246 or conservative modifications thereof, a $V_L$ CDR1 comprising amino acids having the sequence set forth in SEQ ID NO: 247 or conservative modifications thereof, a $V_L$ CDR2 comprising amino acids having the sequence set forth in SEQ ID NO: 248 or conservative modifications thereof, and a $V_L$ CDR3 comprising amino acids having the sequence set forth in SEQ ID NO: 249 or conservative modifications thereof, as shown in Table 21. In certain embodiments, the anti-GPRC5D scFv comprises a $V_H$ CDR1 comprising amino acids having the sequence set forth in SEQ ID NO: 244, a $V_H$ CDR2 comprising amino acids having the sequence set forth in SEQ ID NO: 245, a $V_H$ CDR3 comprising amino acids having the sequence set forth in SEQ ID NO: 246, a $V_L$ CDR1 comprising amino acids having the sequence set forth in SEQ ID NO: 247, a $V_L$ CDR2 comprising amino acids having the sequence set forth in SEQ ID NO: 248, and a $V_L$ CDR3 comprising amino acids having the sequence set forth in SEQ ID NO: 249.

TABLE 21

Antigen A GPRC5D polypeptide having the amino acid sequence of SEQ ID NO: 97

| CDRs | 1 | 2 | 3 |
|---|---|---|---|
| $V_H$ | GYTFTAYS [SEQ ID NO: 244] | INPSSGGA [SEQ ID NO: 245] | ARNVGGHADD [SEQ ID NO: 246] |
| $V_L$ | STDIGGYNY [SEQ ID NO: 247] | EVN [SEQ ID NO: 248] | ASFAGRKTLV [SEQ ID NO: 249] |

Full $V_H$ QVQLVQSGAEVKKPGASVKVSCRASGYTFTAYSLHWVRQAPGQGLE
WMGWINPSSGGAVYAQKFQGRVTMTRDTSISTAYMELSGLRSDDTA
VYYCARNVGGHADDWGQGTLVTVSS [SEQ ID NO: 81]

DNA Caggtgcagctggtgcagtctgggggctgaggtgaaaaagcctggggcctcagtgaaagtctcctgcagggctt
ctggatacaccttcaccgcctactattacactgggtgcgacaggccctggacaaagggcttgagtggatgggat
ggatcaaccctagcagtggtggcgcagtttatgcacagaaatttcagggtagggtcaccatgaccagggacac
gtccatcagcacagcctacatggagctgagtggcctgagatctgacgacacggccgtgtattactgtgcgcgca
acgttggtggtcacgctgatgactggggtcaaggtactctggtgaccgtctcctca [SEQ ID NO: 83]

Full $V_L$ QSALTQPPSASGSPGQSVTISCTGTSTDIGGYNYVSWYQHHPSKAPKL
MIYEVNKRPSGVPDRFSGSKSGNTASLTVSGLQAEDEADYYCASFAG
RKTLVFGGGTKLTVLG [SEQ ID NO: 82]

DNA Caatctgccctgactcagcctccctccgcgtccgggtctcctggacagtcagtcaccatctcctgcactggaacc
agcactgacattggtggttataactatgtctcctggtaccaacaccacccaagcaaagcccccaaactcatgattt
atgaggtcaataageggccctcaggggtccctgatcgcttctcgggctccaagtctggcaacacggcctccctg
accgtctctgggctccaggctgaggatgaggctgattattactgcgcctcatttgagggcaggaagacattggtc
ttcggcggagggaccaagctgaccgtcctaggt [SEQ ID NO: 84]

scFv QSALTQPPSASGSPGQSVTISCTGTSTDIGGYNYVSWYQHHPSKAPKL
MIYEVNKRPSGVPDRFSGSKSGNTASLTVSGLQAEDEADYYCASFAG
RKTLVFGGGTKLTVLGSRGGGGSGGGGSGGGGSLEMAQVQLVQSGA
EVKKPGASVKVSCRASGYTFTAYSLHWVRQAPGQGLEWMGWINPSS
GGAVYAQKFQGRVTMTRDTSISTAYMELSGLRSDDTAVYYCARNVG
GHADDWGQGTLVTVSS [SEQ ID NO: 120]

In certain embodiments, the antibody or other antigen binding protein is an anti-GPRC5D scFv or an antigen-binding fragment thereof having an antigen-binding region that comprises the amino acid sequence of SEQ ID NO: 121 and specifically binds to a GPRC5D polypeptide (e.g., a GPRC5D polypeptide having the amino acid sequence SEQ ID NO:97, or fragments thereof), which is designated as ET150-169 scFv (also referred to as "ET150-19 scFv").

In certain embodiments, the anti-GPRC5D scFv antibody comprises a heavy chain variable region comprising amino acids having the sequence set forth in SEQ ID NO: 85 and a light chain variable region comprising amino acids having the sequence set forth in SEQ ID NO:86, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 22. In certain embodiments, the anti-GPRC5D scFv comprises a $V_H$ comprising amino acids having the sequence set forth in SEQ ID NO:85, as shown in Table 22. In certain embodiments, the anti-GPRC5D scFv comprises a $V_L$ comprising amino acids having the sequence set forth in SEQ ID NO:86, as shown in Table 22. In certain embodiments, the anti-GPRC5D scFv comprises a $V_H$ comprising amino acids having the sequence set forth in SEQ ID NO:85 and a $V_L$ comprising amino acids having the sequence set forth in SEQ ID NO:86, as shown in Table 22. In certain embodiments, the anti-GPRC5D scFv comprises a $V_H$ CDR1 comprising amino acids having the sequence set forth in SEQ ID NO:250 or conservative modifications thereof, a $V_H$ CDR2 comprising amino acids having the sequence set forth in SEQ ID NO: 251 or conservative modifications thereof, and a $V_H$ CDR3 comprising amino acids having the sequence set forth in SEQ ID NO: 252 or conservative modifications thereof, as shown in Table 22. In certain embodiments, the anti-GPRC5D scFv comprises a $V_L$ CDR1 comprising amino acids having the sequence set forth in SEQ ID NO: 253 or conservative modifications thereof, a $V_L$ CDR2 comprising amino acids having the sequence set forth in SEQ ID NO: 254 or conservative modifications thereof, and a $V_L$ CDR3 comprising amino acids having the sequence set forth in SEQ ID NO: 255 or conservative modifications thereof, as shown in Table 22. In certain embodiments, the anti-GPRC5D scFv comprises a $V_H$ CDR1 comprising amino acids having the sequence set forth in SEQ ID NO: 250 or conservative modifications thereof, a $V_H$ CDR2 comprising amino acids having the sequence set forth in SEQ ID NO: 251 or conservative modifications thereof, a $V_H$ CDR3 comprising amino acids having the sequence set forth in SEQ ID NO: 252 or conservative modifications thereof, a $V_L$ CDR1 comprising amino acids having the sequence set forth in SEQ ID NO: 253 or conservative modifications thereof, a $V_L$ CDR2 comprising amino acids having the sequence set forth in SEQ ID NO: 254 or conservative modifications thereof, and a $V_L$ CDR3 comprising amino acids having the sequence set forth in SEQ ID NO: 255 or conservative modifications thereof, as shown in Table 22. In certain embodiments, the anti-GPRC5D scFv comprises a $V_H$ CDR1 comprising amino acids having the sequence set forth in SEQ ID NO: 250, a $V_H$ CDR2 comprising amino acids having the sequence set forth in SEQ ID NO: 251, a $V_H$ CDR3 comprising amino acids having the sequence set forth in SEQ ID NO: 252, a $V_L$ CDR1 comprising amino acids having the sequence set forth in SEQ ID NO: 253, a $V_L$ CDR2 comprising amino acids having the sequence set forth in SEQ ID NO: 254, and a $V_L$ CDR3 comprising amino acids having the sequence set forth in SEQ ID NO: 255.

TABLE 22

Antigen A GPRC5D polypeptide having the amino acid sequence of SEQ ID NO: 97

| CDRs | 1 | 2 | 3 |
|---|---|---|---|
| $V_H$ | GFTFNTYG [SEQ ID NO: 250] | ISANNGHT [SEQ ID NO: 251] | ARGGYHHQMQRYYK ATSVYSDY [SEQ ID NO: 252] |
| $V_L$ | SSNIGNNY [SEQ ID NO: 253] | DNN [SEQ ID NO: 254] | GTWDSSLSGVV [SEQ ID NO: 255] |

Full $V_H$ QVQLVQSGGEVKKPGASVKVSCKASGFTFNTYGISWVRQAPGQGLE
WMGWISANNGHTKSAQRFQDRVAMATDTSTSTAYMELRSLKFDDTA
VYYCARGGYHHQMQRYYKATSVYSDYWGQGTLVTVSS [SEQ ID
NO: 85]

DNA     Caggtccagctggtgcagtctggaggtgaggtgaagaagcctggggcctcagtgaaggtctcctgcaaggctt
ctggtttcacctttaacacctatggcatcagttgggtgcgacaggccectggacaagggcttgagtggatgggat
ggatcagcgctaacaatggtcacacaaagtctgcacagaggttccaggacagagtcgccatggcacagaca
catccacgagcacggcctacatggagctgaggagcctgaaatttgacgacacggccgtgtattactgtgcgcgc
ggtggttaccatcatcagatgcageggtactacaaagctacttctgtttactctgattactggggtcaaggtactctg
gtgaccgtctcctca [SEQ ID NO: 87]

Full $V_L$ QSVVTQPPSVSAAPGQKVTISCSGSSSNIGNNYVSWYQQLPGTAPKLLI
YDNNKRPSGIPDRFSGSKSGTSATLGITGLQTGDEADYYCGTWDSSLS
GVVFGGGTKLTVLG [SEQ ID NO: 86]

DNA     Cagtctgtcgtgacgcagccgccctcagtgtctgcgggcccaggacagaaggtcaccatctcctgctctggaa
gcagctccaacattgggaataattatgtatcctggtaccagcaactcccaggaacagcccccaaactcctcattta
tgacaataataagcgaccctcagggattcctgaccgattctctggctccaagtctggcacgtctgccaccctggg
catcaccggactccagactggggacgaggccgattattactgcggaacatgggatagcagcctgagtggtgtg
gtattcggcggagggaccaagctgaccgtcctaggt [SEQ ID NO: 88]

scFv    QSVVTQPPSVSAAPGQKVTISCSGSSSNIGNNYVSWYQQLPGTAPKLLI
YDNNKRPSGIPDRFSGSKSGTSATLGITGLQTGDEADYYCGTWDSSLS
GVVFGGGTKLTVLGSRGGGGSGGGGSGGGGSLEMAQVQLVQSGGEV

TABLE 22-continued

```
KKPGASVKVSCKASGFTFNTYGISWVRQAPGQGLEWMGWISANNGH
TKSAQRFQDRVAMATDTSTSTAYMELRSLKFDDTAVYYCARGGYHH
QMQRYYKATSVYSDYWGQGTLVTVSS [SEQ ID NO: 121]
```

In certain embodiments, the antibody or other antigen binding protein is an anti-GPRC5D scFv or an antigen-binding fragment thereof having an antigen-binding region that comprises the amino acid sequence of SEQ ID NO: 122 and specifically binds to a GPRC5D polypeptide (e.g., a GPRC5D polypeptide having the amino acid sequence SEQ ID NO:97, or fragments thereof), which is designated as ET150-172 scFv (also referred to as "ET150-22 scFv").

In certain embodiments, the anti-GPRC5D scFv antibody comprises a heavy chain variable region comprising amino acids having the sequence set forth in SEQ ID NO:89 and a light chain variable region comprising amino acids having the sequence set forth in SEQ ID NO:90, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 23. In certain embodiments, the anti-GPRC5D scFv comprises a $V_H$ comprising amino acids having the sequence set forth in SEQ ID NO:89, as shown in Table 23. In certain embodiments, the anti-GPRC5D scFv comprises a $V_L$ comprising amino acids having the sequence set forth in SEQ ID NO:90, as shown in Table 23. In certain embodiments, the anti-GPRC5D scFv comprises a $V_H$ comprising amino acids having the sequence set forth in SEQ ID NO:89 and a $V_L$ comprising amino acids having the sequence set forth in SEQ ID NO:90, as shown in Table 23. In certain embodiments, the anti-GPRC5D scFv comprises a $V_H$ CDR1 comprising amino acids having the sequence set forth in SEQ ID NO:256 or conservative modifications thereof, a $V_H$ CDR2 comprising amino acids having the sequence set forth in SEQ ID NO: 257 or conservative modifications thereof, and a $V_H$ CDR3 comprising amino acids having the sequence set forth in SEQ ID NO: 258 or conservative modifications thereof, as shown in Table 23. In certain embodiments, the anti-GPRC5D scFv comprises a $V_L$ CDR1 comprising amino acids having the sequence set forth in SEQ ID NO: 259 or conservative modifications thereof, a $V_L$ CDR2 comprising amino acids having the sequence set forth in SEQ ID NO: 260 or conservative modifications thereof, and a $V_L$ CDR3 comprising amino acids having the sequence set forth in SEQ ID NO: 261 or conservative modifications thereof, as shown in Table 23. In certain embodiments, the anti-GPRC5D scFv comprises a $V_H$ CDR1 comprising amino acids having the sequence set forth in SEQ ID NO: 256 or conservative modifications thereof, a $V_H$ CDR2 comprising amino acids having the sequence set forth in SEQ ID NO: 257 or conservative modifications thereof, a $V_H$ CDR3 comprising amino acids having the sequence set forth in SEQ ID NO: 258 or conservative modifications thereof, a $V_L$ CDR1 comprising amino acids having the sequence set forth in SEQ ID NO: 259 or conservative modifications thereof, a $V_L$ CDR2 comprising amino acids having the sequence set forth in SEQ ID NO: 260 or conservative modifications thereof, and a $V_L$ CDR3 comprising amino acids having the sequence set forth in SEQ ID NO: 261 or conservative modifications thereof, as shown in Table 23. In certain embodiments, the anti-GPRC5D scFv comprises a $V_H$ CDR1 comprising amino acids having the sequence set forth in SEQ ID NO: 256, a $V_H$ CDR2 comprising amino acids having the sequence set forth in SEQ ID NO: 257, a $V_H$ CDR3 comprising amino acids having the sequence set forth in SEQ ID NO: 258, a $V_L$ CDR1 comprising amino acids having the sequence set forth in SEQ ID NO: 259, a $V_L$ CDR2 comprising amino acids having the sequence set forth in SEQ ID NO: 260, and a $V_L$ CDR3 comprising amino acids having the sequence set forth in SEQ ID NO: 261.

TABLE 23

Antigen A GPRC5D polypeptide having the amino acid sequence of SEQ ID NO: 97

| CDRs | 1 | 2 | 3 |
|---|---|---|---|
| $V_H$ | GYTFTSYY [SEQ ID NO: 256] | INPSGGSS [SEQ ID NO: 257] | ARAGMGMDT [SEQ ID NO: 258] |
| $V_L$ | SSDVGGYNY [SEQ ID NO: 259] | EVS [SEQ ID NO: 260] | SSYAGSNTLV [SEQ ID NO: 261] |

| | |
|---|---|
| Full $V_H$ | QMQLVQSGAEVKKPGASVKVSCKASGYTFTSYYMHWVRQAPGQGL EWMGIINPSGGSSSYAQKFQGRVTMTRDTSTSTVYMELSSLRSEDTAV YYCARAGMGMDTWGQGTLVTVSS [SEQ ID NO: 89] |
| DNA | Cagatgcagctggtgcagtctggggctgaggtgaagaagcctggggcctcagtgaaggtttcctgcaaggcat ctggatacaccttcaccagctactatatgcactgggtgcgacaggcccctggacaagggcttgagtggatggga ataatcaaccctagtggtggtagctcaagctacgcacagaagttccagggcagagtcaccatgaccagggaca cgtccacgagcacagtctacatggagctgagcagcctgagatctgaggacacggccgtgtattactgtgcgcg cgctggtatgggtatggatacttggggtcaaggtactctggtgaccgtctcctca [SEQ ID NO: 91] |
| Full $V_L$ | QSALTQPPSASGSPGQSVTISCTGTSSDVGGYNYVSWYQQHPGKAPKL MIYEVSKRPSGVPDRFSGSKSGNTASLTVSGLQAEDEADYYCSSYAGS NTLVFGGGTKLTVLG [SEQ ID NO: 90] |
| DNA | Cagtctgccctgactcagcctccctccgcgtccgggtctcctggacagtcagtcaccatctcctgcactggaac cagcagtgacgttggtggttataactatgtctcctggtaccaacagcacccaggcaaagcccccaaactcatgat ttatgaggtcagtaagcggccctcaggggtccctgatcgcttctctggctccaagtctggcaacacggcctccct |

TABLE 23-continued

```
          gaccgtctctgggctccaggctgaggatgaggctgattattactgcagctcatatgcaggcagcaacaccttggt
          gttcggcggagggaccaagctgaccgtcctaggt [SEQ ID NO: 92]

scFv      QSALTQPPSASGSPGQSVTISCTGTSSDVGGYNYVSWYQQHPGKAPKL
          MIYEVSKRPSGVPDRFSGSKSGNTASLTVSGLQAEDEADYYCSSYAGS
          NTLVFGGGTKLTVLGSRGGGGSGGGGSGGGGSLEMAQMQLVQSGAE
          VKKPGASVKVSCKASGYTFTSYYMHWVRQAPGQGLEWMGIINPSGG
          SSSYAQKFQGRVTMTRDTSTSTVYMELSSLRSEDTAVYYCARAGMG
          MDTWGQGTLVTVSS [SEQ ID NO: 122]
```

In certain embodiments, the antibody or other antigen binding protein is an anti-GPRC5D scFv or an antigen-binding fragment thereof having an antigen-binding region that comprises the amino acid sequence of SEQ ID NO: 123 and specifically binds to a GPRC5D polypeptide (e.g., a GPRC5D polypeptide having the amino acid sequence SEQ ID NO:97, or fragments thereof), which is designated as ET150-173 scFv (also referred to as "ET150-23 scFv").

In certain embodiments, the anti-GPRC5D scFv antibody comprises a heavy chain variable region comprising amino acids having the sequence set forth in SEQ ID NO:93 and a light chain variable region comprising amino acids having the sequence set forth in SEQ ID NO:94, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 24. In certain embodiments, the anti-GPRC5D scFv comprises a $V_H$ comprising amino acids having the sequence set forth in SEQ ID NO:93, as shown in Table 24. In certain embodiments, the anti-GPRC5D scFv comprises a $V_L$ comprising amino acids having the sequence set forth in SEQ ID NO:94, as shown in Table 24. In certain embodiments, the anti-GPRC5D scFv comprises a $V_H$ comprising amino acids having the sequence set forth in SEQ ID NO:93 and a $V_L$ comprising amino acids having the sequence set forth in SEQ ID NO:94, as shown in Table 24. In certain embodiments, the anti-GPRC5D scFv comprises a $V_H$ CDR1 comprising amino acids having the sequence set forth in SEQ ID NO:262 or conservative modifications thereof, a $V_H$ CDR2 comprising amino acids having the sequence set forth in SEQ ID NO: 263 or conservative modifications thereof, and a $V_H$ CDR3 com-prising amino acids having the sequence set forth in SEQ ID NO: 264 or conservative modifications thereof, as shown in Table 24. In certain embodiments, the anti-GPRC5D scFv comprises a $V_L$ CDR1 comprising amino acids having the sequence set forth in SEQ ID NO: 265 or conservative modifications thereof, a $V_L$ CDR2 comprising amino acids having the sequence set forth in SEQ ID NO: 266 or conservative modifications thereof, and a $V_L$ CDR3 com-prising amino acids having the sequence set forth in SEQ ID NO: 267 or conservative modifications thereof, as shown in Table 24. In certain embodiments, the anti-GPRC5D scFv comprises a $V_H$ CDR1 comprising amino acids having the sequence set forth in SEQ ID NO: 262 or conservative modifications thereof, a $V_H$ CDR2 comprising amino acids having the sequence set forth in SEQ ID NO: 263 or conservative modifications thereof, a $V_H$ CDR3 comprising amino acids having the sequence set forth in SEQ ID NO: 264 or conservative modifications thereof, a $V_L$ CDR1 comprising amino acids having the sequence set forth in SEQ ID NO: 265 or conservative modifications thereof, a $V_L$ CDR2 comprising amino acids having the sequence set forth in SEQ ID NO: 266 or conservative modifications thereof, and a $V_L$ CDR3 comprising amino acids having the sequence set forth in SEQ ID NO: 267 or conservative modifications thereof, as shown in Table 24. In certain embodiments, the anti-GPRC5D scFv comprises a $V_H$ CDR1 comprising amino acids having the sequence set forth in SEQ ID NO: 262, a $V_H$ CDR2 comprising amino acids having the sequence set forth in SEQ ID NO: 263, a $V_H$ CDR3 comprising amino acids having the sequence set forth in SEQ ID NO: 264, a $V_L$ CDR1 comprising amino acids having the sequence set forth in SEQ ID NO: 265, a $V_L$ CDR2 comprising amino acids having the sequence set forth in SEQ ID NO: 266, and a $V_L$ CDR3 comprising amino acids having the sequence set forth in SEQ ID NO: 267.

TABLE 24

| Antigen | A GPRC5D polypeptide having the amino acid sequence of SEQ ID NO: 97 | | |
|---|---|---|---|
| CDRs | 1 | 2 | 3 |
| $V_H$ | GYTFTSYY [SEQ ID NO: 262] | INPSGGST [SEQ ID NO: 263] | ARDVISGFDS [SEQ ID NO: 264] |
| $V_L$ | SSDVGGYNY [SEQ ID NO: 265] | GVS [SEQ ID NO: 266] | SSYAGVNNLM [SEQ ID NO: 267] |
| Full $V_H$ | QVQLVQSGAEVKKPGASVKVSCKASGYTFTSYYMHWVRQAPGQGLE WMGIINPSGGSTSYAQKFQGRVTMTRDTSTSTVYMELSSLRSEDTAV YYCARDVISGFDSWGQGTLVTVSS [SEQ ID NO: 93] | | |
| DNA | Caggtgcagctggtgcaatctggggctgaggtgaagaagcctggggcctcagtgaaggtttcctgcaaggcat ctggatacaccttcaccagctactatatgcactgggtgcgacaggcccctggacaagggcttgagtggatggga ataatcaaccctagtggtggtagcacaagctacgcacagaagttccagggcagagtcaccatgaccagggaca cgtccacgagcacagtctacatggagctgagcagcctgagatctgaggacactgccgtgtattactgtgcgcgc gacgttatctctggtttcgattcttggggtcaaggtactctggtgaccgtctcctca [SEQ ID NO: 95] | | |
| Full $V_L$ | QSALTQPASVSGSPGQSITISCTGTSSDVGGYNYVSWYQQSPGKAPRL MIYGVSKRPSGVPDRFSGSKSGNTASLTVSGLQAEDEADYYCSSYAG VNNLMFGGGTKLTVLG [SEQ ID NO: 94] | | |

TABLE 24-continued

| | |
|---|---|
| DNA | Cagtctgccctgactcagcctgcctccgtgtctgggtctcctggacagtcgatcaccatctcctgcactggaacc<br>agcagtgacgttggtggttataactatgtctcctggtaccaacaatccccaggcaaagcccccagactcatgattt<br>atggggtcagtaagcggccctctggggtccctgatcgcttctctggctccaagtctggcaacacggcctccctga<br>ccgtctctgggctccaggctgaagatgaggctgattattactgcagctcatatgcaggcgtcaacaatttaatgttc<br>ggcggagggaccaagctgaccgtcctaggt [SEQ ID NO: 96] |
| scFv | QSALTQPASVSGSPGQSITISCTGTSSDVGGYNYVSWYQQSPGKAPRL<br>MIYGVSKRPSGVPDRFSGSKSGNTASLTVSGLQAEDEADYYCSSYAG<br>VNNLMFGGGTKLTVLGSRGGGGSGGGGSGGGGSLEMAQVQLVQSG<br>AEVKKPGASVKVSCKASGYTFTSYYMHWVRQAPGQGLEWMGIINPS<br>GGSTSYAQKFQGRVTMTRDTSTSTVYMELSSLRSEDTAVYYCARDVI<br>SGFDSWGQGTLVTVSS [SEQ ID NO: 123] |

In certain embodiments, the antibody or other antigen binding protein is an anti-GPRC5D scFv or an antigen-binding fragment thereof having an antigen-binding region that comprises the amino acid sequence of SEQ ID NO:276 and specifically binds to a GPRC5D polypeptide (e.g., a GPRC5D polypeptide having the amino acid sequence SEQ ID NO:97, or fragments thereof), which is designated as ET150-024 scFv (also referred to as "ET150-174 scFv").

In certain embodiments, the anti-GPRC5D scFv antibody comprises a heavy chain variable region comprising amino acids having the sequence set forth in SEQ ID NO:274 and a light chain variable region comprising amino acids having the sequence set forth in SEQ ID NO:275, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 25. In certain embodiments, the anti-GPRC5D scFv comprises a $V_H$ comprising amino acids having the sequence set forth in SEQ ID NO:274, as shown in Table 25. In certain embodiments, the anti-GPRC5D scFv comprises a $V_L$ comprising amino acids having the sequence set forth in SEQ ID NO:275, as shown in Table 25. In certain embodiments, the anti-GPRC5D scFv comprises a $V_H$ comprising amino acids having the sequence set forth in SEQ ID NO:274 and a $V_L$ comprising amino acids having the sequence set forth in SEQ ID NO:275, as shown in Table 25. In certain embodiments, the anti-GPRC5D scFv comprises a $V_H$ CDR1 comprising amino acids having the sequence set forth in SEQ ID NO:268 or conservative modifications thereof, a $V_H$ CDR2 comprising amino acids having the sequence set forth in SEQ ID NO:269 or conservative modifications thereof, and a $V_H$ CDR3 comprising amino acids having the sequence set forth in SEQ ID NO:270 or conservative modifications thereof, as shown in Table 8. In certain embodiments, the anti-GPRC5D scFv comprises a $V_L$ CDR1 comprising amino acids having the sequence set forth in SEQ ID NO:271 or conservative modifications thereof, a $V_L$ CDR2 comprising amino acids having the sequence set forth in SEQ ID NO:272 or conservative modifications thereof, and a $V_L$ CDR3 comprising amino acids having the sequence set forth in SEQ ID NO:273 or conservative modifications thereof, as shown in Table 25. In certain embodiments, the anti-GPRC5D scFv comprises a $V_H$ CDR1 comprising amino acids having the sequence set forth in SEQ ID NO:268 or conservative modifications thereof, a $V_H$ CDR2 comprising amino acids having the sequence set forth in SEQ ID NO:269 or conservative modifications thereof, a $V_H$ CDR3 comprising amino acids having the sequence set forth in SEQ ID NO:270 or conservative modifications thereof, a $V_L$ CDR1 comprising amino acids having the sequence set forth in SEQ ID NO:271 or conservative modifications thereof, a $V_L$ CDR2 comprising amino acids having the sequence set forth in SEQ ID NO:272 or conservative modifications thereof, and a $V_L$ CDR3 comprising amino acids having the sequence set forth in SEQ ID NO:273 or conservative modifications thereof, as shown in Table 25. In certain embodiments, the anti-GPRC5D scFv comprises a $V_H$ CDR1 comprising amino acids having the sequence set forth in SEQ ID NO:268, a $V_H$ CDR2 comprising amino acids having the sequence set forth in SEQ ID NO:269, a $V_H$ CDR3 comprising amino acids having the sequence set forth in SEQ ID NO:270, a $V_L$ CDR1 comprising amino acids having the sequence set forth in SEQ ID NO:271, a $V_L$ CDR2 comprising amino acids having the sequence set forth in SEQ ID NO:272, and a $V_L$ CDR3 comprising amino acids having the sequence set forth in SEQ ID NO:273.

TABLE 25

| Antigen | A GPRC5D polypeptide having the amino acid sequence of SEQ ID NO: 97 | | |
|---|---|---|---|
| CDRs | 1 | 2 | 3 |
| $V_H$ | GFTFGDYG [SEQ ID NO: 268] | INWNGGST [SEQ ID NO: 269] | ARSKQGY<br>[SEQ ID NO: 270] |
| $V_L$ | SRDAGGYNY [SEQ ID NO: 271] | EVT [SEQ ID NO: 272] | SSYGGSNNFRV<br>[SEQ ID NO: 273] |
| Full $V_H$ | EVQLVESGGGVVRPGGSLRLSCAASGFTFGDYGMSWVRQAPGKGLE<br>WVSGINWNGGSTGYADSVKGRFTISRDNAKNSLYLQMNSLRAEDTA<br>VYYCARSKQDYWGQGTLVTVSS [SEQ ID NO: 274] | | |
| DNA | GAGGTGCAGCTGGTGGAGTCTGGGGGAGGTGTGGTACGGCCTGGG<br>GGGTCCCTGAGACTCTCCTGTGCAGCCTCTGGATTCACCTTTGGTG<br>ATTATGGCATGAGCTGGGTCCGCCAAGCTCCAGGGAAGGGGCTGG<br>AGTGGGTCTCTGGTATTAATTGGAATGGTGGTAGCACAGGTTATGC<br>AGACTCTGTGAAGGGCCGATTCACCATCTCCAGAGACAACGCCAA | | |

TABLE 25-continued

```
        GAACTCCCTGTATCTGCAAATGAACAGTCTGAGAGCCGAGGACAC
        GGCCGTATATTACTGTGCGCGCTCTAAACAGGATTACTGGGGTCAA
        GGTACTCTGGTGACCGTCTCCTCA [SEQ ID NO: 277]

Full V_L  MKKTAIAIAVALAGFATVAQAAELQSALTQPPSASGSPGQSVTISCTGT
        SRDAGGYNYFSWYQQHPGKAPKLLIYEVTKRPSGVPDRFSGSKSGKT
        ASLTVSGLQADDEAVYYCSSYGGSNNFRVFGGGTKLTVLG [SEQ ID
        NO: 275]

DNA     ATGAAAAAGACAGCTATCGCGATTGCAGTGGCACTGGCTGGTTTC
        GCTACCGTGGCCCAGGCGGCCGAGCTCCAGTCTGCCCTGACTCAGC
        CTCCCTCCGCGTCCGGGTCTCCTGGACAGTCAGTCACCATCTCCTG
        CACTGGAACCAGCAGGGACGCTGGTGGTTATAATTATTTCTCCTGG
        TACCAACAACACCCAGGCAAAGCCCCCAAACTCCTGATTTATGAG
        GTCACTAAGCGGCCCTCAGGGGTCCCTGATCGCTTCTCTGGCTCCA
        AGTCTGGCAAGACGGCCTCCCTGACCGTCTCTGGGCTCCAGGCTGA
        CGATGAGGCTGTATATTACTGCAGCTCATATGGAGGCAGCAACAA
        CTTTCGGGTGTTCGGCGGAGGGACCAAGCTGACCGTCCTAGGT
        [SEQ ID NO: 278]

scFv    MKKTAIAIAVALAGFATVAQAAELQSALTQPPSASGSPGQSVTISCTGT
        SRDAGGYNYFSWYQQHPGKAPKLLIYEVTKRPSGVPDRFSGSKSGKT
        ASLTVSGLQADDEAVYYCSSYGGSNNFRVFGGGTKLTVLGSRGGGGS
        GGGGSGGGGSLEMAEVQLVESGGGVVRPGGSLRLSCAASGFTFGDY
        GMSWVRQAPGKGLEWVSGINWNGGSTGYADSVKGRFTISRDNAKNS
        LYLQMNSLRAEDTAVYYCARSKQDYWGQGTLVTVSS [SEQ ID
        NO: 276]

DNA     ATGAAAAAGACAGCTATCGCGATTGCAGTGGCACTGGCTGGTTTC
        GCTACCGTGGCCCAGGCGGCCGAGCTCCAGTCTGCCCTGACTCAGC
        CTCCCTCCGCGTCCGGGTCTCCTGGACAGTCAGTCACCATCTCCTG
        CACTGGAACCAGCAGGGACGCTGGTGGTTATAATTATTTCTCCTGG
        TACCAACAACACCCAGGCAAAGCCCCCAAACTCCTGATTTATGAG
        GTCACTAAGCGGCCCTCAGGGGTCCCTGATCGCTTCTCTGGCTCCA
        AGTCTGGCAAGACGGCCTCCCTGACCGTCTCTGGGCTCCAGGCTGA
        CGATGAGGCTGTATATTACTGCAGCTCATATGGAGGCAGCAACAA
        CTTTCGGGTGTTCGGCGGAGGGACCAAGCTGACCGTCCTAGGTTCT
        AGAGGTGGTGGTGGTAGCGGCGGCGGCGGCTCTGGTGGTGGTGGA
        TCCCTCGAGATGGCCGAGGTGCAGCTGGTGGAGTCTGGGGGAGGT
        GTGGTACGGCCTGGGGGGTCCCTGAGACTCTCCTGTGCAGCCTCTG
        GATTCACCTTTGGTGATTATGGCATGAGCTGGGTCCGCCAAGCTCC
        AGGGAAGGGGCTGGAGTGGGTCTCTGGTATTAATTGGAATGGTGG
        TAGCACAGGTTATGCAGACTCTGTGAAGGGCCGATTCACCATCTCC
        AGAGACAACGCCAAGAACTCCCTGTATCTGCAAATGAACAGTCTG
        AGAGCCGAGGACACGGCCGTATATTACTGTGCGCGCTCTAAACAG
        GATTACTGGGGTCAAGGTACTCTGGTGACCGTCTCCTCA [SEQ ID
        NO: 279]
```

In certain embodiments, the antibody or other antigen binding protein is an anti-GPRC5D scFv or an antigen-binding fragment thereof having an antigen-binding region that comprises the amino acid sequence of SEQ ID NO: 288 and specifically binds to a GPRC5D polypeptide (e.g., a GPRC5D polypeptide having the amino acid sequence SEQ ID NO:97, or fragments thereof), which is designated as ET150-026 scFv (also referred to as "ET150-176 scFv").

In certain embodiments, the anti-GPRC5D scFv antibody comprises a heavy chain variable region comprising amino acids having the sequence set forth in SEQ ID NO:286 and a light chain variable region comprising amino acids having the sequence set forth in SEQ ID NO:287, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 26. In certain embodiments, the anti-GPRC5D scFv comprises a $V_H$ comprising amino acids having the sequence set forth in SEQ ID NO:286, as shown in Table 26. In certain embodiments, the anti-GPRC5D scFv comprises a $V_L$ comprising amino acids having the sequence set forth in SEQ ID NO:287, as shown in Table 26. In certain embodiments, the anti-GPRC5D scFv comprises a $V_H$ comprising amino acids having the sequence set forth in SEQ ID NO:286 and a $V_L$ comprising amino acids having the sequence set forth in SEQ ID NO:287, as shown in Table 26. In certain embodiments, the anti-GPRC5D scFv comprises a $V_H$ CDR1 comprising amino acids having the sequence set forth in SEQ ID NO:280 or conservative modifications thereof, a $V_H$ CDR2 comprising amino acids having the sequence set forth in SEQ ID NO:281 or conservative modifications thereof, and a $V_H$ CDR3 comprising amino acids having the sequence set forth in SEQ ID NO:282 or conservative modifications thereof, as shown in Table 26. In certain embodiments, the anti-GPRC5D scFv comprises a $V_L$ CDR1 comprising amino acids having the sequence set forth in SEQ ID NO:283 or conservative modifications thereof, a $V_L$ CDR2 comprising amino acids having the sequence set forth in SEQ ID NO:284 or conservative modifications thereof, and a $V_L$ CDR3 comprising amino acids having the sequence set forth in SEQ ID NO:285 or conservative modifications thereof, as shown in Table 26. In certain embodiments, the anti-GPRC5D scFv comprises a $V_H$ CDR1 comprising amino acids having the sequence set forth in SEQ ID NO:280 or conservative modifications thereof, a $V_H$ CDR2 comprising amino acids having the sequence set forth in SEQ ID NO:281 or conservative modifications thereof, a $V_H$ CDR3 comprising amino acids having the sequence set forth in SEQ ID NO:282 or conservative modifications thereof, a $V_L$ CDR1 comprising amino acids having the sequence set forth in SEQ ID NO:283 or conservative modifications thereof, a $V_L$ CDR2 comprising amino acids having the sequence set forth in SEQ ID NO:284 or conservative modifications thereof, and a $V_L$ CDR3 comprising amino acids having the sequence set forth in SEQ ID NO:285 or conservative modifications thereof, as shown in Table 26. In certain embodiments, the anti-GPRC5D scFv comprises a $V_H$ CDR1 comprising amino acids having the sequence set forth in SEQ ID NO:280, a $V_H$ CDR2 comprising amino acids having the sequence set forth in SEQ ID NO:281, a $V_H$ CDR3 comprising amino acids having the sequence set forth in SEQ ID NO:282, a $V_L$ CDR1 comprising amino acids having the sequence set forth in SEQ ID NO:283, a $V_L$ CDR2 comprising amino acids having the sequence set forth in SEQ ID NO:284, and a $V_L$ CDR3 comprising amino acids having the sequence set forth in SEQ ID NO:285.

TABLE 26

| Antigen | A GPRC5D polypeptide having the amino acid sequence of SEQ ID NO: 97 | | |
|---|---|---|---|
| CDRs | 1 | 2 | 3 |
| $V_H$ | GFTFSNYA [SEQ ID NO: 280] | ITNSGRST [SEQ ID NO: 281] | ARVTHRRYGSTFDS [SEQ ID NO: 282] |
| $V_L$ | SSNIGSNT [SEQ ID NO: 283] | SNN [SEQ ID NO: 284] | AAWDDSVNGYV [SEQ ID NO: 285] |
| Full $V_H$ | QLQLQESGGGSVQPGGSLRLSCAASGFTFSNYAMSWVRQAPGKGLE WVSAITNSGRSTYYADSVKGRFTISRDNSKNTLSLQMSSLRAEDTAVY YCARVTHRRYGSTFDSRGQGTLVTVSS [SEQ ID NO: 286] | | |
| DNA | CAGCTGCAGCTGCAGGAGTCGGGGGGAGGCTCGGTACAGCCGGGG GGGTCTCTGAGACTGTCCTGTGCAGCCTCTGGATTCACCTTTAGCA ACTATGCCATGAGCTGGGTCCGCCAGGCTCCAGGGAAGGGGCTGG AGTGGGTCTCAGCTATCACTAATAGTGGTCGTAGTACATACTACGC AGACTCCGTGAAGGGCCGGTTCACCATCTCCAGAGACAATTCCAA GAACACGCTGTCTTTGCAAATGAGCAGCCTGAGAGCCGAAGACAC GGCCGTGTATTACTGTGCGCGCGTTACTCATCGTCGTTACGGTTCT ACTTTCGATTCTCGGGGTCAAGGTACTCTGGTGACCGTCTCCTCA ACTAGTGGCCAGGCCGGCCAGC [SEQ ID NO: 289] | | |
| Full $V_L$ | MKKTAIAIAVALAGFATVAQAAELSYELTQPPSASGTPGQRVSISCSGS SSNIGSNTVNWYQQFPGTAPKLLIHSNNQRPSGVPDRFSGSKSGTSASL AISGPQSEDEADYYCAAWDDSVNGYVFGTGTKVTVLG [SEQ ID NO: 287] | | |
| DNA | ATGAAAAAGACAGCTATCGCGATTGCAGTGGCACTGGCTGGTTTC GCTACCGTGGCCCAGGCGGCCGAGCTCTCCTATGAGCTGACTCAGC CACCCTCAGCGTCTGGGACCCCCGGGCAGAGGGTCAGCATCTCTTG TTCTGGAAGCAGCTCCAACATCGGGAGTAATACTGTAAACTGGTAC CAACAGTTCCCCGGAACGGCCCCCAAACTCCTCATCCATAGTAATA ATCAGCGGCCCTCAGGGGTCCCTGACCGATTCTCTGGCTCCAAGTC TGGCACCTCAGCCTCCCTGGCCATCAGTGGGCCCCAGTCTGAGGAT GAGGCTGATTATTACTGTGCAGCTTGGGATGACAGTGTGAATGGTT ATGTCTTCGGAACTGGGACCAAGGTCACCGTCCTAGGT [SEQ ID NO: 290] | | |
| scFv | MKKTAIAIAVALAGFATVAQAAELSYELTQPPSASGTPGQRVSISCSGS SSNIGSNTVNWYQQFPGTAPKLLIHSNNQRPSGVPDRFSGSKSGTSASL AISGPQSEDEADYYCAAWDDSVNGYVFGTGTKVTVLGSRGGGGSGG GGSGGGGSLEMAQLQLQESGGGSVQPGGSLRLSCAASGFTFSNYAMS WVRQAPGKGLEWVSAITNSGRSTYYADSVKGRFTISRDNSKNTLSLQ MSSLRAEDTAVYYCARVTHRRYGSTFDSRGQGTLVTVSS [SEQ ID NO: 288] | | |
| DNA | ATGAAAAAGACAGCTATCGCGATTGCAGTGGCACTGGCTGGTTTC GCTACCGTGGCCCAGGCGGCCGAGCTCTCCTATGAGCTGACTCAGC CACCCTCAGCGTCTGGGACCCCCGGGCAGAGGGTCAGCATCTCTTG TTCTGGAAGCAGCTCCAACATCGGGAGTAATACTGTAAACTGGTAC CAACAGTTCCCCGGAACGGCCCCCAAACTCCTCATCCATAGTAATA ATCAGCGGCCCTCAGGGGTCCCTGACCGATTCTCTGGCTCCAAGTC TGGCACCTCAGCCTCCCTGGCCATCAGTGGGCCCCAGTCTGAGGAT GAGGCTGATTATTACTGTGCAGCTTGGGATGACAGTGTGAATGGTT ATGTCTTCGGAACTGGGACCAAGGTCACCGTCCTAGGTTCTAGAGG TGGTGGTGGTAGCGGCGGCGGCGGCTCGGTGGTGGTGGATCCCTC GAGATGGCCCAGCTGCAGCTGCAGGAGTCGGGGGGAGGCTCGGTA CAGCCGGGGGGGTCTCTGAGACTGTCCTGTGCAGCCTCTGGATTCA CCTTTAGCAACTATGCCATGAGCTGGGTCCGCCAGGCTCCAGGGAA GGGGCTGGAGTGGGTCTCAGCTATCACTAATAGTGGTCGTAGTACA TACTACGCAGACTCCGTGAAGGGCCGGTTCACCATCTCCAGAGAC AATTCCAAGAACACGCTGTCTTTGCAAATGAGCAGCCTGAGAGCC GAAGACACGGCCGTGTATTACTGTGCGCGCGTTACTCATCGTCGTT ACGGTTCTACTTTCGATTCTCGGGGTCAAGGTACTCTGGTGACCGT CTCCTCA [SEQ ID NO: 291] | | |

In certain embodiments, the antibody or other antigen binding protein is an anti-GPRC5D scFv or an antigen-binding fragment thereof having an antigen-binding region that comprises the amino acid sequence of SEQ ID NO: 300 and specifically binds to a GPRC5D polypeptide (e.g., a GPRC5D polypeptide having the amino acid sequence SEQ ID NO:97, or fragments thereof), which is designated as ET150-028 scFv (also referred to as "ET150-178 scFv").

In certain embodiments, the anti-GPRC5D scFv antibody comprises a heavy chain variable region comprising amino acids having the sequence set forth in SEQ ID NO:298 and a light chain variable region comprising amino acids having the sequence set forth in SEQ ID NO:299, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 27. In certain embodiments, the anti-GPRC5D scFv comprises a $V_H$ comprising amino acids having the sequence set forth in SEQ ID NO:298, as shown in Table 27. In certain embodiments, the anti-GPRC5D scFv comprises a $V_L$ comprising amino acids having the sequence set forth in SEQ ID NO:299, as shown in Table 27. In certain embodiments, the anti-GPRC5D scFv comprises a $V_H$ comprising amino acids having the sequence set forth in SEQ ID NO:298 and a $V_L$ comprising amino acids having the sequence set forth in SEQ ID NO:299, as shown in Table 27. In certain embodiments, the anti-GPRC5D scFv comprises a $V_H$ CDR1 comprising amino acids having the sequence set forth in SEQ ID NO:292 or conservative modifications thereof, a $V_H$ CDR2 comprising amino acids having the sequence set forth in SEQ ID NO:293 or conservative modifications thereof, and a $V_H$ CDR3 comprising amino acids having the sequence set forth in SEQ ID NO:294 or conservative modifications thereof, as shown in Table 27. In certain embodiments, the anti-GPRC5D scFv comprises a $V_L$ CDR1 comprising amino acids having the sequence set forth in SEQ ID NO:295 or conservative modifications thereof, a $V_L$ CDR2 comprising amino acids having the sequence set forth in SEQ ID NO:296 or conservative modifications thereof, and a $V_L$ CDR3 comprising amino acids having the sequence set forth in SEQ ID NO:297 or conservative modifications thereof, as shown in Table 27. In certain embodiments, the anti-GPRC5D scFv comprises a $V_H$ CDR1 comprising amino acids having the sequence set forth in SEQ ID NO:292 or conservative modifications thereof, a $V_H$ CDR2 comprising amino acids having the sequence set forth in SEQ ID NO:293 or conservative modifications thereof, a $V_H$ CDR3 comprising amino acids having the sequence set forth in SEQ ID NO:294 or conservative modifications thereof, a $V_L$ CDR1 comprising amino acids having the sequence set forth in SEQ ID NO:295 or conservative modifications thereof, a $V_L$ CDR2 comprising amino acids having the sequence set forth in SEQ ID NO:296 or conservative modifications thereof, and a $V_L$ CDR3 comprising amino acids having the sequence set forth in SEQ ID NO:297 or conservative modifications thereof, as shown in Table 27. In certain embodiments, the anti-GPRC5D scFv comprises a $V_H$ CDR1 comprising amino acids having the sequence set forth in SEQ ID NO:292, a $V_H$ CDR2 comprising amino acids having the sequence set forth in SEQ ID NO:293, a $V_H$ CDR3 comprising amino acids having the sequence set forth in SEQ ID NO:294, a $V_L$ CDR1 comprising amino acids having the sequence set forth in SEQ ID NO:295, a $V_L$ CDR2 comprising amino acids having the sequence set forth in SEQ ID NO:296, and a VY CDR3 comprising amino acids having the sequence set forth in SEQ ID NO:297.

TABLE 27

| Antigen | A GPRC5D polypeptide having the amino acid sequence of SEQ ID NO: 97 | | |
|---|---|---|---|
| CDRs | 1 | 2 | 3 |
| $V_H$ | GGTFRSYA [SEQ ID NO: 292] | IIPMLDIT [SEQ ID NO: 293] | ARTYSRSPFHMEDF [SEQ ID NO: 294] |
| $V_L$ | SSNIGGNT [SEQ ID NO: 295] | RNN [SEQ ID NO: 296] | AAWDASRQGV [SEQ ID NO: 297] |

Full $V_H$ QVQLVQSGAEVKKPGSSVKVSCKASGGTFRSYAITWVRQAPGQGLE
WMGRIIPMLDITNYAQKFQGRVTITADKSTSTAYMELSSLRSEDTAVY
YCARTYSRSPFHMEDFWGQGTLVTVSS [SEQ ID NO: 298]

DNA CAGGTGCAGCTGGTGCAGTCTGGGGGCTGAGGTGAAGAAGCCTGGG
TCCTCGGTGAAGGTCTCCTGCAAGGCTTCTGGAGGCACCTTCCGCA
GCTATGCTATCACCTGGGTGCGACAGGCCCCTGGACAAGGGCTTG
AGTGGATGGGAAGGATCATCCCTATGCTTGATATAACAAACTACG
CACAGAAGTTCCAGGGCAGAGTCACGATTACCGCGGACAAATCCA
CGAGCACAGCCTACATGGAGCTGAGCAGCCTGAGATCTGAGGACA
CGGCCGTGTATTACTGTGCGCGCACTTACTCTCGTTCTCCGTTCCAT
ATGGAAGATTTCTGGGGTCAAGGTACTCTGGTGACCGTCTCCTCA
[SEQ ID NO: 381]

Full $V_L$ MKKTAIAIAVALAGFATVAQAAELQPVLTQPPSASGTPGQRVTISCSG
SSSNIGGNTVSWYQQVPGTAPRLLIFRNNQRPPGVPDRFSGSKSGTSAS
LAISGLRSEDEADYYCAAWDASRQGVFGGGTKLTVLG [SEQ ID
NO: 299]

DNA ATGAAAAAGACAGCTATCGCGATTGCAGTGGCACTGGCTGGTTTC
GCTACCGTGGCCCAGGCGGCCGAGCTCCAGCCTGTGCTGACTCAG
CCACCCTCAGCGTCTGGGACCCCCGGGCAGAGGGTCACCATCTCTT
GTTCTGGAAGCAGCTCCAATATCGGAGGTAACACTGTCAGCTGGTA
CCAGCAGGTCCCAGGAACGGCCCCCAGACTCCTCATTTTTAGGAAT
AATCAACGGCCCCCAGGGGTCCCTGACCGATTCTCTGGCTCCAAGT

TABLE 27-continued

```
        CTGGCACCTCAGCCTCCCTGGCCATCAGTGGGCTCCGGTCTGAGGA
        TGAGGCTGATTATTACTGTGCAGCATGGGACGCCAGTCGACAAGG
        GGTGTTCGGCGGAGGGACCAAGCTGACCGTCCTAGGT [SEQ ID
        NO: 301]

scFv    MKKTAIAIAVALAGFATVAQAAELQPVLTQPPSASGTPGQRVTISCSG
        SSSNIGGNTVSWYQQVPGTAPRLLIFRNNQRPPGVPDRFSGSKSGTSAS
        LAISGLRSEDEADYYCAAWDASRQGVFGGGTKLTVLGSRGGGGSGG
        GGSGGGGSLEMAQVQLVQSGAEVKKPGSSVKVSCKASGGTFRSYAIT
        WVRQAPGQGLEWMGRIIPMLDITNYAQKFQGRVTITADKSTSTAYME
        LSSLRSEDTAVYYCARTYSRSPFHMEDFWGQGTLVTVSS [SEQ ID
        NO: 300]

DNA     ATGAAAAAGACAGCTATCGCGATTGCAGTGGCACTGGCTGGTTTC
        GCTACCGTGGCCCAGGCGGCCGAGCTCCAGCCTGTGCTGACTCAG
        CCACCCTCAGCGTCTGGGACCCCCGGGCAGAGGGTCACCATCTCTT
        GTTCTGGAAGCAGCTCCAATATCGGAGGTAACACTGTCAGCTGGTA
        CCAGCAGGTCCCCAGGAACGGCCCCCAGACTCCTCATTTTTAGGAAT
        AATCAACGGCCCCCAGGGGTCCCTGACCGATTCTCTGGCTCCAAGT
        CTGGCACCTCAGCCTCCCTGGCCATCAGTGGGCTCCGGTCTGAGGA
        TGAGGCTGATTATTACTGTGCAGCATGGGACGCCAGTCGACAAGG
        GGTGTTCGGCGGAGGGACCAAGCTGACCGTCCTAGGTTCTAGAGG
        TGGTGGTGGTAGCGGCGGCGGCGGCTCTGGTGGTGGTGGATCCCTC
        GAGATGGCCCAGGTGCAGCTGGTGCAGTCTGGGGCTGAGGTGAAG
        AAGCCTGGGTCCTCGGTGAAGGTCTCCTGCAAGGCTTCTGGAGGCA
        CCTTCCGCAGCTATGCTATCACCTGGGTGCGACAGGCCCCTGGACA
        AGGGCTTGAGTGGATGGGAAGGATCATCCCTATGCTTGATATAAC
        AAACTACGCACAGAAGTTCCAGGGCAGAGTCACGATTACCGCGGA
        CAAATCCACGAGCACAGCCTACATGGAGCTGAGCAGCCTGAGATC
        TGAGGACACGGCCGTGTATTACTGTGCGCGCACTTACTCTCGTTCT
        CCGTTCCATATGGAAGATTTCTGGGGTCAAGGTACTCTGGTGACCG
        TCTCCTCA [SEQ ID NO: 302]
```

In certain embodiments, the antibody or other antigen binding protein is an anti-GPRC5D scFv or an antigen-binding fragment thereof having an antigen-binding region that comprises the amino acid sequence of SEQ ID NO:312 and specifically binds to a GPRC5D polypeptide (e.g., a GPRC5D polypeptide having the amino acid sequence SEQ ID NO:97, or fragments thereof), which is designated as ET150-029 scFv (also referred to as "ET150-179 scFv").

In certain embodiments, the anti-GPRC5D scFv antibody comprises a heavy chain variable region comprising amino acids having the sequence set forth in SEQ ID NO:310 and a light chain variable region comprising amino acids having the sequence set forth in SEQ ID NO:311, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 28. In certain embodiments, the anti-GPRC5D scFv comprises a $V_H$ comprising amino acids having the sequence set forth in SEQ ID NO:310, as shown in Table 28. In certain embodiments, the anti-GPRC5D scFv comprises a $V_L$ comprising amino acids having the sequence set forth in SEQ ID NO:311, as shown in Table 28. In certain embodiments, the anti-GPRC5D scFv comprises a $V_H$ comprising amino acids having the sequence set forth in SEQ ID NO:310 and a $V_L$ comprising amino acids having the sequence set forth in SEQ ID NO:311, as shown in Table 28. In certain embodiments, the anti-GPRC5D scFv comprises a $V_H$ CDR1 comprising amino acids having the sequence set forth in SEQ ID NO:303 or conservative modifications thereof, a $V_H$ CDR2 comprising amino acids having the sequence set forth in SEQ ID NO:304 or conservative modifications thereof, and a $V_H$ CDR3 comprising amino acids having the sequence set forth in SEQ ID NO:305 or conservative modifications thereof, as shown in Table 28. In certain embodiments, the anti-GPRC5D scFv comprises a $V_L$ CDR1 comprising amino acids having the sequence set forth in SEQ ID NO:306 or conservative modifications thereof, a $V_L$ CDR2 comprising amino acids having the sequence set forth in SEQ ID NO:307 or conservative modifications thereof, and a $V_L$ CDR3 comprising amino acids having the sequence set forth in SEQ ID NO:308 or conservative modifications thereof, as shown in Table 28. In certain embodiments, the anti-GPRC5D scFv comprises a $V_H$ CDR1 comprising amino acids having the sequence set forth in SEQ ID NO:303 or conservative modifications thereof, a $V_H$ CDR2 comprising amino acids having the sequence set forth in SEQ ID NO:304 or conservative modifications thereof, a $V_H$ CDR3 comprising amino acids having the sequence set forth in SEQ ID NO:305 or conservative modifications thereof, a $V_L$ CDR1 comprising amino acids having the sequence set forth in SEQ ID NO:306 or conservative modifications thereof, a $V_L$ CDR2 comprising amino acids having the sequence set forth in SEQ ID NO:307 or conservative modifications thereof, and a $V_L$ CDR3 comprising amino acids having the sequence set forth in SEQ ID NO:308 or conservative modifications thereof, as shown in Table 28. In certain embodiments, the anti-GPRC5D scFv comprises a $V_H$ CDR1 comprising amino acids having the sequence set forth in SEQ ID NO:303, a $V_H$ CDR2 comprising amino acids having the sequence set forth in SEQ ID NO:304, a $V_H$ CDR3 comprising amino acids having the sequence set forth in SEQ ID NO:305, a $V_L$ CDR1 comprising amino acids having the sequence set forth in SEQ ID NO:306, a $V_L$ CDR2 comprising amino acids having the sequence set forth in SEQ ID NO:307, and a $V_L$ CDR3 comprising amino acids having the sequence set forth in SEQ ID NO:308.

TABLE 28

| Antigen | A GPRC5D polypeptide having the amino acid sequence of SEQ ID NO: 97 | | |
|---|---|---|---|
| CDRs | 1 | 2 | 3 |
| $V_H$ | GFTFSSYA[SEQ ID NO: 303] | ISGSGGST [SEQ ID NO: 304] | ARKYQDV [SEQ ID NO: 305] |
| $V_L$ | SSNIGSNT[SEQ ID NO: 306] | RNN [SEQ ID NO: 307] | AAWDDSLSGRV [SEQ ID NO: 308] |

Full $V_H$  EVQLVESGGGLVQPGGSLRLSCAASGFTFSSYAMSWVRQAPGKGLE
WVSAISGSGGSTYYADSVKGRFTISRDNAKNTLYLQMNSLRAEDTAV
YYCARKYQDVWGQGTLVTVSS [SEQ ID NO: 310]

DNA  GAGGTGCAGCTGGTGGAGTCTGGGGGAGGCTTGGTACAGCCTGGG
GGGTCCCTGAGACTCTCCTGTGCAGCCTCTGGATTCACCTTTAGCA
GCTATGCCATGAGCTGGGTCCGCCAGGCTCCAGGGAAGGGGCTGG
AGTGGGTCTCAGCTATTAGTGGTAGTGGTGGTAGCACATACTACGC
AGACTCCGTGAAGGGCCGGTTCACCATCTCCAGAGACAATGCCAA
GAACACGCTGTATCTGCAAATGAACAGCCTGAGAGCCGAGGACAC
GGCCGTATATTACTGTGCGCGCAAATACCAGGATGTTTGGGGTCAA
GGTACTCTGGTGACCGTCTCCTCA [SEQ ID NO: 313]

Full $V_L$  MKKTAIAIAVALAGFATVAQAAELQSVLTQPPSASGTPGQRVTISCSG
SSSNIGSNTVNWYQQLPGTAPKWYRNNQRPSGVPDRFSGSKSGTSAS
LAISGLRSEDEADYYCAAWDDSLSGRVFGGGTKLTVLG [SEQ ID
NO: 311]

DNA  ATGAAAAAGACAGCTATCGCGATTGCAGTGGCACTGGCTGGTTTC
GCTACCGTGGCCCAGGCGGCCGAGCTCCAGTCTGTGCTGACGCAG
CCGCCCTCAGCGTCTGGGACCCCCGGGCAGAGGGTCACCATCTCTT
GTTCTGGAAGCAGCTCCAACATCGGAAGTAATACTGTAAACTGGT
ACCAGCAGCTCCCAGGAACGGCCCCCAAACTCCTCATCTATAGGA
ATAATCAGCGGCCCTCAGGGGTCCCTGACCGATTCTCTGGCTCCAA
GTCTGGCACCTCAGCCTCCCTGGCCATCAGTGGGCTCCGGTCCGAG
GATGAGGCTGATTATTACTGTGCAGCATGGGATGACAGCCTGAGT
GGTAGGGTGTTCGGCGGAGGGACCAAGCTGACCGTCCTAGGT [SEQ
ID NO: 314]

scFv  MKKTAIAIAVALAGFATVAQAAELQSVLTQPPSASGTPGQRVTISCSG
SSSNIGSNTVNWYQQLPGTAPKWYRNNQRPSGVPDRFSGSKSGTSAS
LAISGLRSEDEADYYCAAWDDSLSGRVFGGGTKLTVLGSRGGGGSG
GGSGGGGSLEMAEVQLVESGGGLVQPGGSLRLSCAASGFTFSSYAMS
WVRQAPGKGLEWVSAISGSGGSTYYADSVKGRFTISRDNAKNTLYLQ
MNSLRAEDTAVYYCARKYQDVWGQGTLVTVSS [SEQ ID NO: 312]

DNA  ATGAAAAAGACAGCTATCGCGATTGCAGTGGCACTGGCTGGTTTC
GCTACCGTGGCCCAGGCGGCCGAGCTCCAGTCTGTGCTGACGCAG
CCGCCCTCAGCGTCTGGGACCCCCGGGCAGAGGGTCACCATCTCTT
GTTCTGGAAGCAGCTCCAACATCGGAAGTAATACTGTAAACTGGT
ACCAGCAGCTCCCAGGAACGGCCCCCAAACTCCTCATCTATAGGA
ATAATCAGCGGCCCTCAGGGGTCCCTGACCGATTCTCTGGCTCCAA
GTCTGGCACCTCAGCCTCCCTGGCCATCAGTGGGCTCCGGTCCGAG
GATGAGGCTGATTATTACTGTGCAGCATGGGATGACAGCCTGAGT
GGTAGGGTGTTCGGCGGAGGGACCAAGCTGACCGTCCTAGGTTCT
AGAGGTGGTGGTGGTAGCGGCGGCGGCGGCTCTGGTGGTGGTGGA
TCCCTCGAGATGGCCGAGGTGCAGCTGGTGGAGTCTGGGGGAGGC
TTGGTACAGCCTGGGGGGTCCCTGAGACTCTCCTGTGCAGCCTCTG
GATTCACCTTTAGCAGCTATGCCATGAGCTGGGTCCGCCAGGCTCC
AGGGAAGGGGCTGGAGTGGGTCTCAGCTATTAGTGGTAGTGGTGG
TAGCACATACTACGCAGACTCCGTGAAGGGCCGGTTCACCATCTCC
AGAGACAATGCCAAGAACACGCTGTATCTGCAAATGAACAGCCTG
AGAGCCGAGGACACGGCCGTATATTACTGTGCGCGCAAATACCAG
GATGTTTGGGGTCAAGGTACTCTGGTGACCGTCTCCTCA [SEQ ID
NO: 315]

In certain embodiments, the antibody or other antigen binding protein is an anti-GPRC5D scFv or an antigen-binding fragment thereof having an antigen-binding region that comprises the amino acid sequence of SEQ ID NO:324 and specifically binds to a GPRC5D polypeptide (e.g., a GPRC5D polypeptide having the amino acid sequence SEQ ID NO:97, or fragments thereof), which is designated as ET150-030 scFv (also referred to as "ET150-180 scFv").

In certain embodiments, the anti-GPRC5D scFv antibody comprises a heavy chain variable region comprising amino acids having the sequence set forth in SEQ ID NO:322 and a light chain variable region comprising amino acids having the sequence set forth in SEQ ID NO:323, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 29. In certain embodiments, the anti-GPRC5D scFv comprises a $V_H$ comprising amino acids having the sequence set forth in SEQ ID NO:322, as shown in Table 29. In certain embodiments, the anti-GPRC5D scFv comprises a V$_L$ comprising amino acids having the sequence set forth in SEQ ID NO:323, as shown in Table 29. In certain embodiments, the anti-GPRC5D scFv comprises a V$_H$ comprising amino acids having the sequence set forth in SEQ ID NO:322 and a V$_L$ comprising amino acids having the sequence set forth in SEQ ID NO:323, as shown in Table 29. In certain embodiments, the anti-GPRC5D scFv comprises a V$_H$ CDR1 comprising amino acids having the sequence set forth in SEQ ID NO:316 or conservative modifications thereof, a V$_H$ CDR2 comprising amino acids having the sequence set forth in SEQ ID NO:317 or conservative modifications thereof, and a V$_H$ CDR3 comprising amino acids having the sequence set forth in SEQ ID NO:318 or conservative modifications thereof, as shown in Table 29. In certain embodiments, the anti-GPRC5D scFv comprises a V$_L$ CDR1 comprising amino acids having the sequence set forth in SEQ ID NO:319 or conservative modifications thereof, a V$_L$ CDR2 comprising amino acids having the sequence set forth in SEQ ID NO:320 or conservative modifications thereof, and a V$_L$ CDR3 comprising amino acids having the sequence set forth in SEQ ID NO:321 or conservative modifications thereof, as shown in Table 29. In certain embodiments, the anti- GPRC5D scFv comprises a V$_H$ CDR1 comprising amino acids having the sequence set forth in SEQ ID NO:316 or conservative modifications thereof, a V$_H$ CDR2 comprising amino acids having the sequence set forth in SEQ ID NO:317 or conservative modifications thereof, a V$_H$ CDR3 comprising amino acids having the sequence set forth in SEQ ID NO:318 or conservative modifications thereof, a V$_L$ CDR1 comprising amino acids having the sequence set forth in SEQ ID NO:319 or conservative modifications thereof, a V$_L$ CDR2 comprising amino acids having the sequence set forth in SEQ ID NO:320 or conservative modifications thereof, and a V$_L$ CDR3 comprising amino acids having the sequence set forth in SEQ ID NO:321 or conservative modifications thereof, as shown in Table 29. In certain embodiments, the anti-GPRC5D scFv comprises a V$_H$ CDR1 comprising amino acids having the sequence set forth in SEQ ID NO:316, a V$_H$ CDR2 comprising amino acids having the sequence set forth in SEQ ID NO:317, a V$_H$ CDR3 comprising amino acids having the sequence set forth in SEQ ID NO:318, a V$_L$ CDR1 comprising amino acids having the sequence set forth in SEQ ID NO:319, a V$_L$ CDR2 comprising amino acids having the sequence set forth in SEQ ID NO:320, and a V$_L$ CDR3 comprising amino acids having the sequence set forth in SEQ ID NO:321.

TABLE 29

| Antigen | A GPRC5D polypeptide having the amino acid sequence of SEQ ID NO: 97 | | |
|---|---|---|---|
| CDRs | 1 | 2 | 3 |
| V$_H$ | GFSFSGTA [SEQ ID NO: 316] | ISSTGRST [SEQ ID NO: 317] | ARPVSSMTLSIQSD G [SEQ ID NO: 318] |
| V$_L$ | SSNIGAGYD [SEQ ID NO: 319] | GNS [SEQ ID NO: 320] | QSYDSSLRGYV [SEQ ID NO: 321] |
| Full V$_H$ | QVQLVQSGGGVVQPGRSLRLSCAASGFSFSGTAMHWVRQAPGKGLE WVSTISSTGRSTYYRDSVKGRFTISRDNSKNTLYLQMNSLRGEDTAVY YCARPVSSMTLSIQSDGWGQGTLVTVSS [SEQ ID NO: 322] | | |
| DNA | CAGGTGCAGCTGGTGCAGTCTGGGGGAGGCGTGGTCCAGCCTGGG AGGTCCCTGAGACTCTCCTGTGCAGCCTCTGGATTCAGCTTTAGTG GCACTGCCATGCACTGGGTCCGCCAGGCTCCAGGGAAGGGGCTGG AATGGGTCTCGACTATTAGTAGTACTGGGCGTAGCACATACTACAG AGACTCCGTGAAGGGCCGGTTCACCATCTCCAGAGACAATTCCAA GAACACGCTGTATCTGCAAATGAACAGCCTGAGAGGCGAGGACAC GGCCGTATATTACTGTGCGCGCCCGGTTTCTTCTATGACTCTGTCTA TCCAGTCTGATGGTTGGGGTCAAGGTACTCTGGTGACCGTCTCCTC A [SEQ ID NO: 325] | | |
| Full V$_L$ | MKKTAIAIAVALAGFATVAQAAELQSVLTQPPSVSGAPGQRVTISCTG SSSNIGAGYDVHWYQQLPGRAPKLLIYGNSNRPSGVPDRFSGSKSGTS ASLAITGLQAEDEADYYCQSYDSSLRGYVFGTGTKVTVLG [SEQ ID NO: 323] | | |
| DNA | ATGAAAAAGACAGCTATCGCGATTGCAGTGGCACTGGCTGGTTTC GCTACCGTGGCCCAGGCGGCCGAGCTCCAGTCTGTGTTGACGCAG CCGCCCTCAGTGTCTGGGGCCCCAGGGCAGAGGGTCACCATCTCCT GCACTGGGAGCAGCTCCAACATCGGGGCAGGTTATGATGTACACT GGTACCAGCAGCTTCCAGGAAGAGCCCCCAAACTCCTCATCTATG GTAACAGCAATCGGCCCTCAGGGGTCCCTGACCGATTCTCTGGCTC CAAGTCTGGCACCTCAGCCTCCCTGGCCATCACTGGGCTCCAGGCT GAGGATGAGGCTGATTATTACTGCCAGTCCTATGACAGCAGCCTGA GAGGTTATGTCTTCGGAACTGGGACCAAGGTCACCGTCCTAGGT [SEQ ID NO: 326] | | |
| scFv | MKKTAIAIAVALAGFATVAQAAELQSVLTQPPSVSGAPGQRVTISCTG SSSNIGAGYDVHWYQQLPGRAPKLLIYGNSNRPSGVPDRFSGSKSGTS ASLAITGLQAEDEADYYCQSYDSSLRGYVFGTGTKVTVLGSRGGGGS GGGGSGGGGSLEMAQVQLVQSGGGVVQPGRSLRLSCAASGFSFSGTA MHWVRQAPGKGLEWVSTISSTGRSTYYRDSVKGRFTISRDNSKNTLY LQMNSLRGEDTAVYYCARPVSSMTLSIQSDGWGQGTLVTVSS [SEQ ID NO: 324] | | |

TABLE 29-continued

```
DNA    ATGAAAAAGACAGCTATCGCGATTGCAGTGGCACTGGCTGGTTTC
       GCTACCGTGGCCCAGGCGGCCGAGCTCCAGTCTGTGTTGACGCAG
       CCGCCCTCAGTGTCTGGGGCCCCAGGGCAGAGGGTCACCATCTCCT
       GCACTGGGAGCAGCTCCAACATCGGGGCAGGTTATGATGTACACT
       GGTACCAGCAGCTTCCAGGAAGAGCCCCCAAACTCCTCATCTATG
       GTAACAGCAATCGGCCCTCAGGGGTCCCTGACCGATTCTCTGGCTC
       CAAGTCTGGCACCTCAGCCTCCCTGGCCATCACTGGGCTCCAGGCT
       GAGGATGAGGCTGATTATTACTGCCAGTCCTATGACAGCAGCCTGA
       GAGGTTATGTCTTCGGAACTGGGACCAAGGTCACCGTCCTAGGTTC
       TAGAGGTGGTGGTGGTAGCGGCGGCGGCGGCTCTGGTGGTGGTGG
       ATCCCTCGAGATGGCCCAGGTGCAGCTGGTGCAGTCTGGGGGAGG
       CGTGGTCCAGCCTGGGAGGTCCCTGAGACTCTCCTGTGCAGCCTCT
       GGATTCAGCTTTAGTGGCACTGCCATGCACTGGGTCCGCCAGGCTC
       CAGGGAAGGGGCTGGAATGGGTCTCGACTATTAGTAGTACTGGGC
       GTAGCACATACTACAGAGACTCCGTGAAGGGCCGGTTCACCATCTC
       CAGAGACAATTCCAAGAACACGCTGTATCTGCAAATGAACAGCCT
       GAGAGGCGAGGACACGGCCGTATATTACTGTGCGCGCCCGGTTTCT
       TCTATGACTCTGTCTATCCAGTCTGATGGTTGGGGTCAAGGTACTC
       TGGTGACCGTCTCCTCA [SEQ ID NO: 327]
```

In certain embodiments, the antibody or other antigen binding protein is an anti-GPRC5D scFv or an antigen-binding fragment thereof having an antigen-binding region that comprises the amino acid sequence of SEQ ID NO:336 and specifically binds to a GPRC5D polypeptide (e.g., a GPRC5D polypeptide having the amino acid sequence SEQ ID NO:97, or fragments thereof), which is designated as ET150-031 scFv (also referred to as "ET150-181 scFv").

In certain embodiments, the anti-GPRC5D scFv antibody comprises a heavy chain variable region comprising amino acids having the sequence set forth in SEQ ID NO:334 and a light chain variable region comprising amino acids having the sequence set forth in SEQ ID NO:335, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 30. In certain embodiments, the anti-GPRC5D scFv comprises a $V_H$ comprising amino acids having the sequence set forth in SEQ ID NO:334, as shown in Table 30. In certain embodiments, the anti-GPRC5D scFv comprises a $V_L$ comprising amino acids having the sequence set forth in SEQ ID NO:335, as shown in Table 30. In certain embodiments, the anti-GPRC5D scFv comprises a $V_H$ comprising amino acids having the sequence set forth in SEQ ID NO:334 and a $V_L$ comprising amino acids having the sequence set forth in SEQ ID NO:335, as shown in Table 30. In certain embodiments, the anti-GPRC5D scFv comprises a $V_H$ CDR1 comprising amino acids having the sequence set forth in SEQ ID NO:328 or conservative modifications thereof, a $V_H$ CDR2 comprising amino acids having the sequence set forth in SEQ ID NO:329 or conservative modifications thereof, and a $V_H$ CDR3 comprising amino acids having the sequence set forth in SEQ ID NO:330 or conservative modifications thereof, as shown in Table 30. In certain embodiments, the anti-GPRC5D scFv comprises a $V_L$ CDR1 comprising amino acids having the sequence set forth in SEQ ID NO:331 or conservative modifications thereof, a $V_L$ CDR2 comprising amino acids having the sequence set forth in SEQ ID NO:332 or conservative modifications thereof, and a $V_L$ CDR3 comprising amino acids having the sequence set forth in SEQ ID NO:333 or conservative modifications thereof, as shown in Table 30. In certain embodiments, the anti-GPRC5D scFv comprises a $V_H$ CDR1 comprising amino acids having the sequence set forth in SEQ ID NO:328 or conservative modifications thereof, a $V_H$ CDR2 comprising amino acids having the sequence set forth in SEQ ID NO:329 or conservative modifications thereof, a $V_H$ CDR3 comprising amino acids having the sequence set forth in SEQ ID NO:330 or conservative modifications thereof, a $V_L$ CDR1 comprising amino acids having the sequence set forth in SEQ ID NO:331 or conservative modifications thereof, a $V_L$ CDR2 comprising amino acids having the sequence set forth in SEQ ID NO:332 or conservative modifications thereof, and a $V_L$ CDR3 comprising amino acids having the sequence set forth in SEQ ID NO:333 or conservative modifications thereof, as shown in Table 30. In certain embodiments, the anti-GPRC5D scFv comprises a $V_H$ CDR1 comprising amino acids having the sequence set forth in SEQ ID NO:328, a $V_H$ CDR2 comprising amino acids having the sequence set forth in SEQ ID NO:329, a $V_H$ CDR3 comprising amino acids having the sequence set forth in SEQ ID NO:330, a $V_L$ CDR1 comprising amino acids having the sequence set forth in SEQ ID NO:331, a $V_L$ CDR2 comprising amino acids having the sequence set forth in SEQ ID NO:332, and a $V_L$ CDR3 comprising amino acids having the sequence set forth in SEQ ID NO:333.

TABLE 30

| Antigen | A GPRC5D polypeptide having the amino acid sequence of SEQ ID NO: 97 | | |
|---|---|---|---|
| CDRs | 1 | 2 | 3 |
| $V_H$ | GYTFTSYY [SEQ ID NO: 328] | INPSGGST [SEQ ID NO: 329] | ARGQKYHSQYSRGG TGGGMTQDM [SEQ ID NO: 330] |
| $V_L$ | SSNIGNNY [SEQ ID NO: 331] | DNN [SEQ ID NO: 332] | GTWDSSLRNWV [SEQ ID NO: 333] |

TABLE 30-continued

```
Full V_H   QMQLVQSGAEVKKPGASVKVSCKASGYTFTSYYMEIWVRQAPGQGL
           EWMGIINPSGGSTSYAQKFQGRVTMTRDTSTSTVYMELSSLRSEDTA
           VYYCARGQKYHSQYSRGGTGGGMTQDMWGQGTLVTVSS [SEQ ID
           NO: 334]

DNA        CAGATGCAGCTGGTGCAGTCTGGGGCTGAGGTGAAGAAGCCTGG
           GGCCTCAGTGAAGGTTTCCTGCAAGGCATCTGGATACACCTTCAC
           CAGCTACTATATGCACTGGGTGCGACAGGCCCCTGGACAAGGGCT
           TGAGTGGATGGGAATAATCAACCCTAGTGGTGGTAGCACAAGCTA
           CGCACAAAAGTTCCAGGGCAGAGTCACCATGACCAGGGACACGT
           CCACGAGCACAGTCTACATGGAGCTGAGCAGCCTGAGATCTGAGG
           ACACGGCCGTGTATTACTGTGCGCGCGGTCAGAAATACCATTCTC
           AGTACTCTCGTGGTGGTACTGGTGGTGGTATGACTCAGGATATGT
           GGGGTCAAGGTACTCTGGTGACCGTCTCCTCA [SEQ ID NO: 337]

Full V_L   MKKTAIAIAVALAGFATVAQAAELQSVVTQPPSVSAAPGQRVTISCS
           GGSSNIGNNYVSWFQQLPRTAPKLLIYDNNKRPSGIPDRFSGSKSGTS
           AALDITVLQTGDEADYYCGTWDSSLRNWVFGGGTKLTVLG [SEQ ID
           NO: 335]

DNA        ATGAAAAAGACAGCTATCGCGATTGCAGTGGCACTGGCTGGTTTC
           GCTACCGTGGCCCAGGCGGCCGAGCTCCAGTCTGTCGTGACGCAG
           CCGCCCTCTGTGTCTGCGGCCCCAGGACAGAGGGTCACCATCTCC
           TGCTCTGGAGGTAGTTCCAACATTGGGAATAATTATGTTTCCTGGT
           TCCAACAACTCCCACGAACAGCCCCCAAACTCCTCATTTATGACA
           ATAATAAGCGACCCTCAGGGATTCCTGACCGATTCTCTGGCTCCA
           AGTCTGGCACGTCAGCCGCCCTGGACATCACCGTTCTCCAGACTG
           GGGACGAGGCCGATTATTACTGCGGAACTTGGGATAGCAGCCTGA
           GAAATTGGGTGTTCGGCGGAGGGACCAAGCTGACCGTCCTAGGT
           [SEQ ID NO: 338]

scFv       MKKTAIAIAVALAGFATVAQAAELQSVVTQPPSVSAAPGQRVTISCS
           GGSSNIGNNYVSWFQQLPRTAPKLLIYDNNKRPSGIPDRFSGSKSGTS
           AALDITVLQTGDEADYYCGTWDSSLRNWVFGGGTKLTVLGSRGGG
           GSGGGGSGGGGSLEMAQMQLVQSGAEVKKPGASVKVSCKASGYTF
           TSYYMHWVRQAPGQGLEWMGIINPSGGSTSYAQKFQGRVTMTRDTS
           TSTVYMELSSLRSEDTAVYYCARGQKYHSQYSRGGTGGGMTQDMW
           GQGTLVTVSS [SEQ ID NO: 336]

DNA        ATGAAAAAGACAGCTATCGCGATTGCAGTGGCACTGGCTGGTTTC
           GCTACCGTGGCCCAGGCGGCCGAGCTCCAGTCTGTCGTGACGCAG
           CCGCCCTCTGTGTCTGCGGCCCCAGGACAGAGGGTCACCATCTCC
           TGCTCTGGAGGTAGTTCCAACATTGGGAATAATTATGTTTCCTGGT
           TCCAACAACTCCCACGAACAGCCCCCAAACTCCTCATTTATGACA
           ATAATAAGCGACCCTCAGGGATTCCTGACCGATTCTCTGGCTCCA
           AGTCTGGCACGTCAGCCGCCCTGGACATCACCGTTCTCCAGACTG
           GGGACGAGGCCGATTATTACTGCGGAACTTGGGATAGCAGCCTGA
           GAAATTGGGTGTTCGGCGGAGGGACCAAGCTGACCGTCCTAGGTT
           CTAGAGGTGGTGGTGGTAGCGGCGGCGGCGGCTCTGGTGGTGGTG
           GATCCCTCGAGATGGCCCAGATGCAGCTGGTGCAGTCTGGGGCTG
           AGGTGAAGAAGCCTGGGGCCTCAGTGAAGGTTTCCTGCAAGGCAT
           CTGGATACACCTTCACCAGCTACTATATGCACTGGGTGCGACAGG
           CCCCTGGACAAGGGCTTGAGTGGATGGGAATAATCAACCCTAGTG
           GTGGTAGCACAAGCTACGCACAAAAGTTCCAGGGCAGAGTCACC
           ATGACCAGGGACACGTCCACGAGCACAGTCTACATGGAGCTGAG
           CAGCCTGAGATCTGAGGACACGGCCGTGTATTACTGTGCGCGCGG
           TCAGAAATACCATTCTCAGTACTCTCGTGGTGGTACTGGTGGTGGT
           ATGACTCAGGATATGTGGGGTCAAGGTACTCTGGTGACCGTCTCC
           TCA [SEQ ID NO: 339]
```

In certain embodiments, the antibody or other antigen binding protein is an anti-GPRC5D scFv or an antigen-binding fragment thereof having an antigen-binding region that comprises the amino acid sequence of SEQ ID NO:348 and specifically binds to a GPRC5D polypeptide (e.g., a GPRC5D polypeptide having the amino acid sequence SEQ ID NO:97, or fragments thereof), which is designated as ET150-032 scFv (also referred to as "ET150-182 scFv").

In certain embodiments, the anti-GPRC5D scFv antibody comprises a heavy chain variable region comprising amino acids having the sequence set forth in SEQ ID NO:346 and a light chain variable region comprising amino acids having the sequence set forth in SEQ ID NO:347, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with V_H and V_L regions or CDRs selected from Table 31. In certain embodiments, the anti-GPRC5D scFv comprises a V_H comprising amino acids having the sequence set forth in SEQ ID NO:346, as shown in Table 31. In certain embodiments, the anti-GPRC5D scFv comprises a V_L comprising amino acids having the sequence set forth in SEQ ID NO:347, as shown in Table 31. In certain embodiments, the anti-GPRC5D scFv comprises a V_H comprising amino acids having the sequence set forth in SEQ ID NO:346 and a V_L comprising amino acids having the sequence set forth in SEQ ID NO:347, as shown in Table 31. In certain embodiments, the anti- GPRC5D scFv comprises a $V_H$ CDR1 comprising amino acids having the sequence set forth in SEQ ID NO:340 or conservative modifications thereof, a $V_H$ CDR2 comprising amino acids having the sequence set forth in SEQ ID NO:341 or conservative modifications thereof, and a $V_H$ CDR3 comprising amino acids having the sequence set forth in SEQ ID NO:342 or conservative modifications thereof, as shown in Table 31. In certain embodiments, the anti-GPRC5D scFv comprises a $V_L$ CDR1 comprising amino acids having the sequence set forth in SEQ ID NO:343 or conservative modifications thereof, a $V_L$ CDR2 comprising amino acids having the sequence set forth in SEQ ID NO:344 or conservative modifications thereof, and a $V_L$ CDR3 comprising amino acids having the sequence set forth in SEQ ID NO:345 or conservative modifications thereof, as shown in Table 31. In certain embodiments, the anti-GPRC5D scFv comprises a $V_H$ CDR1 comprising amino acids having the sequence set forth in SEQ ID NO:340 or conservative modifications thereof, a $V_H$ CDR2 comprising amino acids having the sequence set forth in SEQ ID NO:341 or conservative modifications thereof, a $V_H$ CDR3 comprising amino acids having the sequence set forth in SEQ ID NO:342 or conservative modifications thereof, a $V_L$ CDR1 comprising amino acids having the sequence set forth in SEQ ID NO:343 or conservative modifications thereof, a $V_L$ CDR2 comprising amino acids having the sequence set forth in SEQ ID NO:344 or conservative modifications thereof, and a $V_L$ CDR3 comprising amino acids having the sequence set forth in SEQ ID NO:345 or conservative modifications thereof, as shown in Table 31. In certain embodiments, the anti-GPRC5D scFv comprises a $V_H$ CDR1 comprising amino acids having the sequence set forth in SEQ ID NO:340, a $V_H$ CDR2 comprising amino acids having the sequence set forth in SEQ ID NO:341, a $V_H$ CDR3 comprising amino acids having the sequence set forth in SEQ ID NO:342, a $V_L$ CDR1 comprising amino acids having the sequence set forth in SEQ ID NO:343, a $V_L$ CDR2 comprising amino acids having the sequence set forth in SEQ ID NO:344, and a $V_L$ CDR3 comprising amino acids having the sequence set forth in SEQ ID NO:345.

TABLE 31

| Antigen | A GPRC5D polypeptide having the amino acid sequence of SEQ ID NO: 97 | | |
|---|---|---|---|
| CDRs | 1 | 2 | 3 |
| $V_H$ | GYTFSRYY [SEQ ID NO: 340] | MNPNSGNT [SEQ ID NO: 341] | ARGRYHVIDY [SEQ ID NO: 342] |
| $V_L$ | SSDVGGYNH [SEQ ID NO: 343] | EVT [SEQ ID NO: 344] | SSYAGSAHWV [SEQ ID NO: 345] |
| Full $V_H$ | EVQLVQSGAEVKKPGASVKVSCKASGYTFSRYYIHWVRQAPGQGLE WMGWMNPNSGNTGYAQKFQGRVTMTRNTSISTAYMELSSLRSEDTA VYYCARGRYHVIDYWGQGTLVTVSS [SEQ ID NO: 346] | | |
| DNA | GAGGTCCAGCTGGTGCAGTCTGGGGCTGAGGTGAAGAAGCCTGGG GCCTCAGTGAAGGTTTCCTGCAAGGCATCTGGATACACCTTCAGCA GGTACTATATACACTGGGTGCGACAGGCCCCTGGACAAGGGCTTG AGTGGATGGGATGGATGAACCCTAACAGTGGTAACACAGGCTATG CACAGAAGTTCCAGGGCAGAGTCACCATGACCAGGAACACCTCCA TAAGCACAGCCTACATGGAGCTGAGCAGCCTGAGATCTGAGGACA CGGCCGTGTATTACTGTGCGCGCGGTCGTTACCATGTTATCGATTA CTGGGGTCAAGGTACTCTGGTGACCGTCTCCTCA [SEQ ID NO: 349] | | |
| Full $V_L$ | MKKTAIAIAVALAGFATVAQAAELQSVLTQPPSASGSPGQSLTISCTGT SSDVGGYNHVSWYQQYPGKAPKLMIYEVTKRPSGVPDRFSGSKSGNT ASLTVSGLQAEDEADYYCSSYAGSAHWVFGGGTKLTVLG [SEQ ID NO: 347] | | |
| DNA | ATGAAAAAGACAGCTATCGCGATTGCAGTGGCACTGGCTGGTTTC GCTACCGTGGCCCAGGCGGCCGAGCTCCAGTCTGTGTTGACTCAGC CACCCTCCGCGTCCGGGTCTCCTGGACAGTCACTCACCATCTCCTG CACTGGAACCAGCAGTGACGTTGGTGGTTATAACCATGTCTCCTGG TACCAACAGTACCCAGGCAAAGCCCCCAAACTCATGATTTATGAG GTCACTAAGCGGCCCTCAGGGGTCCCTGATCGCTTCTCTGGCTCCA AGTCTGGCAACACGGCCTCCCTGACCGTCTCTGGGCTCCAGGCTGA GGATGAGGCTGATTATTACTGCAGCTCATATGCAGGCAGCGCCCAT TGGGTGTTCGGCGGAGGGACCAAGCTGACCGTCCTAGGT [SEQ ID NO: 350] | | |
| scFv | MKKTAIAIAVALAGFATVAQAAELQSVLTQPPSASGSPGQSLTISCTGT SSDVGGYNHVSWYQQYPGKAPKLMIYEVTKRPSGVPDRFSGSKSGNT ASLTVSGLQAEDEADYYCSSYAGSAHWVFGGGTKLTVLGSRGGGGS GGGGSGGGGSLEMAEVQLVQSGAEVKKPGASVKVSCKASGYTFSRY YIHWVRQAPGQGLEWMGWMNPNSGNTGYAQKFQGRVTMTRNTSIS TAYMELSSLRSEDTAVYYCARGRYHVIDYWGQGTLVTVSS [SEQ ID NO: 348] | | |
| DNA | ATGAAAAAGACAGCTATCGCGATTGCAGTGGCACTGGCTGGTTTC GCTACCGTGGCCCAGGCGGCCGAGCTCCAGTCTGTGTTGACTCAGC CACCCTCCGCGTCCGGGTCTCCTGGACAGTCACTCACCATCTCCTG CACTGGAACCAGCAGTGACGTTGGTGGTTATAACCATGTCTCCTGG TACCAACAGTACCCAGGCAAAGCCCCCAAACTCATGATTTATGAG GTCACTAAGCGGCCCTCAGGGGTCCCTGATCGCTTCTCTGGCTCCA AGTCTGGCAACACGGCCTCCCTGACCGTCTCTGGGCTCCAGGCTGA | | |

TABLE 31-continued

```
GGATGAGGCTGATTATTACTGCAGCTCATATGCAGGCAGCGCCCAT
TGGGTGTTCGGCGGAGGGACCAAGCTGACCGTCCTAGGTTCTAGA
GGTGGTGGTGGTAGCGGCGGCGGCGGCTCTGGTGGTGGTGGATCC
CTCGAGATGGCCGAGGTCCAGCTGGTGCAGTCTGGGGCTGAGGTG
AAGAAGCCTGGGGCCTCAGTGAAGGTTTCCTGCAAGGCATCTGGA
TACACCTTCAGCAGGTACTATATACACTGGGTGCGACAGGCCCCTG
GACAAGGGCTTGAGTGGATGGGATGGATGAACCCTAACAGTGGTA
ACACAGGCTATGCACAGAAGTTCCAGGGCAGAGTCACCATGACCA
GGAACACCTCCATAAGCACAGCCTACATGGAGCTGAGCAGCCTGA
GATCTGAGGACACGGCCGTGTATTACTGTGCGCGCGGTCGTTACCA
TGTTATCGATTACTGGGGTCAAGGTACTCTGGTGACCGTCTCCTCA
[SEQ ID NO: 351]
```

In certain embodiments, the antibody or other antigen binding protein is an anti-GPRC5D scFv or an antigen-binding fragment thereof having an antigen-binding region that comprises the amino acid sequence of SEQ ID NO:360 and specifically binds to a GPRC5D polypeptide (e.g., a GPRC5D polypeptide having the amino acid sequence SEQ ID NO:97, or fragments thereof), which is designated as ET150-033 scFv (also referred to as "ET150-183 scFv").

In certain embodiments, the anti-GPRC5D scFv antibody comprises a heavy chain variable region comprising amino acids having the sequence set forth in SEQ ID NO:358 and a light chain variable region comprising amino acids having the sequence set forth in SEQ ID NO:359, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the anti-GPRC5D scFv antibody is an scFv-Fc fusion protein or full length human IgG with $V_H$ and $V_L$ regions or CDRs selected from Table 32. In certain embodiments, the anti-GPRC5D scFv comprises a $V_H$ comprising amino acids having the sequence set forth in SEQ ID NO:358, as shown in Table 32. In certain embodiments, the anti-GPRC5D scFv comprises a $V_L$ comprising amino acids having the sequence set forth in SEQ ID NO:359, as shown in Table 32. In certain embodiments, the anti-GPRC5D scFv comprises a $V_H$ comprising amino acids having the sequence set forth in SEQ ID NO:358 and a $V_L$ comprising amino acids having the sequence set forth in SEQ ID NO:359, as shown in Table 32. In certain embodiments, the anti-GPRC5D scFv comprises a $V_H$ CDR1 comprising amino acids having the sequence set forth in SEQ ID NO:352 or conservative modifications thereof, a $V_H$ CDR2 comprising amino acids having the sequence set forth in SEQ ID NO:353 or conservative modifications thereof, and a $V_H$ CDR3 comprising amino acids having the sequence set forth in SEQ ID NO:354 or conservative modifications thereof, as shown in Table 32. In certain embodiments, the anti-GPRC5D scFv comprises a $V_L$ CDR1 comprising amino acids having the sequence set forth in SEQ ID NO:355 or conservative modifications thereof, a $V_L$ CDR2 comprising amino acids having the sequence set forth in SEQ ID NO:356 or conservative modifications thereof, and a $V_L$ CDR3 comprising amino acids having the sequence set forth in SEQ ID NO:357 or conservative modifications thereof, as shown in Table 32. In certain embodiments, the anti-GPRC5D scFv comprises a $V_H$ CDR1 comprising amino acids having the sequence set forth in SEQ ID NO:352 or conservative modifications thereof, a $V_H$ CDR2 comprising amino acids having the sequence set forth in SEQ ID NO:353 or conservative modifications thereof, a $V_H$ CDR3 comprising amino acids having the sequence set forth in SEQ ID NO:354 or conservative modifications thereof, a $V_L$ CDR1 comprising amino acids having the sequence set forth in SEQ ID NO:355 or conservative modifications thereof, a $V_L$ CDR2 comprising amino acids having the sequence set forth in SEQ ID NO:356 or conservative modifications thereof, and a $V_L$ CDR3 comprising amino acids having the sequence set forth in SEQ ID NO:357 or conservative modifications thereof, as shown in Table 32. In certain embodiments, the anti-GPRC5D scFv comprises a $V_H$ CDR1 comprising amino acids having the sequence set forth in SEQ ID NO:352, a $V_H$ CDR2 comprising amino acids having the sequence set forth in SEQ ID NO:353, a $V_H$ CDR3 comprising amino acids having the sequence set forth in SEQ ID NO:354, a $V_L$ CDR1 comprising amino acids having the sequence set forth in SEQ ID NO:355, a $V_L$ CDR2 comprising amino acids having the sequence set forth in SEQ ID NO:356, and a $V_L$ CDR3 comprising amino acids having the sequence set forth in SEQ ID NO:357.

TABLE 32

| Antigen | A GPRC5D polypeptide having the amino acid sequence of SEQ ID NO: 97 | | |
|---|---|---|---|
| CDRs | 1 | 2 | 3 |
| $V_H$ | GYTFNTYY [SEQ ID NO: 352] | INPNNGGT [SEQ ID NO: 353] | ARSYDY [SEQ ID NO: 354] |
| $V_L$ | SSNIGSNY [SEQ ID NO: 355] | RNN [SEQ ID NO: 356] | AAWDDSLSGRV [SEQ ID NO: 357] |
| Full $V_H$ | QLQLVQSGAEVKKPGSSVKVSCKASGYTFNTYYLHWVRQAPGQGLE WMGRINPNNGGTNYAQKFQGRVTMTRDTSINTAYMELSRLRSDDTA VYYCARSYDYWGQGTLVTVSS [SEQ ID NO: 358] | | |
| DNA | CAGCTGCAGCTGGTGCAATCTGGGGCTGAGGTGAAGAAGCCTGGG TCCTCGGTGAAGGTCTCCTGCAAGGCTTCTGGATACACCTTCAACA CCTACTATCTGCACTGGGTACGACAGGCCCCTGGACAAGGGCTTGA GTGGATGGGACGGATCAACCCTAACAATGGTGGCACAAACTATGC | | |

TABLE 32-continued

```
                ACAGAAGTTTCAGGGCAGGGTCACCATGACCAGGGACACGTCCAT
                CAACACAGCCTACATGGAGCTGAGCAGGCTGAGATCTGACGACAC
                GGCCGTGTATTACTGTGCGCGCTCTTACGATTACTGGGGTCAAGGT
                ACTCTGGTGACCGTCTCCTCA [SEQ ID NO: 361]

Full V_L        MKKTAIAIAVALAGFATVAQAAELQAVLTQPPSASGTPGQRVTISCSG
                SSSNIGSNYVYWYQQLPGTAPKLLIYRNNQRPSGVPDRFSGSKSGTSA
                SLAISGLRSEDEADYYCAAWDDSLSGRVFGTGTKVTVLG [SEQ ID
                NO: 359]

DNA             ATGAAAAAGACAGCTATCGCGATTGCAGTGGCACTGGCTGGTTTC
                GCTACCGTGGCCCAGGCGGCCGAGCTCCAGGCTGTGCTGACTCAG
                CCACCCTCAGCGTCTGGGACCCCCGGGCAGAGGGTCACCATCTCTT
                GTTCTGGAAGCAGCTCCAACATCGGAAGTAATTATGTATACTGGTA
                CCAGCAGCTCCCAGGAACGGCCCCCAAACTCCTCATCTATAGGAA
                TAATCAGCGGCCCTCAGGGGTCCCTGACCGATTCTCTGGCTCCAAG
                TCTGGCACCTCAGCCTCCCTGGCCATCAGTGGGCTCCGGTCCGAGG
                ATGAGGCTGATTATTACTGTGCAGCATGGGATGACAGCCTGAGTG
                GTCGGGTCTTCGGAACTGGGACCAAGGTCACCGTCCTAGGT [SEQ
                ID NO: 362]

scFv            MKKTAIAIAVALAGFATVAQAAELQAVLTQPPSASGTPGQRVTISCSG
                SSSNIGSNYVYWYQQLPGTAPKWYRNNQRPSGVPDRFSGSKSGTSA
                SLAISGLRSEDEADYYCAAWDDSLSGRVFGTGTKVTVLGSRGGGGSG
                GGGSGGGGSLEMAQLQLVQSGAEVKKPGSSVKVSCKASGYTFNTYY
                LHWVRQAPGQGLEWMGRINPNNGGTNYAQKFQGRVTMTRDTSINTA
                YMELSRLRSDDTAVYYCARSYDYWGQGTLVTVSS [SEQ ID NO: 360]

DNA             ATGAAAAAGACAGCTATCGCGATTGCAGTGGCACTGGCTGGTTTC
                GCTACCGTGGCCCAGGCGGCCGAGCTCCAGGCTGTGCTGACTCAG
                CCACCCTCAGCGTCTGGGACCCCCGGGCAGAGGGTCACCATCTCTT
                GTTCTGGAAGCAGCTCCAACATCGGAAGTAATTATGTATACTGGTA
                CCAGCAGCTCCCAGGAACGGCCCCCAAACTCCTCATCTATAGGAA
                TAATCAGCGGCCCTCAGGGGTCCCTGACCGATTCTCTGGCTCCAAG
                TCTGGCACCTCAGCCTCCCTGGCCATCAGTGGGCTCCGGTCCGAGG
                ATGAGGCTGATTATTACTGTGCAGCATGGGATGACAGCCTGAGTG
                GTCGGGTCTTCGGAACTGGGACCAAGGTCACCGTCCTAGGTTCTAG
                AGGTGGTGGTGGTAGCGGCGGCGGCGGCTCTGGTGGTGGTGGATC
                CCTCGAGATGGCCCAGCTGCAGCTGGTGCAATCTGGGGCTGAGGT
                GAAGAAGCCTGGGTCCTCGGTGAAGGTCTCCTGCAAGGCTTCTGG
                ATACACCTTCAACACCTACTATCTGCACTGGGTACGACAGGCCCCT
                GGACAAGGGCTTGAGTGGATGGGACGGATCAACCCTAACAATGGT
                GGCACAAACTATGCACAGAAGTTTCAGGGCAGGGTCACCATGACC
                AGGGACACGTCCATCAACACAGCCTACATGGAGCTGAGCAGGCTG
                AGATCTGACGACACGGCCGTGTATTACTGTGCGCGCTCTTACGATT
                ACTGGGGTCAAGGTACTCTGGTGACCGTCTCCTCA [SEQ ID NO: 363]
```

The presently disclosed subject matter further provides anti-GPRC5D scFv antibodies comprising a heavy chain variable region, a light chain variable region, a linker peptide between the heavy chain variable region and the light chain variable region, and an His-tag and an HA-tag. In certain embodiments, the amino acid sequence of the His-tag and HA-tag comprises the amino acid sequence of SEQ ID NO:379, which is provided below:

```
                                        [SEQ ID NO: 379]
        TSGQAGQHHHHHHGAYPYDVPDYAS
```

The nucleotide sequence encoding SEQ ID NO: 379 is SEQ ID NO: 380, which is provided below:

```
                                        [SEQ ID NO: 380]
ACTAGTGGCCAGGCCGGCCAGCACCATCACCATCACCATGGCGCATACCC

GTACGACGTTCCGGACTACGCTTCT
```

2. Monoclonal Antibodies

The presently disclosed subject matter provides human antibodies (e.g., human monoclonal antibodies) that specifically bind to GPRC5D (e.g., human GPRC5D) and were isolated and structurally characterized as described in Example 2. The $V_H$ amino acid sequences of human anti-GPRC5D antibodies ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 are shown in SEQ ID NOs: 1, 5, 9, 13, 17, 21, 25, 29, 33, 37, 41, 45, 49, 53, 57, 61, 65, 69, 73, 77, 81, 85, 89, 93, 274, 286, 298, 310, 322, 334, 346 and 358, respectively. The $V_L$ amino acid sequences of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 are shown in SEQ ID NOs: 2, 6, 10, 14, 18, 22, 26, 30, 34, 38, 42, 46, 50, 54, 58, 62, 66, 70, 74, 78, 82, 86, 90, 94, 275, 287, 299, 311, 323, 335, 347 and 359, respectively.

Given that each of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 antibodies can bind to GPRC5D, the $V_H$ and $V_L$ sequences can be "mixed and matched" to create other anti-GPRC5D binding molecules. GPRC5D binding of such "mixed and matched" antibodies can be tested using the binding assays known in the art, including for example, ELISAs, Western blots, RIAs, Biacore® analysis. Preferably, when $V_H$ and $V_L$ chains are mixed and matched, a $V_H$ sequence from a particular $V_H/V_L$ pairing is replaced with a structurally similar $V_H$ sequence. Likewise, a $V_L$ sequence from a particular $V_H/V_L$ pairing is replaced with a structurally similar $V_L$ sequence.

In certain embodiments, the presently disclosed subject matter provides an isolated antibody, or antigen-binding portion thereof comprising: (i) a heavy chain variable region comprising an amino acid sequence selected from the group consisting of SEQ ID NOs: 1, 5, 9, 13, 17, 21, 25, 29, 33, 37, 41, 45, 49, 53, 57, 61, 65, 69, 73, 77, 81, 85, 89, 93, 274, 286, 298, 310, 322, 334, 346 and 358; and (ii) a light chain variable region comprising an amino acid sequence selected from the group consisting of SEQ ID NOs: 2, 6, 10, 14, 18, 22, 26, 30, 34, 38, 42, 46, 50, 54, 58, 62, 66, 70, 74, 78, 82, 86, 90, 94, 275, 287, 299, 311, 323, 335, 347 and 359; wherein the antibody specifically binds GPRC5D, e.g., human GPRC5D.

Preferred heavy and light chain combinations include:
(i) a heavy chain variable region comprising amino acids having a sequence set forth in SEQ ID NO:1, and a light chain variable region comprising amino acids having a sequence set forth in SEQ ID NO:2; or
(ii) a heavy chain variable region comprising amino acids having a sequence set forth in SEQ ID NO:5, and a light chain variable region comprising amino acids having a sequence set forth in SEQ ID NO:6;
(iii) a heavy chain variable region comprising amino acids having a sequence set forth in SEQ ID NO:9, and a light chain variable region comprising amino acids having a sequence set forth in SEQ ID NO:10;
(iv) a heavy chain variable region comprising amino acids having a sequence set forth in SEQ ID NO:13, and a light chain variable region comprising amino acids having a sequence set forth in SEQ ID NO:14;
(v) a heavy chain variable region comprising amino acids having a sequence set forth in SEQ ID NO:17, and a light chain variable region comprising amino acids having a sequence set forth in SEQ ID NO:18;
(vi) a heavy chain variable region comprising amino acids having a sequence set forth in SEQ ID NO:21, and a light chain variable region comprising amino acids having a sequence set forth in SEQ ID NO:22;
(vii) a heavy chain variable region comprising amino acids having a sequence set forth in SEQ ID NO:25, and a light chain variable region comprising amino acids having a sequence set forth in SEQ ID NO:26;
(viii) a heavy chain variable region comprising amino acids having a sequence set forth in SEQ ID NO:29, and a light chain variable region comprising amino acids having a sequence set forth in SEQ ID NO:30;
(ix) a heavy chain variable region comprising amino acids having a sequence set forth in SEQ ID NO:33, and a light chain variable region comprising amino acids having a sequence set forth in SEQ ID NO:34;
(x) a heavy chain variable region comprising amino acids having a sequence set forth in SEQ ID NO:37, and a light chain variable region comprising amino acids having a sequence set forth in SEQ ID NO:38;

(xi) a heavy chain variable region comprising amino acids having a sequence set forth in SEQ ID NO:41, and a light chain variable region comprising amino acids having a sequence set forth in SEQ ID NO:42;
(xii) a heavy chain variable region comprising amino acids having a sequence set forth in SEQ ID NO:45, and a light chain variable region comprising amino acids having a sequence set forth in SEQ ID NO:46;
(xiii) a heavy chain variable region comprising amino acids having a sequence set forth in SEQ ID NO:49, and a light chain variable region comprising amino acids having a sequence set forth in SEQ ID NO:50;
(xiv) a heavy chain variable region comprising amino acids having a sequence set forth in SEQ ID NO:53, and a light chain variable region comprising amino acids having a sequence set forth in SEQ ID NO:54;
(xv) a heavy chain variable region comprising amino acids having a sequence set forth in SEQ ID NO:57, and a light chain variable region comprising amino acids having a sequence set forth in SEQ ID NO:58;
(xvi) a heavy chain variable region comprising amino acids having a sequence set forth in SEQ ID NO:61, and a light chain variable region comprising amino acids having a sequence set forth in SEQ ID NO:62;
(xvii) a heavy chain variable region comprising amino acids having a sequence set forth in SEQ ID NO:65, and a light chain variable region comprising amino acids having a sequence set forth in SEQ ID NO:66;
(xviii) a heavy chain variable region comprising amino acids having a sequence set forth in SEQ ID NO:69, and a light chain variable region comprising amino acids having a sequence set forth in SEQ ID NO:70;
(xix) a heavy chain variable region comprising amino acids having a sequence set forth in SEQ ID NO:73, and a light chain variable region comprising amino acids having a sequence set forth in SEQ ID NO:74;
(xx) a heavy chain variable region comprising amino acids having a sequence set forth in SEQ ID NO:77, and a light chain variable region comprising amino acids having a sequence set forth in SEQ ID NO:78;
(xxi) a heavy chain variable region comprising amino acids having a sequence set forth in SEQ ID NO:81, and a light chain variable region comprising amino acids having a sequence set forth in SEQ ID NO:82;
(xxii) a heavy chain variable region comprising amino acids having a sequence set forth in SEQ ID NO:85, and a light chain variable region comprising amino acids having a sequence set forth in SEQ ID NO:86;
(xxiii) a heavy chain variable region comprising amino acids having a sequence set forth in SEQ ID NO:89, and a light chain variable region comprising amino acids having a sequence set forth in SEQ ID NO:90;
(x) a heavy chain variable region comprising amino acids having a sequence set forth in SEQ ID NO:93, and a light chain variable region comprising amino acids having a sequence set forth in SEQ ID NO:94.
(xvi) a heavy chain variable region comprising amino acids having a sequence set forth in SEQ ID NO:274, and a light chain variable region comprising amino acids having a sequence set forth in SEQ ID NO:275;
(xvii) a heavy chain variable region comprising amino acids having a sequence set forth in SEQ ID NO:286, and a light chain variable region comprising amino acids having a sequence set forth in SEQ ID NO:287;
(xviii) a heavy chain variable region comprising amino acids having a sequence set forth in SEQ ID NO:298, and a light chain variable region comprising amino acids having a sequence set forth in SEQ ID NO:299;

(xix) a heavy chain variable region comprising amino acids having a sequence set forth in SEQ ID NO:310, and a light chain variable region comprising amino acids having a sequence set forth in SEQ ID NO:311;

(xx) a heavy chain variable region comprising amino acids having a sequence set forth in SEQ ID NO:322, and a light chain variable region comprising amino acids having a sequence set forth in SEQ ID NO:323;

(xxi) a heavy chain variable region comprising amino acids having a sequence set forth in SEQ ID NO:334, and a light chain variable region comprising amino acids having a sequence set forth in SEQ ID NO:335;

(xxii) a heavy chain variable region comprising amino acids having a sequence set forth in SEQ ID NO:346, and a light chain variable region comprising amino acids having a sequence set forth in SEQ ID NO:347; or (xxiii) a heavy chain variable region comprising amino acids having a sequence set forth in SEQ ID NO:358, and a light chain variable region comprising amino acids having a sequence set forth in SEQ ID NO:359.

In certain embodiments, the presently disclosed subject matter provides antibodies that comprise the heavy chain and light chain CDR1s, CDR2s and CDR3s of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 antibodies. The amino acid sequences of the $V_H$ CDR1s of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 are shown in SEQ ID NOs: 124, 130, 136, 142, 148, 154, 160, 166, 172, 178, 184, 190, 196, 202, 208, 214, 220, 226, 232, 238, 244, 250, 256, 262, 268, 280, 292, 303, 316, 328, 340 and 352, respectively. The amino acid sequences of the $V_H$ CDR2s of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 antibodies are shown in SEQ ID NOs: 125, 131, 137, 143, 149, 155, 161, 167, 173, 179, 185, 191, 197, 203, 209, 215, 221, 227, 233, 239, 245, 251, 257, 263, 269, 281, 293, 304, 317, 329, 341 and 353, respectively. The amino acid sequences of the $V_H$ CDR3s of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 are shown in SEQ ID NOs: 126, 132, 138, 144, 150, 156, 162, 168, 174, 180, 186, 192, 198, 204, 210, 216, 222, 228, 234, 240, 246, 252, 258, 264, 270, 282, 294, 305, 318, 330, 342 and 354, respectively.

The amino acid sequences of the $V_L$ CDR1s of 1 ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 are shown in SEQ ID NOs: 127, 133, 139, 145, 151, 157, 163, 169, 175, 181, 187, 193, 199, 205, 211, 217, 223, 229, 235, 241, 247, 253, 259, 265, 271, 283, 295, 306, 319, 331, 343 and 355, respectively. The amino acid sequences of the $V_L$ CDR2s of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 are shown in SEQ ID NOs: 128, 134, 140, 146, 152, 158, 164, 170, 176, 182, 188, 194, 200, 206, 212, 218, 224, 230, 236, 242, 248, 254, 260, 266, 272, 284, 296, 307, 320, 332, 344 and 356, respectively. The amino acid sequences of the $V_L$ CDR3s of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 are shown in SEQ ID NOs: 129, 135, 141, 147, 153, 159, 165, 171, 177, 183, 189, 195, 201, 207, 213, 219, 225, 231, 237, 243, 249, 255, 261, 267, 273, 285, 297, 308, 321, 333, 345 and 357, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to GPRC5D and that antigen-binding specificity is provided primarily by the CDR1, CDR2, and CDR3 regions, the $V_H$ CDR1, CDR2, and CDR3 sequences and $V_L$ CDR1, CDR2, and CDR3 sequences can be "mixed and matched" (i.e., CDRs from different antibodies can be mixed and match, although each antibody must contain a $V_H$ CDR1, CDR2, and CDR3 and a V L CDR1, CDR2, and CDR3) to create other anti-GPRC5D binding molecules. GPRC5D binding of such "mixed and matched" antibodies can be tested using the binding assays described above. When $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence preferably is replaced with a structurally similar CDR sequence (s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences of the antibodies disclosed herein ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033.

In certain embodiments, the presently disclosed subject matter provides an isolated antibody, or antigen-binding portion thereof comprising: (ix) a heavy chain variable region CDR1 comprising an amino acid sequence selected from the group consisting of SEQ ID NOs: 124, 130, 136, 142, 148, 154, 160, 166, 172, 178, 184, 190, 196, 202, 208, 214, 220, 226, 232, 238, 244, 250, 256, 262, 268, 280, 292, 303, 316, 328, 340 and 352; (ii) a heavy chain variable region CDR2 comprising an amino acid sequence selected from the group consisting of SEQ ID NOs: 125, 131, 137, 143, 149, 155, 161, 167, 173, 179, 185, 191, 197, 203, 209, 215, 221, 227, 233, 239, 245, 251, 257, 263, 269, 281, 293, 304, 317, 329, 341 and 353; (iii) a heavy chain variable region CDR3 comprising an amino acid sequence selected from the group consisting of SEQ ID NOs: 126, 132, 138, 144, 150, 156, 162, 168, 174, 180, 186, 192, 198, 204, 210, 216, 222, 228, 234, 240, 246, 252, 258, 264, 270, 282, 294, 305, 318, 330, 342 and 354; (iv) a light chain variable region CDR1 comprising an amino acid sequence selected from the group consisting of SEQ ID NOs: 127, 133, 139, 145, 151, 157, 163, 169, 175, 181, 187, 193, 199, 205, 211, 217, 223, 229, 235, 241, 247, 253, 259, 265, 271, 283, 295, 306, 319, 331, 343 and 355; (v) a light chain variable region CDR2 comprising an amino acid sequence selected from the group consisting of SEQ ID NOs: 128, 134, 140, 146, 152, 158, 164, 170, 176, 182, 188, 194, 200, 206, 212, 218, 224, 230, 236, 242, 248, 254, 260, 266, 272, 284, 296, 307, 320, 332, 344 and 356; and (f) a light chain variable region CDR3 comprising an amino acid sequence selected from the group consisting of SEQ ID NOs: 129, 135, 141, 147, 153, 159, 165, 171, 177, 183, 189, 195, 201, 207, 213, 219, 225, 231, 237, 243, 249, 255, 261, 267, 273, 285, 297, 308, 321, 333, 345 and 357; wherein the antibody specifically binds GPRC5D, e.g., human GPRC5D.

In certain embodiments, the antibody comprises:
(i) a heavy chain variable region CDR1 comprising amino acids having the sequence set forth in SEQ ID NO: 124;
(ii) a heavy chain variable region CDR2 comprising amino acids having the sequence set forth in SEQ ID NO: 125;
(iii) a heavy chain variable region CDR3 comprising amino acids having the sequence set forth in SEQ ID NO: 126;
(iv) a light chain variable region CDR1 comprising amino acids having the sequence set forth in SEQ ID NO: 127;
(v) a light chain variable region CDR2 comprising amino acids having the sequence set forth in SEQ ID NO:128; and
(vi) a light chain variable region CDR3 comprising amino acids having the sequence set forth in SEQ ID NO: 129.
In certain embodiments, the antibody comprises:
(i) a heavy chain variable region CDR1 comprising amino acids having the sequence set forth in SEQ ID NO: 130;
(ii) a heavy chain variable region CDR2 comprising amino acids having the sequence set forth in SEQ ID NO: 131;
(iii) a heavy chain variable region CDR3 comprising amino acids having the sequence set forth in SEQ ID NO: 132;
(iv) a light chain variable region CDR1 comprising amino acids having the sequence set forth in SEQ ID NO: 133;
(v) a light chain variable region CDR2 comprising amino acids having the sequence set forth in SEQ ID NO:134; and
(vi) a light chain variable region CDR3 comprising amino acids having the sequence set forth in SEQ ID NO: 135.
In certain embodiments, the antibody comprises:

(i) a heavy chain variable region CDR1 comprising amino acids having the sequence set forth in SEQ ID NO: 136;
(ii) a heavy chain variable region CDR2 comprising amino acids having the sequence set forth in SEQ ID NO: 137;
(iii) a heavy chain variable region CDR3 comprising amino acids having the sequence set forth in SEQ ID NO: 138;
(iv) a light chain variable region CDR1 comprising amino acids having the sequence set forth in SEQ ID NO: 139;
(v) a light chain variable region CDR2 comprising amino acids having the sequence set forth in SEQ ID NO:140; and
(vi) a light chain variable region CDR3 comprising amino acids having the sequence set forth in SEQ ID NO: 141.
In certain embodiments, the antibody comprises:
(i) a heavy chain variable region CDR1 comprising amino acids having the sequence set forth in SEQ ID NO: 142;
(ii) a heavy chain variable region CDR2 comprising amino acids having the sequence set forth in SEQ ID NO: 143;
(iii) a heavy chain variable region CDR3 comprising amino acids having the sequence set forth in SEQ ID NO: 144;
(iv) a light chain variable region CDR1 comprising amino acids having the sequence set forth in SEQ ID NO: 145;
(v) a light chain variable region CDR2 comprising amino acids having the sequence set forth in SEQ ID NO:146; and
(vi) a light chain variable region CDR3 comprising amino acids having the sequence set forth in SEQ ID NO: 147.
In certain embodiments, the antibody comprises:
(i) a heavy chain variable region CDR1 comprising amino acids having the sequence set forth in SEQ ID NO: 148;
(ii) a heavy chain variable region CDR2 comprising amino acids having the sequence set forth in SEQ ID NO: 149;
(iii) a heavy chain variable region CDR3 comprising amino acids having the sequence set forth in SEQ ID NO: 150;
(iv) a light chain variable region CDR1 comprising amino acids having the sequence set forth in SEQ ID NO: 151;
(v) a light chain variable region CDR2 comprising amino acids having the sequence set forth in SEQ ID NO:152; and
(vi) a light chain variable region CDR3 comprising amino acids having the sequence set forth in SEQ ID NO: 153.
In certain embodiments, the antibody comprises:
(i) a heavy chain variable region CDR1 comprising amino acids having the sequence set forth in SEQ ID NO: 154;
(ii) a heavy chain variable region CDR2 comprising amino acids having the sequence set forth in SEQ ID NO: 155;
(iii) a heavy chain variable region CDR3 comprising amino acids having the sequence set forth in SEQ ID NO: 156;
(iv) a light chain variable region CDR1 comprising amino acids having the sequence set forth in SEQ ID NO: 157;
(v) a light chain variable region CDR2 comprising amino acids having the sequence set forth in SEQ ID NO:158; and
(vi) a light chain variable region CDR3 comprising amino acids having the sequence set forth in SEQ ID NO: 159.
In certain embodiments, the antibody comprises:
(i) a heavy chain variable region CDR1 comprising amino acids having the sequence set forth in SEQ ID NO: 160;

(ii) a heavy chain variable region CDR2 comprising amino acids having the sequence set forth in SEQ ID NO: 161;

(iii) a heavy chain variable region CDR3 comprising amino acids having the sequence set forth in SEQ ID NO: 162;

(iv) a light chain variable region CDR1 comprising amino acids having the sequence set forth in SEQ ID NO: 163;

(v) a light chain variable region CDR2 comprising amino acids having the sequence set forth in SEQ ID NO:164; and (vi) a light chain variable region CDR3 comprising amino acids having the sequence set forth in SEQ ID NO: 165.

In certain embodiments, the antibody comprises:

(i) a heavy chain variable region CDR1 comprising amino acids having the sequence set forth in SEQ ID NO: 166;

(ii) a heavy chain variable region CDR2 comprising amino acids having the sequence set forth in SEQ ID NO: 167;

(iii) a heavy chain variable region CDR3 comprising amino acids having the sequence set forth in SEQ ID NO: 168;

(iv) a light chain variable region CDR1 comprising amino acids having the sequence set forth in SEQ ID NO: 169;

(v) a light chain variable region CDR2 comprising amino acids having the sequence set forth in SEQ ID NO:170; and (vi) a light chain variable region CDR3 comprising amino acids having the sequence set forth in SEQ ID NO: 171.

In certain embodiments, the antibody comprises:

(i) a heavy chain variable region CDR1 comprising amino acids having the sequence set forth in SEQ ID NO: 172;

(ii) a heavy chain variable region CDR2 comprising amino acids having the sequence set forth in SEQ ID NO: 173;

(iii) a heavy chain variable region CDR3 comprising amino acids having the sequence set forth in SEQ ID NO: 174;

(iv) a light chain variable region CDR1 comprising amino acids having the sequence set forth in SEQ ID NO: 175;

(v) a light chain variable region CDR2 comprising amino acids having the sequence set forth in SEQ ID NO:176; and (vi) a light chain variable region CDR3 comprising amino acids having the sequence set forth in SEQ ID NO: 177.

In certain embodiments, the antibody comprises:

(i) a heavy chain variable region CDR1 comprising amino acids having the sequence set forth in SEQ ID NO: 178;

(ii) a heavy chain variable region CDR2 comprising amino acids having the sequence set forth in SEQ ID NO: 179;

(iii) a heavy chain variable region CDR3 comprising amino acids having the sequence set forth in SEQ ID NO: 180;

(iv) a light chain variable region CDR1 comprising amino acids having the sequence set forth in SEQ ID NO: 181;

(v) a light chain variable region CDR2 comprising amino acids having the sequence set forth in SEQ ID NO:182; and (vi) a light chain variable region CDR3 comprising amino acids having the sequence set forth in SEQ ID NO: 183.

In certain embodiments, the antibody comprises:

(i) a heavy chain variable region CDR1 comprising amino acids having the sequence set forth in SEQ ID NO: 184;

(ii) a heavy chain variable region CDR2 comprising amino acids having the sequence set forth in SEQ ID NO: 185;

(iii) a heavy chain variable region CDR3 comprising amino acids having the sequence set forth in SEQ ID NO: 186;

(iv) a light chain variable region CDR1 comprising amino acids having the sequence set forth in SEQ ID NO: 187;

(v) a light chain variable region CDR2 comprising amino acids having the sequence set forth in SEQ ID NO:188; and (vi) a light chain variable region CDR3 comprising amino acids having the sequence set forth in SEQ ID NO: 189.

In certain embodiments, the antibody comprises:

(i) a heavy chain variable region CDR1 comprising amino acids having the sequence set forth in SEQ ID NO: 190;

(ii) a heavy chain variable region CDR2 comprising amino acids having the sequence set forth in SEQ ID NO: 191;

(iii) a heavy chain variable region CDR3 comprising amino acids having the sequence set forth in SEQ ID NO: 192;

(iv) a light chain variable region CDR1 comprising amino acids having the sequence set forth in SEQ ID NO: 193;

(v) a light chain variable region CDR2 comprising amino acids having the sequence set forth in SEQ ID NO:194; and (vi) a light chain variable region CDR3 comprising amino acids having the sequence set forth in SEQ ID NO: 195.

In certain embodiments, the antibody comprises:

(i) a heavy chain variable region CDR1 comprising amino acids having the sequence set forth in SEQ ID NO: 196;

(ii) a heavy chain variable region CDR2 comprising amino acids having the sequence set forth in SEQ ID NO: 197;

(iii) a heavy chain variable region CDR3 comprising amino acids having the sequence set forth in SEQ ID NO: 198;

(iv) a light chain variable region CDR1 comprising amino acids having the sequence set forth in SEQ ID NO: 199;

(xxii) a light chain variable region CDR2 comprising amino acids having the sequence set forth in SEQ ID NO:200; and (vi) a light chain variable region CDR3 comprising amino acids having the sequence set forth in SEQ ID NO: 201.

In certain embodiments, the antibody comprises:

(i) a heavy chain variable region CDR1 comprising amino acids having the sequence set forth in SEQ ID NO: 202;

(ii) a heavy chain variable region CDR2 comprising amino acids having the sequence set forth in SEQ ID NO: 203;

(iii) a heavy chain variable region CDR3 comprising amino acids having the sequence set forth in SEQ ID NO: 204;

(iv) a light chain variable region CDR1 comprising amino acids having the sequence set forth in SEQ ID NO: 205;

(xxii) a light chain variable region CDR2 comprising amino acids having the sequence set forth in SEQ ID NO:206; and (vi) a light chain variable region CDR3 comprising amino acids having the sequence set forth in SEQ ID NO: 207.

In certain embodiments, the antibody comprises:

(i) a heavy chain variable region CDR1 comprising amino acids having the sequence set forth in SEQ ID NO: 208;

(ii) a heavy chain variable region CDR2 comprising amino acids having the sequence set forth in SEQ ID NO: 209;

(iii) a heavy chain variable region CDR3 comprising amino acids having the sequence set forth in SEQ ID NO: 210;

(iv) a light chain variable region CDR1 comprising amino acids having the sequence set forth in SEQ ID NO: 211;

(xxii) a light chain variable region CDR2 comprising amino acids having the sequence set forth in SEQ ID NO:212; and (vi) a light chain variable region CDR3 comprising amino acids having the sequence set forth in SEQ ID NO: 213.

In certain embodiments, the antibody comprises:

(i) a heavy chain variable region CDR1 comprising amino acids having the sequence set forth in SEQ ID NO: 214;

(ii) a heavy chain variable region CDR2 comprising amino acids having the sequence set forth in SEQ ID NO: 215;

(iii) a heavy chain variable region CDR3 comprising amino acids having the sequence set forth in SEQ ID NO: 216;

(iv) a light chain variable region CDR1 comprising amino acids having the sequence set forth in SEQ ID NO: 217;

(xxii) a light chain variable region CDR2 comprising amino acids having the sequence set forth in SEQ ID NO:218; and (vi) a light chain variable region CDR3 comprising amino acids having the sequence set forth in SEQ ID NO: 219.

In certain embodiments, the antibody comprises:

(i) a heavy chain variable region CDR1 comprising amino acids having the sequence set forth in SEQ ID NO: 220;

(ii) a heavy chain variable region CDR2 comprising amino acids having the sequence set forth in SEQ ID NO: 221;

(iii) a heavy chain variable region CDR3 comprising amino acids having the sequence set forth in SEQ ID NO: 222;

(iv) a light chain variable region CDR1 comprising amino acids having the sequence set forth in SEQ ID NO: 223;

(xxii) a light chain variable region CDR2 comprising amino acids having the sequence set forth in SEQ ID NO:224; and (vi) a light chain variable region CDR3 comprising amino acids having the sequence set forth in SEQ ID NO: 225.

In certain embodiments, the antibody comprises:

(i) a heavy chain variable region CDR1 comprising amino acids having the sequence set forth in SEQ ID NO: 226;

(ii) a heavy chain variable region CDR2 comprising amino acids having the sequence set forth in SEQ ID NO: 227;

(iii) a heavy chain variable region CDR3 comprising amino acids having the sequence set forth in SEQ ID NO: 228;

(iv) a light chain variable region CDR1 comprising amino acids having the sequence set forth in SEQ ID NO: 229;

(xxii) a light chain variable region CDR2 comprising amino acids having the sequence set forth in SEQ ID NO:230; and (vi) a light chain variable region CDR3 comprising amino acids having the sequence set forth in SEQ ID NO: 231.

In certain embodiments, the antibody comprises:

(i) a heavy chain variable region CDR1 comprising amino acids having the sequence set forth in SEQ ID NO: 232;

(ii) a heavy chain variable region CDR2 comprising amino acids having the sequence set forth in SEQ ID NO: 233;

(iii) a heavy chain variable region CDR3 comprising amino acids having the sequence set forth in SEQ ID NO: 234;

(iv) a light chain variable region CDR1 comprising amino acids having the sequence set forth in SEQ ID NO: 235;

(xxii) a light chain variable region CDR2 comprising amino acids having the sequence set forth in SEQ ID NO:236; and (vi) a light chain variable region CDR3 comprising amino acids having the sequence set forth in SEQ ID NO: 237.

In certain embodiments, the antibody comprises:

(i) a heavy chain variable region CDR1 comprising amino acids having the sequence set forth in SEQ ID NO: 238;

(ii) a heavy chain variable region CDR2 comprising amino acids having the sequence set forth in SEQ ID NO: 239;

(iii) a heavy chain variable region CDR3 comprising amino acids having the sequence set forth in SEQ ID NO: 240;

(iv) a light chain variable region CDR1 comprising amino acids having the sequence set forth in SEQ ID NO: 241;

(xxii) a light chain variable region CDR2 comprising amino acids having the sequence set forth in SEQ ID NO:242; and (vi) a light chain variable region CDR3 comprising amino acids having the sequence set forth in SEQ ID NO: 243.

In certain embodiments, the antibody comprises:

(i) a heavy chain variable region CDR1 comprising amino acids having the sequence set forth in SEQ ID NO: 244;

(ii) a heavy chain variable region CDR2 comprising amino acids having the sequence set forth in SEQ ID NO: 245;

(iii) a heavy chain variable region CDR3 comprising amino acids having the sequence set forth in SEQ ID NO: 246;

(iv) a light chain variable region CDR1 comprising amino acids having the sequence set forth in SEQ ID NO: 247;

(xxii) a light chain variable region CDR2 comprising amino acids having the sequence set forth in SEQ ID NO:248; and (vi) a light chain variable region CDR3 comprising amino acids having the sequence set forth in SEQ ID NO: 249.

In certain embodiments, the antibody comprises:

(i) a heavy chain variable region CDR1 comprising amino acids having the sequence set forth in SEQ ID NO: 250;

(ii) a heavy chain variable region CDR2 comprising amino acids having the sequence set forth in SEQ ID NO: 251;

(iii) a heavy chain variable region CDR3 comprising amino acids having the sequence set forth in SEQ ID NO: 252;

(iv) a light chain variable region CDR1 comprising amino acids having the sequence set forth in SEQ ID NO: 253;

(xxii) a light chain variable region CDR2 comprising amino acids having the sequence set forth in SEQ ID NO:254; and (vi) a light chain variable region CDR3 comprising amino acids having the sequence set forth in SEQ ID NO: 255.

In certain embodiments, the antibody comprises:

(i) a heavy chain variable region CDR1 comprising amino acids having the sequence set forth in SEQ ID NO: 256;

(ii) a heavy chain variable region CDR2 comprising amino acids having the sequence set forth in SEQ ID NO: 257;

(iii) a heavy chain variable region CDR3 comprising amino acids having the sequence set forth in SEQ ID NO: 258;

(iv) a light chain variable region CDR1 comprising amino acids having the sequence set forth in SEQ ID NO: 259;

(xxii) a light chain variable region CDR2 comprising amino acids having the sequence set forth in SEQ ID NO:260; and (vi) a light chain variable region CDR3 comprising amino acids having the sequence set forth in SEQ ID NO: 261.

In certain embodiments, the antibody comprises:

(i) a heavy chain variable region CDR1 comprising amino acids having the sequence set forth in SEQ ID NO: 262;

(ii) a heavy chain variable region CDR2 comprising amino acids having the sequence set forth in SEQ ID NO: 263;

(iii) a heavy chain variable region CDR3 comprising amino acids having the sequence set forth in SEQ ID NO: 264;

(iv) a light chain variable region CDR1 comprising amino acids having the sequence set forth in SEQ ID NO: 265;

(xxii) a light chain variable region CDR2 comprising amino acids having the sequence set forth in SEQ ID NO:266; and (vi) a light chain variable region CDR3 comprising amino acids having the sequence set forth in SEQ ID NO: 267.

In certain embodiments, the antibody comprises:

(i) a heavy chain variable region CDR1 comprising amino acids having the sequence set forth in SEQ ID NO: 268;

(ii) a heavy chain variable region CDR2 comprising amino acids having the sequence set forth in SEQ ID NO: 269;

(iii) a heavy chain variable region CDR3 comprising amino acids having the sequence set forth in SEQ ID NO: 270;

(iv) a light chain variable region CDR1 comprising amino acids having the sequence set forth in SEQ ID NO: 271;

(xxii) a light chain variable region CDR2 comprising amino acids having the sequence set forth in SEQ ID NO:272; and (vi) a light chain variable region CDR3 comprising amino acids having the sequence set forth in SEQ ID NO: 273.

In certain embodiments, the antibody comprises:

(i) a heavy chain variable region CDR1 comprising amino acids having the sequence set forth in SEQ ID NO: 280;

(ii) a heavy chain variable region CDR2 comprising amino acids having the sequence set forth in SEQ ID NO: 281;

(iii) a heavy chain variable region CDR3 comprising amino acids having the sequence set forth in SEQ ID NO: 282;

(iv) a light chain variable region CDR1 comprising amino acids having the sequence set forth in SEQ ID NO: 283;

(xxii) a light chain variable region CDR2 comprising amino acids having the sequence set forth in SEQ ID NO:284; and (vi) a light chain variable region CDR3 comprising amino acids having the sequence set forth in SEQ ID NO: 285.

In certain embodiments, the antibody comprises:

(i) a heavy chain variable region CDR1 comprising amino acids having the sequence set forth in SEQ ID NO: 292;

(ii) a heavy chain variable region CDR2 comprising amino acids having the sequence set forth in SEQ ID NO: 293;

(iii) a heavy chain variable region CDR3 comprising amino acids having the sequence set forth in SEQ ID NO: 294;

(iv) a light chain variable region CDR1 comprising amino acids having the sequence set forth in SEQ ID NO: 295;

(xxii) a light chain variable region CDR2 comprising amino acids having the sequence set forth in SEQ ID NO:296; and (vi) a light chain variable region CDR3 comprising amino acids having the sequence set forth in SEQ ID NO: 297.

In certain embodiments, the antibody comprises:

(i) a heavy chain variable region CDR1 comprising amino acids having the sequence set forth in SEQ ID NO: 303;

(ii) a heavy chain variable region CDR2 comprising amino acids having the sequence set forth in SEQ ID NO: 304;

(iii) a heavy chain variable region CDR3 comprising amino acids having the sequence set forth in SEQ ID NO: 305;

(iv) a light chain variable region CDR1 comprising amino acids having the sequence set forth in SEQ ID NO: 306;

(xxii) a light chain variable region CDR2 comprising amino acids having the sequence set forth in SEQ ID NO: 307; and (vi) a light chain variable region CDR3 comprising amino acids having the sequence set forth in SEQ ID NO: 308.

In certain embodiments, the antibody comprises:

(i) a heavy chain variable region CDR1 comprising amino acids having the sequence set forth in SEQ ID NO: 316;

(ii) a heavy chain variable region CDR2 comprising amino acids having the sequence set forth in SEQ ID NO: 317;

(iii) a heavy chain variable region CDR3 comprising amino acids having the sequence set forth in SEQ ID NO: 318;

(iv) a light chain variable region CDR1 comprising amino acids having the sequence set forth in SEQ ID NO: 319;

(xxii) a light chain variable region CDR2 comprising amino acids having the sequence set forth in SEQ ID NO: 320; and (vi) a light chain variable region CDR3 comprising amino acids having the sequence set forth in SEQ ID NO: 321.

In certain embodiments, the antibody comprises:

(i) a heavy chain variable region CDR1 comprising amino acids having the sequence set forth in SEQ ID NO: 328;

(ii) a heavy chain variable region CDR2 comprising amino acids having the sequence set forth in SEQ ID NO: 329;

(iii) a heavy chain variable region CDR3 comprising amino acids having the sequence set forth in SEQ ID NO: 330;

(iv) a light chain variable region CDR1 comprising amino acids having the sequence set forth in SEQ ID NO: 331;

(xxii) a light chain variable region CDR2 comprising amino acids having the sequence set forth in SEQ ID NO: 332; and (vi) a light chain variable region CDR3 comprising amino acids having the sequence set forth in SEQ ID NO: 333.

In certain embodiments, the antibody comprises:

(i) a heavy chain variable region CDR1 comprising amino acids having the sequence set forth in SEQ ID NO: 340;

(ii) a heavy chain variable region CDR2 comprising amino acids having the sequence set forth in SEQ ID NO: 341;

(iii) a heavy chain variable region CDR3 comprising amino acids having the sequence set forth in SEQ ID NO: 342;

(iv) a light chain variable region CDR1 comprising amino acids having the sequence set forth in SEQ ID NO: 343;

(xxii) a light chain variable region CDR2 comprising amino acids having the sequence set forth in SEQ ID NO: 344; and (vi) a light chain variable region CDR3 comprising amino acids having the sequence set forth in SEQ ID NO: 345.

In certain embodiments, the antibody comprises:

(i) a heavy chain variable region CDR1 comprising amino acids having the sequence set forth in SEQ ID NO: 352;

(ii) a heavy chain variable region CDR2 comprising amino acids having the sequence set forth in SEQ ID NO: 353;

(iii) a heavy chain variable region CDR3 comprising amino acids having the sequence set forth in SEQ ID NO: 354;

(iv) a light chain variable region CDR1 comprising amino acids having the sequence set forth in SEQ ID NO: 355;

(xxii) a light chain variable region CDR2 comprising amino acids having the sequence set forth in SEQ ID NO: 356; and (vi) a light chain variable region CDR3 comprising amino acids having the sequence set forth in SEQ ID NO: 357.

The constant region/framework region of the anti-GPRC5D antibodies disclosed herein can be altered, for example, by amino acid substitution, to modify the properties of the antibody (e.g., to increase or decrease one or more of: antigen binding affinity, Fc receptor binding, antibody carbohydrate, for example, glycosylation, fucosylation etc, the number of cysteine residues, effector cell function, effector cell function, complement function or introduction of a conjugation site).

In certain embodiments, a presently disclosed anti-GPRC5D antibody is a fully-human antibody, e.g., any one of ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033. Fully-human mAbs are preferred for therapeutic use in humans because murine antibodies cause an immunogenicity reaction, known as the HAMA (human anti-mouse antibodies) response (Azinovic I, et al. Survival benefit associated with human anti-mouse antibody (HAMA) in patients with B-cell malignancies. Cancer Immunol Immunother 2006; 55(12):1451-8; Tjandra J J, et al. Development of human anti-murine antibody (HAMA) response in patients. Immunol Cell Biol 1990; 68(6):367-76), when administered to humans, causing serious side effects, including anaphylaxis and hypersensitivity reactions. This immunogenicity reaction is triggered by the human immune system recognizing the murine antibodies as foreign because of slightly different amino acid sequences from natural human antibodies. Humanization methods known in the art (Riechmann L, et al. Reshaping human antibodies for therapy. Nature 1988; 332 (6162): 332:323; Queen C, et al. A humanized antibody that binds to the interleukin 2 receptor. Proc Natl Acad Sci USA 1989; 86 (24): 10029-33) can be employed to reduce the immunogenicity of murine-derived antibodies (Gerd R, et al. Serological Analysis of Human Anti-Human Antibody Responses in Colon Cancer Patients Treated with Repeated Doses of Humanized Monoclonal Antibody A33. Cancer Res 2001; 61, 6851-6859).

The use of phage display libraries has made it possible to select large numbers of Ab repertoires for unique and rare Abs against very defined epitopes (for more details on phage display see McCafferty et al., Phage antibodies: filamentous phage displaying antibody variable domains. Nature, 348: 552-554.) The rapid identification of human Fab or single chain Fv (ScFV) fragments highly specific for tumor antigen-derived peptide-MHC complex molecules has thus become possible (19-22). Recently, immuno-toxins, generated by fusing TCR-like Fab specific for melanoma Ag MART-1 26-35/A2 or gp100 280-288/A2 to a truncated form of *Pseudomonas* endotoxin, have been shown to inhibit human melanoma growth both in vitro and in vivo (Klechevsky E, et al. Antitumor activity of immunotoxins with T-cell receptor-like specificity against human melanoma xenografts. Cancer Res 2008; 68 (15): 6360-6367). In addition, by engineering full-length mAb using the Fab fragments, it is possible to directly generate a therapeutic human mAb, bypassing months of time-consuming work, normally needed for developing therapeutic mAbs. The presently disclosed subject matter involves the development of a fully human mAb that recognizes, for example, a human GPRC5D polypeptide (e.g., a polypeptide having the amino acid sequence set forth in SEQ ID NO:97) for cancer therapy.

3. Homologous Antibodies

In certain embodiments, an antibody of the presently disclosed subject matter comprises heavy and light chain variable regions comprising amino acid sequences that are homologous to the amino acid sequences of the antibodies described herein (e.g., ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 antibodies), and wherein the antibodies retain the desired functional properties of the anti-PGPRC5D antibodies of the presently disclosed subject matter.

For example, the presently disclosed subject matter provides an isolated antibody, or antigen-binding portion thereof, comprising a heavy chain variable region and a light chain variable region, wherein:

(a) the heavy chain variable region comprises an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOs: 1, 5, 9, 13, 17, 21, 25, 29, 33, 37, 41, 45, 49, 53, 57, 61, 65, 69, 73, 77, 81, 85, 89, 93, 274, 286, 298, 310, 322, 334, 346 and 358; and (b) the light chain variable region comprises an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NOs: 2, 6, 10, 14, 18, 22, 26, 30, 34, 38, 42, 46, 50, 54, 58, 62, 66, 70, 74, 78, 82, 86, 90, 94, 275, 287, 299, 311, 323, 335, 347 and 359; and the antibody binds to human GPRC5D with a $K_d$ of $1\times10^{-7}$ M or less.

In certain embodiments, the $V_H$ and/or $V_L$ amino acid sequences can be at least 80%, 81%, 82%, 83%, 84%, 85%, 86%, 87%, 88%, 89%, 90%, 91%, 92%, 93%, 94%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis), followed by testing of the encoded altered antibody for retained function (i.e., the binding affinity) using the binding assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent homology between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the presently disclosed subject matter can further be used as a "query sequence" to perform a search against public databases to, for example, identify related sequences. Such searches can be performed using the XBLAST program (version 2.0) of Altschul, et al. (1990) J. Mol. Biol. 215: 403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. (See www.ncbi.nlm.nih.gov).

4. Antibodies with Conservative Modifications

In certain embodiments, an antibody of the presently disclosed subject matter comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 antibodies), or conservative modifications thereof, and wherein the antibodies retain the desired functional properties of the anti-GPRC5D antibodies of the presently disclosed subject matter.

The presently disclosed subject matter provides an isolated antibody, or antigen-binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs: 126, 132, 138, 144, 150, 156, 162, 168, 174, 180, 186, 192, 198, 204, 210, 216, 222, 228, 234, 240, 246, 252, 258, 264, 270, 282, 294, 305, 318, 330, 342 and 354, and conservative modifications thereof;

(b) the light chain variable region CDR3 sequence comprises an amino acid sequence selected from the group consisting of amino acid sequence of SEQ ID NOs: 129, 135, 141, 147, 153, 159, 165, 171, 177, 183, 189, 195, 201, 207, 213, 219, 225, 231, 237, 243, 249, 255, 261, 267, 273, 285, 297, 308, 321, 333, 345 and 357, and 431, and conservative modifications thereof; and the antibody exhibits binds to human GPRC5D with a $K_d$ of $1 \times 10^{-7}$ M or less.

In certain embodiments, the heavy chain variable region CDR2 sequence comprises an amino acid sequence selected from the group consisting of amino acid sequences of SEQ ID NOs: 125, 131, 137, 143, 149, 155, 161, 167, 173, 179, 185, 191, 197, 203, 209, 215, 221, 227, 233, 239, 245, 251, 257, 263, 269, 281, 293, 304, 317, 329, 341 and 353, and conservative modifications thereof; and the light chain variable region CDR2 sequence comprises an amino acid sequence selected from the group consisting of amino acid sequences of SEQ ID NOs: 128, 134, 140, 146, 152, 158, 164, 170, 176, 182, 188, 194, 200, 206, 212, 218, 224, 230, 236, 242, 248, 254, 260, 266, 272, 284, 296, 307, 320, 332, 344 and 356, and conservative modifications thereof.

In certain embodiments, the heavy chain variable region CDR1 sequence comprises an amino acid sequence selected from the group consisting of amino acid sequences of SEQ ID NOs: 124, 130, 136, 142, 148, 154, 160, 166, 172, 178, 184, 190, 196, 202, 208, 214, 220, 226, 232, 238, 244, 250, 256, 262, 268, 280, 292, 303, 316, 328, 340 and 352, and conservative modifications thereof; and the light chain variable region CDR1 sequence comprises an amino acid sequence selected from the group consisting of amino acid sequences of SEQ ID NOs: 127, 133, 139, 145, 151, 157, 163, 169, 175, 181, 187, 193, 199, 205, 211, 217, 223, 229, 235, 241, 247, 253, 259, 265, 271, 283, 295, 306, 319, 331, 343 and 355, and conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis.

Conservative amino acid substitutions are ones in which the amino acid residue is replaced with an amino acid residue having a similar side chain. Families of amino acid residues having similar side chains have been defined in the art. Exemplary conservative amino acid substitutions are shown in Table 33. Amino acid substitutions may be introduced into an antibody of interest and the products screened for a desired activity, e.g., retained/improved antigen binding, decreased immunogenicity, or improved ADCC or CDC. In certain embodiments, a sequence disclosed herein, e.g., a CDR sequence, a $V_H$ sequence or a $V_L$ sequence, can have up to about one, up to about two, up to about three, up to about four, up to about five, up to about six, up to about seven, up to about eight, up to about nine or up to about ten amino acid residues that are modified and/or substituted.

TABLE 33

| Original Residue | Exemplary conservative amino acid Substitutions |
| --- | --- |
| Ala (A) | Val; Leu; Ile |
| Arg (R) | Lys; Gln; Asn |
| Asn (N) | Gln; His; Asp, Lys; Arg |

137

TABLE 33-continued

| Original Residue | Exemplary conservative amino acid Substitutions |
|---|---|
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe |
| Leu (xii) | Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (xxiii) | Tyr; Phe |
| Tyr (Y) | Trp; Phe; Thr; Ser |
| Val (V) | Ile; Leu; Met; Phe; Ala |

Amino acids may be grouped according to common side-chain properties:

hydrophobic: Norleucine, Met, Ala, Val, Leu, Ile;

neutral hydrophilic: Cys, Ser, Thr, Asn, Gln;

acidic: Asp, Glu;

basic: His, Lys, Arg;

residues that influence chain orientation: Gly, Pro;

aromatic: Trp, Tyr, Phe.

Non-conservative substitutions will entail exchanging a member of one of these classes for another class.

5. Anti-GPRC5D Antibodies that Cross-Compete for Binding to GPRC5D with Anti-GPRC5D Antibodies of the Invention The presently disclosed subject matter provides antibodies that cross-compete with any of the disclosed anti-GPRC5D antibodies for binding to GPRC5D (e.g., human GPRC5D). For example, and not by way of limitation, the cross-competing antibodies can bind to the same epitope region, e.g., same epitope, adjacent epitope, or overlapping as any of the anti-GPRC5D antibodies of the presently disclosed subject matter. In certain embodiments, the reference antibody for cross-competition studies can be any one of the anti-GPRC5D antibodies disclosed herein, e.g., ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 antibodies.

In certain embodiments, the cross-competing antibody binds to an epitope region comprising amino acids 14-22 of SEQ ID NO: 97. In certain embodiments, the cross-competing antibody binds to one, two, three, four, five, six, or seven epitope regions selected from the group consisting of amino acids 5-17, 10-17, 1-27, 15-23, 16-23, 16-25, 85-93, 85-95, 145-167, 157-164, 157-167, 226-239, 230-237, 229-237, 230-243 and 227-237 of SEQ ID NO: 97.

Such cross-competing antibodies can be identified based on their ability to cross-compete with any one of the presently disclosed anti-GPRC5D antibodies in standard GPRC5D binding assays. For example, Biacore® analysis, ELISA assays or flow cytometry can be used to demonstrate cross-competition with the antibodies of the presently disclosed subject matter. The ability of a test antibody to inhibit the binding of, for example, any one of the presently disclosed GPRC5D antibodies (e.g., ET150-153, ET150-166, ET150-170, ET150-171, ET150-175, ET150-154, ET150-156, ET150-157, ET150-159, ET150-160, ET150-161, ET150-162, ET150-163, ET150-151, ET150-152, ET150-155, ET150-158, ET150-168, ET150-165, ET150-167, ET150-169, ET150-172, ET150-173, ET150-024, ET150-026, ET150-028, ET150-029, ET150-030, ET150-031, ET150-032 and ET150-033 antibodies) to human GPRC5D demonstrates that the test antibody can compete with any one of the presently disclosed anti-GPRC5D antibodies for binding to human GPRC5D and thus binds to the same epitope region on human GPRC5D as any one of the presently disclosed anti-GPRC5D antibodies. In certain embodiments, the cross-competing antibody binds to the same epitope on human GPRC5D as any one of the presently disclosed anti-GPRC5D antibodies.

6. Characterization of Antibody Binding to Antigen

Antibodies of the presently disclosed subject can be tested for binding to GPRC5D by, for example, standard ELISA. To determine if the selected anti-GPRC5D antibodies bind to unique epitopes, each antibody can be biotinylated using commercially available reagents (Pierce, Rockford, IL). Competition studies using unlabeled monoclonal antibodies and biotinylated monoclonal antibodies can be performed using GPRC5D coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. Anti-GPRC5D human IgGs can be further tested for reactivity with GPRC5D antigen by Western blotting.

In certain embodiments, $K_d$ is measured by a radiolabeled antigen binding assay (RIA). In certain embodiments, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)).

In certain embodiments, $K_d$ is measured using a BIA-CORE® surface plasmon resonance assay. For example, an assay using a BIACORE®-2000 or a BIACORE®-3000 (BIAcore®, Inc., Piscataway, NJ).

Epitope Mapping

In certain embodiments, the antibody or an antigen-binding fragment thereof binds to a human GPRC5D polypeptide comprising the amino acid sequence set forth in SEQ ID NO: 97. In certain embodiments, the antibody or an antigen-binding fragment thereof binds to one, two, three or four of N-terminal region (amino acids 1-27 of SEQ ID NO:97), ECL1 region (amino acids 85-93 of SEQ ID NO:97), ECL2 region (amino acids 145-167 of SEQ ID NO:97), and ECL3 region (amino acids 226-239 of SEQ ID NO:97). In certain embodiments, an antibody or an antigen-binding fragment thereof of the presently disclosed subject matter binds to an epitope region in the N-terminal region, including, but not limited to, an epitope region comprising amino acids 16-23 of SEQ ID NO:97, and an epitope region comprising amino acids 10-17 of SEQ ID NO:97. In certain embodiments, the epitope region in the N-terminal region comprises amino acids 15-23 of SEQ ID NO:97. In certain embodiments, the epitope region in the N-terminal region comprises amino acids 16-25 of SEQ ID NO:97. In certain embodiments, the epitope region in the N-terminal region comprises amino acids 10-17 of SEQ ID NO:97. In certain embodiments, the epitope region in the N-terminal region comprises amino acids 5-17 of SEQ ID NO:97.

In certain embodiments, an antibody or an antigen-binding fragment thereof of the presently disclosed subject matter binds to an epitope region in the ECL1 region, including, but not limited to, an epitope region comprising amino acids 85-95 of SEQ ID NO:97.

In certain embodiments, an antibody or an antigen-binding fragment thereof of the presently disclosed subject matter binds to an epitope region in the ECL2 region, including, but not limited to, an epitope region comprising amino acids 157-164 of SEQ ID NO:97. In certain embodiments, the epitope region in the ECL2 region comprises amino acids 157-164 of SEQ ID NO:97. In certain embodiments, the epitope region in the ECL2 region comprises amino acids 157-167 of SEQ ID NO:97.

In certain embodiments, an antibody or an antigen-binding fragment thereof of the presently disclosed subject matter binds to an epitope region in the ECL3 region, including, but not limited to, an epitope region comprising amino acids 230-237 of SEQ ID NO:97. In certain embodiments, the epitope region in the ECL3 region comprises amino acids 229-237 of SEQ ID NO:97. In certain embodiments, the epitope region in the ECL3 region comprises amino acids 230-243 of SEQ ID NO:97. In certain embodiments, the epitope region in the ECL3 region comprises amino acids 227-237 of SEQ ID NO:97.

In certain embodiments, the antibody or an antigen-binding fragment thereof binds to an epitope region comprising amino acids 16-25 of SEQ ID NO:97, an epitope region comprising amino acids 157-164 of SEQ ID NO:97, and an epitope region comprising amino acids 229-237 of SEQ ID NO:97. For example, the antibody or an antigen-binding fragment thereof comprises a heavy chain variable region comprising amino acids having the sequence set forth in SEQ ID NO:57 and a light chain variable region comprising amino acids having the sequence set forth in SEQ ID NO:58, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the antibody or an antigen-binding fragment thereof is a scFv. In certain embodiments, the antibody or an antigen-binding fragment thereof is a scFv-Fc fusion protein or full length human IgG with $V_H$ and $V_L$ regions or CDRs selected from Table 15. In certain embodiments, the antibody or an antigen-binding fragment thereof comprises a $V_H$ Comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:57. In certain embodiments, the antibody or an antigen-binding fragment thereof comprises a $V_H$ comprising amino acids having the sequence set forth in SEQ ID NO:57. In certain embodiments, the antibody or an antigen-binding fragment thereof comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:58. In certain embodiments, the antibody or an antigen-binding fragment thereof comprises a $V_L$ comprising amino acids having the sequence set forth in SEQ ID NO:58. In certain embodiments, the antibody or an antigen-binding fragment thereof comprises a $V_H$ comprising amino acids having the sequence set forth in SEQ ID NO:57 and a $V_L$ comprising amino acids having the sequence set forth in SEQ ID NO:58. In certain embodiments, the antibody or an antigen-binding fragment thereof comprises a $V_H$ CDR1 comprising amino acids having the sequence set forth in SEQ ID NO:208 or conservative modifications thereof, a $V_H$ CDR2 comprising amino acids having the sequence set forth in SEQ ID NO: 209 or conservative modifications thereof, and a $V_H$ CDR3 comprising amino acids having the sequence set forth in SEQ ID NO: 210 or conservative modifications thereof. In certain embodiments, the antibody or an antigen-binding fragment thereof comprises a $V_L$ CDR1 comprising amino acids having the sequence set forth in SEQ ID NO: 211 or conservative modifications thereof, a $V_L$ CDR2 comprising amino acids having the sequence set forth in SEQ ID NO: 212 or conservative modifications thereof, and a $V_L$ CDR3 comprising amino acids having the sequence set forth in SEQ ID NO: 213 or conservative modifications thereof. In certain embodiments, the antibody or an antigen-binding fragment thereof comprises a $V_H$ CDR1 comprising amino acids having the sequence set forth in SEQ ID NO: 208 or conservative modifications thereof, a $V_H$ CDR2 comprising amino acids having the sequence set forth in SEQ ID NO: 209 or conservative modifications thereof, a $V_H$ CDR3 comprising amino acids having the sequence set forth in SEQ ID NO: 210 or conservative modifications thereof, a $V_L$ CDR1 comprising amino acids having the sequence set forth in SEQ ID NO: 211 or conservative modifications thereof, a $V_L$ CDR2 comprising amino acids having the sequence set forth in SEQ ID NO: 212 or conservative modifications thereof, and a $V_L$ CDR3 comprising amino acids having the sequence set forth in SEQ ID NO: 213 or conservative modifications thereof. In certain embodiments, the antibody or an antigen-binding fragment thereof comprises a $V_H$ CDR1 comprising amino acids having the sequence set forth in SEQ ID NO: 208, a $V_H$ CDR2 comprising amino acids having the sequence set forth in SEQ ID NO: 209, a $V_H$ CDR3 comprising amino acids having the sequence set forth in SEQ ID NO: 210, a $V_L$ CDR1 comprising amino acids having the sequence set forth in SEQ ID NO: 211, a $V_L$ CDR2 comprising amino acids having the sequence set forth in SEQ ID NO: 212, and a $V_L$ CDR3 comprising amino acids having the sequence set forth in SEQ ID NO: 213. In certain embodiments, the antibody or an antigen-binding fragment thereof is ET150-2 scFv (or ET150-152 scFv).

In certain embodiments, the antibody or an antigen-binding fragment thereof binds to an epitope region comprising amino acids 5-17 of SEQ ID NO:97, an epitope region comprising amino acids 85-95 of SEQ ID NO:97, and an epitope region comprising amino acids 157-164 of SEQ ID NO:97. For example, the antibody or an antigen-binding fragment thereof comprises a heavy chain variable region comprising amino acids having the sequence set forth in SEQ ID NO:61 and a light chain variable region comprising amino acids having the sequence set forth in SEQ ID NO:62, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the antibody or an antigen-binding fragment thereof is a scFv. In certain embodiments, the antibody or an antigen-binding fragment thereof is a scFv-Fc fusion protein or full length human IgG with $V_H$ and $V_L$ regions or CDRs selected from Table 16. In certain embodiments, the antibody or an antigen-binding fragment thereof comprises a $V_H$ Comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:61. In certain embodiments, the antibody or an antigen-binding fragment thereof comprises a $V_H$ comprising amino acids having the sequence set forth in SEQ ID NO:61. In certain embodiments, the antibody or an antigen-binding fragment thereof comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:62. In certain embodiments, the antibody or an antigen-binding fragment thereof comprises a $V_L$ comprising amino acids having the sequence set forth in SEQ ID NO:62. In certain embodiments, the antibody or an antigen-binding fragment thereof comprises a $V_H$ comprising amino acids having the sequence set forth in SEQ ID NO:61 and a $V_L$ comprising amino acids having the sequence set forth in SEQ ID NO:62. In certain embodiments certain embodiments, the antibody or an antigen-binding fragment thereof comprises a $V_H$ CDR1 comprising amino acids having the sequence set forth in SEQ ID NO:214 or conservative modifications thereof, a $V_H$ CDR2 comprising amino acids having the sequence set forth in SEQ ID NO: 215 or conservative modifications thereof, and a $V_H$ CDR3 comprising amino acids having the sequence set forth in SEQ ID NO: 216 or conservative modifications thereof. In certain embodiments, the antibody or an antigen-binding fragment thereof comprises a $V_L$ CDR1 comprising amino acids having the sequence set forth in SEQ ID NO: 217 or conservative modifications thereof, a $V_L$ CDR2 comprising amino acids having the sequence set forth in SEQ ID NO: 218 or conservative modifications thereof, and a $V_L$ CDR3 comprising amino acids having the sequence set forth in SEQ ID NO: 219 or conservative modifications thereof. In certain embodiments, the antibody or an antigen-binding fragment thereof comprises a $V_H$ CDR1 comprising amino acids having the sequence set forth in SEQ ID NO: 214 or conservative modifications thereof, a $V_H$ CDR2 comprising amino acids having the sequence set forth in SEQ ID NO: 215 or conservative modifications thereof, a $V_H$ CDR3 comprising amino acids having the sequence set forth in SEQ ID NO: 216 or conservative modifications thereof, a $V_L$ CDR1 comprising amino acids having the sequence set forth in SEQ ID NO: 217 or conservative modifications thereof, a $V_L$ CDR2 comprising amino acids having the sequence set forth in SEQ ID NO: 218 or conservative modifications thereof, and a $V_L$ CDR3 comprising amino acids having the sequence set forth in SEQ ID NO: 219 or conservative modifications thereof. In certain embodiments, the antibody or an antigen-binding fragment thereof comprises a $V_H$ CDR1 comprising amino acids having the sequence set forth in SEQ ID NO: 214, a $V_H$ CDR2 comprising amino acids having the sequence set forth in SEQ ID NO: 215, a $V_H$ CDR3 comprising amino acids having the sequence set forth in SEQ ID NO: 216, a $V_L$ CDR1 comprising amino acids having the sequence set forth in SEQ ID NO: 217, a $V_L$ CDR2 comprising amino acids having the sequence set forth in SEQ ID NO: 218 and a $V_L$ CDR3 comprising amino acids having the sequence set forth in SEQ ID NO: 219. In certain embodiments, the antibody or an antigen-binding fragment thereof is ET150-155 scFv (or ET150-5 scFv).

In certain embodiments, the antibody or an antigen-binding fragment thereof binds to an epitope region comprising amino acids 15-23 of SEQ ID NO:97, and an epitope region comprising amino acids 230-243 of SEQ ID NO:97. For example, the antibody or an antigen-binding fragment thereof comprises a heavy chain variable region comprising amino acids having the sequence set forth in SEQ ID NO:65 and a light chain variable region comprising amino acids having the sequence set forth in SEQ ID NO:66, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the antibody or an antigen-binding fragment thereof is a scFv. In certain embodiments, the antibody or an antigen-binding fragment thereof is a scFv-Fc fusion protein or full length human IgG with $V_H$ and $V_L$ regions or CDRs selected from Table 17. In certain embodiments, the antibody or an antigen-binding fragment thereof comprises a $V_H$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:65. In certain embodiments, the antibody or an antigen-binding fragment thereof comprises a $V_H$ comprising amino acids having the sequence set forth in SEQ ID NO:65. In certain embodiments, the antibody or an antigen-binding fragment thereof comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:66, as shown in Table 17. In certain embodiments, the antibody or an antigen-binding fragment thereof comprises a $V_L$ comprising amino acids having the sequence set forth in SEQ ID NO:66. In certain embodiments, the antibody or an antigen-binding fragment thereof comprises a $V_H$ Comprising amino acids having the sequence set forth in SEQ ID NO:65 and a $V_L$ comprising amino acids having the sequence set forth in SEQ ID NO:66. In certain embodiments, the antibody or an antigen-binding fragment thereof comprises a $V_H$ CDR1 comprising amino acids having the sequence set forth in SEQ ID NO:220 or conservative modifications thereof, a $V_H$ CDR2 comprising amino acids having the sequence set forth in SEQ ID NO: 221 or conservative modifications thereof, and a $V_H$ CDR3 comprising amino acids having the sequence set forth in SEQ ID NO: 222 or conservative modifications thereof. In certain embodiments, the antibody or an antigen-binding fragment thereof comprises a $V_L$ CDR1 comprising amino acids having the sequence set forth in SEQ ID NO: 223 or conservative modifications thereof, a $V_L$ CDR2 comprising amino acids having the sequence set forth in SEQ ID NO: 224 or conservative modifications thereof, and a $V_L$ CDR3 comprising amino acids having the sequence set forth in SEQ ID NO: 225 or conservative modifications thereof. In certain embodiments, the antibody or an antigen-binding fragment thereof comprises a $V_H$ CDR1 comprising amino acids having the sequence set forth in SEQ ID NO: 220 or conservative modifications thereof, a $V_H$ CDR2 comprising amino acids having the sequence set forth in SEQ ID NO: 221 or conservative modifications thereof, a $V_H$ CDR3 comprising amino acids having the sequence set forth in SEQ ID NO: 222 or conservative modifications thereof, a $V_L$ CDR1 comprising amino acids having the sequence set forth in SEQ ID NO: 223 or conservative modifications thereof, a $V_L$ CDR2 comprising amino acids having the sequence set forth in SEQ ID NO: 224 or conservative modifications thereof, and a $V_L$ CDR3 comprising amino acids having the sequence set forth in SEQ ID NO: 225 or conservative modifications thereof. In certain embodiments, the antibody or an antigen-binding fragment thereof comprises a $V_H$ CDR1 comprising amino acids having the sequence set forth in SEQ ID NO: 220, a $V_H$ CDR2 comprising amino acids having the sequence set forth in SEQ ID NO: 221, a $V_H$ CDR3 comprising amino acids having the sequence set forth in SEQ ID NO: 222, a $V_L$ CDR1 comprising amino acids having the sequence set forth in SEQ ID NO: 223, a $V_L$ CDR2 comprising amino acids having the sequence set forth in SEQ ID NO: 224, and a $V_L$ CDR3 comprising amino acids having the sequence set forth in SEQ ID NO: 225. In certain embodiments, the antibody or an antigen-binding fragment thereof is ET150-8 scFv (or ET150-158 scFv).

In certain embodiments, the antibody or an antigen-binding fragment thereof binds to an epitope region comprising amino acids 10-17 of SEQ ID NO:97, an epitope region comprising amino acids 157-167 of SEQ ID NO:97, and an epitope region comprising amino acids 227-237 of SEQ ID NO:97. For example, the antibody or an antigen-binding fragment thereof comprises a heavy chain variable region comprising amino acids having the sequence set forth in SEQ ID NO:69 and a light chain variable region comprising amino acids having the sequence set forth in SEQ ID NO:70, optionally with (iii) a linker sequence, for example a linker peptide, between the heavy chain variable region and the light chain variable region. In certain embodiments, the linker comprises amino acids having the sequence set forth in SEQ ID NO:98. In certain embodiments, the antibody or an antigen-binding fragment thereof is a scFv. In certain embodiments, the antibody or an antigen-binding fragment thereof is a scFv-Fc fusion protein or full length human IgG with $V_H$ and $V_L$ regions or CDRs selected from Table 18. In certain embodiments, the antibody or an antigen-binding fragment thereof comprises a $V_H$ Comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:69. In certain embodiments, the antibody or an antigen-binding fragment thereof comprises a $V_H$ comprising amino acids having the sequence set forth in SEQ ID NO:69. In certain embodiments, the antibody or an antigen-binding fragment thereof comprises a $V_L$ comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:70. In certain embodiments, the antibody or an antigen-binding fragment thereof comprises a $V_L$ comprising amino acids having the sequence set forth in SEQ ID NO:70. In certain embodiments, the antibody or an antigen-binding fragment thereof comprises a $V_H$ comprising amino acids having the sequence set forth in SEQ ID NO:69 and a $V_L$ comprising amino acids having the sequence set forth in SEQ ID NO:70. In certain embodiments, the antibody or an antigen-binding fragment thereof comprises a $V_H$ CDR1 comprising amino acids having the sequence set forth in SEQ ID NO:226 or conservative modifications thereof, a $V_H$ CDR2 comprising amino acids having the sequence set forth in SEQ ID NO: 227 or conservative modifications thereof, and a $V_H$ CDR3 comprising amino acids having the sequence set forth in SEQ ID NO: 228 or conservative modifications thereof. In certain embodiments, the antibody or an antigen-binding fragment thereof comprises a $V_L$ CDR1 comprising amino acids having the sequence set forth in SEQ ID NO: 229 or conservative modifications thereof, a $V_L$ CDR2 comprising amino acids having the sequence set forth in SEQ ID NO: 230 or conservative modifications thereof, and a $V_L$ CDR3 comprising amino acids having the sequence set forth in SEQ ID NO: 231 or conservative modifications thereof. In certain embodiments, the antibody or an antigen-binding fragment thereof comprises a $V_H$ CDR1 comprising amino acids having the sequence set forth in SEQ ID NO: 226 or conservative modifications thereof, a $V_H$ CDR2 comprising amino acids having the sequence set forth in SEQ ID NO: 227 or conservative modifications thereof, a $V_H$ CDR3 comprising amino acids having the sequence set forth in SEQ ID NO: 228 or conservative modifications thereof, a $V_L$ CDR1 comprising amino acids having the sequence set forth in SEQ ID NO: 229 or conservative modifications thereof, a $V_L$ CDR2 comprising amino acids having the sequence set forth in SEQ ID NO: 230 or conservative modifications thereof, and a $V_L$ CDR3 comprising amino acids having the sequence set forth in SEQ ID NO: 231 or conservative modifications thereof. In certain embodiments, the antibody or an antigen-binding fragment thereof comprises a $V_H$ CDR1 comprising amino acids having the sequence set forth in SEQ ID NO: 226, a $V_H$ CDR2 comprising amino acids having the sequence set forth in SEQ ID NO: 227, a $V_H$ CDR3 comprising amino acids having the sequence set forth in SEQ ID NO: 228, a $V_L$ CDR1 comprising amino acids having the sequence set forth in SEQ ID NO: 229, a $V_L$ CDR2 comprising amino acids having the sequence set forth in SEQ ID NO: 230, and a $V_L$ CDR3 comprising amino acids having the sequence set forth in SEQ ID NO: 231. In certain embodiments, the antibody or an antigen-binding fragment thereof is ET150-18 scFv (or ET150-168 scFv).

7. Immunoconjugates

The presently disclosed subject provides an anti-GPRC5D antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include Taxol® (such as ricin, diphtheria, gelonin), cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, calecheamicin, aureastatin, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an anti-GPRC5D antibody disclosed herein include duocarmycins, calicheamicins, maytansines and auristatins, and derivatives thereof. An example of a calicheamicin antibody conjugate is commercially available (MYLOTARG™ (Gemtuzumab ozogamicin); Wyeth-Ayerst).

Cytoxins can be conjugated to anti-GPRC5D antibody disclosed herein using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Anti-GPRC5D antibodies of the presently disclosed subject matter also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, $^{90}$Y, $^{131}$I, $^{225}$Ac, $^{213}$Bi, $^{223}$Ra and $^{227}$Th. Methods for preparing radioimmunoconjugates are established in the art. Examples of radioimmunoconjugates are commercially available, including ZEVALIN™ (Ibritumomab tiuxetan) (IDEC Pharmaceuticals) and BEXXAR™ (Tositumomab) (Corixa Pharmaceuticals), and similar methods can be used to prepare radioimmunoconjugates using the antibodies of the invention.

The antibody conjugates of the presently disclosed subject matter can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *Pseudomonas* exotoxin, or diphtheria toxin; a protein such as tumor necrosis factor (TNF) or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

8. Bispecific Molecules

The presently disclosed subject matter provides bispecific molecules comprising an anti-GPRC5D antibody, or a fragment thereof, disclosed herein. An antibody of the presently disclosed subject matter, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the presently disclosed subject matter can in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule, a presently disclosed anti-GPRC5D antibody can be functionally linked (e.g., by chemical coupling, genetic fusion, noncovalent association or otherwise) to one or more other binding molecules, such as another antibody, antibody fragment, peptide or binding mimetic, such that a bispecific molecule results.

The presently disclosed subject matter provides bispecific molecules comprising at least a first binding specificity for GPRC5D and a second binding specificity for a second target epitope. The second target epitope can be a GPRC5D epitope, or a non-GPRC5D epitope, e.g., a different antigen. In certain embodiments, the bispecific molecule is multispecific, the molecule can further include a third binding specificity. Where a first portion of a bispecific antibody binds to an antigen on a tumor cell for example and a second portion of a bispecific antibody recognizes an antigen on the surface of a human immune effector cell, the antibody is capable of recruiting the activity of that effector cell by specifically binding to the effector antigen on the human immune effector cell. In certain embodiments, bispecific antibodies, therefore, are able to form a link between effector cells, for example, T cells and tumor cells, thereby enhancing effector function. In certain embodiments, a bispecific antibody of the present disclosure comprises at least a first binding to GPRC5D and at least a second binding to an immune cell. For example, and not by way of limitation, a bispecific antibody of the present disclosure comprises at least a first binding to GPRC5D and at least a second binding to a receptor present on the surface of an immune cell, e.g., CD3.

The bispecific molecules of the presently disclosed subject matter can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5, 5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, IL).

When the binding specificities are antibodies, they can be conjugated via sulfhydryl bonding of the C-terminus hinge regions of the two heavy chains. In certain embodiments, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb x mAb, mAb x Fab, Fab x F(ab')₂ or ligand x Fab fusion protein.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a y counter or a scintillation counter or by autoradiography.

9. Selecting a High Affinity ScFv Against a GPRC5D Polypeptide

The next step is to the selection of phage that bind to the target antigen of interest with high affinity, from phage in a human phage display library that either does not bind or that binds with lower affinity. This is accomplished by iterative binding of phage to the antigen, which is bound to a solid support, for example, beads or mammalian cells followed by removal of non-bound phage and by elution of specifically bound phage. In certain embodiments, antigens are first biotinylated for immobilization to, for example, streptavidin-conjugated Dynabeads™ M-280. The phage library is incubated with the cells, beads or other solid support and non binding phage is removed by washing. Clones that bind are selected and tested.

Once selected, positive scFv clones are tested for their binding to GPRC5D (human GPRC5D) on live 3T3 cell surfaces by flow cytometry. Briefly, phage clones are incubated with 3T3 cells over-expressing GPRC5D. The cells are washed and then with a mouse anti-M13 coat protein mAb. Cells are washed again and labeled with a FITC-goat anti-mouse Ig prior to flow cytometry.

In other embodiments, the anti-GPRC5D antibodies can comprise one or more framework region amino acid substitutions designed to improve protein stability, antibody binding, expression levels or to introduce a site for conjugation of therapeutic agents. These scFv are then used to produce recombinant human monoclonal Igs in accordance with methods known to those of skill in the art.

10. Engineering Full Length mAb Using the Selected ScFv Fragments

Phage display technology allows for the rapid selection and production of antigen-specific scFv and Fab fragments, which are useful in and of themselves, or which can be further developed to provide complete antibodies, antigen binding proteins or antigen binding fragments thereof. Complete mAbs with Fc domains have a number of advantages over the scFv and Fab antibodies. First, only full length Abs exert immunological function such as CDC and ADCC mediated via Fc domain. Second, bivalent mAbs offer stronger antigen-binding affinity than monomeric Fab Abs. Third, plasma half-life and renal clearance will be different with the Fab and bivalent mAb. The particular features and advantages of each can be matched to the planned effector strategy. Fourth, bivalent mAb may be internalized at different rates than scFv and Fab, altering immune function or carrier function. Alpha emitters, for example, do not need to be internalized to kill the targets, but many drugs and toxins will benefit from internalization of the immune complex. In certain embodiments, therefore, once scFv clones specific for GPRC5D were obtained from phage display libraries, a full length IgG mAb using the scFv fragments was produced.

To produce recombinant human monoclonal IgG in Chinese hamster ovary (CHO) cells, a full length IgG mAb can be engineered based on a method known to those of skill in the art (Tomomatsu et al., Production of human monoclonal antibodies against FceRIa by a method combining in vitro immunization with phage display. Biosci Biotechnol Biochem 73(7): 1465-1469 2009). Briefly, antibody variable regions can be subcloned into mammalian expression vectors, with matching Lambda or Kappa light chain constant sequences and IgG1 subclass Fc (for example) (Lidija P, et al. An integrated vector system for the eukaryotic expression of antibodies or their fragments after selection from phage display libraries. Gene 1997; 187(1): 9-18; Lisa J H, et al. Crystallographic structure of an intact IgG1 monoclonal antibody. Journal of Molecular Biology 1998; 275 (5): 861-872). Kinetic binding analysis (Yasmina N A, et al. Probing the binding mechanism and affinity of tanezumab, a recombinant humanized anti-NGF monoclonal antibody, using a repertoire of biosensors. Protein Science 2008; 17(8): 1326-1335) can be used to confirm specific binding of full length IgG to GPRC5D, with a $K_D$ in nanomolar range.

Pharmaceutical Compositions and Methods of Treatment

Anti-GPRC5D antibodies of the presently disclosed subject matter can be administered for therapeutic treatments to a patient suffering from a tumor (e.g., multiple myeloma) in an amount sufficient to prevent, inhibit, or reduce the progression of the tumor. Progression includes, e.g, the growth, invasiveness, metastases and/or recurrence of the tumor. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition.

The identification of medical conditions treatable by anti-GPRC5D antibodies of the presently disclosed subject matter is well within the ability and knowledge of one skilled in the art. For example, human individuals who are either suffering from multiple myeloma or who are at risk of developing multiple myeloma are suitable for administration of the presently disclosed anti-GPRC5D antibodies. A clinician skilled in the art can readily determine, for example, by the use of clinical tests, physical examination and medical/family history, if an individual is a candidate for such treatment.

In certain embodiments, the presently disclosed subject matter provides a method of treating a tumor by administering a presently disclosed anti-GPRC5D antibody in combination with one or more other agents. For example, the presently disclosed subject matter provides a method of treating a tumor by administering a presently disclosed anti-GPRC5D antibody with an antineoplastic agent. The anti-GPRC5D antibody can be chemically or biosynthetically linked to one or more of the antineoplastic agents.

Non-limiting examples of suitable tumors include multiple myeloma and Waldenstrom's Macroglobulinemia. In certain embodiments, the tumor is multiple myeloma.

Any suitable method or route can be used to administer a presently disclosed anti-GPRC5D antibody, and optionally, to coadminister antineoplastic agents. Routes of administration include, for example, oral, intravenous, intraperitoneal, subcutaneous, or intramuscular administration. It should be emphasized, however, that the presently disclosed subject matter is not limited to any particular method or route of administration.

It is noted that presently disclosed anti-GPRC5D antibody can be administered as a conjugate, which binds specifically to the receptor and delivers a toxic, lethal payload following ligand-toxin internalization.

It is understood that anti-GPRC5D antibodies of the presently disclosed subject matter can be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the binding proteins. The compositions of the injection can, as is well known in the art, be formulated so as to provide quick, sustained or delayed release of the active ingredient after administration to the mammal.

The presently disclosed subject matter also provides use of antibodies and nucleic acids that encode them for treatment of a tumor (e.g., multiple myeloma), for diagnostic and prognostic applications as well as use as research tools for the detection of GPRC5D in cells and tissues. Pharmaceutical compositions comprising the disclosed antibodies and nucleic acids are encompassed by the presently disclosed subject matter. Vectors comprising the nucleic acids of the presently disclosed subject matter for antibody-based treatment by vectored immunotherapy are also contemplated by the presently disclosed subject matter. Vectors include expression vectors which enable the expression and secretion of antibodies, as well as vectors which are directed to cell surface expression of the antigen binding proteins, such as chimeric antigen receptors.

Cells comprising the nucleic acids, for example cells that have been transfected with the vectors of the invention are also encompassed by the presently disclosed subject matter.

Kits

The presently disclosed subject matter provides kits for the treatment or prevention of a tumor (e.g., multiple myeloma). In certain embodiments, the kit comprises a therapeutic composition containing an effective amount of an anti-GPRC5D antibody in unit dosage form. In certain embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the anti-GPRC5D antibody is provided together with instructions for administering the cell to a subject having or at risk of developing a tumor (e.g., multiple myeloma). The instructions will generally include information about the use of the composition for the treatment or prevention of a tumor (e.g., multiple myeloma). In other embodiments, the instructions include at least one of the following: description of the therapeutic agent; dosage schedule and administration for treatment or prevention of a neoplasia (e.g., multiple myeloma) or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Methods

Flow cytometry analysis. For cell surface staining, cells can be incubated with appropriate mAbs for 30 minutes on ice, washed, and incubated with secondary antibody reagents when necessary. Flow cytometry data can be collected on a FACS Calibur™ (Becton Dickinson) and analyzed with FlowJo™ V8.7.1 and 9.4.8 software.

Selection and characterization of scFv specific for GPRC5D. A human scFv antibody phage display library is used for the selection of mAb clones. In brief, biotinylated antigens can be first mixed with the human scFv phage library, then the antigen-scFv antibody complexes can be pulled down by streptavidin-conjugated Dynabeads™ M-280 through a magnetic rack. Bound clones can be then eluted and used to infect *E. coli* XL1-Blue. The scFv phage clones expressed in the bacteria can be purified (Yasmina N A, et al. Probing the binding mechanism and affinity of tanezumab, a recombinant humanized anti-NGF monoclonal antibody, using a repertoire of biosensors. Protein Science 2008; 17(8): 1326-1335; Roberts W K, et al. Vaccination with CD20 peptides induces a biologically active, specific immune response in mice. Blood 2002: 99 (10): 3748-3755). Panning can be performed for 3-4 cycles to enrich scFv phage clones binding to GPRC5D specifically. Positive clones can be determined by flow cytometry method against biotinylated single chain GPRC5D. Positive clones can be further tested for their binding to GPRC5D on live cell surfaces by flow cytometry, using a GPRC5D$^+$ cell line, 3T3. The cells can be washed, and the staining can be performed in following steps.

The cells can be first stained with purified scFv phage clones, and followed by staining with a mouse anti-M13 mAb, and finally the goat anti-mouse Ig's conjugate to FITC. Each step of the staining can be done between 30-60 minutes on ice and the cells were washed twice between each step of the staining.

Engineering full length mAb using the selected ScFv fragments. Full-length human IgG of the selected phage clones can be produced in HEK293 and Chinese hamster ovary (CHO) cell lines, as described (Caron P C, Class K, Laird W, Co M S, Queen C, Scheinberg D A. Engineered humanized dimeric forms of IgG are more effective antibodies. J Exp Med 176:1 191-1 195 (1992). In brief, antibody variable regions can be subcloned into mammalian expression vectors, with matching human lambda or kappa light chain constant region and human IgG constant region sequences. Molecular weight of the purified full length IgG antibodies can be measured under both reducing and non-reducing conditions by electrophoresis.

Characterization of the full-length human IgG for GPRC5D. Initially, specificities of the fully human IgG mAbs for the GPRC5D can be determined by staining 3T3 cells transduced to overexpress GPRC5D, followed by secondary goat anti-human IgG mAb conjugate to PE or FITC. The fluorescence intensity can be measured by flow cytometry. The same method can be used to determine the binding of the mAbs to fresh tumor cells and cell lines.

Antibody-dependent cellular cytotoxicity (ADCC). Target cells used for ADCC can be 3T3 cells over-expressing GPRC5D. Anti-GPRC5D antibody or its control human IgG at various concentrations can be incubated with target cells and fresh PBMCs at different effector:target (E:T) ratio for 16 hrs. The supernatant can be harvested and the cytotoxicity can be measured by LDH release assay using Cytotox 96™ nonradioactive kit from Promega following their instruction. Cytotoxicity can also be measured by standard 4 hours 51 Cr-release assay.

EXAMPLES

The following examples are put forth so as to provide those of ordinary skill in the art with a complete disclosure and description of how to make and use the antibodies, bispecific antibodies, compositions comprising thereof, screening, and therapeutic methods of the presently disclosed subject matter, and are not intended to limit the scope of what the inventors regard as their presently disclosed subject matter. It is understood that various other embodiments may be practiced, given the general description provided above.

Example 1—GPRC5D Expression in Various Tissues

Figure 2:
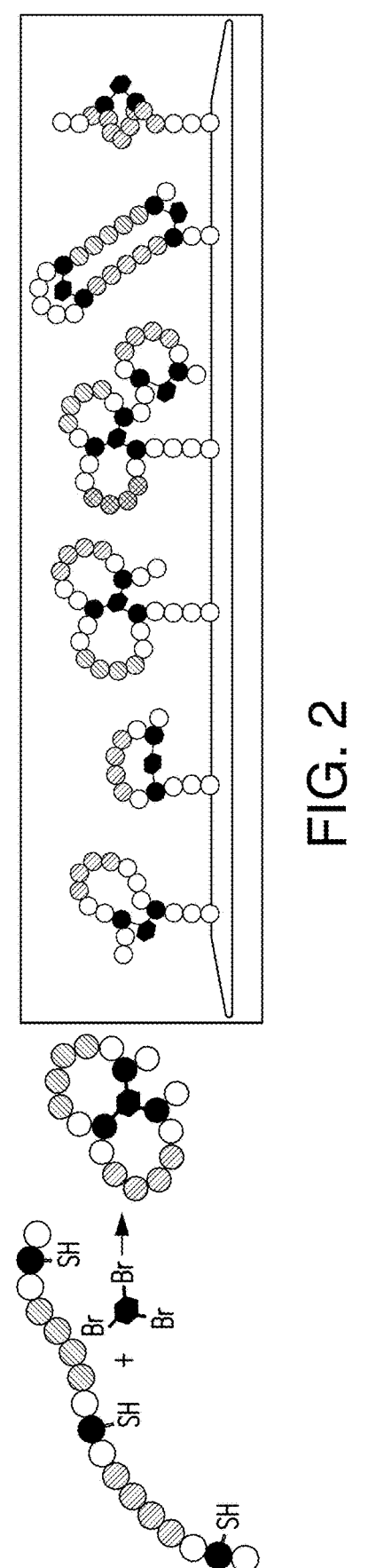
FIG. 2 illustrates the CLIPS™ technology. The CLIPS™ reaction takes place between bromo groups of the CLIPS™ scaffold and thiol sidechains of cysteines. The reaction is fast and specific under mild conditions. Using this elegant chemistry, native protein sequences are transformed into CLIPS™ constructs with a range of structures. From left to right: two different single T2 loops, T3 double loop, conjugated T2+T3 loops, stabilized beta sheet, and stabilized alpha helix (Timmerman et al., J. Mol. Recognit. 2007; 20: 283-29).

The expression of human GPRC5D was evaluated in various malignant and normal tissues by investigating gene expression profiles in databases such as the cancer cell line encyclopedia and BioGPS. As shown in FIG. 2, human GPRC5D was highly expressed in multiple myeloma, but not in other malignant tissues. Normal expression appeared limited to plasma cells. Potential GPRC5D targeted CAR T cell eradication of this normal cell type may not have significant adverse effects based on inventors' patient experience with CD19 targeted CAR T cells. Any lack of physiologic antibody production can be addressed with intravenous immunoglobulin treatment.

Example 2—Selection of ScFv Specific for GPRC5D Using a Fully Human Phage Display Library Phage display against GPRC5D was performed for 4 panning rounds to enrich the scFv phage clones binding to GPRC5D specifically. Four independent pannings with 12 different phage libraries were carried out against GPRC5D overexpressing 3T3 cells identifying 80 positive clones. Individual scFv phage clones positive for the GPRC5D were determined by ELISA and the clones that possessed unique DNA coding sequences were subjected to further characterization. To test if the ScFv bound to GPRC5D on live cells, the positive phage clones were tested for binding to a GPRC5D-positive cell line, 3T3. 72 positive clones were identified out of 80 clones screened FACS; the positive clone rate was 90%. After sequencing, 32 unique and GPRC5D-3T3 positive binding clones were found out of 72 sequenced positive clones; the unique clone rate was 45%.

Example 3—Epitope Mapping of Anti-GPRC5D Antibodies

Four anti-GPRC5D antibodies: ET150-2, ET150-5, ET150-8, and ET150-18 mIgG1. "mIgG1" used in all Examples represents that the variable region is fully human and the Fc part is mouse IgG1. See Table 34.

TABLE 34

| Name | Origin | Concentration | Location | Status |
|---|---|---|---|---|
| ET150-18 mIgG1 | mouse Fc | 1.1 mg/ml | +4° C./22 | ok |
| ET150-2 mIgG1 | mouse Fc | 0.66 mg/ml | +4° C./22 | ok |

TABLE 34-continued

| Name | Origin | Concentration | Location | Status |
|---|---|---|---|---|
| ET150-5 mIgG1 | mouse Fc | 1.9 mg/ml | +4° C./22 | ok |
| ET150-8 mIgG1 | mouse Fc | 2.9 mg/ml | +4° C./22 | ok |

The target protein is human GPRC5D having the amino acid sequence set forth in SEQ ID NO: 97. The N-terminal region of human GPRC5D has amino acids 1-27 of SEQ ID NO:97. The extracellular loop 1 (ECL1) region of human GPRC5D has amino acids 85-93 of SEQ ID NO:97. The extracellular loop 2 (ECL2) region of human GPRC5D has amino acids 145-167 of SEQ ID NO:97. The extracellular loop 3 (ECL3) region of human GPRC5D has amino acids 226-239 of SEQ ID NO:97.

Methods

The principles of CLIPS™ technology. CLIPS™ technology structurally fixes peptides into defined three-dimensional structures. This results in functional mimics of even the most complex binding sites. CLIPS™ technology is now routinely used to shape peptide libraries into single, double or triple looped structures as well as sheet- and helix-like folds (FIG. 2).

Figure 3:
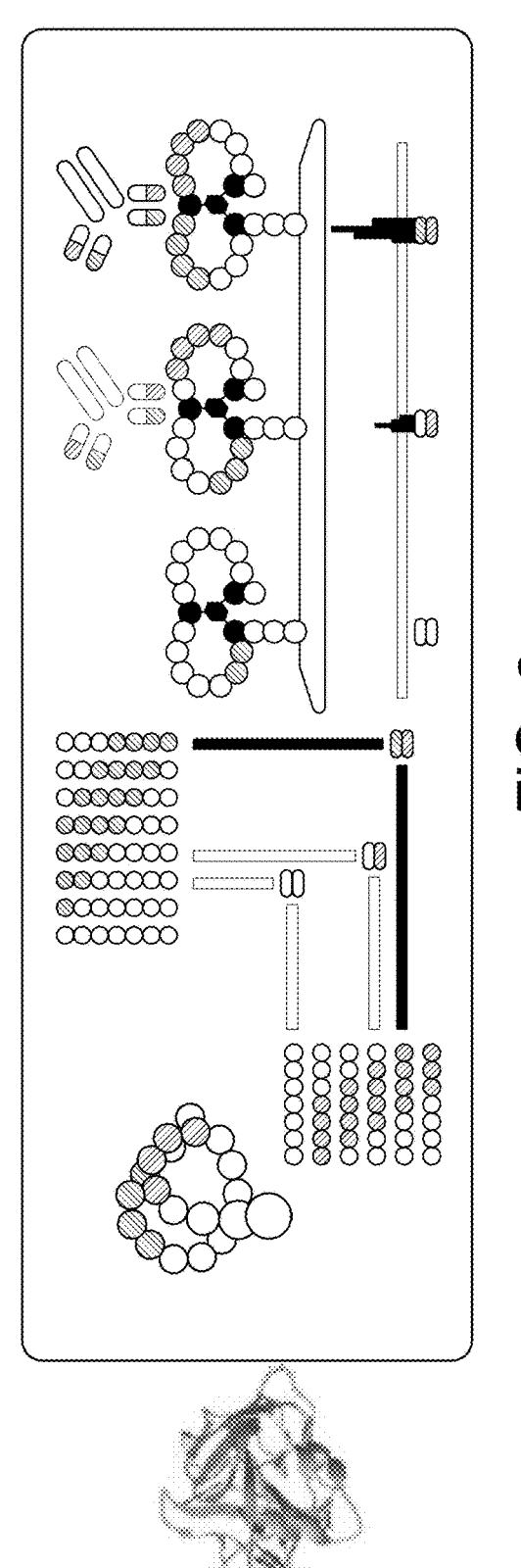
FIG. 3 illustrates combinatorial clips library screening. The target protein (left) containing a discontinuous conformational epitope is converted into a matrix library (middle). Combinatorial peptides are synthesized on a proprietary minicard and chemically converted into spatially defined CLIPS™ constructs (right).

Combinatorial CLIPS™ library screening in detail. CLIPS™ library screening starts with the conversion of the target protein into a library of up to 10,000 overlapping peptide constructs, using a combinatorial matrix design. On a solid carrier, a matrix of linear peptides is synthesized, which are subsequently shaped into spatially defined CLIPS™ constructs (FIG. 3). Constructs representing both parts of the discontinuous epitope in the correct conformation bind the antibody with high affinity, which is detected and quantified. Constructs presenting the incomplete epitope bind the antibody with lower affinity, whereas constructs not containing the epitope do not bind at all. Affinity information is used in iterative screens to define the sequence and conformation of epitopes in detail.

Figure 4:
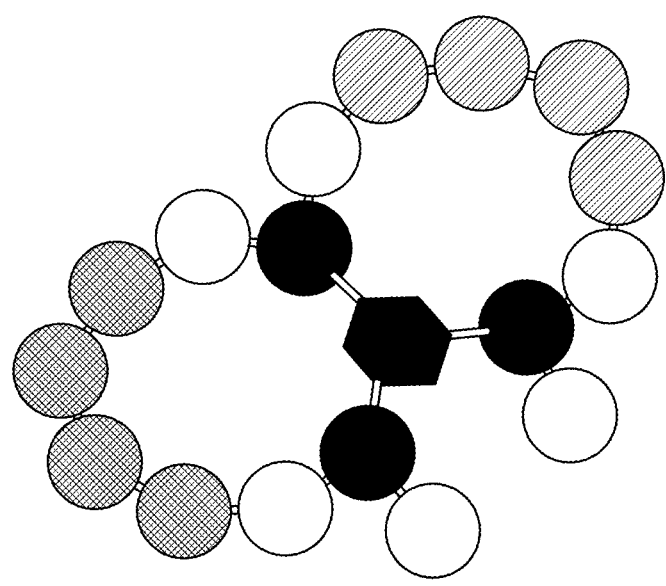
FIG. 4 depicts T3 looped CLIPS™ construct.

Heat map analysis. A heat map is a graphical representation of data where the values taken by a variable in a two-dimensional map are represented as colors. For double-looped CLIPS™ peptides, such a two-dimensional map can be derived from the independent sequences of the first and second loops. For example, the sequences of the 16 CLIPS™ peptides depicted in FIG. 5 are effectively permutations of 4 unique sub-sequences in loop 1 (colored in blue in FIG. 4) and 4 unique sub-sequences in loop 2 (colored in green in FIG. 4). Thus, the observed ELISA data (colored in red in FIG. 5A) can be plotted in a 4×4 matrix, where each X coordinate corresponds to the sequence of the first loop, and each Y coordinate corresponds to the sequence of the second loop. For instance, the ELISA value observed for CLIPS™ peptide CLSSERERVEDLFEYECELLT-SEPIFHCRQEDC (SEQ ID NO: 382) indicated with an arrow in FIG. 4A) can be found at the third row, third column of FIG. 5B (indicated with an arrow and a red square). To further facilitate the visualization, ELISA values can be replaced with colors from a continuous gradient. In this case, extremely low values are colored in green, extremely high values are colored in red, and average values are colored in black (see FIG. 5C). For the aforementioned example, the average value is 0.71. When this color map is applied to the data matrix depicted in FIG. 5B, a color heat map is obtained (see FIG. 5D, the original data is still indicated for extra clarity).

Synthesis of peptides. To reconstruct epitopes of the target molecule a library of peptides was synthesized. An amino functionalized polypropylene support was obtained by grafting with a proprietary hydrophilic polymer formulation, followed by reaction with t-butyloxycarbonyl-hexamethylenediamine (BocHMDA) using dicyclohexylcarbodiimide (DCC) with Nhydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS™ liquid handling stations (Perkin Elmer). Synthesis of structural mimics was done using Pepscan™'s proprietary Chemically Linked Peptides on Scaffolds (CLIPS™) technology. CLIPS™ technology allows to structure peptides into single loops, doubleloops, triple loops, sheet-like folds, helix-like folds and combinations thereof. CLIPS™ templates are coupled to cysteine residues. The side-chains of multiple cysteines in the peptides were coupled to one or two CLIPS™ templates. For example, a 0.5 mM solution of the P2 CLIPS™ (2,6-bis (bromomethyl)pyridine) was dissolved in ammonium bicarbonate (20 mM, pH 7.8)/acetonitrile (1:3 (v/v)). This solution was added onto the peptide arrays. The CLIPS™ template bound to side-chains of two cysteines as present in the solid-phase bound peptides of the peptide-arrays (455 wells plate with 3 μl wells). The peptide arrays were gently shaken in the solution for 30 to 60 minutes while completely covered in solution. Finally, the peptide arrays were washed extensively with excess of $H_2O$ and sonicated in disruptbuffer containing 1% SDS/0.1% beta-mercaptoethanol in PBS (pH 7.2) at 70° C. for 30 minutes, followed by sonication in $H_2O$ for another 45 minutes. The T3 CLIPS™ Carrying peptides were made in a similar way but now with three cysteines.

ELISA Screening. The binding of antibody to each of the synthesized peptides was tested in a PEPSCAN™-based ELISA. The peptide arrays were incubated with primary antibody solution (overnight at 4° C.). After washing, the peptide arrays were incubated with a $1/1000$ dilution of an appropriate antibody peroxidase conjugate (SBA) for one hour at 25° C. After washing, the peroxidase substrate 2,2'-azino-di-3-ethylbenzthiazoline sulfonate (ABTS) and 2 μl/ml of 3 percent $H_2O_2$ were added. After one hour, the color development was measured. The color development was quantified with a charge coupled device (CCD)— camera and an image processing system.

Data processing. The values obtained from the CCD camera ranged from 0 to 3000 mAU, similar to a standard 96-well plate ELISA-reader. The results were quantified and stored into the Peplab™ database. Occasionally a well contained an air-bubble resulting in a false-positive value, the cards were manually inspected and any values caused by an air-bubble were scored as 0.

Synthesis quality control—To verify the quality of the synthesized peptides, a separate set of positive and negative control peptides was synthesized in parallel. These were screened with antibody 57.9 (ref. Posthumus et al., J. Virology, 1990, 64:3304-3309).

Results

Screening. Antibody binding depends on a combination of factors, including concentration of the antibody and the amounts and nature of competing proteins in the ELISA buffer. Also, the pre-coat conditions (the specific treatment of the peptide arrays prior to incubation with the experimental sample) affected binding. These details are summed up in Table 35. For the Pepscan™ Buffer and Preconditioning (SQ), the numbers indicate the relative amount of competing protein (a combination of horse serum and ovalbumin).

TABLE 35

| | Screening conditions | | |
|---|---|---|---|
| Label | Dilution | Sample Buffer | Pre-conditioning |
| ET150-18 mIgG1 | 1 μg/ml | 1% SQ | 1% SQ |
| ET150-2 mIgG1 | 1 μg/ml | 10% SQ | 10% SQ |
| ET150-5 mIgG1 | 1 μg/ml | 10% SQ | 10% SQ |
| ET150-8 mIgG1 | 3 μg/ml | 10% SQ | 10% SQ |

Figure 6:
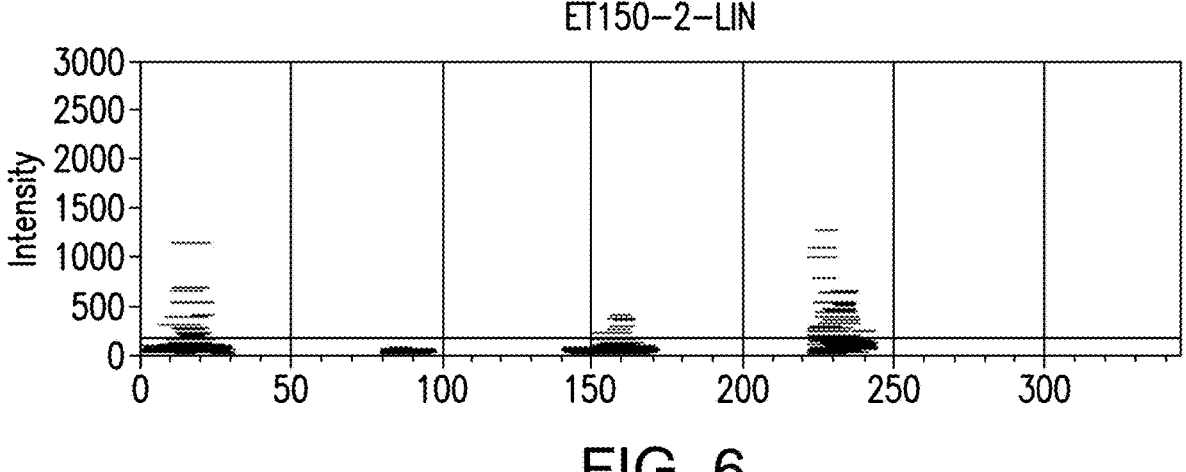
FIG. 6 shows intensity profiles recorded for ET150-2. Lines are drawn from the starting residue to the ending residue of a single peptide on the height at which the signal for that peptide is recorded.
Figure 7:
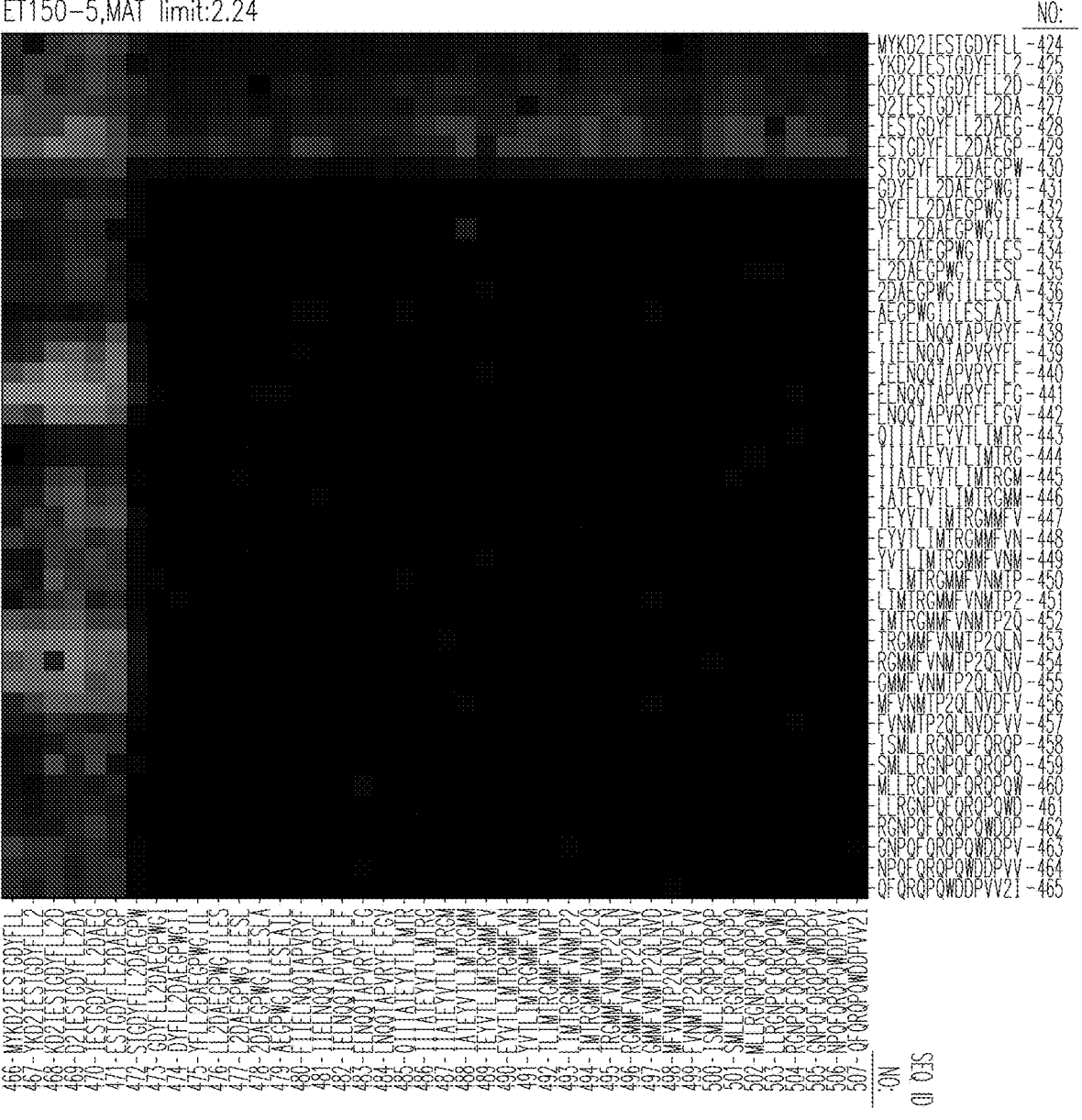
FIG. 7 shows heatmap analysis of data recorded for ET150-5 under high stringency conditions.

Antibody ET150-2. When tested under moderate stringency conditions antibody ET150-2 avidly bound peptides from all sets (FIG. 6). Cumulative data analysis shows that the antibody recognize a discontinuous epitope composed of peptides stretches $_{16}$CDAEGPWGII$_{25}$ (N-term) (SEQ ID NO: 383), $_{157}$MFVNMTPC$_{164}$ (ECL2) (SEQ ID NO: 384) and $_{229}$PQFQRQPQW$_{237}$ (ECL3) (SEQ ID NO: 385), where peptide stretches $_{16}$CDAEGPWGII$_{25}$ (SEQ ID NO: 383) and $_{229}$PQFQRQPQW$_{237}$ (SEQ ID NO: 385) alone suffice for binding. Antibody ET150-5. When tested under high stringency conditions antibody ET150-5 avidly bound peptides from all sets (FIG. 7). Cumulative data analysis shows that the antibody recognizes a discontinuous epitope composed of peptide stretches $_5$CIESTGDYFLLCD$_{17}$ (N-term) (SEQ ID NO: 386), $_{85}$NQQTAPVRYFL$_{95}$ (ECL1) (SEQ ID NO: 387) and $_{157}$MFVNMTPC$_{164}$ (ECL2) (SEQ ID NO: 384), where peptide stretch $_5$CIESTGDYFLLCD$_{17}$ (SEQ ID NO: 386) alone suffices for binding.

Figure 8:
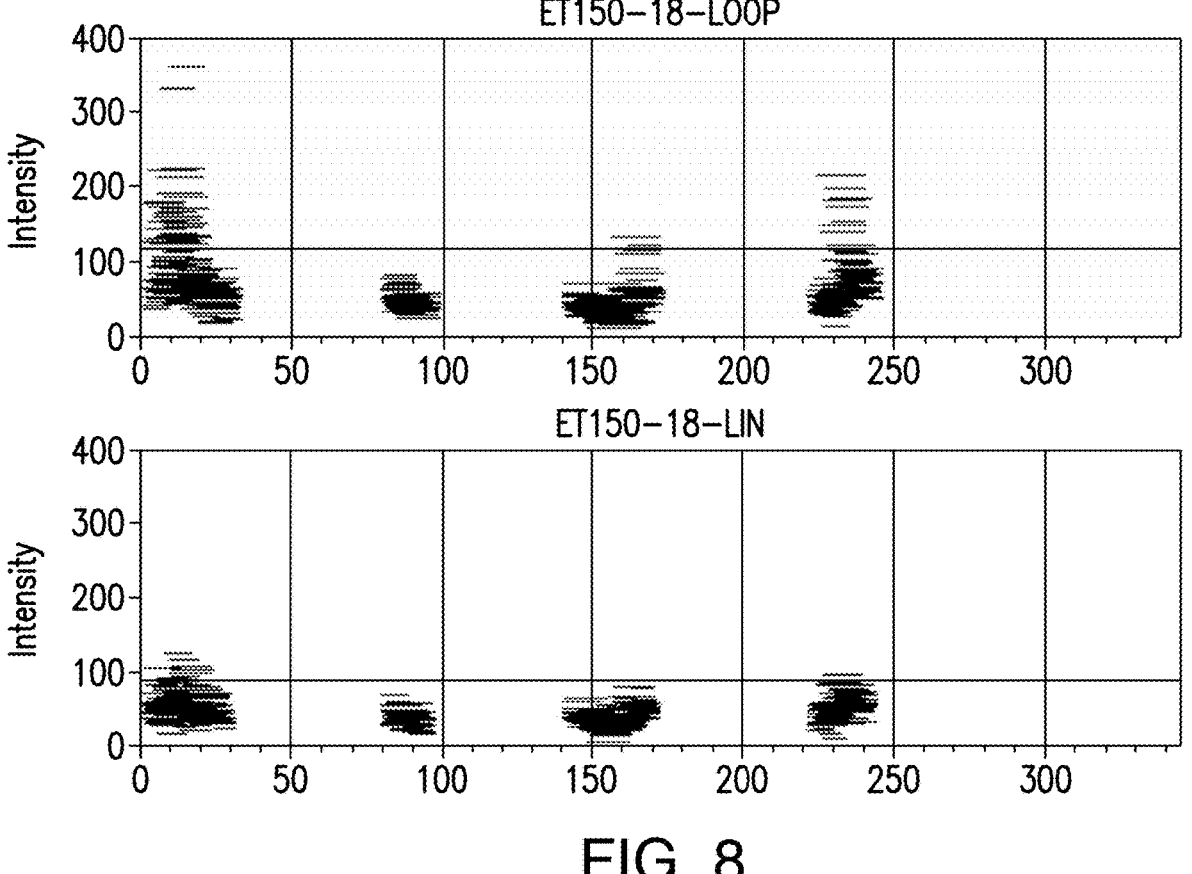
FIG. 8 shows intensity profiles recorded for ET150-18.

Antibody ET150-18. When tested under high stringency conditions antibody ET150-18 bound peptides from set 4 and set 7, containing structurally constrained peptides. No significant binding was recorded on sets containing linear peptides (FIG. 8). Cumulative data analysis shows that the antibody recognizes a discontinuous epitope composed of stretches $_{10}$GDYFLLCD$_{17}$ (N-term) (SEQ ID NO: 388), $_{157}$MFVNMTPCQLN$_{167}$ (ECL2) (SEQ ID NO: 389) and $_{227}$GNPQFQRQPQW$_{237}$ (ECL3) (SEQ ID NO: 390). Peptide stretches $_{10}$GDYFLLCD$_{17}$ (SEQ ID NO: 388) and $_{227}$GNPQFQRQPQW$_{237}$ (SEQ ID NO: 390) represent the epitope's core, as both peptide stretches separately suffice for binding.

Figure 9:
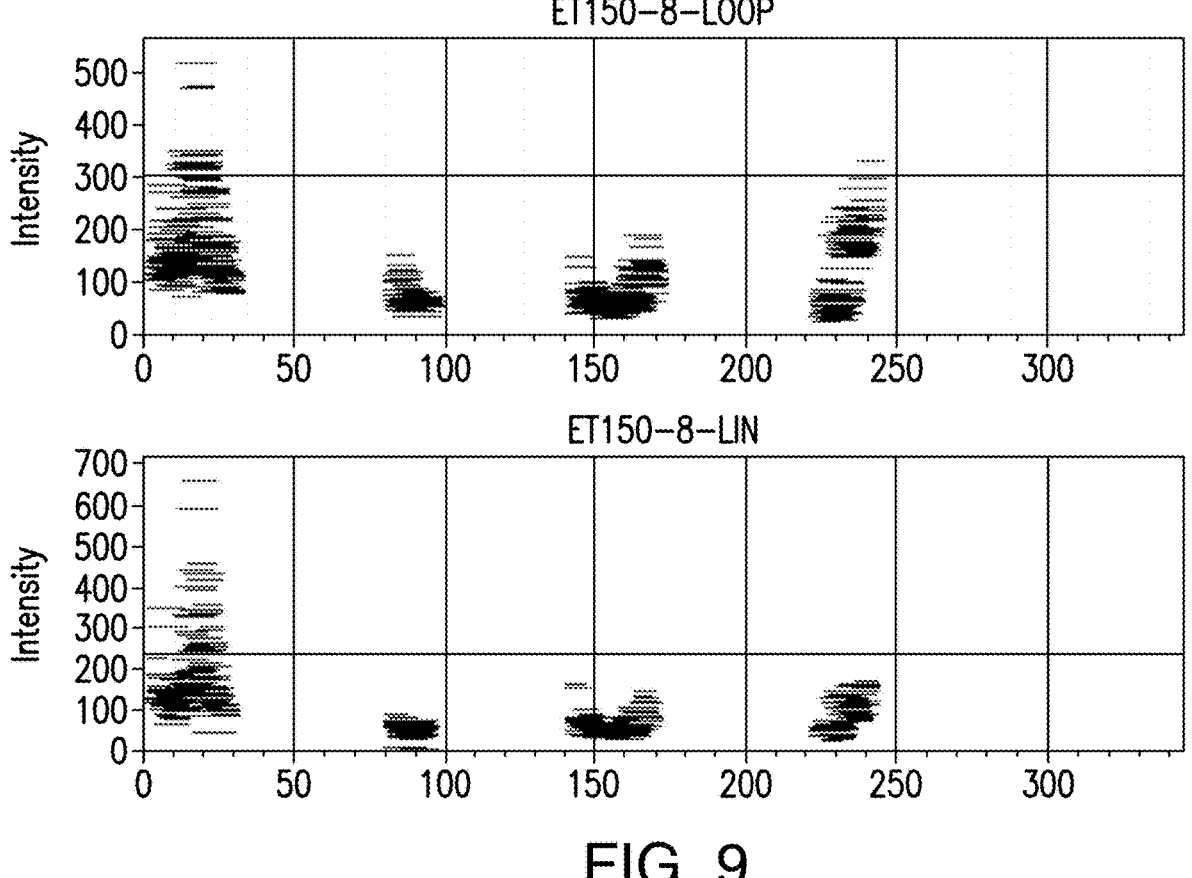
FIG. 9 shows intensity profiles recorded for ET150-8.

Antibody ET150-8. When tested under high stringency conditions antibody ET150-8 bound peptides from all sets, except for set 2 (FIG. 9). Cumulative data analysis shows that the antibody recognizes a discontinuous epitope composed of peptides stretches $_{15}$LCDAEGPWG$_{23}$ (N-term) (SEQ ID NO: 391) and $_{230}$QFQRQPQWDDPVVC$_{243}$ (ECL3) (SEQ ID NO: 392) where peptide stretch $_{15}$LCDAEGPWG$_{23}$ (SEQ ID NO: 391) is the dominant part of the epitope, as it alone suffices for binding. Moreover, comparison of the results obtained on set 1 (linear) and set 4 (loop) shows that introduction of structural constrains to epitope mimics enhances binding of peptides, especially in case of peptides containing sequence $_{230}$QFQRQPQWDDPVVC$_{243}$ (SEQ ID NO: 392).

Conclusions

All antibodies investigated recognized discontinuous epitopes, which were mapped using Pepscan™ arrays. Core tentative epitopes are listed in Table 36. All antibodies commonly recognized overlapping regions at the N-terminus of the protein in combination with regions from one or two ECLs. Two antibodies ET150-18 and ET150-8 showed a requirement for structural constraints to support antibody binding, suggesting that these two antibodies recognize not only discontinuous, but also conformational epitopes. Antibodies ET150-2 and ET150-5 did not show notable discrepancies in peptide binding between linear and looped peptides.

TABLE 36

| | | List of epitopes | | |
|---|---|---|---|---|
| Antibody | N-terminus | ECL1 | ECL2 | ECL3 |
| ET150-2 | $_{16}$CDAEGPWGII$_{25}$*$^{)}$ (SEQ ID NO: 383) | – | $_{157}$MFVNMTPC$_{164}$ (SEQ ID NO: 384) | $_{229}$PQFQRQPQW$_{237}$*$^{)}$ (SEQ ID NO: 385) |
| ET150-5 | $_{5}$CIESTGDYFLLCD$_{17}$*$^{)}$ (SEQ ID NO: 386) | $_{85}$NQQTAPVRYFL$_{95}$ (SEQ ID NO: 387) | $_{157}$MFVNMTPC$_{164}$ (SEQ ID NO: 384) | – |
| ET150-8 | $_{15}$LCDAEGPWG$_{23}$*$^{)}$ (SEQ ID NO: 391) | – | – | $_{230}$QFQRQPQWDDPVVC$_{243}$ (SEQ ID NO: 392) |
| ET150-18 | $_{10}$GDYFLLCD$_{17}$*$^{)}$ (SEQ ID NO: 388) | – | $_{157}$MFVNMTPCQLN$_{167}$ (SEQ ID NO: 389) | $_{227}$GNPQFQRQPQW$_{237}$*$^{)}$ (SEQ ID NO: 390) |

*$^{)}$dominant part

Figure 10:
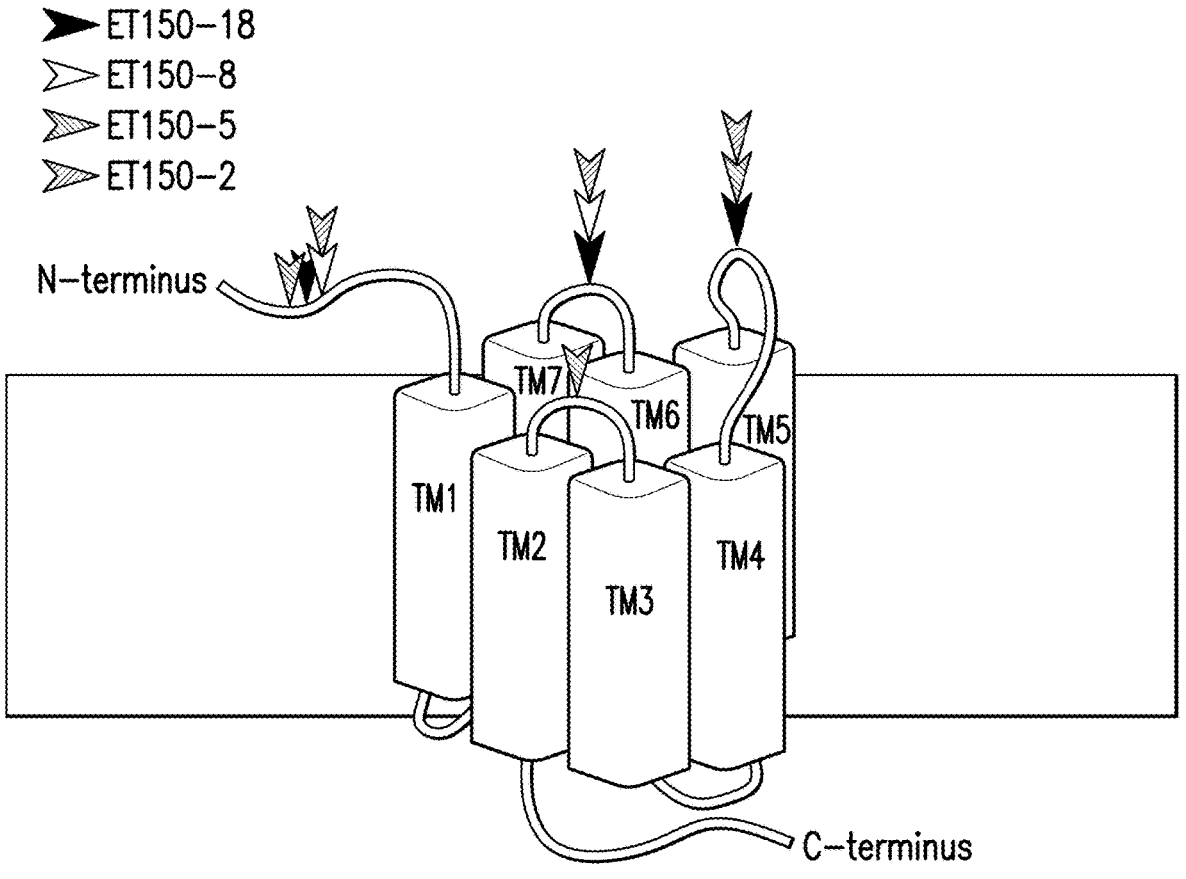
FIG. 10 depicts schematic drawing of a GPCR containing seven transmembrane helices (TM) and 3 extracellular regions (ECLs). Colored arrows binding sites for each antibody is depicted.

FIG. 10 is an illustration of the results of the study with respect to overall organization of GPCRs. As the N-terminus is highly flexible and unstructured, it likely transiently interacts with ECLs forming discontinuous immunodominant regions.

Figure 11:
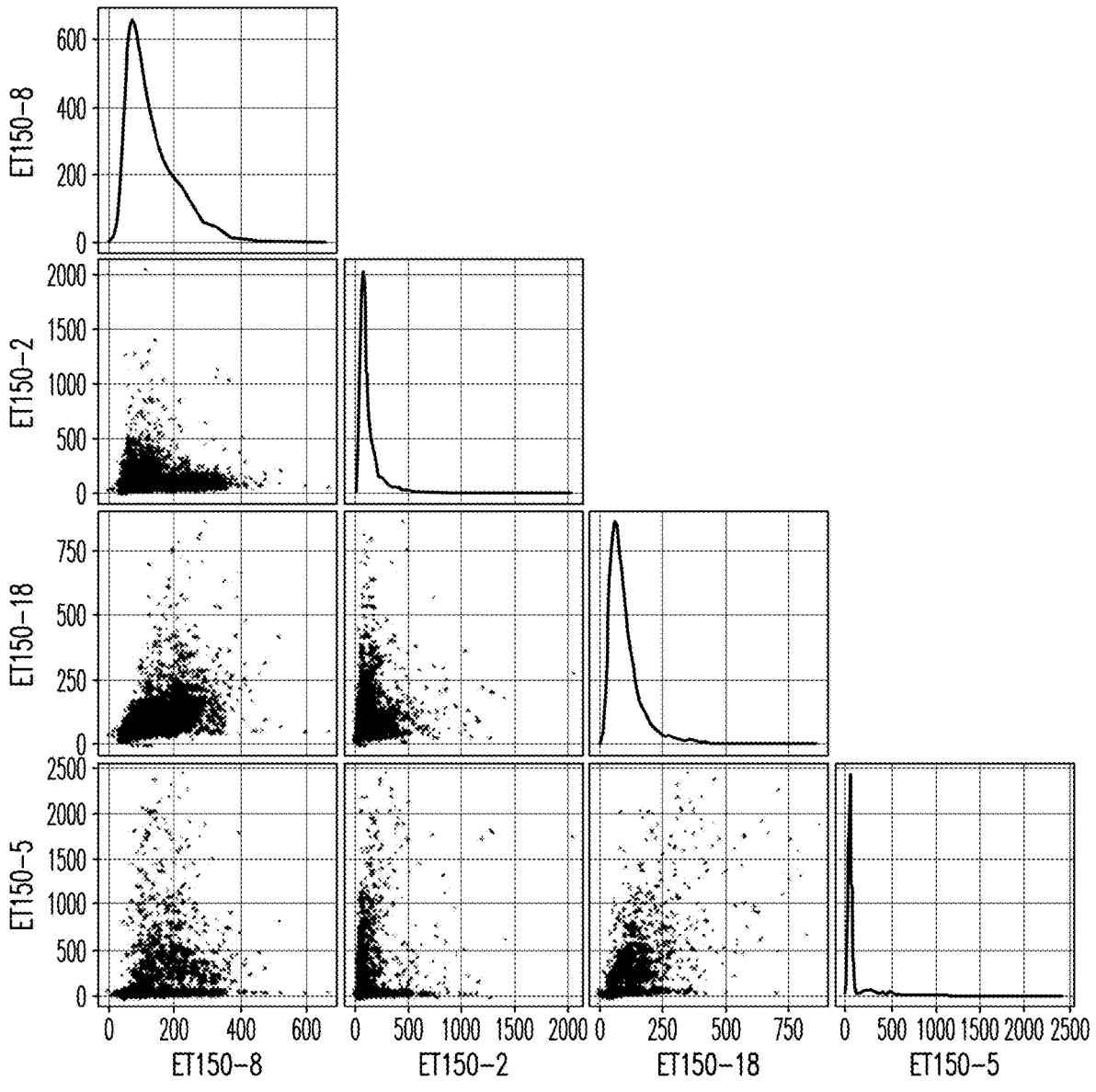
FIG. 11 depicts scatterplot analysis of all data recorded for each sample. On the diagonal is the statistical data distribution.

Differences and commonalities in peptide binding can be illustrated with a scatter plot analysis in FIG. 11. Data points in the top left and bottom right corners point to the differences in the binding. Despite significant epitope overlap, the fine specificities of epitopes of the individual antibodies differ to a large extent.

Example 4—Screening Data for Anti-GPRC5D Antibodies

FACS Screening. FIG. 12 shows FACS analysis of the GPRC5D-specific phage antibody clones (ET150-1, ET150-2, ET150-5, ET150-8, ET150-18). Phage clones were incubated with 3T3-GPRC5D cell line, then with anti-M13 mouse antibody. Finally APC-labeled anti-mouse IgG 2nd antibody was added to the reaction after washing again. The binding was measured by FACS and expressed as mean fluorescence intensity (MFI). Cells incubated with M13 K07 helper phage and cells only were used as negative controls.

Example 5—Binding Affinity of Anti-GPRC5D Antibodies

Figure 13:
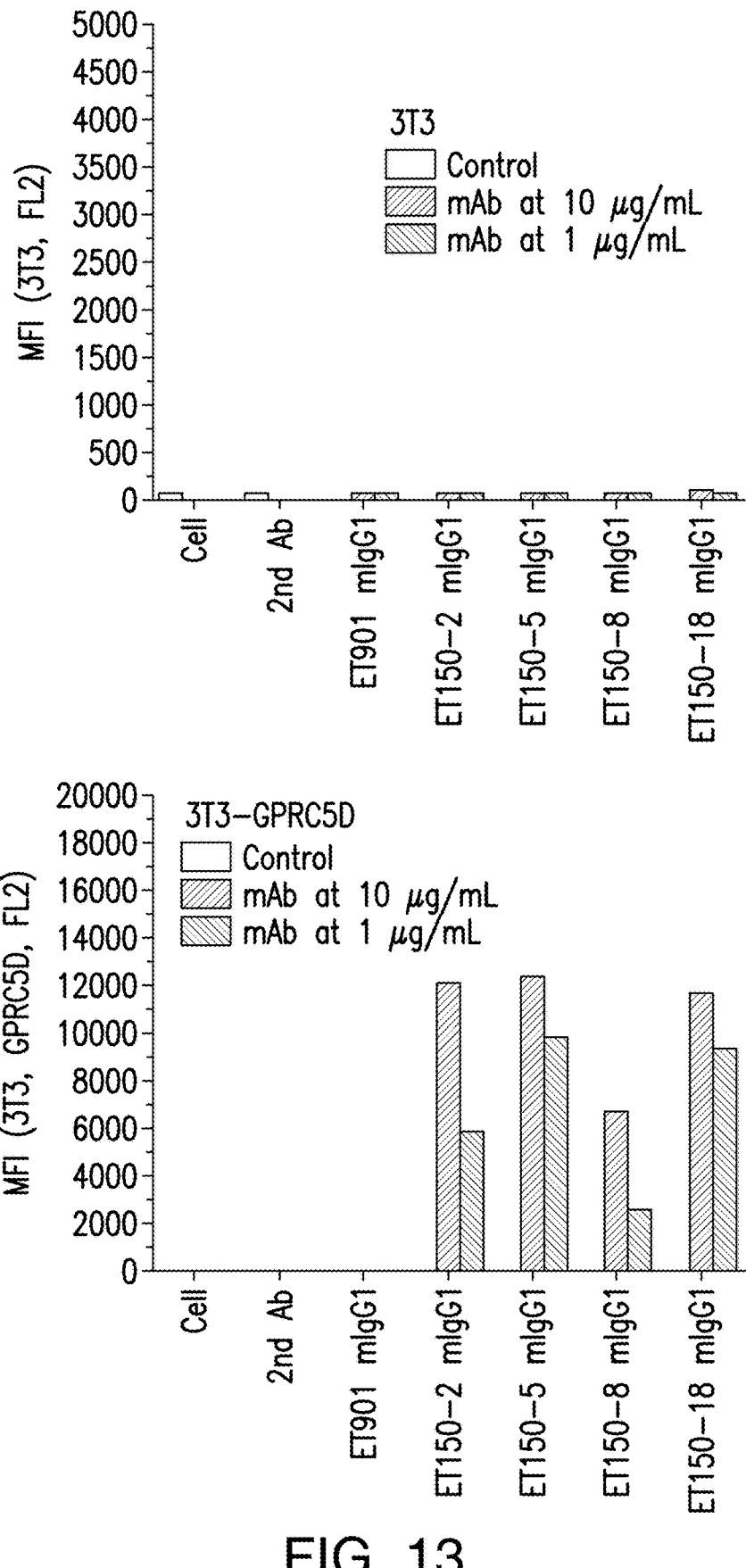
FIG. 13 depicts FACS analysis of anti-GPRC5D antibodies.

FIG. 13 shows FACS analysis of GPRC5D-specific phage antibody clones (ET150-2, ET150-5, ET150-8, ET150-18). Each antibody (ET150-1, ET150-2, ET150-5, ET150-8, ET150-18) was incubated with 3T3 or 3T3-GPRC5D cells at 10 or 1 μg/mL, then with anti-M13 mouse antibody. Finally PE-labeled anti-mouse IgG 2nd antibody was added to the reaction. The binding was measured by FACS and expressed as mean fluorescence intensity (MFI) (FIG. 13). Cells incubated with 2nd antibody alone, ET901 mIgG1 isotype control and cells only were used as negative controls.

Example 6—Bispecific Antibodies Specific for GPRC5D and CD3

Figure 14:
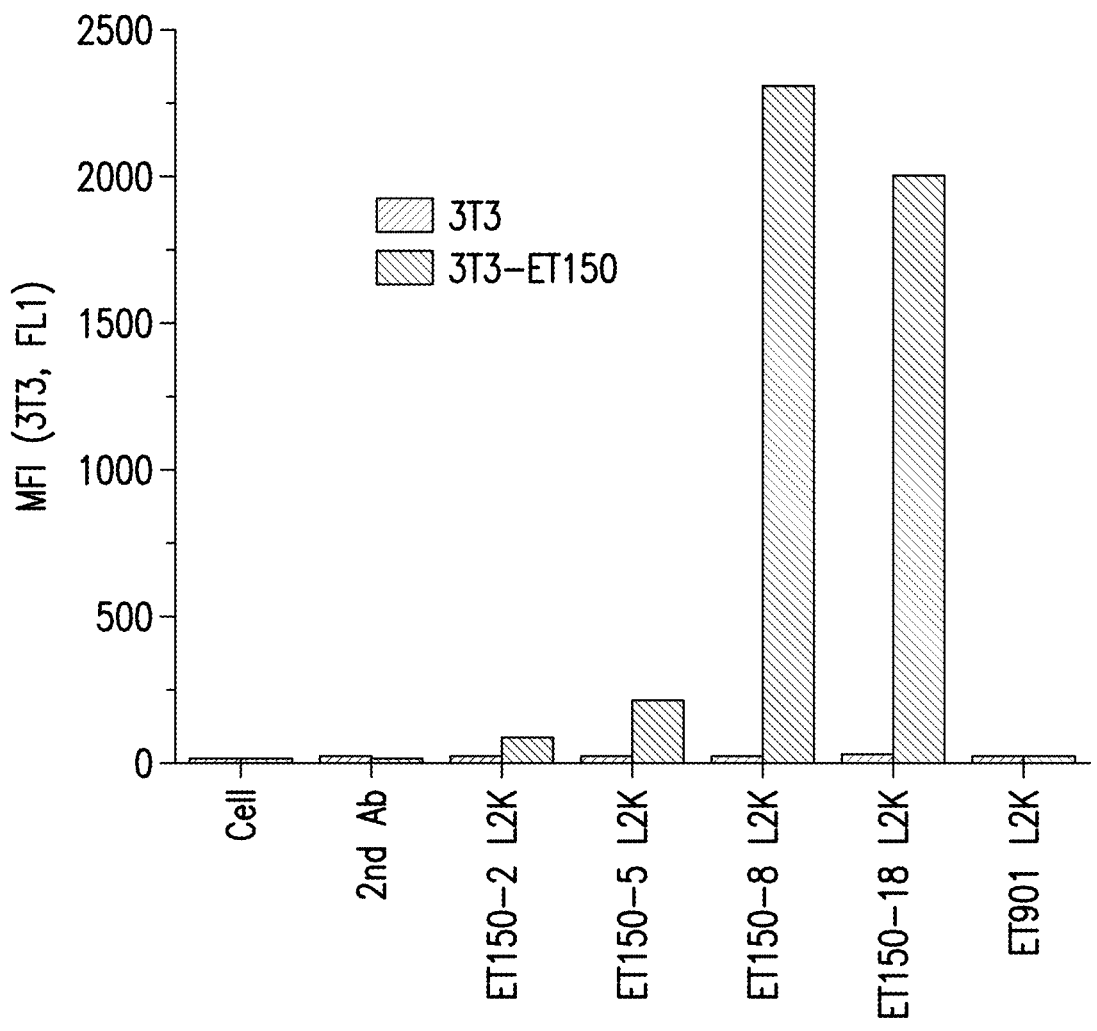
FIG. 14 depicts the FACS analysis of anti-GPRC5D/CD3 bispecific antibodies.

FIG. 14 shows FACS analysis of the anti-GPRC5D/anti-CD3 bispecific antibodies generated using the ET150-2, ET150-5, ET150-8, ET150-18 clones disclosed herein. Each antibody was incubated with 3T3 or 3T3-GPRC5D cells at 10 μg/ml, followed by the incubation with a FITC-conjugated anti-His tag antibody. The binding was measured by FACS and expressed as mean fluorescence intensity (MFI). Cells incubated with 2nd antibody alone, ET901 bispecific antibody control and cells only were used as negative controls. As shown in FIG. 14, the anti-GPRC5D/CD3 bispecific antibodies generated using the disclosed scFvs specifically bound to 3T3 cells expressing GPRC5D.

Although the foregoing presently disclosed subject matter has been described in some detail by way of illustration and example for purposes of clarity of understanding, the descriptions and examples should not be construed as limiting the scope of the presently disclosed subject matter. The disclosures of all patent and scientific literature cited herein are expressly incorporated in their entirety by reference.

What is claimed is:

1. An anti-human G-protein coupled receptor family C group 5 member D (GPRC5D) single chain variable fragment (scFv) comprising a light chain variable region, a heavy chain variable region, and a peptide linker, wherein:

(i) the heavy chain variable region comprises a CDR1 comprising amino acids having the sequence set forth in SEQ ID NO: 124; a CDR2 comprising amino acids having the sequence set forth in SEQ ID NO: 125; and a CDR3 comprising amino acids having the sequence set forth in SEQ ID NO: 126; and the light chain variable region comprises a CDR1 comprising amino acids having the sequence set forth in SEQ ID NO: 127; a CDR2 comprising amino acids having the sequence of DNN; and a CDR3 comprising amino acids having the sequence set forth in SEQ ID NO: 129;

(ii) the heavy chain variable region comprises a CDR1 comprising amino acids having the sequence set forth in SEQ ID NO: 130; a CDR2 comprising amino acids having the sequence set forth in SEQ ID NO: 131; and a CDR3 comprising amino acids having the sequence set forth in SEQ ID NO: 132; and the light chain variable region comprises a CDR1 comprising amino acids having the sequence set forth in SEQ ID NO: 133; a CDR2 comprising amino acids having the sequence of DDN; and a CDR3 comprising amino acids having the sequence set forth in SEQ ID NO: 135;

(iii) the heavy chain variable region comprises a CDR1 comprising amino acids having the sequence set forth in SEQ ID NO: 136; a CDR2 comprising amino acids having the sequence set forth in SEQ ID NO: 137; and a CDR3 comprising amino acids having the sequence set forth in SEQ ID NO: 138; and the light chain variable region comprises a CDR1 comprising amino acids having the sequence set forth in SEQ ID NO: 139; a CDR2 comprising amino acids having the sequence of AAS; and a CDR3 comprising amino acids having the sequence set forth in SEQ ID NO: 141;

(iv) the heavy chain variable region comprises a CDR1 comprising amino acids having the sequence set forth in SEQ ID NO: 142; a CDR2 comprising amino acids having the sequence set forth in SEQ ID NO: 143; and a CDR3 comprising amino acids having the sequence set forth in SEQ ID NO: 144; and the light chain variable region comprises a CDR1 comprising amino acids having the sequence set forth in SEQ ID NO: 145; a CDR2 comprising amino acids having the sequence of DVS; and a CDR3 comprising amino acids having the sequence set forth in SEQ ID NO: 147;

(v) the heavy chain variable region comprises a CDR1 comprising amino acids having the sequence set forth in SEQ ID NO: 148; a CDR2 comprising amino acids having the sequence set forth in SEQ ID NO: 149; a CDR3 comprising amino acids having the sequence set forth in SEQ ID NO: 150; and the light chain variable region comprises a CDR1 comprising amino acids having the sequence set forth in SEQ ID NO: 151; a CDR2 comprising amino acids having the sequence of RNH; and a CDR3 comprising amino acids having the sequence set forth in SEQ ID NO: 153;

(vi) the heavy chain variable region comprises a CDR1 comprising amino acids having the sequence set forth in SEQ ID NO: 154; a CDR2 comprising amino acids having the sequence set forth in SEQ ID NO: 155; and a CDR3 comprising amino acids having the sequence set forth in SEQ ID NO: 156; and the light chain variable region comprises a CDR1 comprising amino acids having the sequence set forth in SEQ ID NO: 157; a CDR2 comprising amino acids having the sequence of RNN; and a CDR3 comprising amino acids having the sequence set forth in SEQ ID NO: 159;

(vii) the heavy chain variable region comprises a CDR1 comprising amino acids having the sequence set forth in SEQ ID NO: 160; a CDR2 comprising amino acids having the sequence set forth in SEQ ID NO: 161; a CDR3 comprising amino acids having the sequence set forth in SEQ ID NO: 162; a light chain variable region CDR1 comprising amino acids having the sequence set forth in SEQ ID NO: 163; a light chain variable region CDR2 comprising amino acids having the sequence of EVS; and a light chain variable region CDR3 comprising amino acids having the sequence set forth in SEQ ID NO: 165;

(viii) the heavy chain variable region comprises a CDR1 comprising amino acids having the sequence set forth in SEQ ID NO: 166; a CDR2 comprising amino acids having the sequence set forth in SEQ ID NO: 167; and a CDR3 comprising amino acids having the sequence set forth in SEQ ID NO: 168; and the light chain variable region comprises CDR1 comprising amino acids having the sequence set forth in SEQ ID NO: 169; a CDR2 comprising amino acids having the sequence of RNN; and a CDR3 comprising amino acids having the sequence set forth in SEQ ID NO: 171;

(ix) the heavy chain variable region comprises a CDR1 comprising amino acids having the sequence set forth in SEQ ID NO: 172; a CDR2 comprising amino acids having the sequence set forth in SEQ ID NO: 173; and a CDR3 comprising amino acids having the sequence set forth in SEQ ID NO: 174; and the light chain variable region comprises a CDR1 comprising amino acids having the sequence set forth in SEQ ID NO: 175; a CDR2 comprising amino acids having the sequence of RNN; and a CDR3 comprising amino acids having the sequence set forth in SEQ ID NO: 177;

(x) the heavy chain variable region comprises a CDR1 comprising amino acids having the sequence set forth in SEQ ID NO: 178; a CDR2 comprising amino acids having the sequence set forth in SEQ ID NO: 179; and a CDR3 comprising amino acids having the sequence set forth in SEQ ID NO: 180; and the light chain variable region comprises a CDR1 comprising amino acids having the sequence set forth in SEQ ID NO: 181; a CDR2 comprising amino acids having the sequence of DVS; and a CDR3 comprising amino acids having the sequence set forth in SEQ ID NO: 183;

(xi) the heavy chain variable region comprises a CDR1 comprising amino acids having the sequence set forth in SEQ ID NO: 184; a CDR2 comprising amino acids having the sequence set forth in SEQ ID NO: 185; and a CDR3 comprising amino acids having the sequence set forth in SEQ ID NO: 186; and the light chain variable region comprises a CDR1 comprising amino acids having the sequence set forth in SEQ ID NO: 187; a CDR2 comprising amino acids having the sequence of RNN; and a CDR3 comprising amino acids having the sequence set forth in SEQ ID NO: 189;

(xii) the heavy chain variable region comprises a CDR1 comprising amino acids having the sequence set forth in SEQ ID NO: 190; a CDR2 comprising amino acids having the sequence set forth in SEQ ID NO: 191; and a CDR3 comprising amino acids having the sequence set forth in SEQ ID NO: 192; and the light chain variable region comprises a CDR1 comprising amino acids having the sequence set forth in SEQ ID NO: 193; a CDR2 comprising amino acids having the sequence of EVT; and a CDR3 comprising amino acids having the sequence set forth in SEQ ID NO: 195;

(xiii) the heavy chain variable region comprises a CDR1 comprising amino acids having the sequence set forth in SEQ ID NO: 196; a CDR2 comprising amino acids having the sequence set forth in SEQ ID NO: 197; and a CDR3 comprising amino acids having the sequence set forth in SEQ ID NO: 198; and the light chain variable region comprises a CDR1 comprising amino acids having the sequence set forth in SEQ ID NO: 199; a CDR2 comprising amino acids having the sequence of GNS; and a CDR3 comprising amino acids having the sequence set forth in SEQ ID NO: 201;

(xiv) the heavy chain variable region comprises a CDR1 comprising amino acids having the sequence set forth in SEQ ID NO: 202; a CDR2 comprising amino acids having the sequence set forth in SEQ ID NO: 203; and a CDR3 comprising amino acids having the sequence set forth in SEQ ID NO: 204; and the light chain variable region comprises a CDR1 comprising amino acids having the sequence set forth in SEQ ID NO: 205; a CDR2 comprising amino acids having the sequence of DVS; and a CDR3 comprising amino acids having the sequence set forth in SEQ ID NO: 207;

(xv) the heavy chain variable region comprises a CDR1 comprising amino acids having the sequence set forth in SEQ ID NO: 208; a CDR2 comprising amino acids having the sequence set forth in SEQ ID NO: 209; and a CDR3 comprising amino acids having the sequence set forth in SEQ ID NO: 210; and the light chain variable region comprises a CDR1 comprising amino acids having the sequence set forth in SEQ ID NO: 211; a CDR2 comprising amino acids having the sequence of DVF; and a CDR3 comprising amino acids having the sequence set forth in SEQ ID NO: 213;

(xvi) the heavy chain variable region comprises a CDR1 comprising amino acids having the sequence set forth in SEQ ID NO: 214; a CDR2 comprising amino acids having the sequence set forth in SEQ ID NO: 215; and a CDR3 comprising amino acids having the sequence set forth in SEQ ID NO: 216; and the light chain variable region comprises a CDR1 comprising amino acids having the sequence set forth in SEQ ID NO: 217; a CDR2 comprising amino acids having the sequence of RSN; and a CDR3 comprising amino acids having the sequence set forth in SEQ ID NO: 219;

(xvii) the heavy chain variable region comprises a CDR1 comprising amino acids having the sequence set forth in SEQ ID NO: 220; a CDR2 comprising amino acids having the sequence set forth in SEQ ID NO: 221; and a CDR3 comprising amino acids having the sequence set forth in SEQ ID NO: 222; and the light chain variable region comprises a CDR1 comprising amino acids having the sequence set forth in SEQ ID NO: 223; a CDR2 comprising amino acids having the sequence of GKN; and a CDR3 comprising amino acids having the sequence set forth in SEQ ID NO: 225;

(xviii) the heavy chain variable region comprises a CDR1 comprising amino acids having the sequence set forth in SEQ ID NO: 226; a CDR2 comprising amino acids having the sequence set forth in SEQ ID NO: 227; and a CDR3 comprising amino acids having the sequence set forth in SEQ ID NO: 228; and the light chain variable region comprises a CDR1 comprising amino acids having the sequence set forth in SEQ ID NO: 229; a CDR2 comprising amino acids having the sequence of DND; and a CDR3 comprising amino acids having the sequence set forth in SEQ ID NO: 231;

(xix) the heavy chain variable region comprises a CDR1 comprising amino acids having the sequence set forth in SEQ ID NO: 232; a CDR2 comprising amino acids having the sequence set forth in SEQ ID NO: 233; and a CDR3 comprising amino acids having the sequence set forth in SEQ ID NO: 234; and the light chain variable region comprises a CDR1 comprising amino acids having the sequence set forth in SEQ ID NO: 235; a CDR2 comprising amino acids having the sequence of EVS; and a CDR3 comprising amino acids having the sequence set forth in SEQ ID NO: 237;

(xx) the heavy chain variable region comprises a CDR1 comprising amino acids having the sequence set forth in SEQ ID NO: 238; a CDR2 comprising amino acids having the sequence set forth in SEQ ID NO: 239; and a CDR3 comprising amino acids having the sequence set forth in SEQ ID NO: 240; and the light chain variable region comprises a CDR1 comprising amino acids having the sequence set forth in SEQ ID NO: 241; a CDR2 comprising amino acids having the sequence of EVN; and a CDR3 comprising amino acids having the sequence set forth in SEQ ID NO: 243;

(xxi) the heavy chain variable region comprises a CDR1 comprising amino acids having the sequence set forth in SEQ ID NO: 244; a CDR2 comprising amino acids having the sequence set forth in SEQ ID NO: 245; and a CDR3 comprising amino acids having the sequence set forth ACTIVE 513198183.1 6 in SEQ ID NO: 246; and the light chain variable region comprises a CDR1 comprising amino acids having the sequence set forth in SEQ ID NO: 247; a CDR2 comprising amino acids having the sequence of EVN; and a CDR3 comprising amino acids having the sequence set forth in SEQ ID NO: 249;

(xxii) the heavy chain variable region comprises a CDR1 comprising amino acids having the sequence set forth in SEQ ID NO: 250; a CDR2 comprising amino acids having the sequence set forth in SEQ ID NO: 251; and a CDR3 comprising amino acids having the sequence set forth in SEQ ID NO: 252; and the light chain variable region comprises a CDR1 comprising amino acids having the sequence set forth in SEQ ID NO: 253; a CDR2 comprising amino acids having the sequence of DNN; and a CDR3 comprising amino acids having the sequence set forth in SEQ ID NO: 255;

(xxiii) the heavy chain variable region comprises a CDR1 comprising amino acids having the sequence set forth in SEQ ID NO: 256; a CDR2 comprising amino acids having the sequence set forth in SEQ ID NO: 257; and a CDR3 comprising amino acids having the sequence set forth in SEQ ID NO: 258; and the light chain variable region comprises a CDR1 comprising amino acids having the sequence set forth in SEQ ID NO: 259; a CDR2 comprising amino acids having the sequence of EVS; and a CDR3 comprising amino acids having the sequence set forth in SEQ ID NO: 261;

(xxiv) the heavy chain variable region comprises a CDR1 comprising amino acids having the sequence set forth in SEQ ID NO: 262; a CDR2 comprising amino acids having the sequence set forth in SEQ ID NO: 263; and a CDR3 comprising amino acids having the sequence set forth in SEQ ID NO: 264; and the light chain variable region comprises a CDR1 comprising amino acids having the sequence set forth in SEQ ID NO: 265; a CDR2 comprising amino acids having the sequence of GVS; and a CDR3 comprising amino acids having the sequence set forth in SEQ ID NO: 267;

(xxv) the heavy chain variable region comprises a CDR1 comprising amino acids having the sequence set forth in SEQ ID NO: 268; a CDR2 comprising amino acids having the sequence set forth in SEQ ID NO: 269; and a CDR3 comprising amino acids having the sequence set forth in SEQ ID NO: 270; and the light chain variable region comprises a CDR1 comprising amino acids having the sequence set forth in SEQ ID NO: 271; a CDR2 comprising amino acids having ACTIVE 513198183.1 7 the sequence of EVT; and a CDR3 comprising amino acids having the sequence set forth in SEQ ID NO: 273;

(xxvi) the heavy chain variable region comprises a CDR1 comprising amino acids having the sequence set forth in SEQ ID NO: 280; a CDR2 comprising amino acids having the sequence set forth in SEQ ID NO: 281; and a CDR3 comprising amino acids having the sequence set forth in SEQ ID NO: 282; and the light chain variable region comprises a CDR1 comprising amino acids having the sequence set forth in SEQ ID NO: 283; a CDR2 comprising amino acids having the sequence of SNN; and a CDR3 comprising amino acids having the sequence set forth in SEQ ID NO: 285;

(xxvii) the heavy chain variable region comprises a CDR1 comprising amino acids having the sequence set forth in SEQ ID NO: 292; a CDR2 comprising amino acids having the sequence set forth in SEQ ID NO: 293; and a CDR3 comprising amino acids having the sequence set forth in SEQ ID NO: 294; and the light chain variable region comprises a CDR1 comprising amino acids having the sequence set forth in SEQ ID NO: 295; a CDR2 comprising amino acids having the sequence of RNN; and a CDR3 comprising amino acids having the sequence set forth in SEQ ID NO: 297;

(xxviii) the heavy chain variable region comprises a CDR1 comprising amino acids having the sequence set forth in SEQ ID NO: 303; a CDR2 comprising amino acids having the sequence set forth in SEQ ID NO: 304; and a CDR3 comprising amino acids having the sequence set forth in SEQ ID NO: 305; and the light chain variable region comprises a CDR1 comprising amino acids having the sequence set forth in SEQ ID NO: 306; a CDR2 comprising amino acids having the sequence of RNN; and a CDR3 comprising amino acids having the sequence set forth in SEQ ID NO: 308;

(xxix) the heavy chain variable region comprises a CDR1 comprising amino acids having the sequence set forth in SEQ ID NO: 316; a CDR2 comprising amino acids having the sequence set forth in SEQ ID NO: 317; and a CDR3 comprising amino acids having the sequence set forth in SEQ ID NO: 318; and the light chain variable region comprises a CDR1 comprising amino acids having the sequence set forth in SEQ ID NO: 319; a CDR2 comprising amino acids having the sequence of GNS; and a CDR3 comprising amino acids having the sequence set forth in SEQ ID NO: 321;

(xxx) the heavy chain variable region comprises a CDR1 comprising amino acids having the sequence set forth in SEQ ID NO: 328; a CDR2 comprising amino acids having the sequence set forth in SEQ ID NO: 329; and a CDR3 comprising amino acids having the sequence set forth in SEQ ID NO: 330; and the light chain variable region comprises a CDR1 comprising amino acids having the sequence set forth in SEQ ID NO: 331; a CDR2 comprising amino acids having the sequence of DNN; and a CDR3 comprising amino acids having the sequence set forth in SEQ ID NO: 333;

(xxxi) the heavy chain variable region comprises a CDR1 comprising amino acids having the sequence set forth in SEQ ID NO: 340; a CDR2 comprising amino acids having the sequence set forth in SEQ ID NO: 341; and a CDR3 comprising amino acids having the sequence set forth in SEQ ID NO: 342; and the light chain variable region comprises a CDR1 comprising amino acids having the sequence set forth in SEQ ID NO: 343; a CDR2 comprising amino acids having the sequence of EVT; and a CDR3 comprising amino acids having the sequence set forth in SEQ ID NO: 345; or (xxxii) the heavy chain variable region comprises a CDR1 comprising amino acids having the sequence set forth in SEQ ID NO: 352; a CDR2 comprising amino acids having the sequence set forth in SEQ ID NO: 353; and a CDR3 comprising amino acids having the sequence set forth in SEQ ID NO: 354; and the light chain variable region comprises a CDR1 comprising amino acids having the sequence set forth in SEQ ID NO: 355; a CDR2 comprising amino acids having the sequence of RNN; and a CDR3 comprising amino acids having the sequence set forth in SEQ ID NO: 357.

2. The anti-human GPRC5D scFv of claim 1, wherein:

(a) the heavy chain variable region comprises the amino acid sequence selected from the group consisting of SEQ ID NOS: 1, 5, 9, 13, 17, 21, 25, 29, 33, 37, 41, 45, 49, 53, 57, 61, 65, 69, 73, 77, 81, 85, 89, 93, 274, 286, 298, 310, 322, 334, 346 and 358; and (b) the light chain variable region comprises the amino acid sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, 94, 275, 287, 299, 311, 323, 335, 347 and 359.

3. The anti-human GPRC5D scFv of claim 1, wherein the heavy chain variable region and the light chain variable region are selected from the group consisting of:

(i) a heavy chain variable region comprising amino acids having the sequence set forth in SEQ ID NO:1, and a light chain variable region comprising amino acids having the sequence set forth in SEQ ID NO:2;

(ii) a heavy chain variable region comprising amino acids having the sequence set forth in SEQ ID NO:5, and a light chain variable region comprising amino acids having the sequence set forth in SEQ ID NO:6;

(iii) a heavy chain variable region comprising amino acids having the sequence set forth in SEQ ID NO:9, and a light chain variable region comprising amino acids having the sequence set forth in SEQ ID NO:10;

(iv) a heavy chain variable region comprising amino acids having the sequence set forth in SEQ ID NO:13, and a light chain variable region comprising amino acids having the sequence set forth in SEQ ID NO:14;

(v) a heavy chain variable region comprising amino acids having the sequence set forth in SEQ ID NO:17, and a light chain variable region comprising amino acids having the sequence set forth in SEQ ID NO:18;

(vi) a heavy chain variable region comprising amino acids having the sequence set forth in SEQ ID NO:21, and a light chain variable region comprising amino acids having the sequence set forth in SEQ ID NO:22;

(vii) a heavy chain variable region comprising amino acids having the sequence set forth in SEQ ID NO:25, and a light chain variable region comprising amino acids having the sequence set forth in SEQ ID NO:26;

(viii) a heavy chain variable region comprising amino acids having the sequence set forth in SEQ ID NO:29, and a light chain variable region comprising amino acids having the sequence set forth in SEQ ID NO: 30;

(ix) a heavy chain variable region comprising amino acids having the sequence set forth in SEQ ID NO:33, and a light chain variable region comprising amino acids having the sequence set forth in SEQ ID NO:34;

(x) a heavy chain variable region comprising amino acids having the sequence set forth in SEQ ID NO:37, and a light chain variable region comprising amino acids having the sequence set forth in SEQ ID NO:38;

(xi) a heavy chain variable region comprising amino acids having the sequence set forth in SEQ ID NO:41, and a light chain variable region comprising amino acids having the sequence set forth in SEQ ID NO:42;

(xii) a heavy chain variable region comprising amino acids having the sequence set forth in SEQ ID NO:45, and a light chain variable region comprising amino acids having the sequence set forth in SEQ ID NO:46;

(xiii) a heavy chain variable region comprising amino acids having the sequence set forth in SEQ ID NO:49, and a light chain variable region comprising amino acids having the sequence set forth in SEQ ID NO:50;

(xiv) a heavy chain variable region comprising amino acids having the sequence set forth in SEQ ID NO:53, and a light chain variable region comprising amino acids having the sequence set forth in SEQ ID NO:54;

(xv) a heavy chain variable region comprising amino acids having the sequence set forth in SEQ ID NO:57, and a light chain variable region comprising amino acids having the sequence set forth in SEQ ID NO:58;

(xvi) a heavy chain variable region comprising amino acids having the sequence set forth in SEQ ID NO:61, and a light chain variable region comprising amino acids having the sequence set forth in SEQ ID NO:62;

(xvii) a heavy chain variable region comprising amino acids having the sequence set forth in SEQ ID NO:65, and a light chain variable region comprising amino acids having the sequence set forth in SEQ ID NO:66;

(xviii) a heavy chain variable region comprising amino acids having the sequence set forth in SEQ ID NO:69, and a light chain variable region comprising amino acids having the sequence set forth in SEQ ID NO:70;

(xix) a heavy chain variable region comprising amino acids having the sequence set forth in SEQ ID NO:73, and a light chain variable region comprising amino acids having the sequence set forth in SEQ ID NO:74;

(xx) a heavy chain variable region comprising amino acids having the sequence set forth in SEQ ID NO:77, and a light chain variable region comprising amino acids having the sequence set forth in SEQ ID NO:78;

(xxi) a heavy chain variable region comprising amino acids having the sequence set forth in SEQ ID NO:81, and a light chain variable region comprising amino acids having the sequence set forth in SEQ ID NO: 82;

(xxii) a heavy chain variable region comprising amino acids having the sequence set forth in SEQ ID NO:85, and a light chain variable region comprising amino acids having the sequence set forth in SEQ ID NO:86;

(xxiii) a heavy chain variable region comprising amino acids having the sequence set forth in SEQ ID NO:89, and a light chain variable region comprising amino acids having the sequence set forth in SEQ ID NO:90;

(xxiv) a heavy chain variable region comprising amino acids having the sequence set forth in SEQ ID NO:93, and a light chain variable region comprising amino acids having the sequence set forth in SEQ ID NO:94;

(xxv) a heavy chain variable region comprising amino acids having the sequence set forth in SEQ ID NO:274, and a light chain variable region comprising amino acids having the sequence set forth in SEQ ID NO:275;

(xxvi) a heavy chain variable region comprising amino acids having the sequence set forth in SEQ ID NO:286, and a light chain variable region comprising amino acids having the sequence set forth in SEQ ID NO:287;

(xxvii) a heavy chain variable region comprising amino acids having the sequence set forth in SEQ ID NO:298, and a light chain variable region comprising amino acids having the sequence set forth in SEQ ID NO:299;

(xxviii) a heavy chain variable region comprising amino acids having the sequence set forth in SEQ ID NO:310, and a light chain variable region comprising amino acids having the sequence set forth in SEQ ID NO:311;

(xxix) a heavy chain variable region comprising amino acids having the sequence set forth in SEQ ID NO:322, and a light chain variable region comprising amino acids having the sequence set forth in SEQ ID NO:323;

(xxx) a heavy chain variable region comprising amino acids having the sequence set forth in SEQ ID NO:334, and a light chain variable region comprising amino acids having the sequence set forth in SEQ ID NO:335;

(xxxi) a heavy chain variable region comprising amino acids having the sequence set forth in SEQ ID NO:346, and a light chain variable region comprising amino acids having the sequence set forth in SEQ ID NO:347; or (xxxii) a heavy chain variable region comprising amino acids having the sequence set forth in SEQ ID NO:358, and a light chain variable region comprising amino acids the sequence set forth in SEQ ID NO:359.

4. The anti-human GPRC5D scFv of claim 1, wherein the GPRC5D comprises the amino acid sequence set forth in SEQ ID NO:97.

5. The anti-human GPRC5D scFv of claim 1, wherein the scFv comprises the amino acid sequence selected from the group consisting of SEQ ID NOS: 100-123, 276, 288, 300, 312, 324, 336, 348 and 360.

6. A composition comprising the anti-human GPRC5D scFv antibody of claim 1, and a pharmaceutically acceptable carrier.

7. An immunoconjugate comprising the anti-human GPRC5D scFv antibody of claim 1, linked to a therapeutic agent.

8. The immunoconjugate of claim 7, wherein said therapeutic agent is a drug.

9. A composition comprising the immunoconjugate of claim 7 and a pharmaceutically acceptable carrier.

10. A bispecific molecule comprising the anti-human GPRC5D scFv of claim 1, linked to a second functional moiety.

11. The bispecific molecule of claim 10, wherein the second functional moiety has a different binding specificity than said anti-human GPRC5D scFv.

12. The bispecific molecule of claim 11, wherein the second functional moiety has a binding specificity for an immune cell.

13. The bispecific molecule of claim 11, wherein the second functional moiety has a binding specificity for CD3.

14. A composition comprising the bispecific molecule of claim 10 and a pharmaceutically acceptable carrier.

15. A nucleic acid that encodes an anti-human GPRC5D scFv of claim 1.

16. An expression vector comprising the nucleic acid molecule of claim 15.

17. A host cell comprising the expression vector of claim 16.

18. A method for detecting GPRC5D in a whole cell or tissue, comprising:

contacting a cell or tissue with the anti-human GPRC5D scFv of claim 7, wherein said anti-human GPRC5D scFv comprises a detectable label; and determining the amount of the labeled anti-human GPRC5D scFv bound to said cell or tissue by measuring the amount of detectable label associated with said cell or tissue, wherein the amount of bound anti-human GPRC5D scFv indicates the amount of GPRC5D in said cell or tissue.

19. The anti-human GPRC5D scFv of claim 1, wherein the heavy chain variable region comprises a CDR1 comprising the amino acid sequence set forth in SEQ ID NO:220, a CDR2 comprising the amino acid sequence set forth in SEQ ID NO:221, and a CDR3 comprising the amino acid sequence set forth in SEQ ID NO:222; and the light chain variable region comprises a CDR1 comprising the amino acid sequence set forth in SEQ ID NO:223, a CDR2 comprising the amino acid sequence of GKN, and a CDR3 comprising the amino acid sequence set forth in SEQ ID NO:225.

20. The anti-human GPRC5D scFv of claim 1, comprising the amino acid sequence set forth in SEQ ID NO:116.

21. The immunoconjugate of claim 7, wherein said therapeutic agent is a cytotoxin.

22. The immunoconjugate of claim 7, wherein said therapeutic agent is a radioactive isotope.

* * * * *